United States Patent
Himmelsbach et al.

(10) Patent No.: US 9,492,436 B2
(45) Date of Patent: Nov. 15, 2016

(54) AZABENZIMIDAZOLE DERIVATIVES

(71) Applicants: Frank Himmelsbach, Mittelbiberach (DE); Elke Langkopf, Biberach an der Riss (DE); Holger Wagner, Mettenberg (DE); Nobert Redemann, Biberach an der Riss (DE)

(72) Inventors: Frank Himmelsbach, Mittelbiberach (DE); Elke Langkopf, Biberach an der Riss (DE); Holger Wagner, Mettenberg (DE); Nobert Redemann, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/331,359

(22) Filed: Jul. 15, 2014

(65) Prior Publication Data

US 2015/0025065 A1    Jan. 22, 2015

(30) Foreign Application Priority Data

Jul. 17, 2013 (EP) ..................... 13176929

(51) Int. Cl.

| | |
|---|---|
| *C07D 471/02* | (2006.01) |
| *A61K 31/437* | (2006.01) |
| *A61K 31/496* | (2006.01) |
| *A61K 31/497* | (2006.01) |
| *A61K 31/501* | (2006.01) |
| *A61K 31/506* | (2006.01) |
| *A61K 31/541* | (2006.01) |
| *A61K 45/06* | (2006.01) |
| *C07D 493/04* | (2006.01) |
| *C07D 519/00* | (2006.01) |

(52) U.S. Cl.
CPC .......... *A61K 31/437* (2013.01); *A61K 31/496* (2013.01); *A61K 31/497* (2013.01); *A61K 31/501* (2013.01); *A61K 31/506* (2013.01); *A61K 31/541* (2013.01); *A61K 45/06* (2013.01); *C07D 493/04* (2013.01); *C07D 519/00* (2013.01)

(58) Field of Classification Search
None
See application file for complete search history.

(56) References Cited

FOREIGN PATENT DOCUMENTS

| | | |
|---|---|---|
| WO | 2008008895 A1 | 1/2008 |
| WO | 2012116145 A1 | 8/2012 |

OTHER PUBLICATIONS

International Search Report PCT/EP2014/065004 mailed Oct. 2, 2014.

*Primary Examiner* — Heidi Reese
(74) *Attorney, Agent, or Firm* — Michael P. Morris; Usha R. Patel

(57) ABSTRACT

The present invention relates to compounds of general formula I,

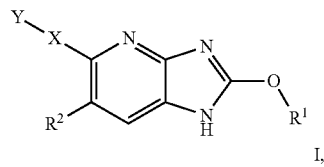

wherein the group $R^1$, $R^2$, X and Y are defined as in claim 1, which have valuable pharmacological properties, in particular bind to the AMP-activated protein kinase (AMPK) and modulate its activity. The compounds are suitable for treatment and prevention of diseases which can be influenced by this receptor, such as metabolic diseases, in particular diabetes type 2.

11 Claims, No Drawings

AZABENZIMIDAZOLE DERIVATIVES

FIELD OF THE INVENTION

The present invention relates to novel azabenzimidazole derivatives that are agonists of the AMP-activated protein kinase (AMPK), to processes for their preparation, to pharmaceutical compositions containing these compounds and to their medical use for the prophylaxis and/or treatment of diseases which can be influenced by the modulation of the function of AMPK. Particularly, the pharmaceutical compositions of the invention are suitable for the prophylaxis and/or therapy of metabolic diseases, such as diabetes, more specifically type 2 diabetes mellitus, and conditions associated with the disease, including insulin resistance, obesity, cardiovascular disease and dyslipidemia.

BACKGROUND OF THE INVENTION

Metabolic diseases are diseases caused by an abnormal metabolic process and may either be congenital due to an inherited enzyme abnormality or acquired due to a disease of an endocrine organ or failure of a metabolically important organ such as the liver or the pancreas.

Diabetes mellitus is a disease state or process derived from multiple causative factors and is defined as a chronic hyperglycemia associated with resulting damages to organs and dysfunctions of metabolic processes. Depending on its etiology, one differentiates between several forms of diabetes, which are either due to an absolute (lacking or decreased insulin secretion) or to a relative lack of insulin. Diabetes mellitus Type I (IDDM, insulin-dependent diabetes mellitus) generally occurs in adolescents under 20 years of age. It is assumed to be of auto-immune etiology, leading to an insulitis with the subsequent destruction of the beta cells of the islets of Langerhans which are responsible for the insulin synthesis. In addition, in latent autoimmune diabetes in adults (LADA; Diabetes Care. 8: 1460-1467, 2001) beta cells are being destroyed due to autoimmune attack. The amount of insulin produced by the remaining pancreatic islet cells is too low, resulting in elevated blood glucose levels (hyperglycemia). Diabetes mellitus Type II generally occurs at an older age. It is above all associated with a resistance to insulin in the liver and the skeletal muscles, but also with a defect of the islets of Langerhans. High blood glucose levels (and also high blood lipid levels) in turn lead to an impairment of beta cell function and to an increase in beta cell apoptosis.

Persistent or inadequately controlled hyperglycemia is associated with a wide range of pathologies. Diabetes is a very disabling disease, because today's common antidiabetic drugs do not control blood sugar levels well enough to completely prevent the occurrence of high and low blood sugar levels. Out of range blood sugar levels are toxic and cause long-term complications for example retinopathy, renopathy, neuropathy and peripheral vascular disease. There is also a host of related conditions, such as obesity, hypertension, stroke, heart disease and hyperlipidemia, for which persons with diabetes are substantially at risk.

Obesity is associated with an increased risk of follow-up diseases such as cardiovascular diseases, hypertension, diabetes, hyperlipidemia and an increased mortality. Diabetes (insulin resistance) and obesity are part of the "metabolic syndrome" which is defined as the linkage between several diseases (also referred to as syndrome X, insulin-resistance syndrome, or deadly quartet). These often occur in the same patients and are major risk factors for development of diabetes type II and cardiovascular disease. It has been suggested that the control of lipid levels and glucose levels is required to treat diabetes type II, heart disease, and other occurrences of metabolic syndrome (see e.g., Diabetes 48: 1836-1841, 1999; JAMA 288: 2209-2716, 2002).

Sensing and regulating cellular the energy status in response to environmental and/or nutritional stress is highly important and AMP-activated protein kinase (AMPK) is a major contributor for this task (Hardie et al. (2001) Bioessays 23: 1112; Kemp et al. (2003) Biochem. Soc. Transactions 31: 162). Cellular energy depletion leads to the activation of AMP-activated protein kinase (AMPK) thereby inhibiting ATP consuming and upregulating ATP generating pathways. On a cellular level several substrates are regulated by AMP-activated protein kinase (AMPK) such as acetyl-CoA-carboxylase (ACC) and HMG-CoA-reductase (Carling et al. (1987) FEBS Letters 223: 217), hormone-sensitive lipase (Garton et al. (1989) Eur. J. Biochem. 179: 249), malonyl-CoA-decarboxylase (Saha et al. (2000) J. Biol. Chem. 275: 24279) and glycerol-3-phosphate acyltransferase (Muoio et al. (1999) Biochem. J. 338: 783).

AMP-activated protein kinase (AMPK) mediated phosphorylation of ACC leads to inhibition of ACC, which then results in a decrease of fatty acid synthesis while fatty acid oxidation is increased. AMP-activated protein kinase (AMPK) mediated phosphorylation and inhibition of HMG-CoA-reductase leads to a decrease in cholesterol synthesis. Triacylglycerol synthesis and fatty acid oxidation is regulated by AMP-activated protein kinase (AMPK) via glycerol-3-phosphate acyltransferase. In addition AMP-activated protein kinase (AMPK) stimulates glucose transport in skeletal muscle and regulates the expression of genes involved in fatty acid and glucose metabolism (Hardie et al. (2001) Bioessays 23: 1112; Kemp et al. (2003) Biochem. Soc. Transactions 31: 162). Glucose homeostasis is mediated in liver and muscle by AMP-activated protein kinase (AMPK), wherein activation of AMP-activated protein kinase (AMPK) leads to an increase in GLUT 4-dependent glucose uptake (Sakamoto et al. (2008) Am. J. Physiol. Endocrinol. Metab. 295: E29-E37; Karagounis et al. (2009) Int. J. Biochem. Cell Biol. 41: 2360-2363; Pehmoller et al. (2009) Am. J. Physiol. Endocrinol. Metab. 297: E665-E675).

Besides energy regulation on a cellular level AMP-activated protein kinase (AMPK) also regulates whole body energy metabolism. Independently of the cellular AMP level AMP-activated protein kinase (AMPK) can be activated by the adipocyte derived hormones leptin (Minokoski et al. (2002) Nature 415: 339) and adiponectin (Yamauchi et al. (2002) Nature Medicine 8: 1288).

From the points discussed above activation of AMP-activated protein kinase (AMPK) in vivo is expected to result in hepatic stimulation of fatty acid oxidation; inhibition of cholesterol synthesis, lipogenesis and triglyceride synthesis; stimulation of skeletal muscle fatty acid oxidation and glucose uptake; improved insulin action; increase in energy expenditure and hence a decrease body weight.

OBJECT OF THE PRESENT INVENTION

The object of the present invention is to provide new compounds, hereinafter described as compounds of formula I, in particular new azabenzimidazole derivatives, which are active with regard to the AMP-activated protein kinase (AMPK), notably are agonists of the AMP-activated protein kinase (AMPK).

A further object of the present invention is to provide new compounds, in particular new azabenzimidazole derivatives, which have an activating effect on the AMP-activated protein kinase (AMPK) in vitro and/or in vivo and possess suitable pharmacological and pharmacokinetic properties to use them as medicaments.

A further object of the present invention is to provide effective agonists of AMP-activated protein kinase (AMPK), in particular for the treatment of metabolic disorders, for example diabetes, dyslipidemia and/or obesity.

A further object of the present invention is to provide methods for treating a disease or condition mediated by the activation the AMP-activated protein kinase (AMPK) in a patient.

A further object of the present invention is to provide a pharmaceutical composition comprising at least one compound according to the invention.

A further object of the present invention is to provide a combination of at least one compound according to the invention with one or more additional therapeutic agents.

Further objects of the present invention become apparent to the one skilled in the art by the description hereinbefore and in the following and by the examples.

AMP-activated protein kinase (AMPK) modulators are known in the art, for example, the compounds disclosed in WO 2012033149 and WO 2012116145. The azabenzimidazole derivatives of the present invention may provide several advantages, such as enhanced potency, high metabolic and/or chemical stability, high selectivity and/or tolerability and in consequence low toxicity, reduced risk to cause adverse events or undesirable side effects, and enhanced solubility.

SUMMARY OF THE INVENTION

In a first aspect the invention relates to compounds of formula I

I wherein
$R^1$ is selected from the group $R^1$-G1 consisting of $C_{3-10}$-cycloalkyl and heterocyclyl, both optionally substituted with 1 to 3 groups independently selected from HO—, NC—, $HO_2C$—, $HO_2C$—$H_2C$—, $C_{1-4}$-alkyl, $C_{1-4}$-alkyl-O—, and HO—$C_{1-4}$-alkyl-,
  wherein heterocyclyl denotes a saturated mono-, bi- or spirocyclic ring system having 5 to 10 ring member atoms of which 1 or 2 not vicinal ring members are O atoms;
$R^2$ is selected from the group $R^2$-G1 consisting of F, Cl, Br, $C_{1-4}$-alkyl, and $C_{1-4}$-alkyl-O—,
  wherein any alkyl group and subgroup is optionally substituted with 1 or more F atoms;
X is selected from the group X-G1 consisting of a bond, a divalent heterocyclyl group, an arylene, and a heteroarylene group,
  wherein heterocyclyl denotes a saturated monocyclic 5 to 7-membered ring system containing 1 or 2 N atoms, optionally substituted with 1 to 3 groups independently selected from F, $C_{1-4}$-alkyl and $C_{1-4}$-alkyl-O—, and
  wherein said arylene and heteroarylene groups are optionally substituted with 1 to 3 groups independently selected from F, Cl, Br, I, NC—, HO—, $HO_2C$—, $C_{1-4}$-alkyl, $C_{1-4}$-alkyl-O—, $F_3C$—, and $F_3CO$—;
Y is selected from the group Y-G1 consisting of a $C_{5-7}$-cycloalkyl, $C_{5-7}$-cycloalkenyl, heterocyclyl, aryl, and heteroaryl group, which are mandatorily substituted with a group selected from $R^SR^{S'}(O=)S=N$—, $R^SR^{S'}(O=)S=N$—$C_{1-3}$-alkyl-, $R^SR^{S'}(O=)S=N$—$C(=O)$—, $(R^N)N=S(=O)(R^S)$—, $(R^N)N=S(=O)(R^S)$—$C_{1-3}$-alkyl-, and $R^SR^{S'}(R^{N'}-N=)S=N$—,
  wherein said $C_{5-7}$-cycloalkyl, $C_{5-7}$-cycloalkenyl, and heterocyclyl groups are optionally substituted with 1 to 3 groups independently selected from F, $C_{1-4}$-alkyl- and $C_{1-4}$-alkyl-O—, and
  wherein said aryl and heteroaryl groups are optionally substituted with 1 to 3 groups independently selected from F, Cl, Br, I, NC—, HO—, $HO_2C$—, $C_{1-4}$-alkyl, $C_{1-4}$-alkyl-O—, $F_3C$—, and $F_3CO$—, and
  wherein $R^N$ is selected from H, NC—, $C_{1-4}$-alkyl, $C_{1-4}$-alkyl-$C(=O)$—, $C_{1-4}$-alkyl-O—$C(=O)$—, $C_{3-7}$-cycloalkyl, $C_{3-7}$-cycloalkyl-$C_{1-3}$-alkyl-, $C_{3-7}$-cycloalkyl-$C(=O)$—, heterocyclyl, heterocyclyl-$CH_2$—, heterocyclyl-$C(=O)$—, aryl, aryl-$C_{1-3}$-alkyl-, aryl-$C(=O)$—, heteroaryl, heteroaryl-$C_{1-3}$-alkyl-, and heteroaryl-$C(=O)$—, and $R^{N'}$ is selected from H, NC—, $C_{1-4}$-alkyl-, aryl, aryl-$C_{1-3}$-alkyl-, heteroaryl, heteroaryl-$C_{1-3}$-alkyl-,
  wherein any alkyl, cycloalkyl and heterocyclyl group is optionally substituted with 1 to 3 groups independently selected from F, $C_{1-3}$-alkyl-O—, $(C_{1-3}$-alkyl$)_2$-N—, $HO_2C$—, $C_{1-3}$-alkyl-$C(=O)$—, and $C_{1-3}$-alkyl-$S(=O)_2$—, and wherein any aryl and heteroaryl group is optionally substituted with 1 to 3 groups independently selected from F, Cl, Br, I, HO—, NC—, $HO_2C$—, $C_{1-3}$-alkyl, $C_{1-3}$-alkyl-O—, $H_2N$—, $C_{1-3}$-alkyl-NH—, $(C_{1-3}$-alkyl$)_2$-N—, and $C_{1-3}$-alkyl-$S(=O)_2$—, and
  wherein $R^{N'}$ is selected from H, NC—, $C_{1-4}$-alkyl, $C_{3-7}$-cycloalkyl, aryl-$C_{1-3}$-alkyl-, heteroaryl, heteroaryl-$C_{1-3}$-alkyl-,
  wherein any alkyl and cycloalkyl optionally substituted with 1 to 3 groups independently selected from F, $C_{1-3}$-alkyl-O—, $(C_{1-3}$-alkyl$)_2$-N—, $HO_2C$—, $C_{1-3}$-alkyl-$C(=O)$—, and $C_{1-3}$-alkyl-$S(=O)_2$—,
  and wherein any aryl and heteroaryl group is optionally substituted with 1 to 3 groups independently selected from F, Cl, Br, I, HO—, NC—, $HO_2C$—, $C_{1-3}$-alkyl, $C_{1-3}$-alkyl-O—, $H_2N$—, $C_{1-3}$-alkyl-NH—, $(C_{1-3}$-alkyl$)_2$-N—, and $C_{1-3}$-alkyl-$S(=O)_2$—, and
  wherein $R^S$ and $R^{S'}$ are independently selected from $C_{1-4}$-alkyl, $C_{3-7}$-cycloalkyl, $C_{3-7}$-cycloalkyl-$C_{1-3}$-alkyl-, heterocyclyl, heterocyclyl-$C_{1-3}$-alkyl-, aryl, aryl-$CH_2$—, heteroaryl, and heteroaryl-$C_{1-3}$-alkyl-
  wherein any alkyl, cycloalkyl and heterocyclyl group is optionally substituted with 1 to 3 groups independently selected from $C_{1-3}$-alkyl-O—, $(C_{1-3}$-alkyl$)_2$-N—, $HO_2C$—, $C_{1-3}$-alkyl-$C(=O)$—, and $C_{1-3}$-alkyl-$S(=O)_2$—, and
  wherein any aryl and heteroaryl group is optionally substituted with 1 to 3 groups independently selected from F, Cl, Br, I, HO—, NC—, $C_{1-3}$-alkyl, $C_{1-3}$-alkyl-O—, $H_2N$—, $C_{1-3}$-alkyl-NH—, $(C_{1-3}$-alkyl$)_2$-N—, and $C_{1-3}$-alkyl -$S(=O)_2$,
  or $R^S$ and $R^{S'}$ together with the S-atom these groups are attached to form a 5-7 membered saturated monocyclic ring system containing 0 to 1 heteroatoms selected from —$NR^{N''}$— and O, optionally substituted with 1 to 3 groups independently selected from F, HO—, $C_{1-3}$- alkyl, $C_{1\text{-}3}$-alkyl-O—, $H_2N$—, $C_{1\text{-}3}$-alkyl-NH—, ($C_{1\text{-}3}$-alkyl)$_2$-N—, and $C_{1\text{-}3}$-alkyl-S($=$O)$_2$—, and wherein $R^{N'''}$ is selected from H, $H_3C$—, $H_5C_2$—, and cyclopropyl;

a saturated or partly unsaturated heterocyclyl group containing a —S($=$O)($=$N—$R^N$)— group, optionally substituted with 1 to 3 groups independently selected from F, HO—, NC—, $C_{1\text{-}4}$-alkyl- and $C_{1\text{-}4}$-alkyl-O—, wherein $R^N$ is defined as mentioned hereinbefore;

wherein any heterocyclyl group mentioned hereinbefore, if not specified otherwise, denotes a saturated or partially unsaturated monocyclic or bicyclic fused, bridged or spiro group having 5 to 12 ring member atoms of which 4 to 11 ring members are C atoms and 1 to 3 ring members are heteroatoms selected from N and $NR^{N'''}$, or 1 or 2 ring members are heteroatoms selected from N and $NR^{N'''}$ and 1 ring member is selected from O and S($=$O)$_r$ with r=0, 1 or 2, or 1 ring member is N and 2 ring members are independently selected from O and S($=$O)$_r$ with r=0, 1 or 2, with the proviso that no O—O, S—S or S—O bond is formed, wherein 1 $CH_2$ ring member attached to a ring member N atom is optionally replaced by a —C($=$O)— group, and wherein $R^{N'''}$ is defined as mentioned hereinbefore;

wherein any arylene group mentioned hereinbefore denotes a bivalent aryl group;

wherein any heteroarylene group mentioned hereinbefore denotes a bivalent heteroaryl group;

wherein any aryl group mentioned hereinbefore, if not specified otherwise, denotes a carbocyclic aromatic monocyclic group containing 6 carbon atoms which may be further fused to a second 5- or 6-membered carbocyclic group which may be aromatic, saturated or unsaturated;

wherein any heteroaryl group mentioned hereinbefore, if not specified otherwise, denotes tetrazolyl, a 5-membered heteroaromatic ring containing 1 ring member selected from $NR^{N'''}$, O and S, or 1 N and 1 ring member selected from $NR^{N'''}$, O and S, or 1 $NR^{N'''}$, O or S and 2 N, wherein $R^{N'''}$ is defined as mentioned hereinbefore, or a 6-membered heteroaromatic ring containing 1 to 3 N atoms; and wherein in any definition mentioned hereinbefore and if not specified otherwise, any alkyl group or sub-group may be straight-chained or branched, the isoforms, tautomers, stereoisomers, metabolites, prodrugs, solvates, hydrates, and the salts thereof, particularly the physiologically acceptable salts thereof with inorganic or organic acids or bases, or the combinations thereof.

The expression "optionally substituted with 1 or more F atoms" means that none or one up to successively all H atoms bound to carbon atoms of the respective group or submoiety may be replaced by F atoms, preferably 1 to 5 H atoms or, more preferred, 1 to 3 H atoms may be replaced by F atoms.

The extension -Gn used within the definitions is meant to identify genus n of the respective substituent. For example, $R^1$-G1 defines genus 1 of the substituent $R^1$.

In a further aspect this invention relates to a pharmaceutical composition, comprising one or more compounds of general formula I or one or more pharmaceutically acceptable salts thereof according to the invention, optionally together with one or more inert carriers and/or diluents.

In a further aspect this invention relates to a method for treating diseases or conditions which are mediated by activating the AMP-activated protein kinase (AMPK) in a patient in need thereof characterized in that a compound of general formula I or a pharmaceutically acceptable salt thereof is administered to the patient.

According to another aspect of the invention, there is provided a method for treating a metabolic disease or disorder, such as diabetes, dyslipidemia and/or obesity, in a patient in need thereof characterized in that a therapeutically effective amount of a compound of general formula I or a pharmaceutically acceptable salt thereof is administered to the patient.

According to another aspect of the invention, there is provided the use of a compound of the general formula I or a pharmaceutically acceptable salt thereof for the manufacture of a medicament for a therapeutic method as described hereinbefore and hereinafter.

According to another aspect of the invention, there is provided a compound of the general formula I or a pharmaceutically acceptable salt thereof for use in a therapeutic method as described hereinbefore and hereinafter.

In a further aspect this invention relates to a method for treating a disease or condition mediated by the activation of the AMP-activated protein kinase (AMPK) in a patient that includes the step of administering to the patient in need of such treatment a therapeutically effective amount of a compound of the general formula I or a pharmaceutically acceptable salt thereof in combination with a therapeutically effective amount of one or more additional therapeutic agents.

In a further aspect this invention relates to the use of a compound of the general formula I or a pharmaceutically acceptable salt thereof in combination with one or more additional therapeutic agents for the treatment of diseases or conditions which are mediated by the activation of the AMP-activated protein kinase (AMPK).

In a further aspect this invention relates to a pharmaceutical composition which comprises a compound according to general formula I or a pharmaceutically acceptable salt thereof and one or more additional therapeutic agents, optionally together with one or more inert carriers and/or diluents.

Other aspects of the invention become apparent to the one skilled in the art from the specification and the experimental part as described hereinbefore and hereinafter.

DETAILED DESCRIPTION

Unless otherwise stated, the groups, residues, and substituents, particularly $R^1$, $R^2$, X, and Y are defined as above and hereinafter. If residues, substituents, or groups occur several times in a compound, they may have the same or different meanings. Some preferred meanings of individual groups and substituents of the compounds according to the invention will be given hereinafter. Any and each of these definitions may be combined with each other.

$R^1$:

$R^1$-G1:

The group $R^1$ is preferably selected from the group $R^1$-G1 as defined hereinbefore.

$R^1$-G2:

According to one embodiment the group $R^1$ is selected from the group $R^1$-G2 consisting of

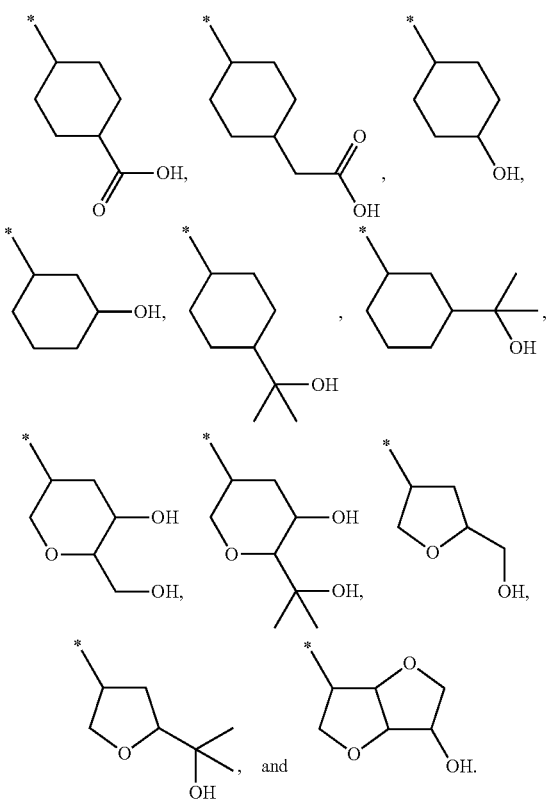

R¹-G3:

According to one embodiment the group R¹ is selected from the group R¹-G3 consisting of

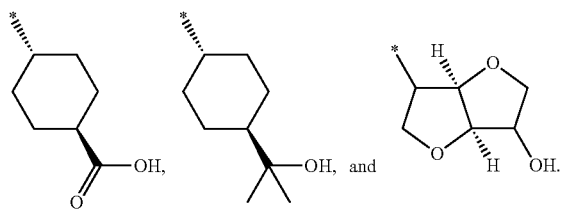 [SMILES: *[C@H]1CC[C@H](C(=O)O)CC1 ; *[C@H]1CC[C@H](C(C)(C)O)CC1 ; *C1CO[C@@H]2C(O)CO[C@H]12]

R¹-G4:

According to embodiment R¹-G4 the group R¹ is

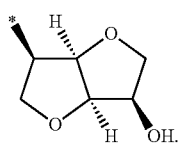 [SMILES: *[C@@H]1CO[C@H]2[C@@H]1OC[C@H]2O]

R²:

R²-G1:

The group R² is preferably selected from the group R²-G1 as defined hereinbefore.

R²-G2:

In another embodiment the group R² is selected from the group R²-G2 consisting of F, Cl, $H_3C-$, $H_3C-O-$, $F_3C-$, and $F_3C-O-$.

R²-G3:

In another embodiment the group R² is selected from the group R²-G3 consisting of $C_1$, $H_3C-$, and $F_3C-$.

R²-G4:

In another embodiment the group R² is selected from the group R²-G4 consisting of Cl, and $H_3C-$.

X:

X-G1:

The group X is preferably selected from the group X-G1 as defined hereinbefore.

X-G2:

In another embodiment the group X is selected from the group X-G2 consisting of a bond, a divalent piperidinyl, a divalent piperazinyl, a phenylene, pyridinylene, pyrimidinylene, and pyridazinylene group,
  wherein said divalent piperidinyl and piperazinyl group is optionally substituted with F, $H_3C-$, or $H_3C-O-$, and
  wherein said phenylene, pyridinylene, pyrimidinylene, and pyridazinylene group are optionally substituted with F, Cl, Br, NC—, $HO_2C-$, $H_3C-$, $H_3C-O-$, $F_3C-$, or $F_3CO-$.

X-G3:

In another embodiment the group X is selected from the group X-G3 consisting of a bond, a divalent piperazinyl, a phenylene, and a pyridinylene group, bound via para positions and optionally substituted with F or $H_3C-$.

X-G4:

In another embodiment the group X is selected from the group X-G4 consisting of a bond, a divalent piperazinyl, and a phenylene group, both bound via para positions.

X-G5:

In another embodiment the group X is selected from the group X-G5 consisting of a pyridinylene and a pyrimidinylene group, both bound via para positions.

Y:

Y-G1:

The group Y is preferably selected from the group Y-G1 as defined hereinbefore.

Y-G2a:

In another embodiment the group Y is selected from the group Y-G2a consisting of cyclohexyl, cyclohexenyl, piperidinyl, phenyl, pyridinyl, and pyrimidinyl, which are mandatorily substituted with a group selected from $R^S R^{S'}(O=)S=N-$, $R^S R^{S'}(O=)S=N-C_{1-3}$-alkyl-, $R^S R^{S'}(O=)S=N-C(=O)-$, $(R^N)N=S(=O)(R^S)-$, $(R^N)N=S(=O)(R^S)-C_{1-3}$-alkyl-, and $R^S R^S (R^{N'}-N=)S=N-$,
  wherein $R^N$, $R^{N'}$ and $R^S$ and $R^{S'}$ are defined as mentioned under Y-G1, and
  wherein said cyclohexyl, cyclohexenyl, piperidinyl and piperazinyl groups are optionally substituted with F, $H_3C-$, and $H_3C-O-$, and
  wherein said phenyl, pyridinyl, and pyrimidinyl groups are optionally substituted with F, Cl, Br, NC—, $HO_2C-$, $H_3C-$, $H_3C-O-$, $F_3C-$, or $F_3CO-$.

Y-G2b:

In another embodiment the group Y is selected from the group Y-G2b consisting of a saturated or partly unsaturated monocyclic 5-7 membered ring system, optionally substituted with F, $H_3C-$, and $H_3C-O-$,
  wherein mandatorily one ring member is a $-S(=O)(=N-R^N)-$ group and optionally one ring member is a $-NR^{N''}-$ group,
  wherein $R^N$ and $R^{N''}$ are defined as mentioned under Y-G1.

Y-G3a:

In another embodiment the group Y is selected from the group Y-G3a consisting of cyclohexyl, piperidinyl, phenyl and pyridinyl, which are mandatorily substituted with a group selected from $R^S R^{S'}(O=)S=N-$, $R^S R^{S'}(O=)S=N-CH_2-$, $R^S R^{S'}(O=)S=N-C(=O)-$, $(R^N)N=S(=O)(R^S)-$, $(R^N)N=S(=O)(R^S)-CH_2-$, and $R^S R^{S'}(R^{N'}-N=)S=N-$,
- wherein $R^N$ is selected from H, NC—, $H_3C-$, $(CH_3)_3C-O-C(=O)-$, $F_3C-C(=O)-$, and $R^{N'}$ is H,
- wherein $R^S$ and $R^{S'}$ are independently selected from $H_3C-$, $H_5C_2-$, $(H_3C)_2CH-$, cyclopropyl, tetrahydropyranyl, phenyl, and pyridinyl, or $R^S$ and $R^{S'}$ linked together are selected from $-(CH_2)_4-$, $-(CH_2)_5-$, and $-(CH_2)_2-O-(CH_2)_2-$, and
- wherein any cyclohexyl, piperidinyl, phenyl and pyridinyl groups mentioned under Y or $R^S$ and $R^{S'}$ optionally are substituted with F, $H_3C-$, or $H_3C-O-$.

Y-G3b:

In another embodiment the group Y is selected from the group Y-G3b consisting of

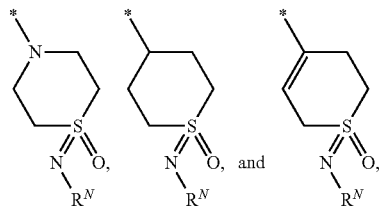

wherein $R^N$ is selected from H, NC—, $H_3C-$, $(H_3C)_3C-O-C(=O)-$, and $F_3C-C(=O)-$.

Y-G4a:

According to embodiment Y-G4a the group Y is phenyl or pyridinyl, both mandatorily substituted with a group selected from

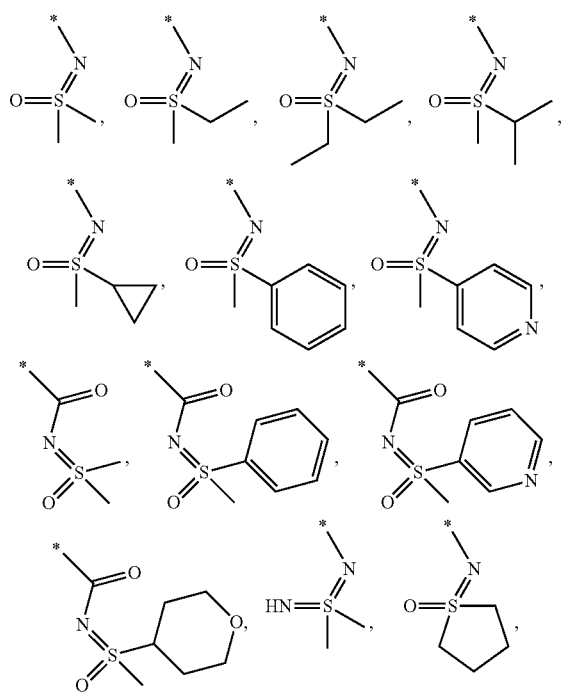

Y-G4b:

According to embodiment Y-G4b the group Y is

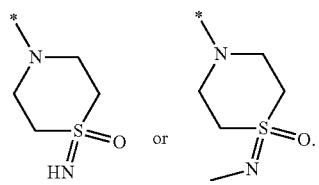

Y-G5a:

In another embodiment the group Y is selected from the group Y-G5a consisting a bicyclic fused partially unsaturated heterocyclyl group having 8 to 10 ring member atoms of which 6 to 8 ring members are C atoms and 1 or 2 ring members are heteroatoms selected from N and $NR^{N''}$,
- wherein an unsaturated ring member (preferably a phenyl or pyridinyl ring) as part of the bicyclic fused heterocyclyl group is mandatorily substituted with a group selected from $R^S R^{S'}(O=)S=N-$ or $R^S R^{S'}(O=)S=N-CH_2-$,
- wherein $R^S$ and $R^{S'}$ are independently selected from $H_3C-$, $H_5C_2-$ and $(H_3C)_2CH-$, $R^N$ is selected from H, NC—, and $H_3C-$, and
- wherein $R^{N''}$ is selected from H, $H_3C-$, and $H_5C_2-$.

Y-G5b:

In another embodiment the group Y is selected from the group Y-G5b consisting of a bicyclic fused or bridged saturated heterocyclyl group having 8 to 10 ring member atoms of which 6 to 8 ring members are C atoms and 1 ring member is a heteroatom selected from N and $NR^{N''}$ and 1 $CH_2$ ring member is replaced by a $-S(=O)(=N-R^N)-$ group,
- wherein $R^N$ is selected from H, NC—, and $H_3C-$, and
- wherein $R^{N''}$ is selected from H, $H_3C-$, and $H_5C_2-$.

Y-G6:

According to embodiment Y-G6 the group Y is pyrazinyl or pyrazidinyl, both mandatorily substituted with a group selected from $R^S R^{S'}(O=)S=N-$ or $R^S R^{S'}(O=)S=N-CH_2-$,
- wherein $R^S$ and $R^{S'}$ are independently selected from $H_3C-$, $H_5C_2-$ and $(H_3C)_2CH-$, $R^N$ is selected from H, NC—, and $H_3C-$.

Examples of preferred subgeneric embodiments (E) according to the present invention are set forth in the following table, wherein each substituent group of each embodiment is defined according to the definitions set forth hereinbefore and wherein all other substituents of the formula I are defined according to the definitions set forth hereinbefore:

| Embodiment | R¹- | R²- | X- | Y- |
|---|---|---|---|---|
| E-1 | R¹-G1 | R²-G1 | X-G1 | Y-G1 |
| E-2 | R¹-G2 | R²-G1 | X-G1 | Y-G1 |
| E-3 | R¹-G2 | R²-G1 | X-G2 | Y-G2a |
| E-4 | R¹-G3 | R²-G2 | X-G1 | Y-G3a |
| E-5 | R¹-G3 | R²-G2 | X-G2 | Y-G3a |
| E-6 | R¹-G3 | R²-G2 | X-G3 | Y-G3a |
| E-7 | R¹-G3 | R²-G3 | X-G3 | Y-G3a |
| E-8 | R¹-G3 | R²-G2 | X-G2 | Y-G4a |
| E-9 | R¹-G3 | R²-G2 | X-G3 | Y-G4a |
| E-10 | R¹-G3 | R²-G3 | X-G3 | Y-G4a |
| E-11 | R¹-G4 | R²-G3 | X-G3 | Y-G4a |
| E-12 | R¹-G2 | R²-G1 | X-G2 | Y-G2b |
| E-13 | R¹-G3 | R²-G2 | X-G1 | Y-G3b |
| E-14 | R¹-G3 | R²-G2 | X-G2 | Y-G3b |
| E-15 | R¹-G3 | R²-G2 | X-G3 | Y-G3b |
| E-16 | R¹-G3 | R²-G3 | X-G3 | Y-G3b |
| E-17 | R¹-G3 | R²-G2 | X-G2 | Y-G4b |
| E-18 | R¹-G3 | R²-G2 | X-G3 | Y-G4b |
| E-19 | R¹-G3 | R²-G3 | X-G3 | Y-G4b |
| E-20 | R¹-G4 | R²-G3 | X-G3 | Y-G4b |
| E-21 | R¹-G3 | R²-G4 | X-G3 | Y-G3a |
| E-22 | R¹-G3 | R²-G4 | X-G3 | Y-G4a |
| E-23 | R¹-G4 | R²-G4 | X-G3 | Y-G4a |
| E-24 | R¹-G3 | R²-G4 | X-G3 | Y-G3b |
| E-25 | R¹-G3 | R²-G4 | X-G3 | Y-G4b |
| E-26 | R¹-G4 | R²-G4 | X-G3 | Y-G4b |
| E-27 | R¹-G3 | R²-G4 | X-G3 | Y-G5a |
| E-28 | R¹-G4 | R²-G4 | X-G4 | Y-G5a |
| E-29 | R¹-G3 | R²-G4 | X-G5 | Y-G3a |
| E-30 | R¹-G4 | R²-G4 | X-G5 | Y-G4a |
| E-31 | R¹-G3 | R²-G4 | X-G3 | YG5b |
| E-32 | R¹-G4 | R²-G4 | X-G4 | YG5b |
| E-33 | R¹-G3 | R²-G4 | X-G3 | YG6 |
| E-34 | R¹-G4 | R²-G4 | X-G4 | YG6 |

According to embodiment E-21 those compounds of formula I are preferred, wherein
R¹ is selected from the group consisting of

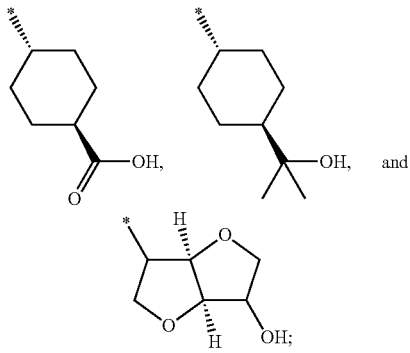

R² is selected from the group consisting of Cl, and H₃C—;
X is selected from the group consisting of a bond, a divalent piperazinyl, phenylene, and a pyridinylene, bound via para positions and optionally substituted with F or H₃C—;
Y is selected from the group consisting of cyclohexyl, piperidinyl, phenyl and pyridinyl, which are mandatorily substituted with a group selected from $R^S R^{S'}(O=)S=N—$, $R^S R^{S'}(O=)S=N—CH_2—$, $R^S R^{S'}(O=)S=N—C(=O)—$, $(R^N)N=S(=O)(R^S)—$, $(R^N)N=S(=O)(R^S)—CH_2—$, and $R^S R^{S'}(R^{N'}—N=)S=N—$,
wherein $R^N$ is selected from H, NC—, H₃C—, (CH₃)₃C—O—C(=O)—, F₃C—C(=O)—, and $R^{N'}$ is H, and
wherein $R^S$ and $R^{S'}$ are independently selected from H₃C—, H₅C₂—, (H₃C)₂CH—, cyclopropyl, tetrahydropyranyl, phenyl, and pyridinyl, or $R^S$ and $R^{S'}$ linked together are selected from —(CH₂)₄—, —(CH₂)₅—, and —(CH₂)₂—O—(CH₂)₂—, and wherein any cyclohexyl, piperidinyl, phenyl and pyridinyl groups mentioned under Y or $R^S$ and $R^{S'}$ optionally are substituted with F, H₃C—, or H₃C—O—,
and the pharmaceutically acceptable salts thereof.

According to embodiment E-24 those compounds of formula I are preferred, wherein
R¹ is selected from the group consisting of

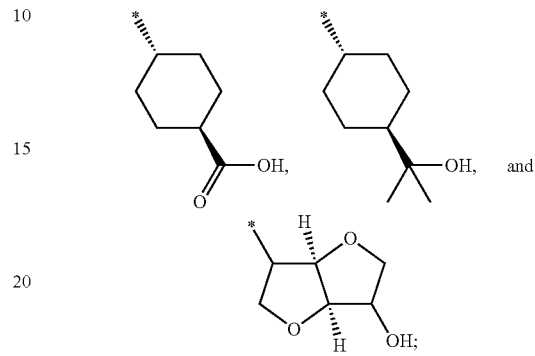

R² is selected from the group consisting of Cl, and H₃C—;
X is selected from the group consisting of a bond, a divalent piperazinyl, phenylene, and pyridinylene, bound via para positions and optionally substituted with F or H₃C—;
Y is selected from the group consisting of

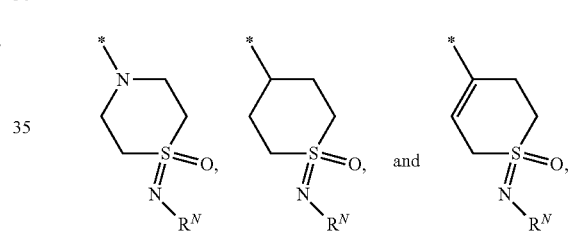

wherein $R^N$ is selected from H, NC—, H₃C—, (H₃C)₃C—O—C(=O)—, and F₃C—C(=O)—,
and the pharmaceutically acceptable salts thereof.

Particularly preferred compounds, including their tautomers and stereoisomers, the salts thereof, or any solvates or hydrates thereof, are described in the experimental section hereinafter.

The compounds according to the invention and their intermediates may be obtained using methods of synthesis which are known to the one skilled in the art and described in the literature of organic synthesis. Preferably the compounds are obtained analogously to the methods of preparation explained more fully hereinafter, in particular as described in the experimental section. In some cases the sequence adopted in carrying out the reaction schemes may be varied. Variants of these reactions that are known to the skilled man but are not described in detail here may also be used. The general processes for preparing the compounds according to the invention will become apparent to the skilled man on studying the schemes that follow. Starting compounds are commercially available or may be prepared by methods that are described in the literature or herein, or may be prepared in an analogous or similar manner. Before the reaction is carried out any corresponding functional groups in the compounds may be protected using conventional protecting groups. These protecting groups may be cleaved again at a suitable stage within the reaction sequence using methods familiar to the skilled man.

The compounds of the invention I are preferably accessed from a precursor 1 that bears the protected imidazopyridine-nitrogen (Scheme 1); $R^1$, $R^2$, X and Y have the meaning as defined hereinbefore and hereinafter. The benzyl protecting group is cleaved advantageously using hydrogen in the presence of a transition metal, preferably palladium on carbon in a solvent such as methanol, ethanol, tetrahydrofurane, 1,4-dioxane. Benzyl groups bearing electron donating groups on the phenyl ring, such as methoxy, may also be removed under acidic conditions such as $H_2SO_4$, $CF_3CO_2H$, $MeSO_3$. Amino-acetal derivatives can be cleaved under acidic conditions such as HCl, $H_2SO_4$, $CF_3CO_2H$, $MeSO_3$, $KHSO_4$, $HCO_2H$, $BF_3 \times OEt_2$ in a solvent such as dichloromethane, water, tetrahydrofurane, 1,4-dioxane or mixtures thereof at −10 to 100° C. In addition to cleavage under acidic conditions, amino-acetal derivatives bearing a $Si(CH_3)_3$ group can also be cleaved in the presence of tetrabutylammonium fluoride.

The tert.-butyloxy-carbonyl-protecting group can be cleaved under acidic conditions such as HCl, $H_2SO_4$, $CF_3CO_2H$, $MeSO_3H$, $KHSO_4$, $HCO_2H$, $BF_3 \times OEt_2$ in a solvent such as dichloromethane, water, tetrahydrofuran, 1,4-dioxane or mixtures thereof at −10 to 100° C. The trifluoroacetyl-protecting group can be cleaved under basic conditions such as NaOH, KOH, NaOMe, NaOEt, NaOtBu in a solvent such as water, tetrahydrofuran, 1,4-dioxane or mixtures thereof at −10 to 50° C.

Compounds 1 can be prepared from imidazopyridine derivatives 2 and boronic acid derivatives 3 (Scheme 2); $R^1$, $R^2$, X and Y' have the meaning defined hereinbefore and hereinafter.

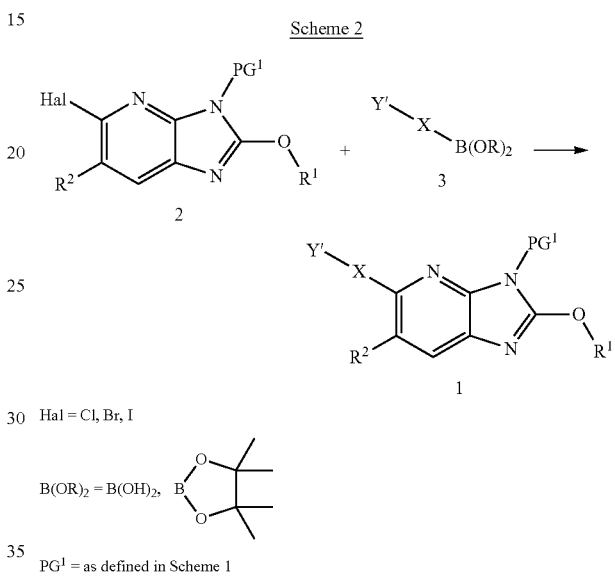

Scheme 2

Hal = Cl, Br, I $B(OR)_2 = B(OH)_2$, [pinacol boronate]

$PG^1$ = as defined in Scheme 1

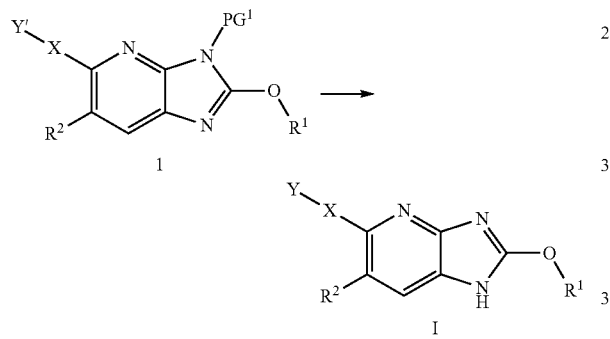

Scheme 1

$PG^1$ = CH$_2$-phenyl, wherein phenyl is optionally substituted with one or two OCH$_3$ groups;
CH$_2$—O—C$_{1-3}$-alkyl, wherein alkyl is optionally substituted with Si(CH$_3$)$_3$
Y' = Y or Y—PG$^2$ The N atom of the sulfoximine or sulfondiimine moiety within Y might be protected with a suitable protecting group $PG^2$, e.g. a tert-butoxycarbonyl, acetyl, or 2,2,2-trifluoroacetyl group. The protecting group $PG^2$ is either removed together with $PG^1$ in one reaction step or in an additional deprotection step, depending on the nature of $PG^1$ and $PG^2$.

The reaction is preferably conducted with a palladium derived catalyst, e.g. [1,1'-bis(diphenylphosphino)-ferrocene]-dichloropalladium(II)-CH$_2$Cl$_2$-complex (PdCl$_2$(dppf)$_x$CH$_2$Cl$_2$) in the presence of a base, e.g. sodium carbonate, in a mixture of water and tetrahydrofurane, 1,4-dioxane or N,N-dimethylformamide at 40 to 120° C.

Alternatively, compounds 1 can be prepared in a stepwise approach by successively linking X and Y' to the imidazopyridine (Scheme 3) using essentially the same reaction conditions as described for Scheme 2; $R^1$, $R^2$, X, and Y' have the meaning defined hereinbefore and hereinafter.

Scheme 3

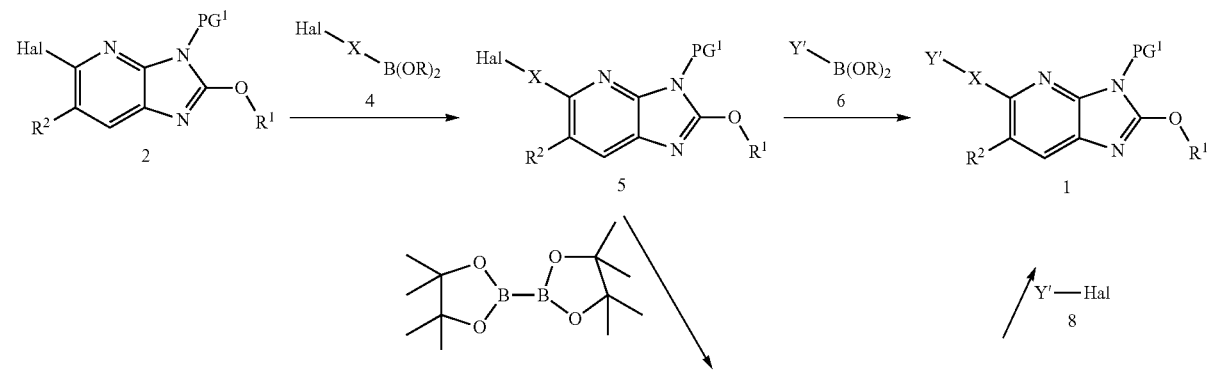

-continued

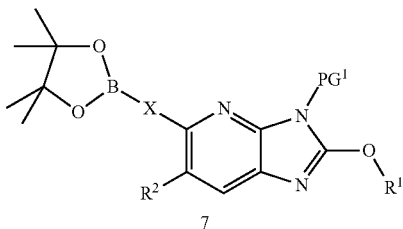

7

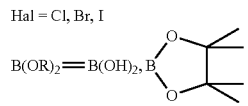

Hal = Cl, Br, I
$B(OR)_2 = B(OH)_2$, B(pinacol)
$PG^1$ = as defined in Scheme 1

If Y' denotes an N-containing heterocyclyl moiety, which is linked to X via an N atom, intermediate 5 (Scheme 3) can be coupled directly with the N-containing heterocycle Y' to form the carbon-nitrogen bond. The reaction is preferably conducted with a palladium derived catalyst, e.g. 2-(2'-di-tert-butylphosphine)biphenyl palladium(II) acetate, in the presence of a base, e.g. sodium tert-butoxide, in a mixture of sodium tert-butanol and toluene at 40 to 120° C.

Compounds 1' bearing a sulfoximine or sulfondiimine linked via the nitrogen to an aryl or heteroaryl group Y" can be prepared from halogen compounds 9 via direct coupling of the sulfoximine or sulfondiime (Scheme 4); $R^1$, $R^2$, X, Y, $R^{N'}$, $R^S$ and $R^{S'}$ have the meaning defined hereinbefore and hereinafter.

Scheme 4

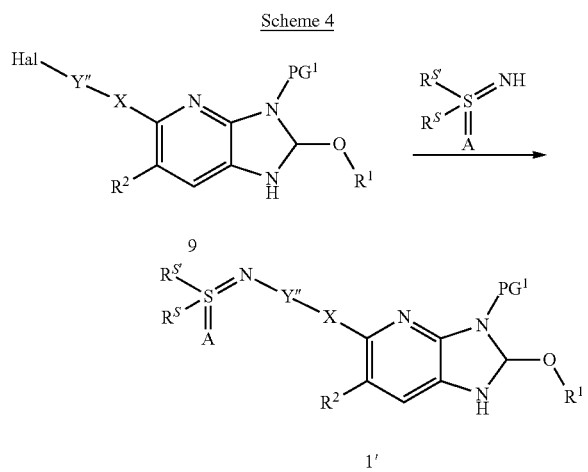

1'

$PG^1$ = as defined in Scheme 1
Hal = Cl, Br, I
A = O, $NR^{N'}$
$(R^S)(R^{S'})S(=A)=N-Y''$ denotes Y The coupling reaction is preferably conducted with a palladium derived catalyst and a suitable ligand, e.g. palladium(II) acetate (2 mg) and 2-dicyclohexylphosphino-2',6'-di-isopropoxy-1,1'-biphenyl (RuPhos), tris(dibenzylideneacetone)dipalladium(0) and 2-(di-t-butylphosphino) biphenyl, or palladium(II) acetate and racemic 2,2'-bis-(diphenylphosphino)-1,1'-binaphthyl in the presence of a base, e.g. $Cs_2CO_3$ or sodium tert-butoxide in a suitable solvent such as 1,4-dioxane or toluene at 40 to 120° C.

Compounds 1" bearing a sulfoximine linked via the nitrogen to a carbonyl on Y''' can be prepared via reaction of the corresponding carboxylic acid derivatives 10 with the sulfoximine (Scheme 5); $R^1$, $R^2$, X, Y, RN, $R^S$ and $R^{S'}$ have the meaning defined hereinbefore and hereinafter.

Scheme 5

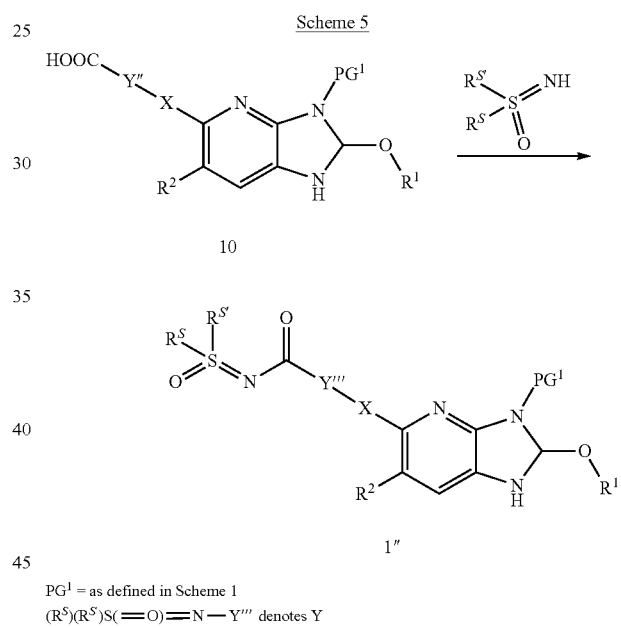

1"

$PG^1$ = as defined in Scheme 1
$(R^S)(R^{S'})S(=O)=N-Y'''$ denotes Y

The reaction is preferably conducted with a coupling reagent, e.g. 1-[bis(dimethylamino)-methylene]-1H-1,2,3-triazolo[4,5-b]pyridinium-3-oxide hexafluorophosphate, (benzotriazo-1-yloxy)-tris(dimethylamino)-phosphonium hexafluorophosphate, (benzotriazol-1-yloxyl)-tris(pyrrolidino)-phosphonium hexafluorophosphate or 1-ethyl-(3-(3-dimethylamino)propyl)-carbodiimide hydrochloride in the presence of a base, e.g. N,N-diisopropylethylamine, triethylamine, pyridine or 4-(N,N-dimethlyamino)pyridine in a suitable solvent, e.g. N,N-dimethylformamide or dichloromethane at 0 to 120° C.

Precursors 9 and 10 can be prepared by reaction of the corresponding aryl- or heteroarylboronic acid derivatives 11 and 12 with intermediate 5 (Scheme 6) using essentially the same reaction conditions as described for Scheme 2; $R^1$, $R^2$, and X have the meaning defined hereinbefore and hereinafter.

Scheme 6

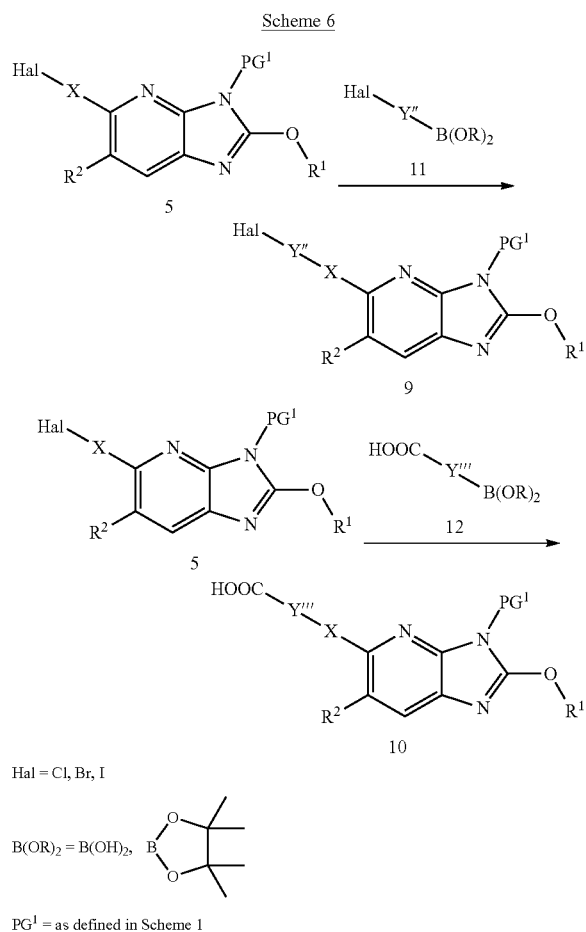

Hal = Cl, Br, I

B(OR)₂ = B(OH)₂, pinacol boronate

PG¹ = as defined in Scheme 1

If X denotes an N-containing heterocyclyl moiety, e.g. piperazinyl, which is linked to the imidazopyridine via an N atom, it can be coupled directly with imidazopyridine derivative 2 to form the carbon-nitrogen bond. Intermediate 13 can then be coupled via the second N atom with Intermediate 8 to give Compound 1''' (Scheme 7); R¹, R² and Y' have the meaning defined hereinbefore and hereinafter.

Scheme 7

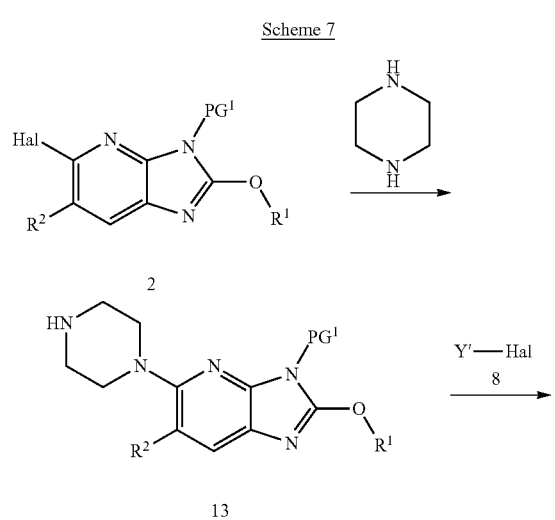

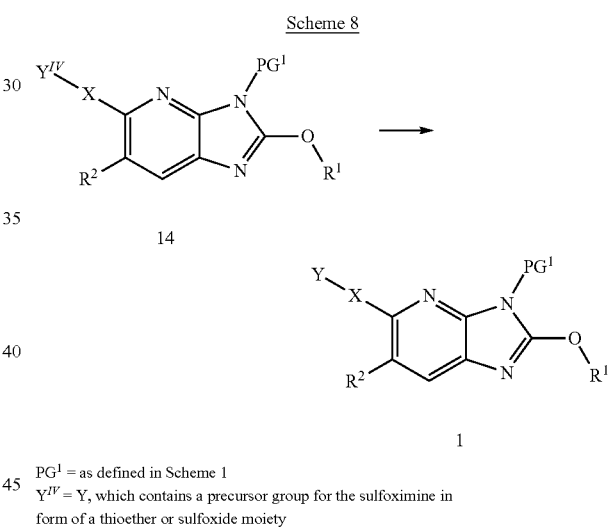

Hal = Cl, Br, I

PG¹ = as defined in Scheme 1

The coupling reactions are preferably conducted with a palladium derived catalyst and a suitable ligand, e.g. tris(dibenzylideneacetone)dipalladium(0) and 2-dicyclohexylphosphino-2',4',6'-triisopropylbiphenyl (Xphos) or dichlorobis(tri-o-tolylphosphine)-palladium(II) and 2,2'-bis(diphenylphosphino)-1,1'-binaphthyl (BINAP), in the presence of a base, e.g. cesium carbonate, in 1,4-dioxane or toluene at 40 to 150° C.

Compounds 1, wherein Y denotes Y-PG², can be prepared from compounds 14 (Scheme 8); R¹, R², and X have the meaning defined hereinbefore and hereinafter.

Scheme 8

PG¹ = as defined in Scheme 1

Y^IV = Y, which contains a precursor group for the sulfoximine in form of a thioether or sulfoxide moiety The thioether functionality in Y^IV can be transformed into a sulfoximine group protected by PG² by a two-step procedure. First step is the oxidation into a sulfoxide functionality, which is conducted by oxidation with meta-chloro-perbenzoic acid (MCPBA) in dichloromethane, sodium metaperiodate in methanol/water, or preferentially by oxidation with H₂O₂ in hexafluoro-isopropanol. Second step is the oxidation of the sulfoxide to the sulfoximine, which is preferentially conducted by reaction with PhI(CH₃COO)₂ and CF₃C(O)NH₂ in the presence of MgO and a Rh-catalyst as e.g. [Rh(CH₃COO)₂]₂, in dichloromethane or 1,2-dichloroethane at 0 to 60° C., which gives the sulfoximine protected as a trilfluoroacetamide.

The trifluoroacetyl-protecting group can be cleaved under basic conditions such as NaOH, KOH, NaOMe, NaOEt, NaOtBu in a solvent such as water, tetrahydrofurane, 1,4-dioxane or mixtures thereof at −10 to 50° C., to give the free sulfoximine, which can be reacted with (tBuO-C(O))₂O (BOC anhydride) or alternatively with PhCH₂O—C(O)Cl in the presence a base like NaH, KH, NEt₃, (iPr)₂Net or pyridine, but preferentially NaH, in a solvent like dichloromethane, 1,2-dichloroethane, tetrahydrofurane, 1,4-dioxane, toluene or mixtures thereof, at −10 to 90° C. give the benzyloxy-carbonyl- or tert.-butyloxy-carbonyl-protected sulfoximine.

The synthetic routes presented may rely on the use of protecting groups. For example, potentially reactive groups present, such as hydroxy, carbonyl, carboxy, amino, alkylamino, or imino, may be protected during the reaction by conventional protecting groups which are cleaved again after the reaction. Suitable protecting groups for the respective functionalities and their removal are well known to the one skilled in the art and are described in the literature of organic synthesis.

The compounds of general formula I may be resolved into their enantiomers and/or diastereomers as mentioned below. Thus, for example, cis/trans mixtures may be resolved into their cis and trans isomers and racemic compounds may be separated into their enantiomers.

The cis/trans mixtures may be resolved, for example, by chromatography into the cis and trans isomers thereof. The compounds of general formula I which occur as racemates may be separated by methods known per se into their optical antipodes and diastereomeric mixtures of compounds of general formula I may be resolved into their diastereomers by taking advantage of their different physico-chemical properties using methods known per se, e.g. chromatography and/or fractional crystallization; if the compounds obtained thereafter are racemates, they may be resolved into the enantiomers as mentioned below.

The racemates are preferably resolved by column chromatography on chiral phases or by crystallization from an optically active solvent or by reacting with an optically active substance which forms salts or derivatives such as esters or amides with the racemic compound. Salts may be formed with enantiomerically pure acids for basic compounds and with enantiomerically pure bases for acidic compounds. Diastereomeric derivatives are formed with enantiomerically pure auxiliary compounds, e.g. acids, their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids commonly used for such a purpose as well as optically active alcohols applicable as auxiliary residues are known to those skilled in the art.

As mentioned above, the compounds of formula I may be converted into salts, particularly for pharmaceutical use into the pharmaceutically acceptable salts. As used herein, "pharmaceutically acceptable salts" refer to derivatives of the disclosed compounds wherein the parent compound is modified by making acid or base salts thereof.

The compounds according to the invention are advantageously also obtainable using the methods described in the examples that follow, which may also be combined for this purpose with methods known to the skilled man from the literature.

Terms And Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula (I)", "compound(s) of the invention" and the like denote the compounds of the formula (I) according to the present invention including their tautomers, stereoisomers and mixtures thereof and the salts thereof, in particular the pharmaceutically acceptable salts thereof, and the solvates and hydrates of such compounds, including the solvates and hydrates of such tautomers, stereoisomers and salts thereof.

The terms "treatment" and "treating" embrace both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy. In addition the terms "treatment" and "treating" comprise prophylactic treatment, i.e. a treatment of patients at risk to develop a condition mentioned hereinbefore, thus reducing said risk.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

The terms "modulated" or "modulating", or "modulate(s)", as used herein, unless otherwise indicated, refer to the activation of the AMP-activated protein kinase (AMPK) with one or more compounds of the present invention.

The terms "mediated" or "mediating" or "mediate", as used herein, unless otherwise indicated, refer to the (i) treatment, including prevention of the particular disease or condition, (ii) attenuation, amelioration, or elimination of one or more symptoms of the particular disease or condition, or (iii) prevention or delay of the onset of one or more symptoms of the particular disease or condition described herein.

The term "substituted" as used herein, means that any one or more hydrogens on the designated atom, radical or moiety is replaced with a selection from the indicated group, provided that the atom's normal valence is not exceeded, and that the substitution results in an acceptably stable compound.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk may be used in sub-formulas to indicate the bond which is connected to the core molecule as defined.

The numeration of the atoms of a substituent starts with the atom which is closest to the core or to the group to which the substituent is attached.

For example, the term "3-carboxypropyl-group" represents the following substituent:

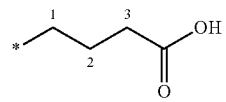

wherein the carboxy group is attached to the third carbon atom of the propyl group.

The terms "1-methylpropyl-", "2,2-dimethylpropyl-" or "cyclopropylmethyl-" group represent the following groups:

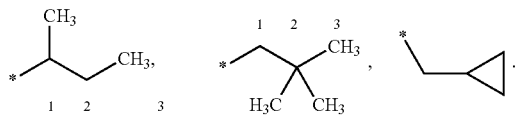

The asterisk may be used in sub-formulas to indicate the bond which is connected to the core molecule as defined.

Unless specifically indicated, throughout the specification and the appended claims, a given chemical formula or name shall encompass tautomers and all stereo, optical and geometrical isomers (e.g. enantiomers, diastereomers, E/Z isomers etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof.

Salts of other acids than those mentioned above which for example are useful for purifying or isolating the compounds of the present invention (e.g. trifluoro acetate salts) also comprise a part of the invention.

The term halogen generally denotes fluorine, chlorine, bromine and iodine.

The term "$C_{1-n}$-alkyl", wherein n is an integer from 1 to n, either alone or in combination with another radical denotes an acyclic, saturated, branched or linear hydrocarbon radical with 1 to n C atoms. For example the term $C_{1-4}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, and $H_3C$—$C(CH_3)_2$—.

Solubility

The aqueous solubility of the compounds of the invention is determined by comparing the amount dissolved in buffer to the amount in an acetonitrile/water (1/1) solution. Starting from a 10 mM DMSO stock solution aliquots are diluted with acetonitrile/water (1/1) or buffer resp. After 24 h of shaking, the solutions are filtrated and analyzed by LC-UV. The amount dissolved in buffer is compared to the amount in the acetonitrile solution.

Solubility is usually being measured from 0.001 to 0.125 mg/ml at a DMSO concentration of 2.5%. If more than 90% of the compound is dissolved in buffer, the value is marked with ">".

| Example | pH | Solubility [mg/ml] |
|---|---|---|
| 2 | 2.2 | 0.017 |
| | 4.5 | 0.002 |
| | 6.8 | 0.001 |
| 7 | 2.2 | 0.015 |
| | 4.5 | <0.001 |
| | 6.8 | <0.001 |
| 10 | 2.2 | 0.105 |
| | 4.5 | <0.001 |
| | 6.8 | <0.001 |
| 22 | 2.2 | <0.080 |
| | 4.5 | >0.007 |
| | 6.8 | <0.001 |
| 23 | 2.2 | 0.069 |
| | 4.5 | 0.002 |
| | 6.8 | 0.001 |
| 27 | 2.2 | 0.077 |
| | 4.5 | <0.001 |
| | 6.8 | <0.001 |
| 28 | 2.2 | 0.092 |
| | 4.5 | <0.001 |
| | 6.8 | <0.001 |
| 31 | 2.2 | >0.122 |
| | 4.5 | 0.105 |
| | 6.8 | 0.089 |
| 34 | 2.2 | 0.004 |
| | 4.5 | 0.005 |
| | 6.8 | 0.013 |
| 36 | 2.2 | 0.099 |
| | 4.5 | <0.001 |
| | 6.8 | <0.001 |
| 45 | 2.2 | >0.119 |
| | 4.5 | 0.005 |
| | 6.8 | <0.001 |
| 50 | 2.2 | >0.128 |
| | 4.5 | >0.117 |
| | 6.8 | 0.088 |
| 51 | 2.2 | >0.146 |
| | 4.5 | 0.028 |
| | 6.8 | 0.002 |
| 52 | 2.2 | 0.042 |
| | 4.5 | <0.001 |
| | 6.8 | <0.001 |

Plasma Protein Binding

Equilibrium dialysis (ED) technique is used to determine the approximate in vitro fractional binding of test compounds to plasma proteins (human, rat mouse):

Incubation:

Teflon dialysis cells or RED-devices are used. Each cell consists of a donor and an acceptor chamber, separated by an ultrathin semipermeable membrane (cutoff 5-10 kDa, high permeability).

Stock solutions for each test compound are prepared in DMSO. Plasma (anticoagulant EDTA) is spiked with test compound and then transferred into the donor chamber, while dialysis buffer (PBS containing Dextran, pH 7.4) is dispensed into the acceptor chamber.

Dextran (Leuconostoc ssp, MW approx. 40000, No. 31389, Fluka) concentration [g/L] in PBS for species:
human: 40 g/L buffer
rat: 37 g/L buffer
mouse 32 g/L buffer.

Incubation is carried out for up to 6 hours (standard 3 h) under rotation at 37° C. After the dialysis period aliquots of both dialysates are analysed using HPLC-MS/MS.

Calculation:
Percent bound is calculated according to the equation:

$$\% \text{ bound} = (Cp - Cb/Cp) \times 100$$

Cp=plasma concentration
Cb=buffer concentration
Percent free is calculated according to the equation:

$$\% \text{ free} = 100 - \% \text{ bound}$$

Dextran (Leuconostoc ssp, MW approx. 40000, No. 31389, Fluka) concentration [g/L] in PBS for species:
human: 40 g/L buffer
rat: 37 g/L buffer
mouse 32 g/L buffer

| | Plasma Protein Binding [% bound] | | |
|---|---|---|---|
| Example | human | rat | mouse |
| 2 | 98.55 | 98.67 | 98.68 |
| 10 | 98.92 | 98.23 | 98.64 |
| 45 | 98.48 | 98.94 | 99.23 |

Pharmacological Activity

The activity of the compounds of the invention may be demonstrated using the following in vitro AMPK activation assay:

Activated AMPK complex 1 (containing alpha1beta1gamma1) was obtained from baculovirus expression system. The gene encoding AMPK alpha1 was cloned into the pACG2T vector (BD Biosciences) to obtain a N-terminal Glutathion S transferase (GST)-fusion protein. The genes encoding AMPK beta 1 and gamma1 were cloned into the p2Bac dual multiple cloning site vector (Invitrogen) with beta1 under the control of the p10 promoter and gamma1 under the control of the PH promoter. The transfer vectors containing AMPK were co-transfected individually with AcPNV BacMagic-3 DNA (EMD Millipore) in Sf9 cells and the recombinant baculoviruses were harvested after 5 days, followed by 3 rounds of amplification of the virus stock in Sf9 cells. AMPK (alpha1beta1gamma1) was expressed in High Five 5 cells by co-infection of recombinant alpha1 virus and recombinant beta1/gamma1 virus for 72 h at 27° C. Cells were harvested by centrifugation and lysed by 3 freeze/thaw cycles in PBS with 10% glycerol and protease inhibitor cocktail (Roche). After centrifugation AMPK a1b1g1 in the supernatant was captured by immobilized glutathione (GE Healthcare), impurities were washed away with PBS and AMPK alpha1beta1gamma1 was eluted with PBS containing 20 mM reduced gluthathione. The protein buffer was then exchanged to PBS with 10% glycerol and protein concentration was determined by UV absorbance.

The white 384-well Optiplates (cat.no. 6007299) were purchased from PerkinElmer. The V9101 ADP-Glo Kinase Assay and ultra pure ATP (V915A) was purchased from Promega. The substrate for AMPK (NH2-HMRSAMSGL-HLVKRR_CONH2) was purchased from Upstate (12-355).

All other materials were of highest grade commercially available.

Compounds were tested in either serial dilutions or single dose concentrations. The serial compound dilutions were prepared in 100% DMSO automatically. The final DMSO concentration in the assay was 0.1%.

The Compound Stock Solutions were 10 mM in 100% DMSO. The compounds were solubilised at room temperature.

In the 384-well plates 1.25 ul of test compound in assay buffer was mixed with 1.25 ul of AMPK and 1.25 µl of the peptide (final concentration of 1 µM) and 1.25 µl of ATP (final concentration of 30 µM), both dissolved in assay buffer. This step was followed by an incubation time of 60 min. Then 5 µl of ADP Glo Reagent was added. This was followed by 40 min of incubation. Then 10 µl of Kinase Detection Reagent was admixed. The plates were sealed and after an incubation period of 30 min, the luminescence signal was measured in an Envision reader. All incubation steps were accomplished at room temperature.

Assay Buffer:
20 mM HEPES pH 7.0, 0.025% BSA, 15 mM MgCl2, 0.01% Brij

Each assay microtiter plate contained wells with vehicle controls instead of compound (0.1% DMSO in water) as reference for the low signal (100% CTL, low signal), and wells with serial dilutions of AMP (final 30 µM) as reference for high signals.

The luminescence signal generated was proportional to the ADP concentration produced and was correlated with AMPK activity. The analysis of the data was performed by the calculation of the percentage of ATP consumption of AMPK in the presence of the test compound compared to the consumption of ATP in the presence of AMPK without compound.

$$(RLU(\text{sample})/RLU(\text{low control})) * 100 \ [RLU=\text{relative luminescence units}]$$

An activator of the AMPK enzyme gave values above 100% CTL.

EC50 values based on dose response curves are calculated with the XIFIT software using the 4 Parameter Logistic Model or Sigmoidal Dose-Response Model.

The compounds according to the invention typically have $EC_{50}$ values in the range from about 0.1 nM to about 10 µM, preferably less than 1 µM, more preferably less than 100 nM.

$EC_{50}$ values for compounds according to the invention are shown in the following table. The number of the compound corresponds to the number of the Example in the experimental section.

| Example | $EC_{50}$ [nM] |
|---|---|
| 1 | 275 |
| 2 | 3 |
| 3 | 402 |
| 4 | 22 |
| 5 | 62 |
| 6 | 2 |
| 7 | 1 |
| 8 | 4 |
| 9 | 14 |
| 10 | 4 |
| 11 | 3 |
| 12 | 581 |
| 13 | 4 |
| 14 | 6 |
| 15 | 41 |
| 16 | 245 |

-continued

| Example | EC$_{50}$ [nM] |
|---|---|
| 17 | 1 |
| 18 | 34 |
| 19 | 55 |
| 20 | 776 |
| 21 | 43 |
| 22 | 45 |
| 23 | 10 |
| 24 | 215 |
| 25 | 1199 |
| 26 | 145 |
| 27 | 4 |
| 28 | 2 |
| 29 | 725 |
| 30 | 2 |
| 31 | 17 |
| 32 | 13 |
| 33 | 265 |
| 34 | 3 |
| 35 | 87 |
| 36 | 15 |
| 37 | 47 |
| 38 | 704 |
| 39 | 8 |
| 40 | 50 |
| 41 | 209 |
| 42 | 410 |
| 43 | 293 |
| 44 | 66 |
| 45 | 29 |
| 46 | 37 |
| 47 | 67 |
| 48 | 16 |
| 49 | 26 |
| 50 | 304 |
| 51 | 92 |
| 52 | 3 |
| 53 | 56 |
| 54 | 114 |
| 55 | 26 |
| 56 | 41 |
| 57 | 118 |

In view of their ability to modulate the activity of the AMP-activated protein kinase (AMPK), in particular an agonistic activity, the compounds of general formula I according to the invention, including the corresponding salts thereof, are theoretically suitable for the treatment of all those diseases or conditions which may be affected or which are mediated by the activation of the AMP-activated protein kinase (AMPK).

Accordingly, the present invention relates to a compound of general formula I as a medicament.

Furthermore, the present invention relates to the use of a compound of general formula I or a pharmaceutical composition according to this invention for the treatment and/or prevention of diseases or conditions which are mediated by the activation of the AMP-activated protein kinase (AMPK) in a patient, preferably in a human.

In yet another aspect the present invention relates to a method for treating a disease or condition mediated by the activation of the AMP-activated protein kinase (AMPK) in a mammal that includes the step of administering to a patient, preferably a human, in need of such treatment a therapeutically effective amount of a compound or a pharmaceutical composition of the present invention.

Diseases and conditions mediated by agonists of the AMP-activated protein kinase (AMPK) embrace metabolic diseases or conditions. According to one aspect the compounds and pharmaceutical compositions of the present invention are particularly suitable for treating diabetes mellitus, in particular Type 2 diabetes, Type 1 diabetes, complications of diabetes (such as e.g. retinopathy, nephropathy or neuropathies, diabetic foot, ulcers or macroangiopathies), metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, oedema and hyperuricaemia.

The compounds and pharmaceutical compositions of the present invention are also suitable for preventing beta-cell degeneration such as e.g. apoptosis or necrosis of pancreatic beta cells. The compounds and pharmaceutical compositions of the present invention are also suitable for improving or restoring the functionality of pancreatic cells, and also for increasing the number and size of pancreatic beta cells.

Therefore according to another aspect the invention relates to compounds of formula I and pharmaceutical compositions according to the invention for use in preventing, delaying, slowing the progression of and/or treating metabolic diseases, particularly in improving the glycaemic control and/or beta cell function in the patient.

In another aspect the invention relates to compounds of formula I and pharmaceutical compositions according to the invention for use in preventing, delaying, slowing the progression of and/or treating type 2 diabetes, overweight, obesity, complications of diabetes and associated pathological conditions.

In addition the compounds and pharmaceutical compositions according to the invention are suitable for use in one or more of the following therapeutic processes:

for preventing, delaying, slowing the progression of or treating metabolic diseases, such as for example type 1 diabetes, type 2 diabetes, insufficient glucose tolerance, insulin resistance, hyperglycaemia, hyperlipidaemia, hypercholesterolaemia, dyslipidaemia, syndrome X, metabolic syndrome, obesity, high blood pressure, chronic systemic inflammation, retinopathy, neuropathy, nephropathy, atherosclerosis, endothelial dysfunction or bone-related diseases (such as osteoporosis, rheumatoid arthritis or osteoarthritis);

for improving glycaemic control and/or reducing fasting plasma glucose, postprandial plasma glucose and/or the glycosylated haemoglobin HbA1c;

for preventing, delaying, slowing or reversing the progression of disrupted glucose tolerance, insulin resistance and/or metabolic syndrome to type 2 diabetes;

for preventing, delaying, slowing the progression of or treating a condition or a disease selected from among the complications of diabetes, such as for example retinopathy, nephropathy or neuropathies, diabetic foot, ulcers or macroangiopathies;

for reducing weight or preventing weight gain or assisting weight loss;

for preventing or treating the degradation of pancreatic beta cells and/or improving and/or restoring the functionality of pancreatic beta cells and/or restoring the functionality of pancreatic insulin secretion;

for maintaining and/or improving insulin sensitivity and/or preventing or treating hyperinsulinaemia and/or insulin resistance.

In particular, the compounds and pharmaceutical compositions according to the invention are suitable for the treatment of obesity, diabetes (comprising type 1 and type 2 diabetes, preferably type 2 diabetes mellitus) and/or complications of diabetes (such as for example retinopathy, nephropathy or neuropathies, diabetic foot, ulcers or macroangiopathies).

The compounds according to the invention are most particularly suitable for treating type 2 diabetes mellitus.

The dose range of the compounds of general formula I applicable per day is usually from 0.001 to 10 mg per kg body weight, for example from 0.01 to 8 mg per kg body weight of the patient. Each dosage unit may conveniently contain from 0.1 to 1000 mg, for example 0.5 to 500 mg.

The actual therapeutically effective amount or therapeutic dosage will of course depend on factors known by those skilled in the art such as age and weight of the patient, route of administration and severity of disease. In any case the compound or composition will be administered at dosages and in a manner which allows a therapeutically effective amount to be delivered based upon patient's unique condition.

The compounds, compositions, including any combinations with one or more additional therapeutic agents, according to the invention may be administered by oral, transdermal, inhalative, parenteral or sublingual route. Of the possible methods of administration, oral or intravenous administration is preferred.

Pharmaceutical Compositions

Suitable preparations for administering the compounds of formula I, optionally in combination with one or more further therapeutic agents, will be apparent to those with ordinary skill in the art and include for example tablets, pills, capsules, suppositories, lozenges, troches, solutions, syrups, elixirs, sachets, injectables, inhalatives and powders etc. Oral formulations, particularly solid forms such as e.g. tablets or capsules are preferred. The content of the pharmaceutically active compound(s) is advantageously in the range from 0.1 to 90 wt.-%, for example from 1 to 70 wt.-% of the composition as a whole.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers. The particular excipients, carriers and/or diluents that are suitable for the desired preparations will be familiar to the skilled man on the basis of his specialist knowledge. The preferred ones are those that are suitable for the particular formulation and method of administration that are desired. The preparations or formulations according to the invention may be prepared using methods known per se that are familiar to the skilled man, such as for example by mixing or combining at least one compound of formula I according to the invention, or a pharmaceutically acceptable salt of such a compound, and one or more excipients, carriers and/or diluents.

Combination Therapy

The compounds of the invention may further be combined with one or more, preferably one additional therapeutic agent. According to one embodiment the additional therapeutic agent is selected from the group of therapeutic agents useful in the treatment of diseases or conditions described hereinbefore, in particular associated with metabolic diseases or conditions such as for example diabetes mellitus, obesity, diabetic complications, hypertension, hyperlipidemia. Additional therapeutic agents which are suitable for such combinations include in particular those which for example potentiate the therapeutic effect of one or more active substances with respect to one of the indications mentioned and/or which allow the dosage of one or more active substances to be reduced.

Therefore a compound of the invention may be combined with one or more additional therapeutic agents selected from the group consisting of antidiabetic agents, agents for the treatment of overweight and/or obesity and agents for the treatment of high blood pressure, heart failure and/or atherosclerosis.

Antidiabetic agents are for example metformin, sulphonylureas, nateglinide, repaglinide, thiazolidinediones, PPAR-(alpha, gamma or alpha/gamma) agonists or modulators, alpha-glucosidase inhibitors, DPPIV inhibitors, SGLT2-inhibitors, insulin and insulin analogues, GLP-1 and GLP-1 analogues or amylin and amylin analogues, cycloset, 11β-HSD inhibitors. Other suitable combination partners are inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, alpha2-antagonists, CCR-2 antagonists or glucokinase activators. One or more lipid lowering agents are also suitable as combination partners, such as for example HMG-CoA-reductase inhibitors, fibrates, nicotinic acid and the derivatives thereof, PPAR-(alpha, gamma or alpha/gamma) agonists or modulators, PPAR-delta agonists, ACAT inhibitors or cholesterol absorption inhibitors such as, bile acid-binding substances such as, inhibitors of ileac bile acid transport, MTP inhibitors, or HDL-raising compounds such as CETP inhibitors or ABC1 regulators.

Therapeutic agents for the treatment of overweight and/or obesity are for example antagonists of the cannabinoid) receptor, MCH-1 receptor antagonists, MC4 receptor agonists, NPY5 or NPY2 antagonists, β3-agonists, leptin or leptin mimetics, agonists of the 5HT2c receptor.

Therapeutic agents for the treatment of high blood pressure, chronic heart failure and/or atherosclerosis are for example A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Angiotensin II receptor antagonists are preferably used for the treatment or prevention of high blood pressure and complications of diabetes, often combined with a diuretic such as hydrochlorothiazide.

The dosage for the combination partners mentioned above is usually 1/5 of the lowest dose normally recommended up to 1/1 of the normally recommended dose.

Preferably, compounds of the present invention and/or pharmaceutical compositions comprising a compound of the present invention optionally in combination with one or more additional therapeutic agents are administered in conjunction with exercise and/or a diet.

Therefore, in another aspect, this invention relates to the use of a compound according to the invention in combination with one or more additional therapeutic agents described hereinbefore and hereinafter for the treatment of diseases or conditions which may be affected or which are mediated by the activation of the AMP-activated protein kinase (AMPK), in particular diseases or conditions as described hereinbefore and hereinafter.

In yet another aspect the present invention relates a method for treating a disease or condition mediated by the activation of the AMP-activated protein kinase (AMPK) in a patient that includes the step of administering to the patient, preferably a human, in need of such treatment a therapeutically effective amount of a compound of the present invention in combination with a therapeutically effective amount of one or more additional therapeutic agents described in hereinbefore and hereinafter, The use of the compound according to the invention in combination with the additional therapeutic agent may take place simultaneously or at staggered times.

The compound according to the invention and the one or more additional therapeutic agents may both be present together in one formulation, for example a tablet or capsule, or separately in two identical or different formulations, for example as a so-called kit-of-parts.

Consequently, in another aspect, this invention relates to a pharmaceutical composition which comprises a compound according to the invention and one or more additional therapeutic agents described hereinbefore and hereinafter, optionally together with one or more inert carriers and/or diluents.

Other features and advantages of the present invention will become apparent from the following more detailed Examples which illustrate, by way of example, the principles of the invention.

EXAMPLES

Preliminary Remarks:

As a rule, $^1$H-NMR and/or mass spectra have been obtained for the compounds prepared. The $R_f$ values are determined using Merck silica gel 60 $F_{254}$ plates and UV light at 254 nm.

The terms "ambient temperature" and "room temperature" are used interchangeably and designate a temperature of about 20° C.

Analytical HPLC parameters employed for characterization of products (TFA denotes trifluoroacetic acid and FA denotes formic acid):

Method: 1
Device: Agilent 1200 with DA and MS detector
Column: XBridge C18, 3 × 30 mm, 2.5 μm
Column Supplier: Waters

| Gradient/ Solvent Time [min] | % Solvent [H$_2$O, 0.1% TFA] | % Solvent [Acetonitrile] | Flow [mL/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

Method: 2
Device: Agilent 1200 with DA and MS detector
Column: XBridge C18, 3 × 30 mm, 2.5 μm
Column Supplier: Waters

| Gradient/ Solvent Time [min] | % Solvent [H$_2$O, 0.1% TFA] | % Solvent [Acetonitrile] | Flow [mL/min] | Temperature [° C.] |
|---|---|---|---|---|
| 0.00 | 50 | 50 | 2.2 | 60 |
| 0.20 | 50 | 50 | 2.2 | 60 |
| 1.20 | 0 | 100 | 2.2 | 60 |
| 1.25 | 0 | 100 | 3 | 60 |
| 1.40 | 0 | 100 | 3 | 60 |

Method: 3
Device: Agilent 1200 with DA and MS detector
Column: XBridge C18, 3 × 30 mm, 2.5 μm
Column Supplier: Waters

| Gradient/ Solvent Time [min] | % Solvent [H$_2$O, 0.1% TFA] | % Solvent [CH$_3$CN] | Flow [mL/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

Method: 4
Device: Agilent 1200 with DA and MS detector
Column: Sunfire C18, 3 × 30 mm, 2.5 μm
Column Supplier: Waters

| Gradient/ Solvent Time [min] | % Solvent [H$_2$O, 0.1% TFA] | % Solvent [CH$_3$CN] | Flow [mL/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

Method: 5
Device: Agilent 1200 with DA and MS detector
Column: XBridge C18, 3 × 30 mm, 2.5 μm
Column Supplier: Waters

| Gradient/ Solvent Time [min] | % Solvent [H$_2$O, 0.1% NH$_4$OH] | % Solvent [CH$_3$CN] | Flow [mL/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

Method: 6
Device: Agilent 1200 with DA and MS detector
Column: Sunfire C18, 3 × 30 mm, 2.5 μm
Column Supplier: Waters

| Gradient/ Solvent Time [min] | % Solvent [H$_2$O, 0.1% TFA] | % Solvent [CH$_3$CN] | Flow [mL/min] | Temperature [° C.] |
|---|---|---|---|---|
| 0.00 | 50 | 50 | 2.2 | 60 |
| 0.20 | 50 | 50 | 2.2 | 60 |
| 1.20 | 0 | 100 | 2.2 | 60 |
| 1.25 | 0 | 100 | 3 | 60 |
| 1.40 | 0 | 100 | 3 | 60 |

| Method: 7 |||||
|---|---|---|---|---|
| Device: Agilent 1200 with DA and MS detector |||||
| Column: Sunfire C18, 3 × 30 mm, 2.5 µm |||||
| Column Supplier: Waters |||||
| Gradient/ Solvent Time [min] | % Solvent [H$_2$O, 0.1% HCOOH] | % Solvent [CH$_3$CN] | Flow [mL/min] | Temperature [° C.] |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

The Examples that follow are intended to illustrate the present invention without restricting it:

Intermediate 1

(3R,3aR,6R,6aR)-6-(6-Chloro-5-iodo-3-(2-trimethylsilanyl-ethoxymethyl)-3H-imidazo[4,5-b]pyridin-2-yloxy)hexahydrofuro[3,2-b]furan-3-ol

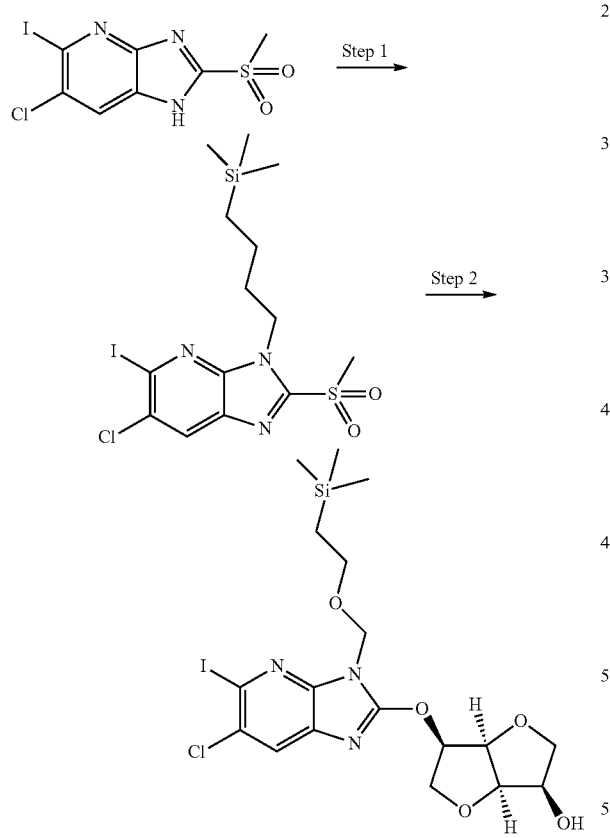

Step 1: 6-Chloro-5-iodo-2-(methylsulfonyl)-3-(2-trimethylsilanyl-ethoxymethyl)-3H-imidazo[4,5-b]pyridine 6-Chloro-5-iodo-2-(methylsulfonyl)-1H-imidazo[4,5-b]pyridine (for preparation see WO 2012116145; 1.5 g) and triethylamine (875 µL) are dissolved in tetrahydrofurane (12 mL), cooled to 0° C. and treated with (2-(chloromethoxy)ethyl)trimethylsilane (SEM-Cl; 890 µL). The mixture is stirred for 30 minutes while warming to room temperature. Then the mixture is partitioned between saturated aqueous NH$_4$Cl and ethylacetate. The organic phase is washed with water and brine. After drying (MgSO$_4$) the solvents are evaporated in vacuo to give the title compound. LC (method 1): t$_R$=1.22 min; Mass spectrum (ESI$^+$): m/z=488 [M+H]$^+$.

Step 2: (3R,3aR,6R,6aR)-6-(6-Chloro-5-iodo-3-(2-trimethylsilanyl-ethoxymethyl)-3H-imidazo[4,5-b]pyridin-2-yloxy)hexahydrofuro[3,2-b]furan-3-ol (3R,3aR,6R,6aR)-Hexahydrofuro[3,2-b]furan-3,6-diol (1.84 g) is dissolved in N,N-dimethylformamide (10 mL) and treated with 1,8-diazabicyclo[5.4.0]undec-7-ene (DBU; 1.9 mL). A solution of 6-chloro-5-iodo-2-(methylsulfonyl)-3-(2-trimethylsilanyl-ethoxymethyl)-3H-imidazo[4,5-b]pyridine (2.05 g) in N,N-dimethylformamide (20 mL) is added drop wise and the mixture is stirred for 2 hours at room temperature. The mixture is partitioned between water and ethylacetate and the organic phase is washed with brine and dried (MgSO$_4$). The solvents are evaporated in vacuo and the residue is chromatographed on silica gel (cyclohexane/ethyl acetate 80:20→0:100) to give the title compound. LC (method 1): t$_R$=1.17 min; Mass spectrum (ESI$^+$): m/z=554 [m+H]$^+$.

Intermediate 2

N-(4-(6-Chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)phenyl)-S,S-dimethylsulfoximide

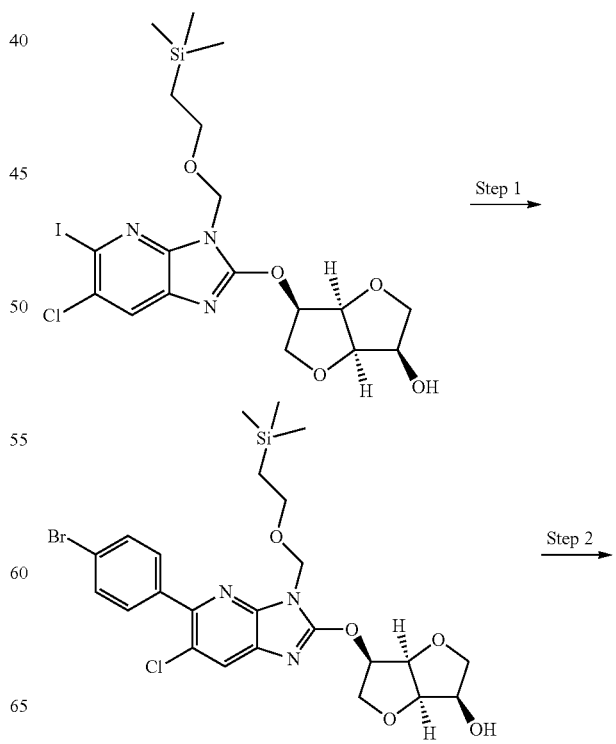

-continued

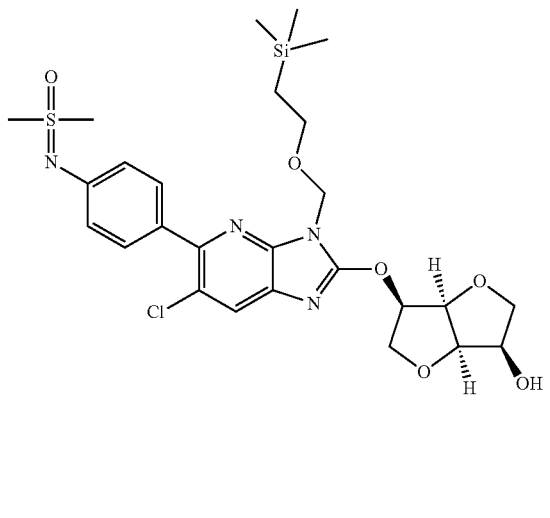

Step 1: (3R,3aR,6R,6aR)-6-[5-(4-Bromo-phenyl)-6-chloro-3-(2-trimethylsilanyl-ethoxymethyl)-3H-imidazo[4,5-b]pyridin-2-yloxy]-hexahydro-furo[3,2-b]furan-3-ol A mixture of (3R,3aR,6R,6aR)-6-(6-chloro-5-iodo-3-(2-trimethylsilanyl-ethoxymethyl)-3H-imidazo[4,5-b]pyridin-2-yloxy)hexahydrofuro[3,2-b]furan-3-ol (300 mg), 4-bromophenylboronic acid (120 mg), Na$_2$CO$_3$ (2 M aqueous solution, 810 μL), and 1,4-dioxane (4 mL) is purged for 5 minutes with argon. [1,1'-Bis(diphenylphosphino)-ferrocene]-dichloropalladium(II)-CH$_2$Cl$_2$-complex (PdCl$_2$(dppf)$_x$CH$_2$Cl$_2$) (30 mg) is added and the mixture is stirred for 3 h at 90° C. The reaction mixture is diluted with ethylacetate and washed with water and brine, dried over MgSO$_4$ and concentrated in vacuo. The residue is chromatographed on silica gel (cyclohexane/ethyl acetate 40:60→20:80) to give the title compound. LC (method 1): t$_R$=1.26 min; Mass spectrum (ESI$^+$): m/z=582 [M+H]$^+$.

Step 2: N-(4-(6-Chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)phenyl)-S,S-dimethylsulfoximide A microwave vial charged with a stir bar, (3R,3aR,6R,6aR)-6-[5-(4-bromo-phenyl)-6-chloro-3-(2-trimethylsilanyl-ethoxymethyl)-3H-imidazo[4,5-b]pyridin-2-yloxy]-hexahydro-furo[3,2-b]furan-3-ol (292 mg), S,S-dimethylsulfoximine (58 mg), 2-(di-t-butylphosphino)biphenyl (30 mg), sodium tert-butoxide (69 mg), and 1,4-dioxane (4 mL) is purged with argon for 3 minutes. Tris(dibenzylideneacetone)dipalladium(0) (35 mg) is added, the vial is sealed, and the mixture is stirred for 2 h at 80° C. After cooling to room temperature, the mixture is filtered through a pad of celite and the pad is rinsed with ethyl acetate. The combined filtrates are concentrated in vacuo and the residue is chromatographed on silica gel [dichloromethane/(dichloromethane/methanol/7 M ammonia in methanol 50:48:2) 98:2→90:10] to give the title compound. LC (method 1): t$_R$=0.98 min; Mass spectrum (ESI$^+$): m/z=595 [M+H]$^+$.

Intermediate 3

N-(4'-(6-Chloro-2-((3R,3aR,6R,6aR)-6-hydroxyhexahydrofuro[3,2-b]furan-3-yloxy)-3-2-trimethylsilanyl-ethoxymethyl)-3H-imidazo[4,5-b]pyridin-5-yl)biphenyl-4-yl)-S,S-dimethylsulfoximide

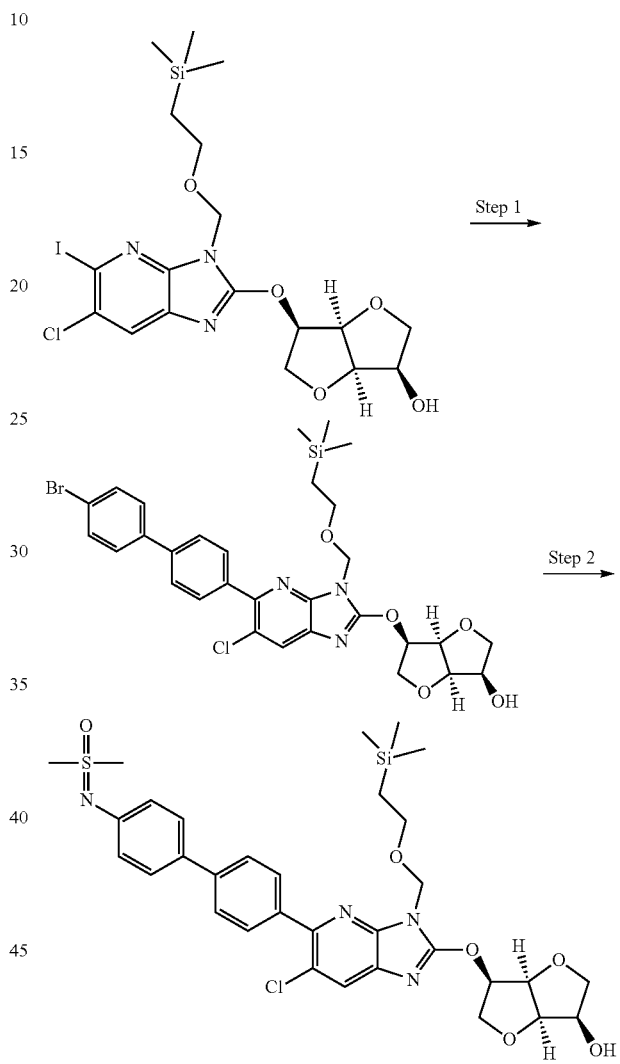

Step 1: (3R,3aR,6R,6aR)-6-[5-(4'-Bromo-biphenyl-4-yl)-6-chloro-3-(2-trimethylsilanyl-ethoxymethyl)-3H-imidazo[4,5-b]pyridin-2-yloxy]-hexahydro-furo[3,2-b]furan-3-ol The title compound is prepared from (3R,3aR,6R,6aR)-6-(6-chloro-5-iodo-3-(2-trimethylsilanyl-ethoxymethyl)-3H-imidazo[4,5-b]pyridin-2-yloxy)hexahydrofuro[3,2-b]furan-3-ol and 4'-bromo-4-biphenylboronic acid following a procedure analogous to that described for Intermediate 2 (Step 1). LC (method 2): t$_R$=1.08 min; Mass spectrum (ESI$^+$): m/z=658 [M+H]$^+$.

Step 2: N-(4'-(6-Chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)biphenyl-4-yl)-S,S-dimethylsulfoximide The title compound is prepared from (3R,3aR,6R,6aR)-6-[5-(4'-bromo-biphenyl-4-yl)-6-chloro-3-(2-trimethylsilanyl-ethoxymethyl)-3H-imidazo[4,5-b]pyridin-2-yloxy]-hexahydro-furo[3,2-b]furan-3-ol and S,S-dimethylsulfoximine following a procedure analogous to that described for Intermediate 2 (Step 2). LC (method 2): $t_R$=0.31 min; Mass spectrum (ESI$^+$): m/z=671 [M+H]$^+$.

Intermediate 4

4-(6-Chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)benzoyl dimethylsulfoximide

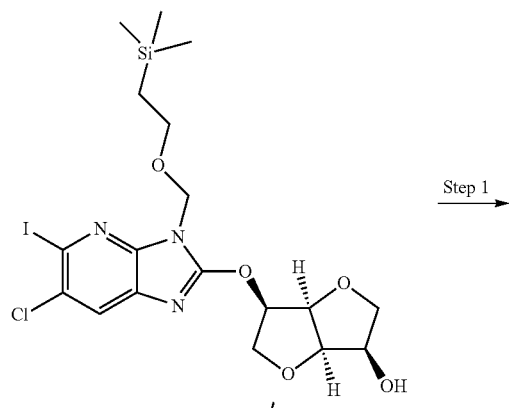

Step 1

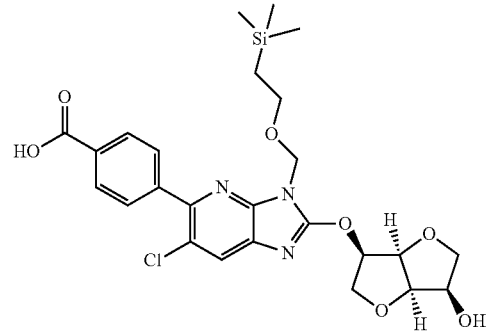

Step 2

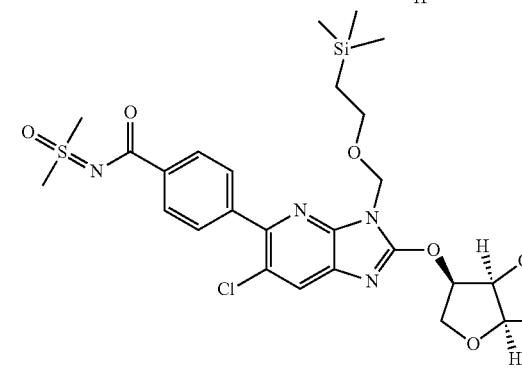

Step 1: 4-[6-Chloro-2-((3R,3aR,6R,6aR)-6-hydroxy-hexahydro-furo[3,2-b]furan-3-yloxy)-3-(2-trimethylsilanyl-ethoxymethyl)-3H-imidazo[4,5-b]pyridin-5-yl]-benzoic acid The title compound is prepared from (3R,3aR,6R,6aR)-6-(6-chloro-5-iodo-3-(2-trimethylsilanyl-ethoxymethyl)-3H-imidazo[4,5-b]pyridin-2-yloxy)hexahydrofuro[3,2-b]furan-3-ol and 4-carboxyphenylboronic acid following a procedure analogous to that described for Intermediate 2 (Step 1). LC (method 1): $t_R$=1.02 min; Mass spectrum (ESI$^+$): m/z=548 [M+H]$^+$.

Step 2: 4-(6-Chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)benzoyl dimethylsulfoximide A mixture of 4-[6-chloro-2-((3R,3aR,6R,6aR)-6-hydroxy-hexahydro-furo[3,2-b]furan-3-yloxy)-3-(2-trimethylsilanyl-ethoxymethyl)-3H-imidazo[4,5-b]pyridin-5-yl]-benzoic acid (95 mg), N,N-diisopropylethylamine (75 µL), and 1-[bis(dimethylamino)-methylene]-1H-1,2,3-triazolo[4,5-b]pyridinium-3-oxide hexafluorophosphate (79 mg) in N,N-dimethylformamide (3 mL) is stirred at room temperature for 5 min. S,S-Dimethylsulfoximine (19 mg) is added and the mixture is stirred at room temperature over night. The reaction mixture is diluted with ice cold water and extracted with ethyl acetate. The combined extracts are washed with brine, dried over MgSO$_4$, and concentrated in vacuo. The crude product is used for the next reaction step without further purification. LC (method 1): $t_R$=1.01 min; Mass spectrum (ESI$^+$): m/z=623 [M+H]$^+$.

Intermediate 5

(3R,3aR,6R,6aR)-6-(6-chloro-5-(4-(S-(N-acetyl-imino)-S-oxo-thiomorpholin-4-yl)-phenyl)-(2-trimethylsilanyl-ethoxymethyl)-3H-imidazo[4,5-b]pyridin-2-yloxy)-hexahydro-furo[3,2-b]furan-3-ol

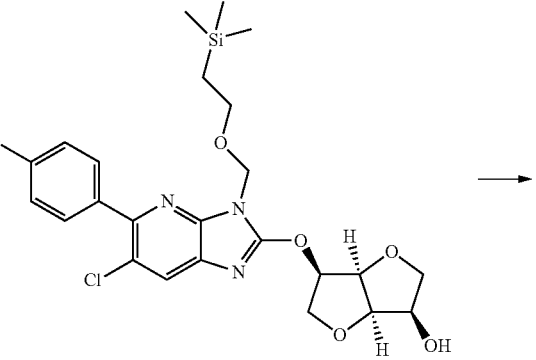

37

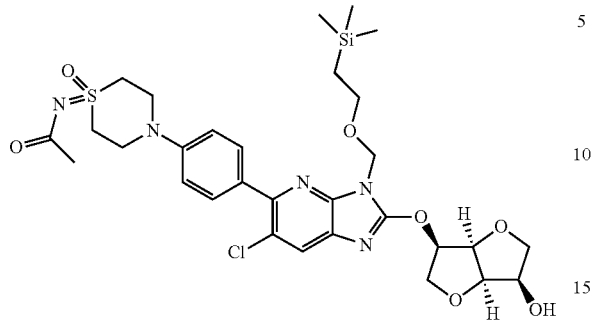

A microwave vial charged with (3R,3aR,6R,6aR)-6-[5-(4-bromo-phenyl)-6-chloro-3-(2-trimethylsilanyl-ethoxymethyl)-3H-imidazo[4,5-b]pyridin-2-yloxy]-hexahydro-furo[3,2-b]furan-3-ol (100 mg), S-(N-acetylimino)-S-oxo-thiomorpholine trifluoroacetic acid salt (60 mg), sodium tert-butoxide (25 mg), sodium tert-butanol (400 mg) and toluene (2 mL) is purged with argon for 3 minutes. 2-(2'-Di-tert-butylphosphine)biphenyl palladium(II) acetate (4 mg) is added, the vial is sealed, and the mixture is heated to 140° C. for 15 min in a microwave oven. After cooling to room temperature, the mixture is diluted with water and extracted with ethylacetate. The combined extracts are washed with brine, dried over MgSO$_4$, and concentrated in vacuo. The crude product is used for the next reaction step without further purification. LC (method 1): t$_R$=0.99 min; Mass spectrum (ESI$^+$): m/z=678 [M+H]$^+$.

Intermediate 6

(3R,3aR,6R,6aR)-6-(6-chloro-5-(4-(S-methylimino-5-oxo-thiomorpholin-4-yl)-phenyl)-(2-trimethylsilanyl-ethoxymethyl)-3H-imidazo[4,5-b]pyridin-2-yloxy)-hexahydro-furo[3,2-b]furan-3-ol

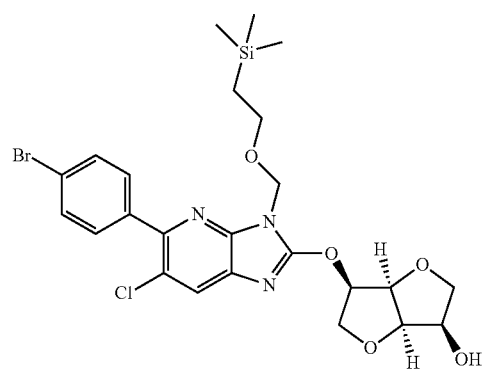

38

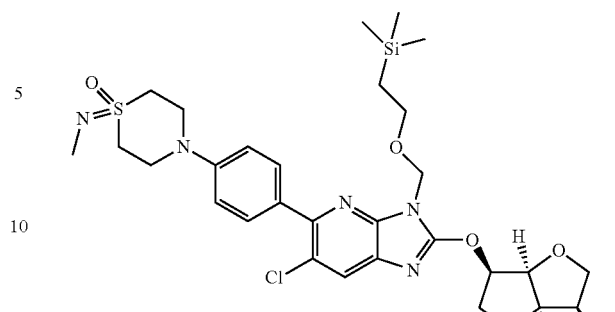

The title compound is prepared from (3R,3aR,6R,6aR)-6-[5-(4-bromo-phenyl)-6-chloro-3-(2-trimethylsilanyl-ethoxymethyl)-3H-imidazo[4,5-b]pyridin-2-yloxy]-hexahydrofuro[3,2-b]furan-3-ol and S-methylimino-5-oxo-thiomorpholine trifluoroacetic acid salt following a procedure analogous to that described for Intermediate 5. LC (method 1): t$_R$=0.95 min; Mass spectrum (ESI$^+$): m/z=650 [M+H]$^+$.

Intermediate 7

N-4'-(6-chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)biphenyl-4-carbonyl-S,S-dimethylsulfoximide

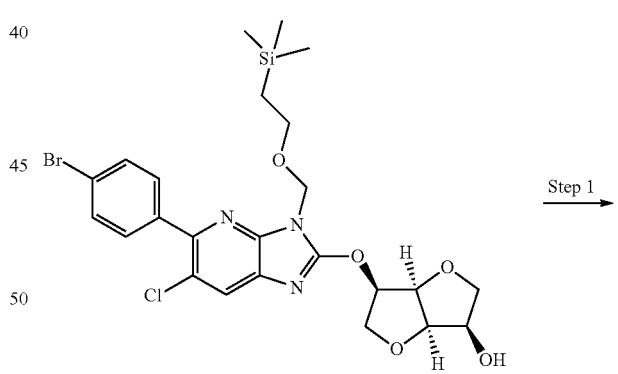

Step 1

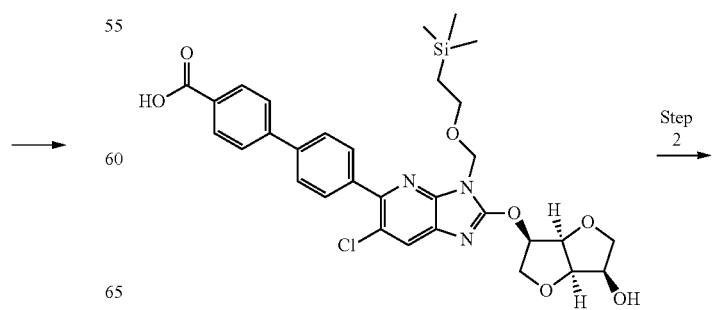

Step 2

-continued

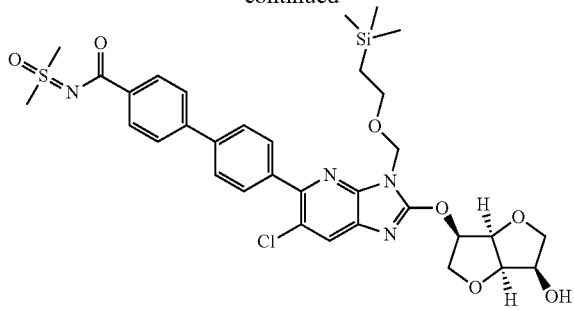

Step 1: 4'-(6-Chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)biphenyl-4-carboxylic acid The title compound is prepared from (3R,3aR,6R,6aR)-6-[5-(4-bromo-phenyl)-6-chloro-3-(2-trimethylsilanyl-ethoxymethyl)-3H-imidazo[4,5-b]pyridin-2-yloxy]-hexahydrofuro[3,2-b]furan-3-ol and 4-carboxyphenylboronic acid following a procedure analogous to that described for Intermediate 2 (Step 1). LC (method 1): $t_R$=1.10 min; Mass spectrum (ESI$^+$): m/z=624 [M+H]$^+$.

Step 2: N-4'-(6-chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)biphenyl-4-carbonyl-S,S-dimethylsulfoximide The title compound is prepared from (4'-(6-chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)biphenyl-4-carboxylic acid and S,S-dimethylsulfoximine following a procedure analogous to that described for Intermediate 4 (Step 2). LC (method 1): $t_R$=1.08 min; Mass spectrum (ESI$^+$): m/z=699 [M+H]$^+$.

Intermediate 8

S-(4'-(6-Chloro-2-((3R,3aR,6R,6aR)-6- hydroxyhexahydrofuro[3,2-b]furan-3-yloxy)-3-(2-trimethylsilanyl-ethoxymethyl)-3H-imidazo[4,5-b]pyridin-5-yl)biphenyl-4-yl)-S-methyl-N-cyano-sulfoximide

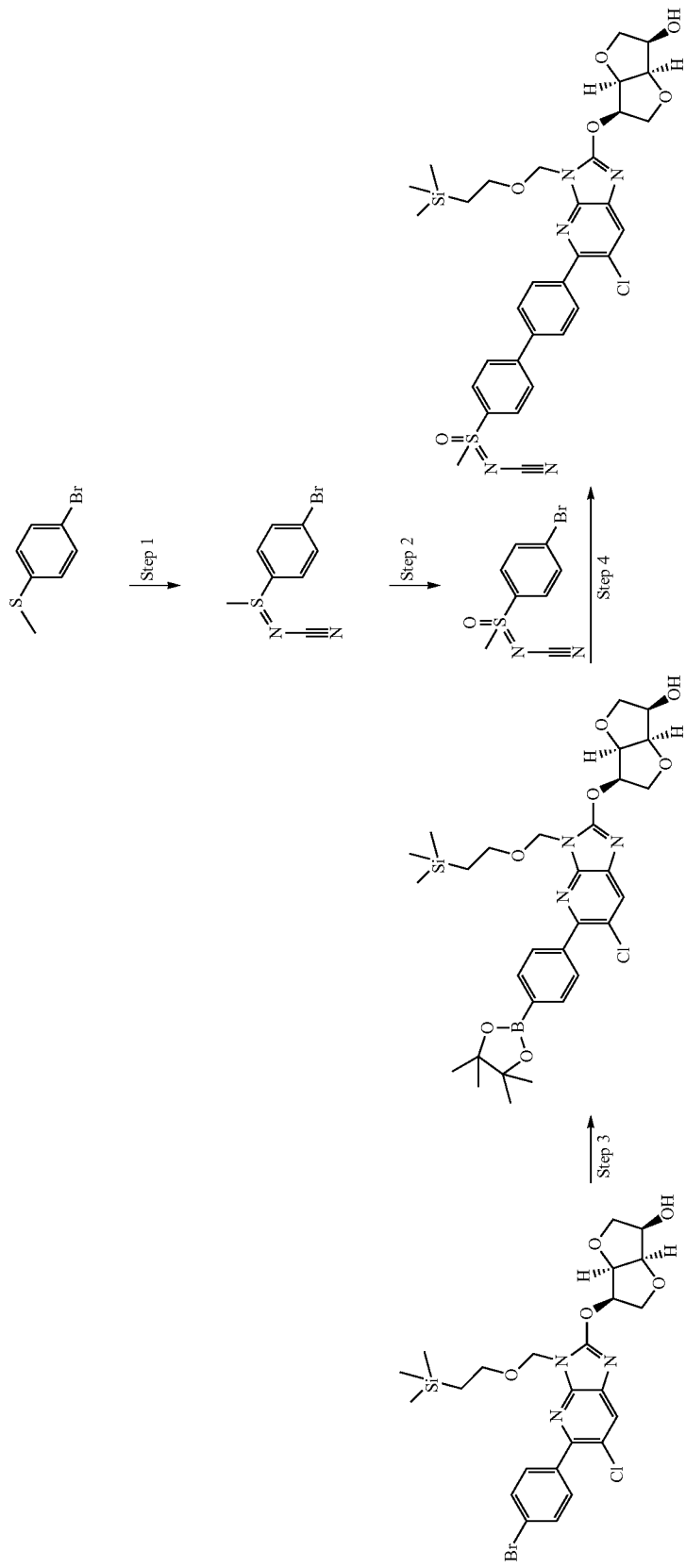

Step 1:
N-Cyano-S-methyl-S-(4-bromophenyl)sulfilimine

A mixture of 4-bromothioanisole (3.75 g), cyanamide (1.01 g), potassium tert-butoxide (2.49 g), and N-bromosuccinimide (4.93 g) in methanol (75 mL) is stirred at room temperature under an argon atmosphere for 2 h. The reaction mixture is concentrated in vacuo, diluted with water, and extracted ethyl acetate. The combined extracts ware washed with brine, dried over $MgSO_4$, and concentrated in vacuo. The residue is triturated with ethyl acetate and the precipitate is filtered off, washed with small amounts of ethyl acetate and tert-butylmethyl ether, and dried to yield the title compound. LC (method 1): $t_R$=1.10 min; Mass spectrum ($ESI^+$): m/z=243 $[M+H]^+$.

Step 2:
N-Cyano-S-methyl-S-(4-bromophenyl)sulfoximine

3-Chloroperoxybenzoidc acid (4.75 g) and potassium carbonate (7.61 g) are added to an ice-cooled mixture of N-cyano-S-methyl-S-(4-bromophenyl)sulfilimine (4.46 g) and ethanol (100 mL). The ice/water bath is removed and the reaction mixture is stirred at room temperature overnight. The reaction mixture is concentrated in vacuo, diluted with water, and extracted ethyl acetate. The combined extracts ware washed with brine, dried over $MgSO_4$, and concentrated in vacuo. The residue is triturated with ethyl acetate (20 mL) and the precipitate is filtered off, washed with small amounts of ethyl acetate and tert-butylmethyl ether, and dried to yield the title compound. The mother liquor is concentrated in vacuo and the residue is chromatographed on silica gel (dichloromethane/methanol 98:2→95:5) to give the another batch of the title compound. LC (method 1): $t_R$=0.79 min; Mass spectrum ($ESI^+$): m/z=259 $[M+H]^+$.

Step 3: (3R,3aR,6R,6aR)-6-(6-Chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol A mixture of (3R,3aR,6R,6aR)-6-[5-(4-bromo-phenyl)-6-chloro-3-(2-trimethylsilanyl-ethoxymethyl)-3H-imidazo[4,5-b]pyridin-2-yloxy]-hexahydro-furo[3,2-b]furan-3-ol (490 mg), 4,4,5,5,4',4',5',5'-octamethyl-[2,2']bi[[1,3,2]dioxaborolanyl] (640 mg), potassium acetate (413 mg), and 1,4-dioxane (15 mL) is purged for 5 minutes with argon. [1,1'-Bis(diphenylphosphino)-ferrocene]-dichloropalladium(II)-$CH_2Cl_2$-complex ($PdCl_2(dppf)xCH_2Cl_2$) (69 mg) is added and the mixture is stirred for 20 h at 80° C. More $PdCl_2(dppf)xCH_2Cl_2$ is added and the mixture is stirred at 90° C. for 6 h until conversion is complete. The reaction mixture concentrated in vacuo and chromatographed on silica gel (cyclohexane/ethyl acetate 30:70→0:100) to give the title compound. LC (method 2): $t_R$=0.91 min; Mass spectrum ($ESI^+$): m/z=630 $[M+H]^+$.

Step 4: S-(4'-(6-Chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)biphenyl-4-yl)-S-methyl-N-cyanosulfoximide The title compound is prepared from (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol and N-cyano-S-methyl-S-(4-bromophenyl)sulfoximine following a procedure analogous to that described for Intermediate 2 (Step 1). LC (method 1): $t_R$=1.08 min; Mass spectrum ($ESI^+$): m/z=682 $[m+H]^+$.

Intermediate 9

(3R,3aR,6R,6aR)-6-{6-Chloro-5-[4'-(1-oxo-tetrahydro-1λ4-thiophen-1-ylideneamino)-biphenyl-4-yl]-3-(2-trimethylsilanyl-ethoxy-methyl)-3H-imidazo[4,5-b]pyridin-2-yloxy}-hexahydro-furo[3,2-b]furan-3-ol

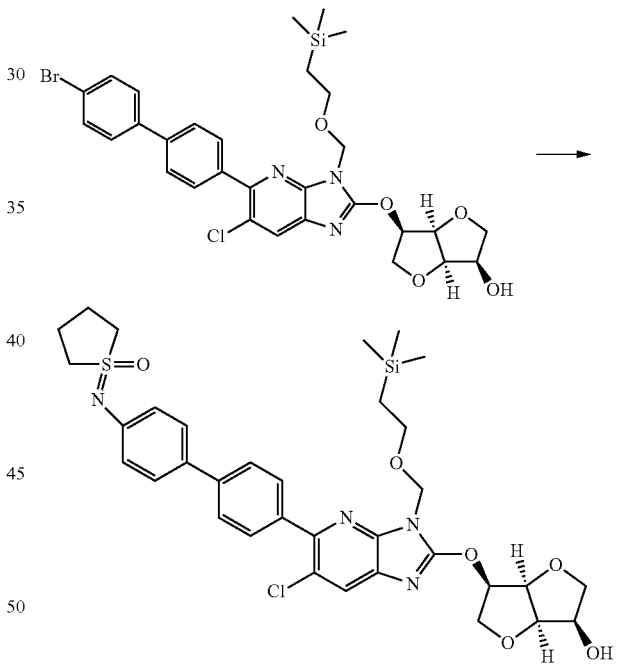

A mixture of (3R,3aR,6R,6aR)-6-[5-(4'-bromo-biphenyl-4-yl)-6-chloro-3-(2-trimethyl-silanyl-ethoxymethyl)-3H-imidazo[4,5-b]pyridin-2-yloxy]-hexahydro-furo[3,2-b]furan-3-ol and S,S-tetramethylenesulfoximide (22 mg), $Cs_2CO_3$ (79 mg), and toluene (2 mL) is purged for 5 minutes with argon. Palladium(II) acetate (2 mg) and 2-dicyclohexylphosphino-2',6'-diisopropoxybiphenyl (RuPhos, 6 mg) are added and the mixture is stirred under an argon atmosphere for 12 h at 110° C. After cooling to room temperature, the mixture is filtered through a pad of celite and the pad is rinsed with ethyl acetate. The combined filtrates are concentrated in vacuo and the residue is purified by HPLC on reversed phase to give the title compound. Mass spectrum ($ESI^+$): m/z=697 $[M+H]^+$.

47

Intermediate 10

(S)-N-(4-(6-Chloro-2-((3R,3aR,6R,6aR)-6-hydroxy-hexahydrofuro[3,2-b]furan-3-yloxy)-3-(2-trimethyl-silanyl-ethoxy-methyl)-3H-imidazo[4,5-b]pyridin-5-yl)phenyl)-S-methyl-S-phenylsulfoximide

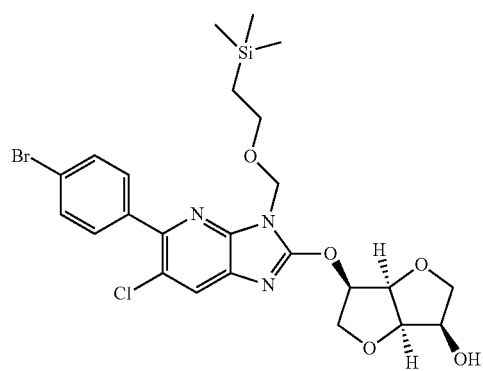

48

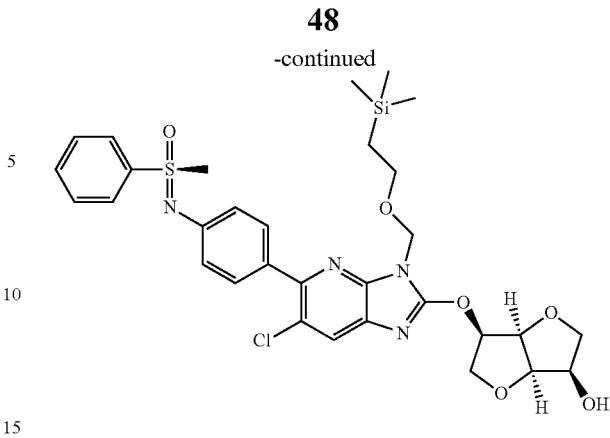

The title compound is prepared from (3R,3aR,6R,6aR)-6-[5-(4-bromo-phenyl)-6-chloro-3-(2-trimethylsilanyl-ethoxymethyl)-3H-imidazo[4,5-b]pyridin-2-yloxy]-hexahydrofuro[3,2-b]furan-3-ol and (S)-S-methyl-S-phenylsulfoximine following a procedure analogous to that described for Intermediate 2 (step 2). LC (method 3): $t_R$=1.07 min; Mass spectrum (ESI$^+$): m/z=657 [M+H]$^+$.

Intermediate 11

(3R,3aR,6R,6aR)-6-(6-Chloro-5-(4-(5-(N,S-dimethylsulfonimidoyl)pyridin-2-yl)phenyl)-3-(2-trimethyl-silanyl-ethoxy-methyl)-3H-imidazo[4,5-b]pyridin-2-yloxy)hexahydrofuro[3,2-b]furan-3-ol

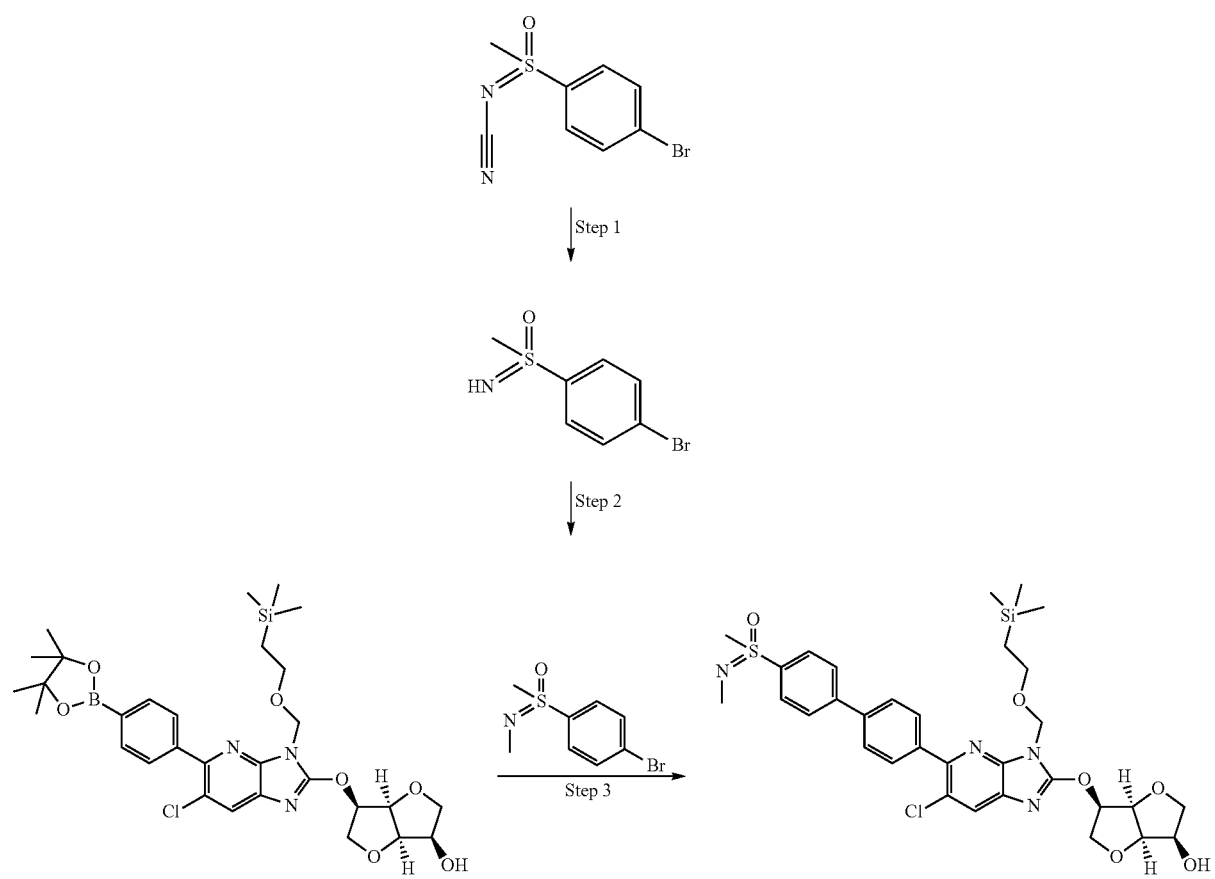 [SMILES: CS(=O)(=NC#N)c1ccc(Br)cc1 ; CS(=N)(=O)c1ccc(Br)cc1 ; CC1(C)OB(c2ccc(-c3nc4c(cc3Cl)nc(O[C@@H]3CO[C@H]5[C@@H]3OC[C@H]5O)n4COCC[Si](C)(C)C)cc2)OC1(C)C ; CN=S(C)(=O)c1ccc(Br)cc1 ; CN=S(C)(=O)c1ccc(-c2ccc(-c3nc4c(cc3Cl)nc(O[C@@H]3CO[C@H]5[C@@H]3OC[C@H]5O)n4COCC[Si](C)(C)C)cc2)cc1]

Step 1: S-(4-Bromophenyl)-S-methyl-sulfoximine

Trifluoroacetic anhydride (1.26 g) is added to an ice-cooled mixture of N-cyano-S-methyl-S-(4-bromophenyl)sulfoximine (518 mg) and dichloromethane (35 mL). The reaction mixture is allowed to warm to room temperature and stirred for 1.5 h. The solvent is evaporated in vacuo and the residue is dissolved in methanol (14 mL), $K_2CO_3$ (1.38 g) is added, and the resulting mixture is stirred at room temperature for 1.5 days. The reaction mixture is concentrated in vacuo, diluted with water, and extracted ethyl acetate. The combined extracts ware washed with brine, dried over $MgSO_4$, and concentrated in vacuo. The residue is chromatographed on silica gel (dichloromethane/methanol 98:2→95:5) to give the title compound. LC (method 1): $t_R$=0.66 min; Mass spectrum (ESI$^+$): m/z=234 [M+H]$^+$.

Step 2: S-(4-Bromophenyl)-N,S-dimethyl-sulfoximine

Sodium hydride (55-60% in mineral oil, 54 mg) is added to S-(4-bromophenyl)-S-methyl-sulfoximine (97 mg) in 1,2-dimethoxyethane (3 mL) and the resulting mixture is stirred at room temperature for 5 min. Methyl iodide (294 mg) is added and the reaction mixture is stirred for 6 h at room temperature. More methyl iodide (50 µL) is added and the reaction mixture is stirred over night. The mixture is concentrated in vacuo, diluted with water, and extracted ethyl acetate. The combined extracts are washed with brine, dried over $MgSO_4$, and concentrated in vacuo. The residue is chromatographed on silica gel (dichloromethane/methanol 98:2) to give the title compound. LC (method 1): $t_R$=0.69 min; Mass spectrum (ESI$^+$): m/z=248 [M+H]$^+$.

Step 3: (3R,3aR,6R,6aR)-6-(6-Chloro-5-(4-(5-(N,S-dimethylsulfonimidoyl)pyridin-2-yl)phenyl)-3-(2-trimethylsilanyl-ethoxy-methyl)-3H-imidazo[4,5-b]pyridin-2-yloxy)-hexahydrofuro[3,2-b]furan-3-ol The title compound is prepared from (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol and S-(4-bromophenyl)-N,S-dimethyl-sulfoximine following a procedure analogous to that described for Intermediate 2 (Step 1). LC (method 1): $t_R$=1.04 min; Mass spectrum (ESI$^+$): m/z=671 [M+H]$^+$.

Intermediate 12

N-(4'-(6-Chloro-2-((3R,3aR,6R,6aR)-6-hydroxy-hexahydrofuro[3,2-b]furan-3-yloxy)-3-(2-trimethyl-silanyl-ethoxymethyl)-3H-imidazo[4,5-b]pyridin-5-yl)biphenyl-4-yl)-S,S-diethylsulfoximide

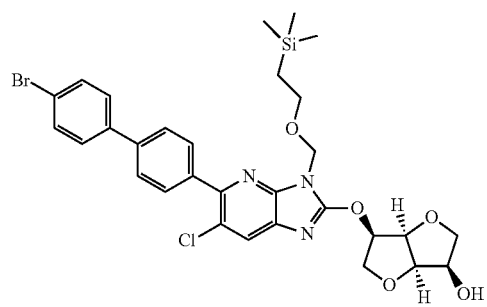

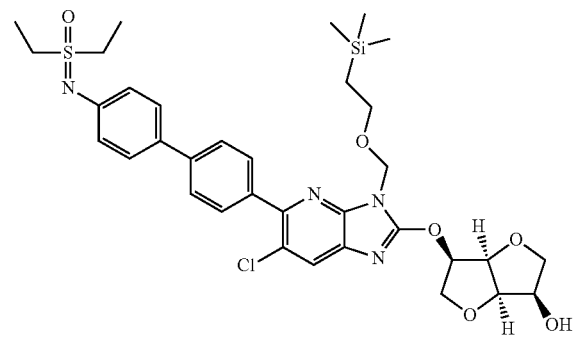

The title compound is prepared from (3R,3aR,6R,6aR)-6-[5-(4'-bromo-biphenyl-4-yl)-6-chloro-3-(2-trimethylsilanyl-ethoxymethyl)-3H-imidazo[4,5-b]pyridin-2-yloxy]-hexahydrofuro[3,2-b]furan-3-ol and S,S-diethylsulfoximine following a procedure analogous to that described for Intermediate 2 (Step 2). LC (method 1): $t_R$=1.13 min; Mass spectrum (ESI$^+$): m/z=699 [M+H]$^+$.

Intermediate 13

(R)-N-(4-(6-Chloro-2-((3R,3aR,6R,6aR)-6-hydroxy-hexahydrofuro[3,2-b]furan-3-yloxy)-3-(2-trimethyl-silanyl-ethoxy-methyl)-3H-imidazo[4,5-b]pyridin-5-yl)phenyl)-S-methyl-S-phenylsulfoximide

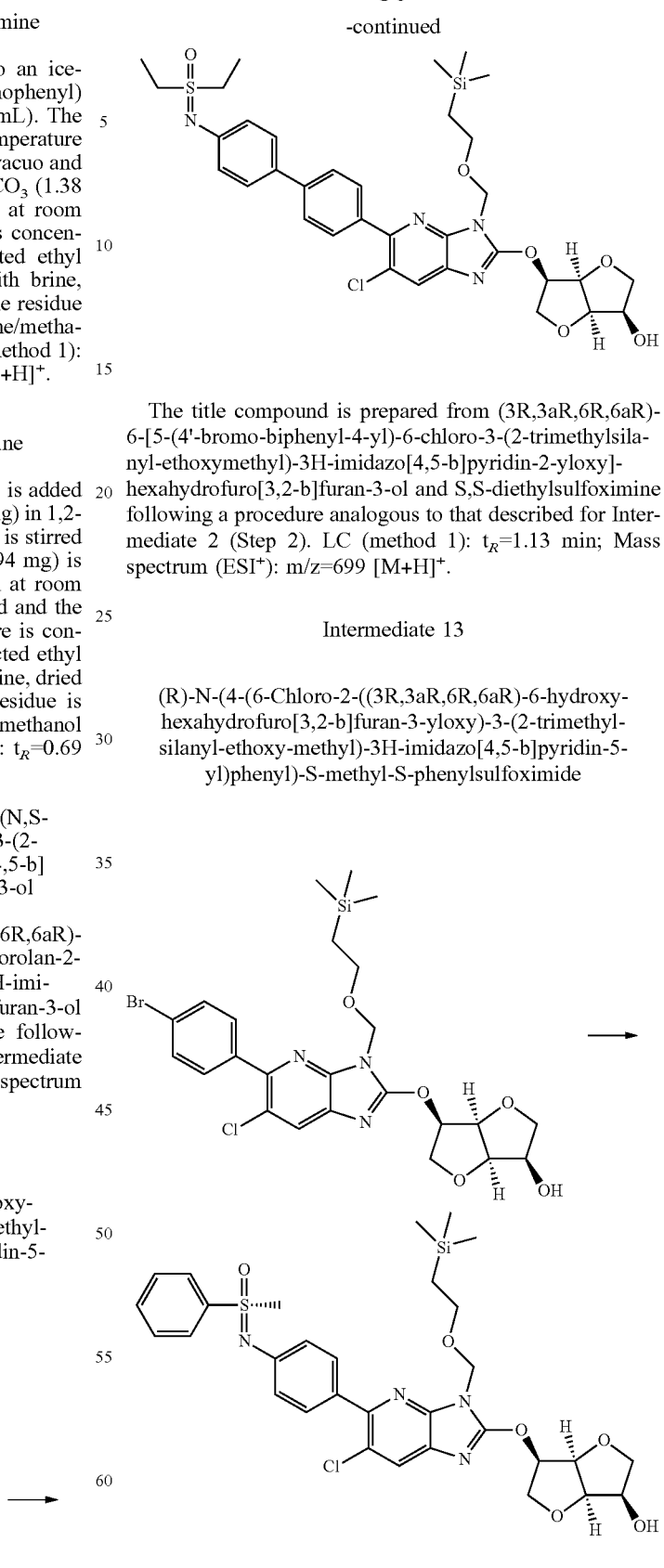

The title compound is prepared from (3R,3aR,6R,6aR)-6-[5-(4-bromo-phenyl)-6-chloro-3-(2-trimethylsilanylethoxymethyl)-3H-imidazo[4,5-b]pyridin-2-yloxy]-hexahydrofuro[3,2-b]furan-3-ol and (R)-S-methyl-S-phenylsulfoximine following a procedure analogous to that described for Intermediate 2 (step 2). LC (method 3): $t_R$=1.06 min; Mass spectrum (ESI$^+$): m/z=657 [M+H]$^+$.

Intermediate 14

N-(4'-(6-Chloro-2-((3R,3aR,6R,6aR)-6-hydroxy-hexahydrofuro[3,2-b]furan-3-yloxy)-3-(2-trimethyl-silanyl-ethoxymethyl)-3H-imidazo[4,5-b]pyridin-5-yl)biphenyl-4-yl)-S-ethyl-S-methylsulfoximide

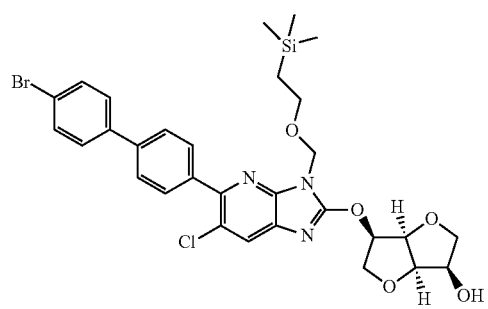

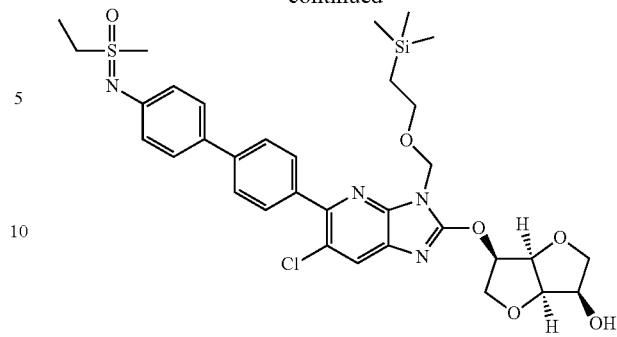

The title compound is prepared from (3R,3aR,6R,6aR)-6-[5-(4'-bromo-biphenyl-4-yl)-6-chloro-3-(2-trimethylsilanyl-ethoxymethyl)-3H-imidazo[4,5-b]pyridin-2-yloxy]-hexahydrofuro[3,2-b]furan-3-ol and S-ethyl-S-methylsulfoximine following a procedure analogous to that described for Intermediate 2 (Step 2). LC (method 1): $t_R$=1.11 min; Mass spectrum (ESI$^+$): m/z=685 [M+H]$^+$.

Intermediate 15

N-(4'-(6-Chloro-2-((3R,3aR,6R,6aR)-6-hydroxy-hexahydrofuro[3,2-b]furan-3-yloxy)-3-(2-trimethyl-silanyl-ethoxymethyl)-3H-imidazo[4,5-b]pyridin-5-yl)biphenyl-3-yl)-S,S-dimethylsulfoximide

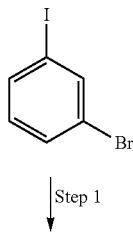

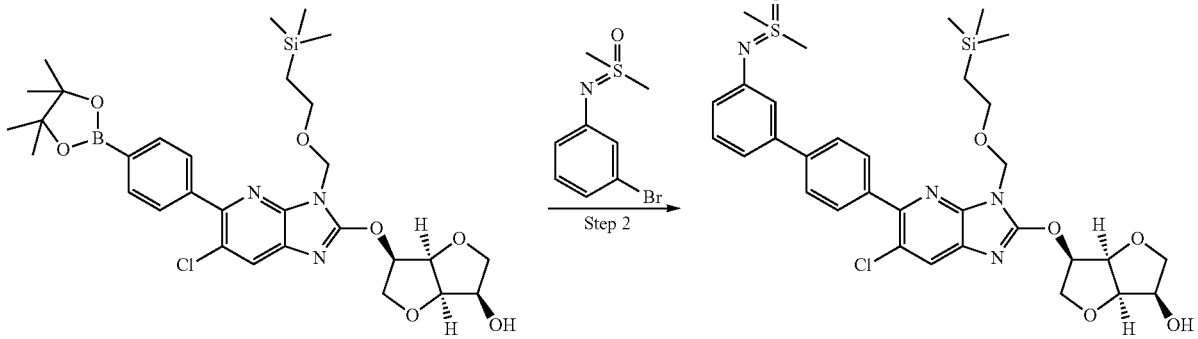

Step 1: N-(3-Bromophenyl)-S,S-dimethylsulfoximine

A mixture of 1-bromo-3-iodo-benzene (250 μL), S,S-dimethylsulfoximine (219 mg), and Cs$_2$CO$_3$ (895 mg) in 1,4-dioxane (12 mL) in a microwave vial is purged with argon for 5 minutes. Tris(dibenzylideneacetone)dipalladium (0) (35 mg) and 4,5-bis(diphenylphosphino)-9,9-dimethylxanthene (XantPhos, 85 mg) are added, the vial is sealed, and the mixture is stirred at 105° C. for 3 hours. The product mixture is filtered over celite, using methanol as the eluent. The filtrate is concentrated in vacuo and the residue is purified by HPLC on reversed phase to give the title compound. LC (method 4): t$_R$=0.74 min; Mass spectrum (ESI$^+$): m/z=248 [M+H]$^+$.

Step 2: N-(4'-(6-Chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)biphenyl-3-yl)-S,S-dimethylsulfoximide The title compound is prepared from (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol and N-(3-bromophenyl)-S,S-dimethylsulfoximine following a procedure analogous to that described for Intermediate 2 (Step 1). LC (method 3): t$_R$=1.07 min; Mass spectrum (ESI$^+$): m/z=671 [M+H]$^+$.

Intermediate 16

N-(4'-(6-Chloro-2-((3R,3aR,6R,6aR)-6-hydroxyhexahydrofuro[3,2-b]furan-3-yloxy)-3-2-trimethylsilanyl-ethoxymethyl)-3H-imidazo[4,5-b]pyridin-5-yl)biphenyl-4-yl)-S-cyclopropyl-S-methylsulfoximide

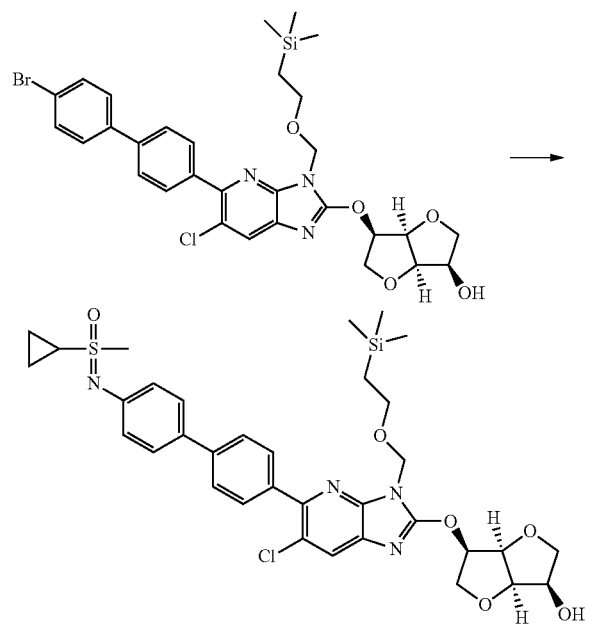

The title compound is prepared from (3R,3aR,6R,6aR)-6-[5-(4'-bromo-biphenyl-4-yl)-6-chloro-3-(2-trimethylsilanyl-ethoxymethyl)-3H-imidazo[4,5-b]pyridin-2-yloxy]-hexahydrofuro[3,2-b]furan-3-ol and S-cyclopropyl-S-methylsulfoximine following a procedure analogous to that described for Intermediate 9. LC (method 1): t$_R$=1.13 min; Mass spectrum (ESI$^+$): m/z=698 [M+H]$^+$.

Intermediate 17

(S)-N-4-(6-Chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)benzoyl-S-methyl-S-phenylsulfoximine

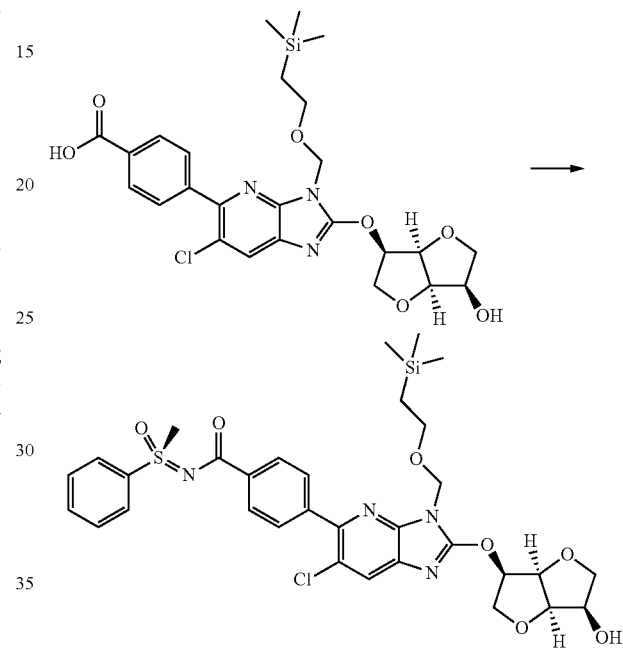

The title compound is prepared from 4-[6-chloro-2-((3R,3aR,6R,6aR)-6-hydroxy-hexahydro-furo[3,2-b]furan-3-yloxy)-3-(2-trimethylsilanyl-ethoxymethyl)-3H-imidazo-[4,5-b]pyridin-5-yl]-benzoic acid and (S)-S-methyl-S-phenylsulfoximine following a procedure analogous to that described for Intermediate 4 (Step 2). LC (method 1): t$_R$=1.10 min; Mass spectrum (ESI$^+$): m/z=685 [M+H]$^+$.

Intermediate 18

N-(4'-(6-chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)biphenyl-4-yl)-S,S-dimethyl-sulfondiimine

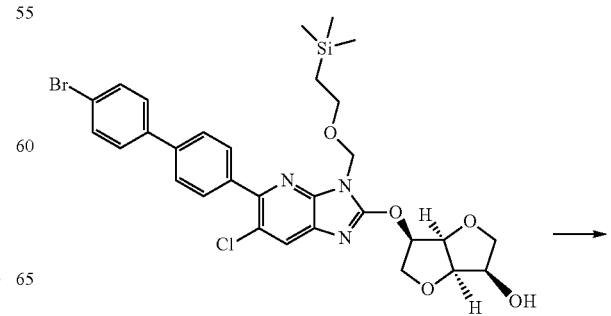

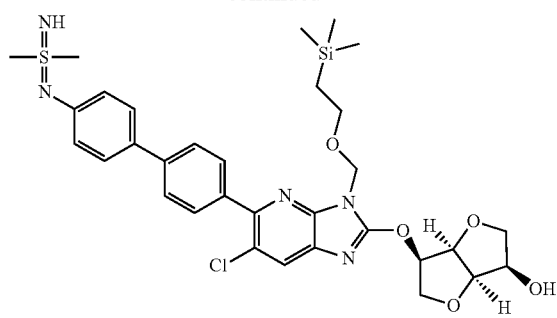

The title compound is prepared from (3R,3aR,6R,6aR)-6-[5-(4'-bromo-biphenyl-4-yl)-6-chloro-3-(2-trimethylsilanyl-ethoxymethyl)-3H-imidazo[4,5-b]pyridin-2-yloxy]-hexahydrofuro[3,2-b]furan-3-ol and S,S-dimethylsulfondiimine following a procedure analogous to that described for Intermediate 2 (Step 2). LC (method 1): $t_R$=1.02 min; Mass spectrum (ESI$^+$): m/z=671 [M+H]$^+$.

Intermediate 19

N-(4'-(6-Chloro-2-((3R,3aR,6R,6aR)-6-hydroxy-hexahydrofuro[3,2-b]furan-3-yloxy)-3-(2-trimethyl-silanyl-ethoxymethyl)-3H-imidazo[4,5-b]pyridin-5-yl)biphenyl-4-yl)-S-isopropyl-S-methylsulfoximide

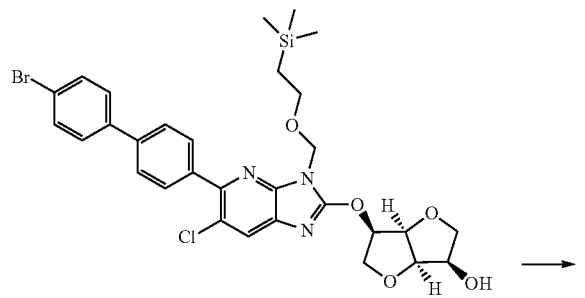

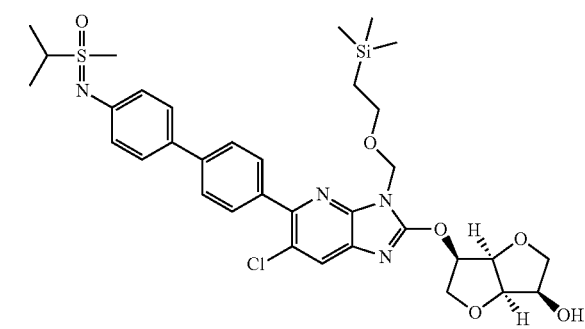

The title compound is prepared from (3R,3aR,6R,6aR)-6-[5-(4'-bromo-biphenyl-4-yl)-6-chloro-3-(2-trimethylsilanyl-ethoxymethyl)-3H-imidazo[4,5-b]pyridin-2-yloxy]-hexahydrofuro[3,2-b]furan-3-ol and S-isopropyl-S-methylsulfoximine following a procedure analogous to that described for Intermediate 9. LC (method 1): $t_R$=1.14 min; Mass spectrum (ESI$^+$): m/z=700 [M+H]$^+$.

Intermediate 20

N-4-(6-Chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)benzoyl-S-methyl-S-(pyridin-3-yl)-sulfoximine

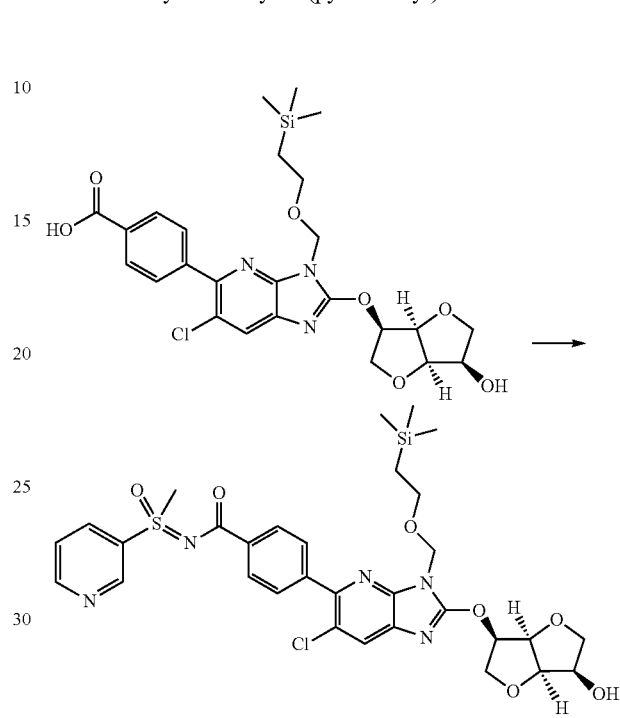

The title compound is prepared from 4-[6-chloro-2-((3R,3aR,6R,6aR)-6-hydroxy-hexahydrofuro[3,2-b]furan-3-yloxy)-3-(2-trimethylsilanyl-ethoxymethyl)-3H-imidazo[4,5-b]pyridin-5-yl]-benzoic acid and S-methyl-S-(pyridin-3-yl)-sulfoximine following a procedure analogous to that described for Intermediate 4 (Step 2). LC (method 1): $t_R$=1.03 min; Mass spectrum (ESI$^+$): m/z=686 [M+H]$^+$.

Intermediate 21

N-4-(6-Chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)benzoyl-S-methyl-S-tetrahydro-2H-pyran-4-yl)-sulfoximine

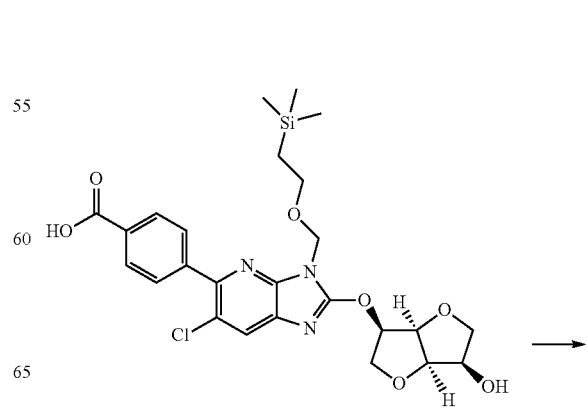

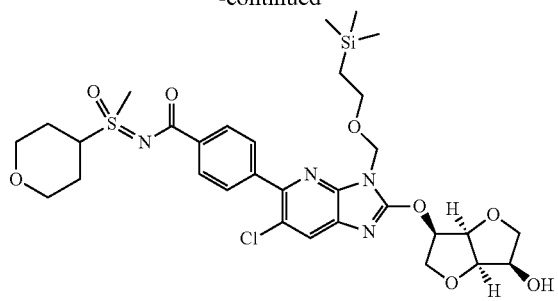

The title compound is prepared from 4-[6-chloro-2-((3R,3aR,6R,6aR)-6-hydroxy-hexahydrofuro[3,2-b]furan-3-yloxy)-3-(2-trimethylsilanyl-ethoxymethyl)-3H-imidazo-[4,5-b]pyridin-5-yl]-benzoic acid and S-methyl-S-(tetrahydro-2H-pyran-4-yl)-sulfoximine following a procedure analogous to that described for Intermediate 4 (Step 2). LC (method 1): $t_R$=1.03 min; Mass spectrum (ESI$^+$): m/z=693 [M+H]$^+$.

Intermediate 22

4-[6-Chloro-2-((3R,3aR,6R,6aR)-6-hydroxy-hexahydro-furo[3,2-b]furan-3-yloxy)-3-(2-trimethylsilanyl-ethoxymethyl)-3H-imidazo[4,5-b]pyridin-5-yl]-N-(4-oxo-4λ6-[1,4]oxathian-4-ylidene)-benzamide

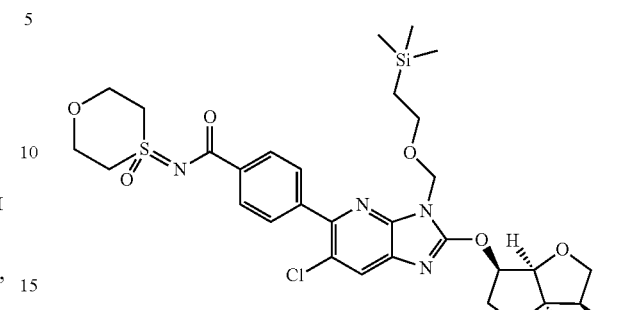

The title compound is prepared from 4-[6-chloro-2-((3R,3aR,6R,6aR)-6-hydroxy-hexahydro-furo[3,2-b]furan-3-yloxy)-3-(2-trimethylsilanyl-ethoxymethyl)-3H-imidazo-[4,5-b]pyridin-5-yl]-benzoic acid and 4-imino-1,4-oxathiane-4-oxide following a procedure analogous to that described for Intermediate 4 (Step 2). LC (method 1): $t_R$=1.03 min; Mass spectrum (ESI$^+$): m/z=665 [M+H]$^+$.

Intermediate 23

N-(5-(4-(6-Chloro-2-((3R,3aR,6R,6aR)-6-hydroxy-hexahydrofuro[3,2-b]furan-3-yloxy)-3-(2-trimethyl-silanyl-ethoxymethyl)-3H-imidazo[4,5-b]pyridin-5-yl)phenyl)pyridin-2-yl)-S,S-dimethylsulfoximide

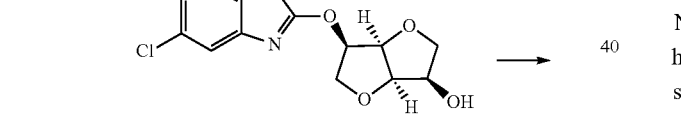

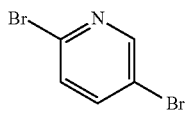

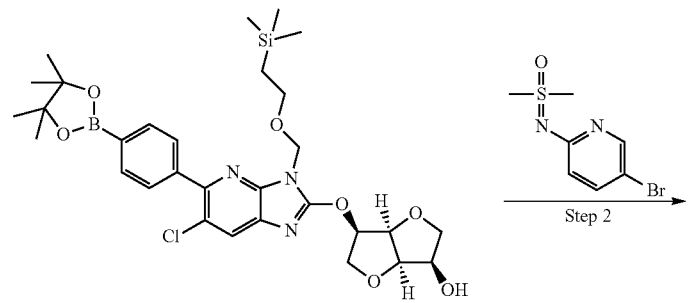

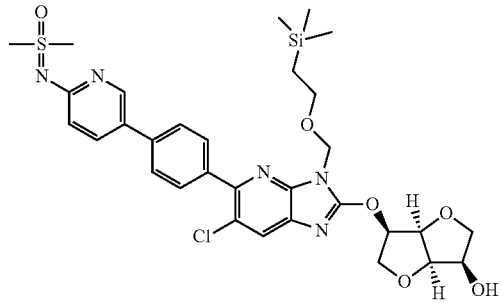

Step 1: N-(5-Bromo-pyridin-2-yl)-S,S-dimethylsulfoximine

A mixture of 2,5-dibromo-pyridine (200 mg), S,S-dimethylsulfoximine (83 mg), and $Cs_2CO_3$ (385 mg) in 1,4-dioxane (3 mL) in a microwave vial is purged with argon for 5 minutes. Palladium(II) acetate (9.5 mg) and racemic 2,2'-bis-(diphenylphosphino)-1,1'-binaphthyl (42 mg) are added, the vial is sealed, and the mixture heated to 130° C. for 30 minutes. The product mixture is filtered over celite, using ethyl acetate as the eluent. The filtrate is concentrated in vacuo and the residue is triturated with tert-butylmethyl ether. The precipitate is filtered off and dried to give the title compound. LC (method 1): $t_R$=0.58 min; Mass spectrum (ESI$^+$): m/z=249 [M+H]$^+$.

Step 2: N-(5-(4-(6-Chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)phenyl)pyridin-2-yl)-S,S-dimethylsulfoximide The title compound is prepared from (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol and N-(5-bromo-pyridin-2-yl)-S,S-dimethylsulfoximine following a procedure analogous to that described for Intermediate 2 (Step 1). LC (method 1): $t_R$=0.95 min; Mass spectrum (ESI$^+$): m/z=672 [M+H]$^+$.

Intermediate 24

(3R,3aR,6R,6aR)-6-(6-Chloro-5-(4'-(N-tert-butoxycarbonyl-S-methylsulfonimidoyl)biphenyl-4-yl)-3-(2-trimethylsilanyl-ethoxy-methyl)-3H-imidazo[4,5-b]pyridin-2-yloxy)-hexahydrofuro[3,2-b]furan-3-ol

Step 1: S-(4-Bromophenyl)-N-tert-butoxycarbonyl-S-methyl-sulfoximine

Sodium hydride (55-60% in mineral oil, 54 mg) is added to S-(4-bromophenyl)-S-methyl-sulfoximine (210 mg) in tetrahydrofuran (5 mL) cooled in an ice-bath and the resulting mixture is stirred for 30 min. Di-tert-butyldicarbonate (392 mg) is added and the reaction mixture is stirred for 20 minutes. The ice-bath is removed and the mixture is stirred for 4 h at room temperature. The mixture diluted with water and a small amount of citric acid and extracted ethyl acetate. The combined extracts are washed with brine, dried over $MgSO_4$, and concentrated in vacuo. The residue is chromatographed on silica gel (cyclohexane/ethyl acetate 70:30→50:50) to give the title compound. LC (method 1): $t_R$=0.96 min; Mass spectrum (ESI$^+$): m/z=334 [M+H]$^+$.

Step 2: (3R,3aR,6R,6aR)-6-(6-Chloro-5-(4'-(N-tert-butoxycarbonyl-S-methylsulfonimidoyl)biphenyl-4-yl)-3-(2-trimethylsilanyl-ethoxy-methyl)-3H-imidazo[4,5-b]pyridin-2-yloxy)hexahydrofuro[3,2-b]furan-3-ol The title compound is prepared from (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol and S-(4-bromophenyl)-N-tert-butoxycarbonyl-S-methyl-sulfoximine following a procedure analogous to that described for Intermediate 2 (Step 1). LC (method 1): $t_R$=1.16 min; Mass spectrum (ESI$^+$): m/z=757 [M+H]$^+$.

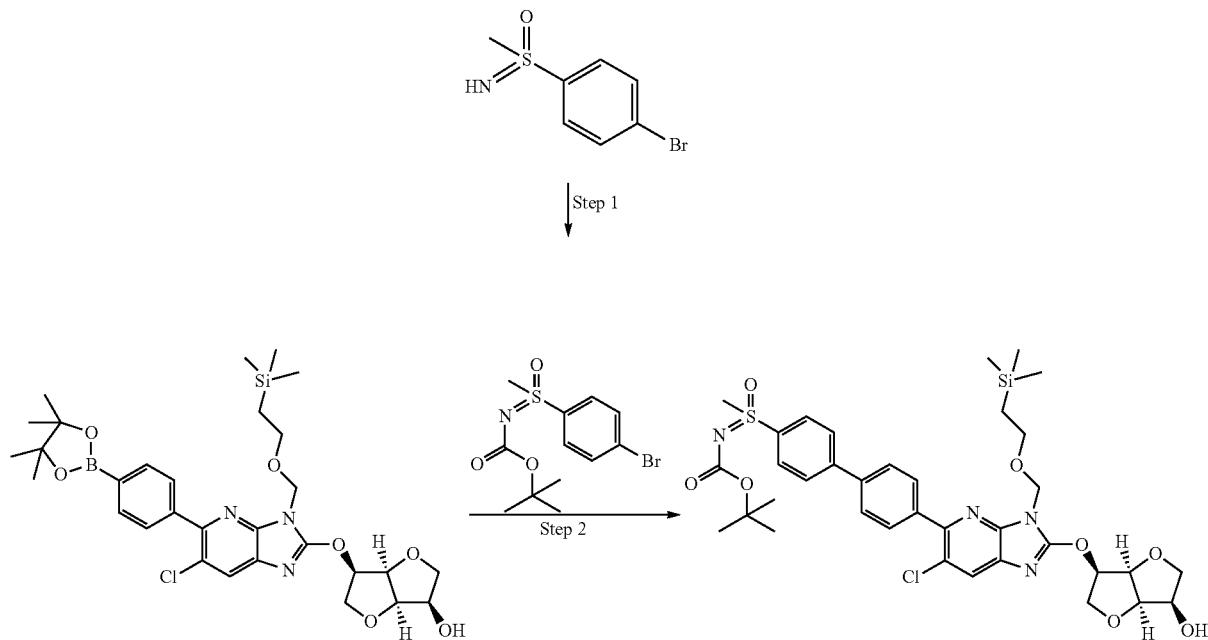

Intermediate 25

4-[6-Chloro-2-((3R,3aR,6R,6aR)-6-hydroxy-hexahydro-furo[3,2-b]furan-3-yloxy)-3-(2-trimethylsilanyl-ethoxymethyl)-3H-imidazo[4,5-b]pyridin-5-yl]-N-(1-oxo-hexahydro-1λ6-thiopyran-1-ylidene)-benzamide

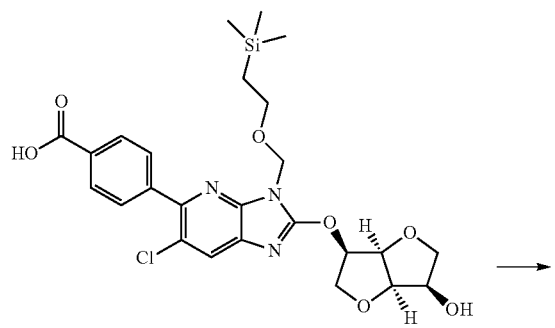

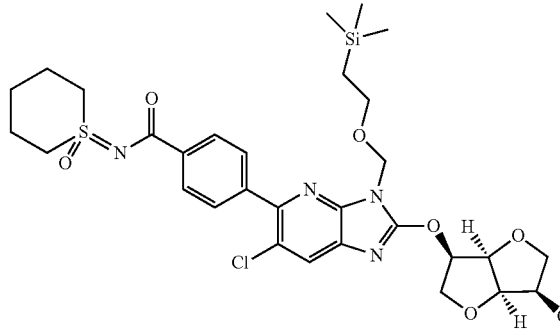

The title compound is prepared from 4-[6-chloro-2-((3R,3aR,6R,6aR)-6-hydroxy-hexahydro-furo[3,2-b]furan-3-yloxy)-3-(2-trimethylsilanylethoxymethyl)-3H-imidazo-[4,5-b]pyridin-5-yl]-benzoic acid and 1-oxo-1-imino-1-thiacyclohexane following a procedure analogous to that described for Intermediate 4 (Step 2). LC (method 1): $t_R$=1.07 min; Mass spectrum (ESI$^+$): m/z=663 [M+H]$^+$.

Intermediate 26

(R)-N-4-(6-Chloro-2-((3R,3aR,6R,6aR)-6-hydroxy-hexahydrofuro[3,2-b]furan-3-yloxy)-3-(2-trimethylsilanyl-ethoxymethyl)-3H-imidazo[4,5-b]pyridin-5-yl)benzoyl-S-methyl-S-phenylsulfoximine

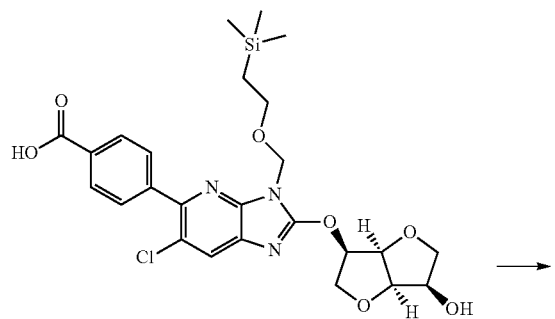

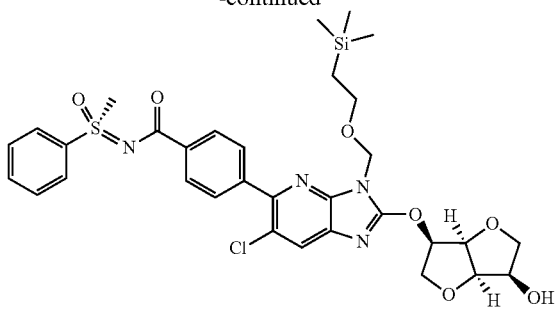

The title compound is prepared from 4-[6-chloro-2-((3R,3aR,6R,6aR)-6-hydroxy-hexahydro-furo[3,2-b]furan-3-yloxy)-3-(2-trimethylsilanyl-ethoxymethyl)-3H-imidazo-[4,5-b]pyridin-5-yl]-benzoic acid and (R)-S-methyl-S-phenylsulfoximine following a procedure analogous to that described for Intermediate 4 (Step 2). LC (method 1): $t_R$=1.10 min; Mass spectrum (ESI$^+$): m/z=685 [M+H]$^+$.

Intermediate 27

N-(4-(6-Chloro-2-((3R,3aR,6R,6aR)-6-hydroxy-hexahydrofuro[3,2-b]furan-3-yloxy)-3-(2-trimethyl-silanyl-ethoxy-methyl)-3H-imidazo[4,5-b]pyridin-5-yl)phenyl)-S-methyl-S-(Pyridin-4-yl)-sulfoximide

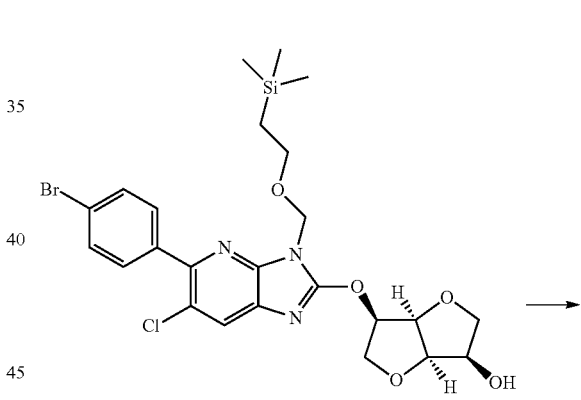

The title compound is prepared from (3R,3aR,6R,6aR)-6-[5-(4-bromo-phenyl)-6-chloro-3-(2-trimethylsilanyl-ethoxymethyl)-3H-imidazo[4,5-b]pyridin-2-yloxy]-hexahydrofuro[3,2-b]furan-3-ol and S-methyl-S-(pyridin-4-yl)-sulfoximine following a procedure analogous to that described for Intermediate 9. LC (method 1): $t_R$=1.33 min; Mass spectrum (ESI$^+$): m/z=658 [M+H]$^+$.

Intermediate 28

(3R,3aR,6R,6aR)-6-(6-chloro-5-(4-(5-(N-tert-butoxycarbonyl-S-methylsulfonimido-yl)Pyridin-2-yl)phenyl)-3-(2-trimethylsilanyl-ethoxy-methyl)-3H-imidazo[4,5-b]pyridin-2-yloxy)hexahydrofuro[3,2-b]furan-3-ol sodium thiosulfate (10% aqueous solution), potassium carbonate (10% aqueous solution), and brine, dried over MgSO$_4$ and concentrated in vacuo. The crude product is used for the next reaction step without further purification.

LC (method 3): t$_R$=0.57 min; Mass spectrum (ESI$^+$): m/z=220 [M+H]$^+$.

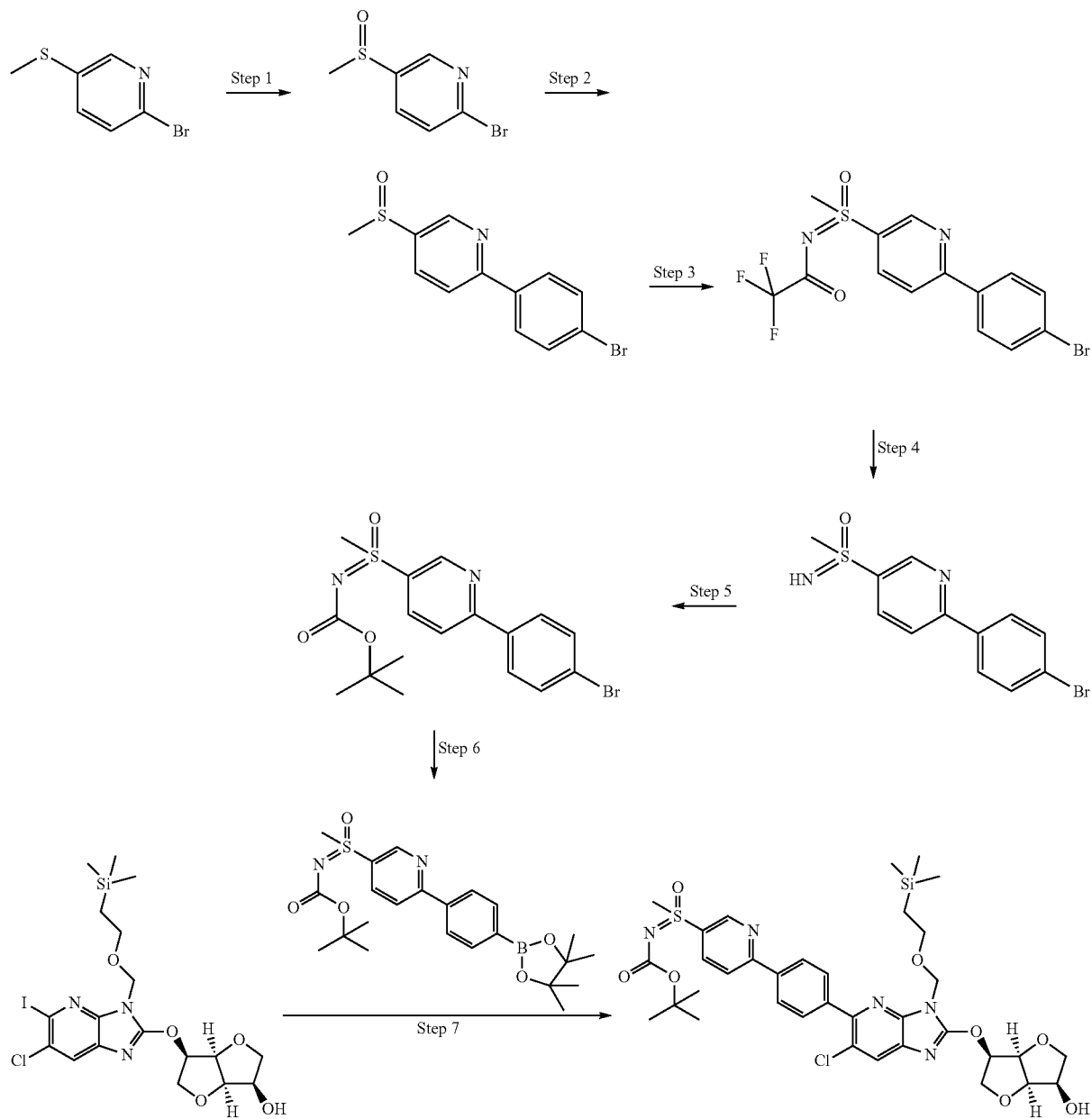

Step 1: 2-Bromo-S-methylsulfinyl-pyridine

A mixture of 2-bromo-S-methylsulfanyl-pyridine (8.67 g), sodium periodate (12.72 g), concentrated acetic acid (115 mL), and water (30 µL) is stirred at room temperature for 2 h. The reaction mixture is diluted with water and extracted with ethyl acetate. The combined extracts are washed with

Step 2: 2-(4-Bromo-phenyl)-S-methylsulfinyl-pyridine

A mixture of 2-bromo-S-methylsulfinyl-pyridine (1.50 g) and 4-bromobenzene boronic acid (1.20 g), Na$_2$CO$_3$ (2 M aqueous solution, 8.18 mL), and 1,4-dioxane (15 mL) is purged with argon for 5 minutes. [1,1'-Bis(diphenylphosphino)-ferrocene]-dichloropalladium(II)-CH$_2$Cl$_2$-complex (PdCl$_2$(dppf)$_x$CH$_2$Cl$_2$) (223 mg) is added and the mixture is stirred over night at 80° C. The reaction mixture is concentrated in vacuo and the residue is chromatographed on silica gel (cyclohexane/ethyl acetate 50:50→0:100) to give the title compound. LC (method 3): t$_R$=0.88 min; Mass spectrum (ESI$^+$): m/z=296 [M+H]$^+$.

Step 3: 2-(4-Bromophenyl)-5-(N-(2,2,2-trifluoroacetyl)-S-methylsulfonimidoyl)pyridine A mixture of 2-(4-bromo-phenyl)-S-methylsulfinyl-pyridine (500 mg), 2,2,2-trifluoroacetamide (382 mg), iodobenzene diacetate (815 mg), magnesium oxide (272 mg), rhodium(II) acetate dimer (19 mg), and K$_2$CO$_3$ (1.17 g) in dichloromethane (25 mL) is stirred at room temperature overnight. The reaction mixture is filtered through a pad of celite. The filtrate is washed with water and brine, dried over MgSO$_4$, and concentrated in vacuo. The residue is chromatographed on silica gel (cyclohexane/ethyl acetate 70:30→0:100) to give the title compound. LC (method 3): t$_R$=1.09 min; Mass spectrum (ESI$^+$): m/z=407 [M+H]$^+$.

Step 4: 2-(4-Bromophenyl)-5-(S-methylsulfonimidoyl)pyridine

A mixture of 2-(4-bromophenyl)-5-(N-(2,2,2-trifluoroacetyl)-S-methyl-sulfonimido-yl)pyridine (478 mg), and K$_2$CO$_3$ (800 mg) in methanol (5 mL) is stirred at room temperature for 1 h. The reaction mixture is diluted with dichloromethane, washed with water, dried over MgSO$_4$, and concentrated in vacuo. The crude product is used for the next reaction step without further purification. LC (method 3): t$_R$=0.87 min; Mass spectrum (ESI$^+$): m/z=311 [M+H]$^+$.

Step 5: 2-(4-Bromophenyl)-5-(N-tert-butoxycarbonyl-S-methylsulfonimidoyl)pyridine The title compound is prepared from 2-(4-bromophenyl)-5-(S-methyl-sulfon-imidoyl)pyridine following a procedure analogous to that described for Intermediate 24 (Step 1). LC (method 3): t$_R$=1.05 min; Mass spectrum (ESI$^+$): m/z=411 [M+H]$^+$.

Step 6: 5-(N-tert-Butoxycarbonyl-S-methylsulfonimidoyl)-2-(4-(4,4,5,5-tetramethyl-1,3,2-dioxaborolan-2-yl)phenyl)pyridine The title compound is prepared from 2-(4-bromophenyl)-5-(N-tert-butoxycarbonyl-S-methylsulfonimidoyl)pyridine following a procedure analogous to that described for Intermediate 8 (Step 3). LC (method 1): t$_R$=1.15 min; Mass spectrum (ESI$^+$): m/z=459 [M+H]$^+$.

Step 7: (3R,3aR,6R,6aR)-6-(6-chloro-5-(4-(5-(N-tert-butoxycarbonyl-S-methylsulfonimidoyl)pyridin-2-yl)phenyl)-3-(2-trimethylsilanyl-ethoxy-methyl)-3H-imidazo[4,5-b]pyridin-2-yloxy)hexahydrofuro[3,2-b]furan-3-ol The title compound is prepared from (3R,3aR,6R,6aR)-6-(6-chloro-5-iodo-3-(2-trimethylsilanyl-ethoxymethyl)-3H-imidazo[4,5-b]pyridin-2,-yloxy)hexahydrofuro [3,2-b]furan-3-ol and 5-(N-tert-butoxycarbonyl-S-methylsulfonimidoyl)-2-(4-(4,4,5,5-tetramethyl-1,3,2-dioxaborolan-2-yl)phenyl)pyridine following a procedure analogous to that described for Intermediate 2(Step 1). LC (method 2): t$_R$=0.55 min; Mass spectrum (ESI$^+$): m/z=758 [M+H]$^+$.

Intermediate 29

(3R,3aR,6R,6aR)-6-(6-Chloro-5-(4-(5-(N,S-dimethylsulfonimidoyl)pyridin-2-yl)phenyl)-3-(2-trimethylsilanyl-ethoxy-methyl)-3H-imidazo[4,5-b]pyridin-2-yloxy)hexahydrofuro-[3,2-b]furan-3-ol

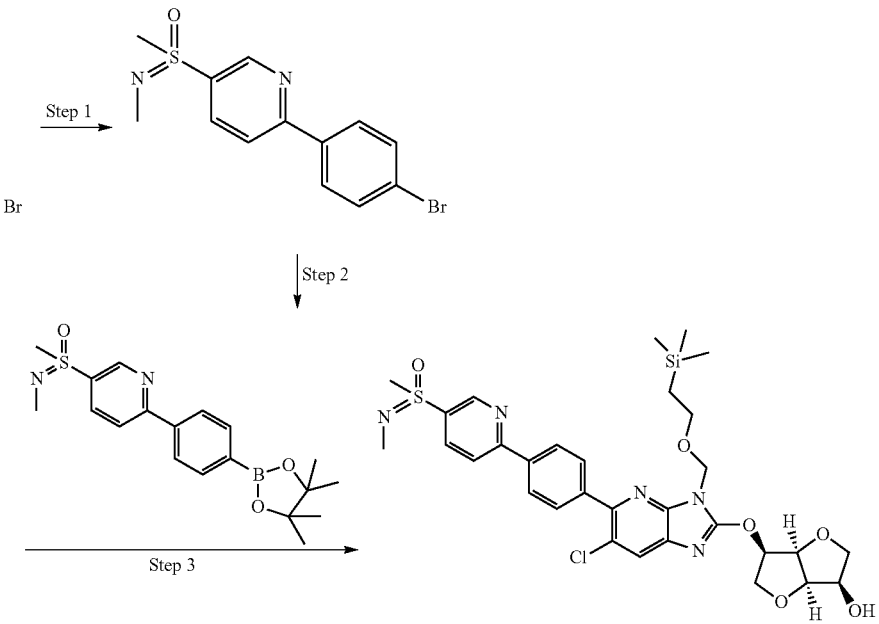

Step 1: 2-(4-Bromophenyl)-5-(N,S-dimethylsulfon-imidoyl)pyridine

The title compound is prepared from 2-(4-bromophenyl)-5-(S-methyl-sulfonimidoyl)pyridine following a procedure analogous to that described for Intermediate 11 (Step 2). LC (method 3): $t_R$=0.92 min; Mass spectrum (ESI$^+$): m/z=325 [M+H]$^+$.

Step 2: 5-(N,S-dimethylsulfonimidoyl)-2-(4-(4,4,5,5-tetramethyl-1,3,2-dioxaborolan-2-yl)phenyl)pyridine The title compound is prepared from 2-(4-bromophenyl)-5-(N,S-dimethylsulfonimidoyl)pyridine following a procedure analogous to that described for Intermediate 8 (Step 3). LC (method 3): $t_R$=1.00 min; Mass spectrum (ESI$^+$): m/z=373 [M+H]$^+$.

Step 3: (3R,3aR,6R,6aR)-6-(6-Chloro-5-(4-(5-(N,S-dimethylsulfonimidoyl)pyridin-2-yl)phenyl)-3-(2-trimethylsilanyl-ethoxy-methyl)-3H-imidazo[4,5-b]pyridin-2-yloxy)hexahydrofuro[3,2-b]furan-3-ol The title compound is prepared from 3R,3aR,6R,6aR)-6-(6-chloro-5-iodo-3-(2-trimethylsilanyl-ethoxymethyl)-3H-imidazo[4,5-b]pyridin-2-yloxy)hexahydrofuro[3,2-b]furan-3-ol and 5-(N,S-dimethylsulfonimidoyl)-2-(4-(4,4,5,5-tetramethyl-1,3,2-dioxaborolan-2-yl)phenyl)pyridine following a procedure analogous to that described for Intermediate 2 (Step 1). LC (method 3): $t_R$=1.02 min; Mass spectrum (ESI$^+$): m/z=672 [M+H]$^+$.

Intermediate 30

(3R,3aR,6R,6aR)-6-(5,6-Dichloro-3-(2-trimethylsilanyl-ethoxymethyl)-3H-imidazo[4,5-b]pyridin-2-yloxy)hexahydrofuro[3,2-b]furan-3-ol

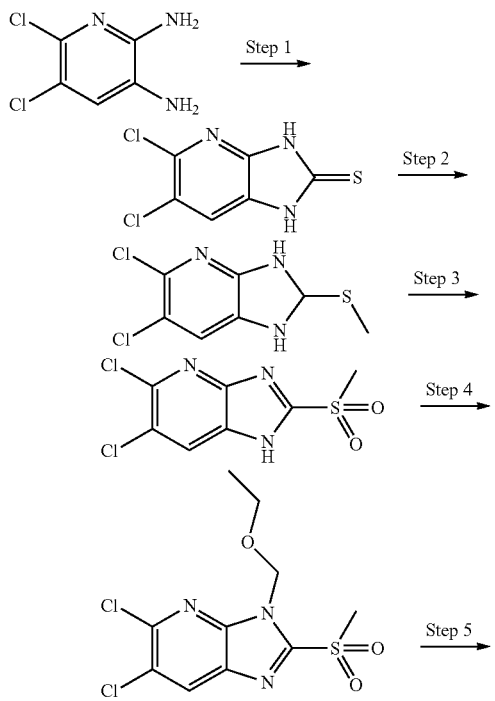

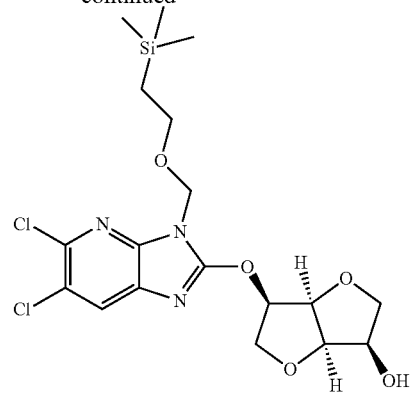

Step 1: 5,6-Dichloro-1,3-dihydro-imidazo[4,5-b]pyridine-2-thione

Thiophosgene (4.0 mL) is added drop wise to an ice-cooled mixture of 5,6-dichloro-pyridine-2,3-diamine (9.18 g) and triethylamine (14.4 mL) in tetrahydrofuran (170 mL). After 1 h the ice bath is removed and the reaction mixture is stirred for 1 h at room temperature. Ethyl acetate (500 mL) and hydrochloric acid (1 N, 200 mL) are added. The organic phase is separated, washed with brine, dried over MgSO$_4$, and concentrated in vacuo to give the title compound, which is used for the next reaction step without further purification. LC (method 1): $t_R$=0.77 min; Mass spectrum (ESI$^+$): m/z=220 [M+H]$^+$.

Step 2: 5,6-Dichloro-2-methylsulfanyl-2,3-dihydro-1H-imidazo[4,5-b]pyridine

A mixture of 5,6-dichloro-1,3-dihydro-imidazo[4,5-b]pyridine-2-thione (10.57 g) and KOH (3.30 g) in ethanol (170 mL) is stirred at room temperature for 30 min. Methyl iodide (3.30 mL) is added and the reaction mixture is stirred for 3 h at room temperature. The reaction mixture is acidified with hydrochloric acid (1 N) and the precipitate is filtered off, rinsed with water, and dried in a desiccator to give the title compound, which is used for the next reaction step without further purification. LC (method 1): $t_R$=0.83 min; Mass spectrum (ESI$^+$): m/z=234 [M+H]$^+$.

Step 3: 5,6-Dichloro-2-methylsulfonyl-1H-imidazo[4,5-b]pyridine

Oxone (20.06 g) is added to 5,6-dichloro-2-methylsulfanyl-2,3-dihydro-1H-imidazo[4,5-b]pyridine (3.82 g) in a mixture of water (50 mL) and acetonitrile (50 mL) and the resulting mixture is stirred at room temperature overnight. The reaction mixture is filtered, diluted with aqueous KHSO$_4$ solution and extracted with ethyl acetate. The combined extracts are washed with brine, dried over MgSO$_4$, and concentrated in vacuo to give the title compound, which is used for the next reaction step without further purification. LC (method 1): $t_R$=0.79 min; Mass spectrum (ESI$^+$): m/z=266 [M+H]$^+$.

Step 4: 5,6-Dichloro-2-methylsulfonyl-3-(2-trimethylsilanyl-ethoxymethyl)-3H-imidazo[4,5-b]pyridine The title compound is prepared from 5,6-dichloro-2-methylsulfonyl-1H-imidazo[4,5-b]pyridine following a procedure analogous to that described for Intermediate 1 (Step 1). LC (method 1): $t_R$=1.21 min; Mass spectrum (ESI$^+$): m/z=396 [M+H]$^+$.

Step 5: (3R,3aR,6R,6aR)-6-(5,6-Dichloro-3-(2-trimethylsilanyl-ethoxymethyl)-3H-imidazo[4,5-b]pyridin-2-yloxy)hexahydrofuro[3,2-b]furan-3-ol The title compound is prepared from 5,6-dichloro-2-methylsulfonyl-3-(2-trimethylsilanyl-ethoxymethyl)-3H-imidazo[4,5-b]pyridine following a procedure analogous to that described for Intermediate 1 (Step 2). LC (method 1): $t_R$=1.15 min; Mass spectrum (ESI$^+$): m/z=462 [M+H]$^+$.

Intermediate 31

(3R,3aR,6R,6aR)-6-(6-Chloro-5-(4-(4-(N,S-dimethylsulfonimidoyl)phenyl)piperazin-1-yl)-3-(2-trimethylsilanyl-ethoxy-methyl)-3H-imidazo[4,5-b]pyridin-2-yloxy)hexahydro-furo[3,2-b]furan-3-ol

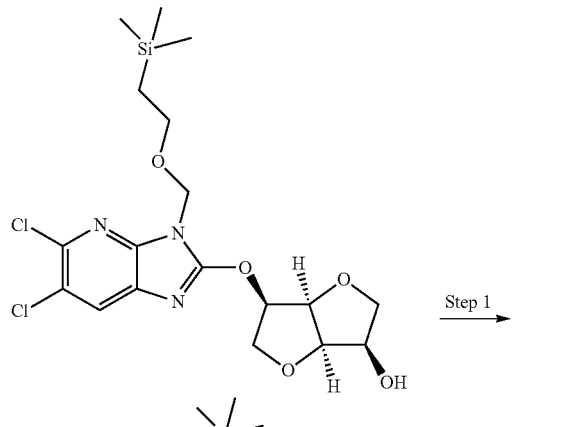

Step 1: (3R,3aR,6R,6aR)-6-(6-Chloro-5-piperazin-1-yl-3-(2-trimethylsilanyl-ethoxy-methyl)-3H-imidazo[4,5-b]pyridin-2-yloxy)hexahydrofuro[3,2-b]furan-3-ol A mixture of (3R,3aR,6R,6aR)-6-(5,6-dichloro-3-(2-trimethylsilanyl-ethoxymethyl)-3H-imidazo[4,5-b]pyridin-2-yloxy)hexahydrofuro[3,2-b]furan-3-ol (400 mg), piperazine (373 mg), and cesium carbonate (564 mg) in 1,4-dioxane (8 mL) is purged for 5 minutes with argon. Tris(dibenzylideneacetone)dipalladium(0) (40 mg) and 2-dicyclo-hexylphosphino-2',4',6'-triisopropylbiphenyl (XPhos, 62 mg) are added and the mixture is stirred at 80° C. overnight. The reaction mixture is diluted with water and extracted with dichloromethane. The organic phase is washed with brine, dried over MgSO$_4$, and concentrated in vacuo. The residue is chromatographed on silica gel [dichloromethane/(dichloromethane/methanol/7 M ammonia in methanol 50:48:2) 84:16→60:40] to give the title compound. LC (method 1): $t_R$=0.84 min; Mass spectrum (ESI$^+$): m/z=512 [M+H]$^+$.

Step 2: (3R,3aR,6R,6aR)-6-(6-Chloro-5-(4-(4-(N,S-dimethylsulfonimidoyl)phenyl)piperazin-1-yl)-3-(2-trimethylsilanyl-ethoxy-methyl)-3H-imidazo[4,5-b]pyridin-2-yloxy)-hexahydrofuro[3,2-b]furan-3-ol A mixture of (3R,3aR,6R,6aR)-6-(6-chloro-5-piperazin-1-yl-3-(2-trimethylsilanyl-ethoxymethyl)-3H-imidazo[4,5-b]pyridin-2-yloxy)hexahydrofuro[3,2-b]furan-3-ol (50 mg) and cesium carbonate (32 mg) in toluene is purged for 5 minutes with argon. Dichlorobis(tri-o-tolylphosphine)palladium(II) (2 mg) and 2,2'-bis(diphenylphosphino)-1,1'-binaphthyl (BINAP, 5 mg) are added and the mixture is heated to 150° C. for 40 min in a microwave oven. The reaction mixture concentrated in vacuo and the residue is purified by HPLC to give the title compound. LC (method 1): $t_R$=0.97 min; Mass spectrum (ESI$^+$): m/z=679 [M+H]$^+$.

Intermediate 32

N-(2-(4-(6-Chloro-2-(((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)phenyl)pyridin-5-yl)-S,S-dimethylsulfoximide

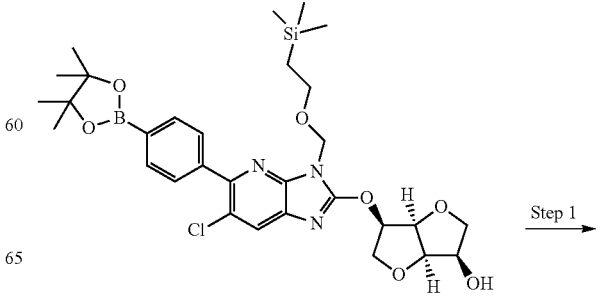

-continued

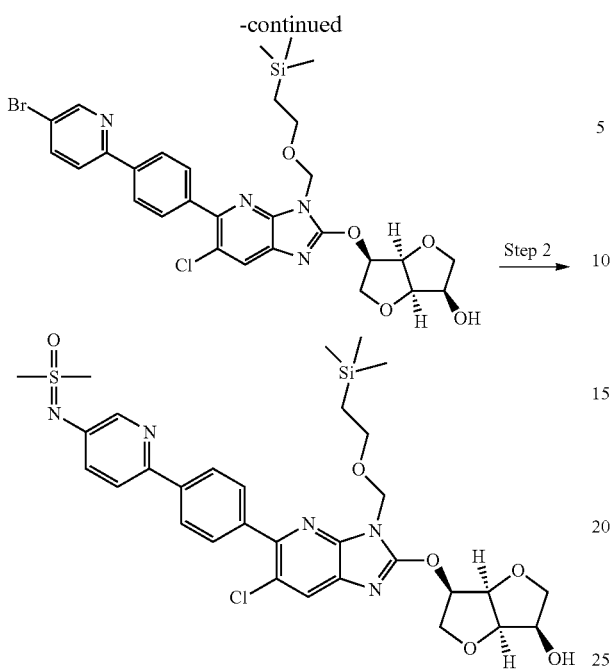

Step 1: (3R,3aR,6R,6aR)-6-(5-(4-(5-Bromopyridin-2-yl)phenyl)-6-chloro-3-(2-trimethylsilanyl-ethoxymethyl)-3H-imidazo[4,5-b]pyridin-2-yloxy)hexahydrofuro[3,2-b]furan-3-ol The title compound is prepared from (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol and 2,5-dibromopyridine following a procedure analogous to that described for Intermediate 2 (Step 1). Mass spectrum (ESI$^+$): m/z=659, 661 [M+H]$^+$.

Step 2: N-(2-(4-(6-Chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)phenyl)-pyridin-5-yl)-S,S-dimethylsulfoximide The title compound is prepared from (3R,3aR,6R,6aR)-6-(5-(4-(5-bromopyridin-2-yl)phenyl)-6-chloro-3-(2-trimethylsilanyl-ethoxymethyl)-3H-imidazo[4,5-b]pyridin-2-yloxy)hexahydrofuro[3,2-b]furan-3-ol and S,S-dimethylsulfoximine following a procedure analogous to that described for Intermediate 9. LC (method 1): $t_R$=0.93 min; Mass spectrum (ESI$^+$): m/z=672 [M+H]$^+$.

Intermediate 33

N-(1-(4-(6-Chloro-2-((3R,3aR,6R,6aR)-6-hydroxy-hexahydrofuro[3,2-b]furan-3-yloxy)-3-(2-trimethyl-silanyl-ethoxymethyl)-3H-imidazo[4,5-b] pyridin-5-yl)phenyl)piperidin-4-ylmethyl)-S,S-dimethylsulfoximide

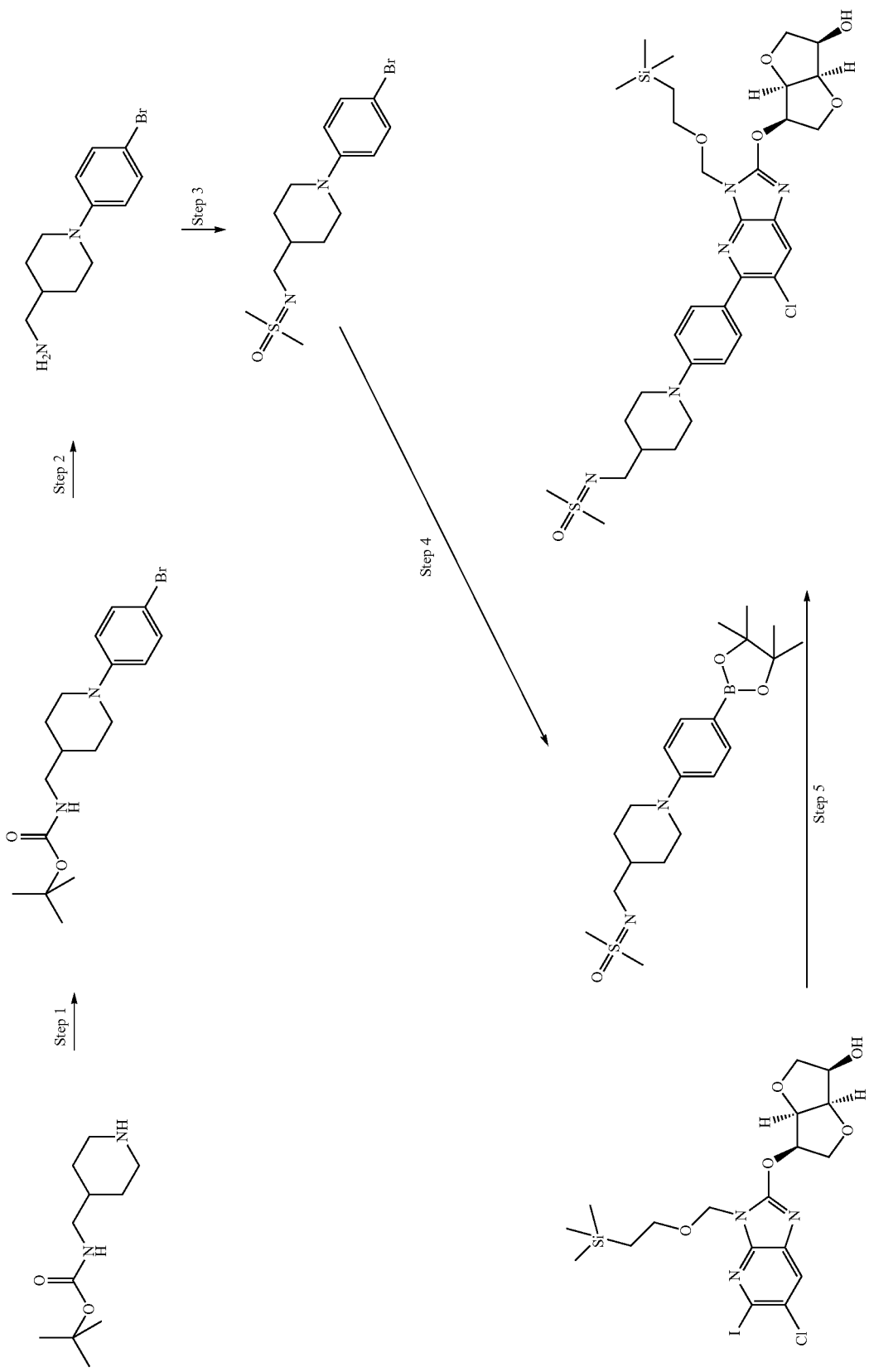

Step 1: [1-(4-Bromo-phenyl)-piperidin-4-ylmethyl]-carbamic acid tert-butyl ester A mixture of 1-bromo-4-iodo-benzene (1.32 g), piperidin-4-ylmethyl-carbamic acid tert-butyl ester (1.00 g), and Cs$_2$CO$_3$ (2.28 g) in 1,4-dioxane (30 mL) is purged with argon for 5 minutes. Tris(dibenzylideneacetone)dipalladium (0) (90 mg) and 4,5-bis(diphenylphosphino)-9,9-dimethyl-xanthene (XantPhos, 216 mg) are added. The mixture is stirred at 110° C. overnight and then cooled to room temperature, diluted with ethyl acetate and washed with aqueous NH$_4$Cl solution (10%). The organic phase is washed with brine, dried over MgSO$_4$, and concentrated in vacuo. The residue is chromatographed on silica gel (cyclohexane/ethyl acetate 93:7→70:30) to give the title compound. LC (method 4): $t_R$=0.94 min; Mass spectrum (ESI$^+$): m/z=369, 371 [M+H]$^+$.

Step 2: C-[1-(4-Bromo-phenyl)-piperidin-4-yl]-methylamine

The title compound is prepared from [1-(4-bromo-phenyl)-piperidin-4-ylmethyl]-carbamic acid tert-butyl ester by treatment with trifluoroacetic acid in dichloromethane at room temperature. LC (method 4): $t_R$=0.63 min; Mass spectrum (ESI$^+$): m/z=269, 271 [M+H]$^+$.

Step 3: N-[1-(4-Bromo-phenyl)-piperidin-4-ylmethyl]-S,S-dimethylsulfoximide

Dimethyl sulfone (285 mg) is heated to 130° C. under an argon atmosphere, 4-bromobenzenediazonium tetrafluoroborate (272 mg) is added portion wise, and the resulting mixture is stirred for 30 min at 130° C. The mixture is allowed to cool to room temperature and dissolved in acetonitrile (2 mL). N,N-Diisopropylethylamine (0.19 mL) and C-[1-(4-bromo-phenyl)-piperidin-4-yl]-methylamine (300 mg) are added and the resulting mixture is stirred at room temperature for 1.5 h. The mixture is diluted with acetonitrile (2 mL), acidified with trifluoroacetic acid, filtered and purified by HPLC on reversed phase to give the title compound. LC (method 4): $t_R$=0.68 min; Mass spectrum (ESI$^+$): m/z=346 [M+H]$^+$.

Step 4: N-{1-[4-(4,4,5,5-Tetramethyl-[1,3,2]dioxaborolan-2-yl)-phenyl]-piperidin-4-ylmethyl}-S,S-dimethylsulfoximide The title compound is prepared from N-[1-(4-bromo-phenyl)-piperidin-4-ylmethyl]-S,S-dimethylsulfoximide following a procedure analogous to that described for Intermediate 8 (Step 3). LC (method 5): $t_R$=1.08 min; Mass spectrum (ESI$^+$): m/z=393 [M+H]$^+$.

Step 5: N-(1-(4-(6-Chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)phenyl)piperidin-4-ylmethyl)-S,S-dimethylsulfoximide The title compound is prepared by Suzuki coupling of 3R,3aR,6R,6aR)-6-(6-chloro-5-iodo-3-(2-trimethylsilanyl-ethoxymethyl)-3H-pyridin-2-yloxy)-hexahydrofuro[3,2-b]furan-3-ol with N-{1-[4-(4,4,5,5-tetramethyl-[1,3,2]dioxaborolan-2-yl)-phenyl]-piperidin-4-ylmethyl}-S,S-dimethylsulfoximide using bis(di-tert-butyl (4-dimethylaminophenyl)phosphine)-dichloropalladium(II) as catalyst, K$_2$CO$_3$ as base and ethanol/water as solvent. LC (method 4): $t_R$=0.83 min; Mass spectrum (ESI$^+$): m/z=692 [M+H]$^+$.

Intermediate 34

N-(4-{5-[6-Chloro-2-((3R,3aR,6R,6aR)-6-hydroxy-hexahydrofuro[3,2-b]furan-3-yloxy)-3-(2-trimethyl-silanyl-ethoxymethyl)-3H-imidazo[4,5-b]pyridin-5-yl]-pyridin-2-yl}-phenyl)-S,S-dimethylsulfoximide

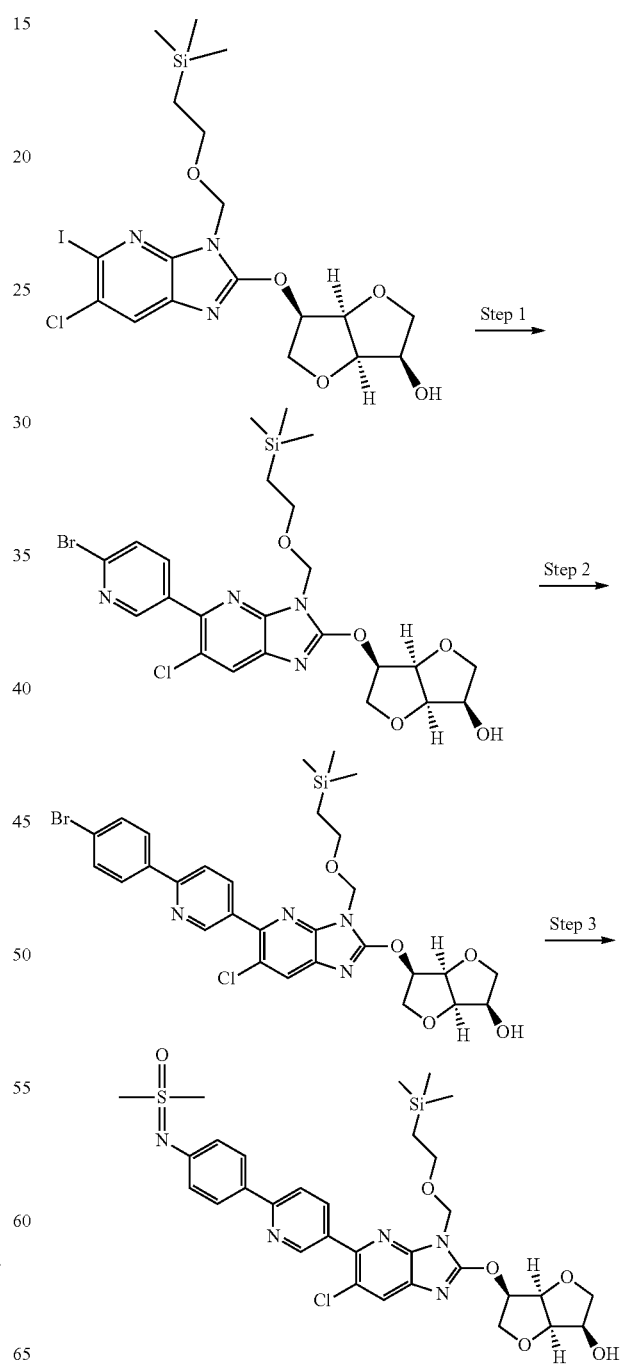

Step 1: (3R,3aR,6R,6aR)-6-[5-(6-Bromo-pyridin-3-yl)-6-chloro-3-(2-trimethylsilanyl-ethoxymethyl)-3H-imidazo[4,5-b]pyridin-2-yloxy]-hexahydro-furo[3,2-b]furan-3-ol The title compound is prepared from 3R,3aR,6R,6aR)-6-(6-chloro-5-iodo-3-(2-trimethylsilanyl-ethoxymethyl)-3H-imidazo-[4,5-b]pyridin-2-yloxy)hexahydrofuro[3,2-b]furan-3-ol and 2-bromopyridine-5-boronic acid following a procedure analogous to that described for Intermediate 2 (Step 1). LC (method 6): $t_R$=0.76 min; Mass spectrum (ESI$^+$): m/z=583, 585 [M+H]$^+$.

Step 2: (3R,3aR,6R,6aR)-6-[5-[6-(4-Bromo-phenyl)-pyridin-3-yl]-6-chloro-3-(2-trimethylsilanyl-ethoxymethyl)-3H-imidazo[4,5-b]pyridin-2-yloxy]-hexahydro-furo[3,2-b]furan-3-ol The title compound is prepared from (3R,3aR,6R,6aR)-6-[5-(6-bromo-pyridin-3-yl)-6-chloro-3-(2-trimethylsilanyl-ethoxymethyl)-3H-imidazo[4,5-b]pyridin-2-yloxy]-hexahydro-furo[3,2-b]furan-3-ol and 4-bromo-benzeneboronic acid following a procedure analogous to that described for Intermediate 2 (Step 1). LC (method 4): $t_R$=1.30 min; Mass spectrum (ESI$^+$): m/z=661, 663 [M+H]$^+$.

Step 3: N-(4-{5-[6-chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl]-pyridin-2-yl}-phenyl)-S,S-dimethylsulfoximide The title compound is prepared from (3R,3aR,6R,6aR)-6-[5-[6-(4-bromo-phenyl)-pyridin-3-yl]-6-chloro-3-(2-trimethylsilanyl-ethoxymethyl)-3H-imidazo[4,5-b]pyridin-2-yloxy]-hexahydro-furo[3,2-b]furan-3-ol and S,S-dimethylsulfoximine following a procedure analogous to that described for Intermediate 2 (Step 2). LC (method 5): $t_R$=1.02 min; Mass spectrum (ESI$^+$): m/z=672 [M+H]$^+$.

Intermediate 35

2-[(3R,3aR,6R,6aS)-6-(tert-Butyl-dimethyl-silanyloxy)-hexahydro-furo[3,2-b]furan-3-yloxy]-6-chloro-5-iodo-3-(2-trimethylsilanyl-ethoxymethyl)-3H-imidazo[4,5-b]pyridine

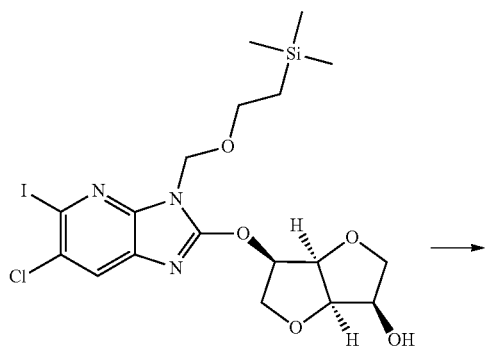

→

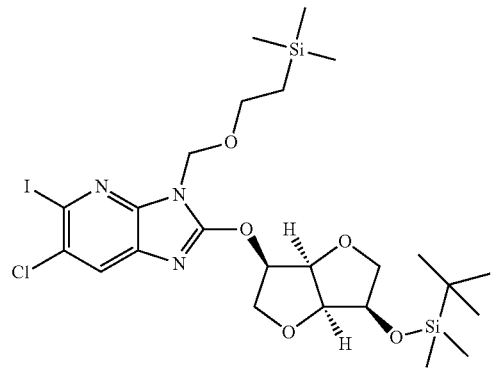

tert-Butyl-chloro-dimethyl-silane (430 mg) is added to a mixture of 3R,3aR,6R,6aR)-6-(6-chloro-5-iodo-3-(2-trimethylsilanyl-ethoxymethyl)-3H-imidazo-[4,5-b]pyridin-2-yloxy)hexahydrofuro[3,2-b]furan-3-ol (1.05 g) and imidazole (260 mg) in N,N-dimethylformamide (5.00 mL) under an argon atmosphere and the mixture is stirred at room temperature overnight. Ethyl acetate and saturated aqueous NH$_4$Cl solution are added. The organic phase is separated, washed with water and brine, dried over MgSO$_4$, and concentrated in vacuo. The residue is chromatographed on silica gel (cyclohexane/ethyl acetate 99:1→70:30) to give the title compound. LC (method 2): $t_R$=1.23 min; Mass spectrum (ESI$^+$): m/z=668 [M+H]$^+$.

Intermediate 36

N-(cis-4-{4-[2-[(3R,3aR,6R,6aS)-6-(tert-Butyl- dimethyl-silanyloxy)-hexahydro-furo[3,2-b]furan-3-yloxy]-6-chloro-3-(2-trimethylsilanyl-ethoxymethyl)- 3H-imidazo[4,5-b]pyridin-5-yl]-phenyl}-cyclohexanyl)-(methyl)oxido-$\lambda^4$- sulfanylidene])-2,2,2-trifluoro-acetamide

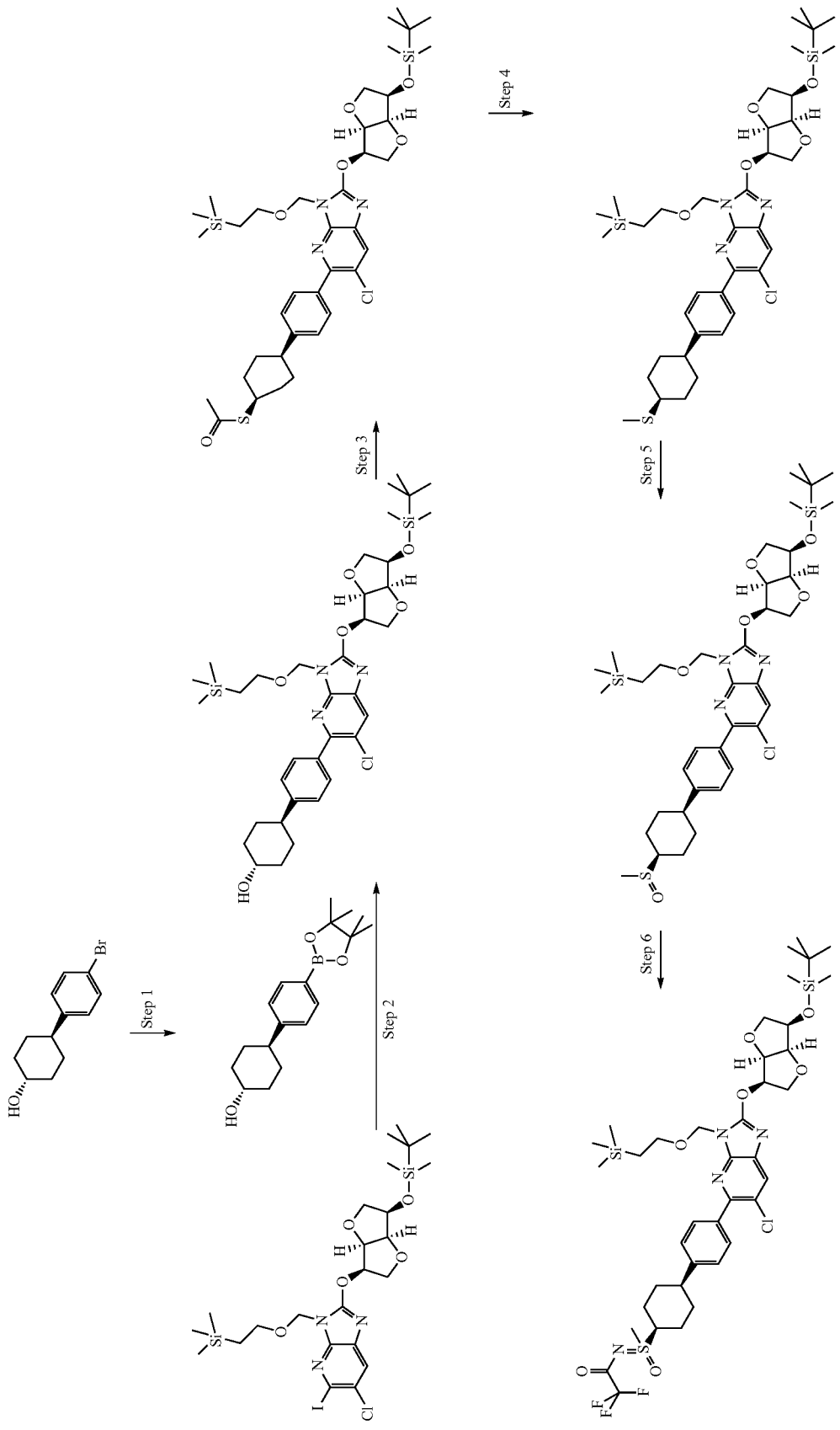

Step 1: trans-4-[4-(4,4,5,5-Tetramethyl-[1,3,2]dioxaborolan-2-yl)-phenyl]-cyclo-hexanol The title compound is prepared from trans-4-(4-bromophenyl)-cyclohexanol following a procedure analogous to that described for Intermediate 8 (Step 3), using bis(di-tert-butyl(4-dimethylaminophenyl)phosphine)-dichloropalladium(II) as catalyst. LC (method 1): $t_R$=1.07 min; Mass spectrum (ESI$^+$): m/z=303 [M+H]$^+$.

Step 2: trans-4-{4-[2-[(3R,3aR,6R,6aS)-6-(tert-Butyl-dimethyl-silanyloxy)-hexahydro-furo[3,2-b]furan-3-yloxy]-6-chloro-3-(2-trimethylsilanyl-ethoxymethyl)-3H-imidazo[4,5-b]pyridin-5-yl]-phenyl}-cyclohexanol The title compound is prepared by Suzuki coupling of 2-[(3R,3aR,6R,6aS)-6-(tert-butyl-dimethyl-silanyloxy)-hexahydro-furo[3,2-b]furan-3-yloxy]-6-chloro-5-iodo-3-(2-trimethylsilanyl-ethoxymethyl)-3H-imidazo[4,5-b]pyridine with trans-4-[4-(4,4,5,5-tetramethyl-[1,3,2]dioxaborolan-2-yl)-phenyl]-cyclohexanol using bis(di-tert-butyl(4-dimethylaminophenyl)phosphine)-dichloropalladium(II) as catalyst, K$_2$CO$_3$ as base, and ethanol/water as solvent. LC (method 2): $t_R$=1.14 min; Mass spectrum (ESI$^+$): m/z=716 [M+H]$^+$.

Step 3: cis-Thioacetic acid S-(4-{4-[2-[(3R,3aR,6R,6aS)-6-(tert-butyl-dimethyl-silanyloxy)-hexahydro-furo[3,2-b]furan-3-yloxy]-6-chloro-3-(2-trimethylsilanyl-ethoxymethyl)-3H-imidazo[4,5-b]pyridin-5-yl]-phenyl}-cyclohexyl ester Methanesulfonyl chloride (38 µl) is added drop wise to an ice-cooled mixture of trans-4-{4-[2-[(3R,3aR,6R,6aS)-6-(tert-butyl-dimethyl-silanyloxy)-hexahydro-furo[3,2-b]furan-3-yloxy]-6-chloro-3-(2-trimethylsilanyl-ethoxymethyl)-3H-imidazo[4,5-b]pyridin-5-yl]-phenyl}-cyclohexanol (313 mg) and triethylamine (80 µl) in dichloromethane (3.00 mL) under an argon atmosphere. The reaction mixture is allowed to warm room temperature and stirred overnight. Dichloromethane is added and the organic phase is separated, washed with water and brine, dried over MgSO$_4$, and concentrated in vacuo. The residue is purified by silica gel chromatography (cyclohexane/ethyl acetate 99:1→50:50). The mesylate is dissolved in N,N-dimethylformamide (2.00 mL), potassium thioacetate (66 mg) is added, and the mixture is stirred overnight at 70° C. Ethyl acetate is added and the organic phase is separated, washed with water and brine, dried over MgSO$_4$, and concentrated in vacuo. The residue is chromatographed on silica gel (cyclohexane/ethyl acetate 99:1→70:30) to give the title compound. LC (method 2): $t_R$=1.32 min; Mass spectrum (ESI$^+$): m/z=774 [M+H]$^+$.

Step 4: cis-2-[(3R,3aR,6R,6aS)-6-(tert-Butyl-dimethyl-silanyloxy)-hexahydro-furo[3,2-b]furan-3-yloxy]-6-chloro-5-[4-(4-methylsulfanyl-cyclohexyl)-phenyl]-3-(2-trimethylsilanyl-ethoxymethyl)-3H-imidazo[4,5-b]pyridine A mixture of cis-thioacetic acid S-(4-{4-[2-[(3R,3aR,6R,6aS)-6-(tert-butyl-dimethyl-silanyloxy)-hexahydro-furo[3,2-b]furan-3-yloxy]-6-chloro-3-(2-trimethylsilanyl-ethoxymethyl)-3H-imidazo[4,5-b]pyridin-5-yl]-phenyl}-cyclohexyl ester (114 mg), K$_2$CO$_3$ (62 mg), and methyl iodide (30 µl) in methanol (2.00 mL) is stirred for 2 h at room temperature under an argon atmosphere. The mixture is concentrated in vacuo and ethyl acetate is added to the residue. The organic phase is separated, washed with water and brine, dried over MgSO$_4$, and concentrated in vacuo to give the title compound. LC (method 2): $t_R$=1.35 min; Mass spectrum (ESI$^+$): m/z=746 [M+H]$^+$.

Step 5: cis-2-[(3R,3aR,6R,6aS)-6-(tert-Butyl-dimethyl-silanyloxy)-hexahydro-furo[3,2-b]furan-3-yloxy]-6-chloro-5-[4-(4-methanesulfinyl-cyclohexyl)-phenyl]-3-(2-trimethylsilanyl-ethoxymethyl)-3H-imidazo[4,5-b]pyridine Aqueous hydrogen peroxide solution (35%, 17 µl) is added to a solution of cis-2-[(3R,3aR,6R,6aS)-6-(tert-butyl-dimethyl-silanyloxy)-hexahydro-furo[3,2-b]furan-3-yloxy]-6-chloro-5-[4-(4-methylsulfanyl-cyclohexyl)-phenyl]-3-(2-trimethylsilanyl-ethoxymethyl)-3H-imidazo[4,5-b]pyridine (63 mg) in hexafluoroisopropanol (1 mL). The reaction mixture is stirred at room temperature for 1 h, quenched with aqueous Na$_2$S$_2$O$_3$ solution and saturated aqueous NaHCO$_3$ solution, and extracted with ethyl acetate. The organic phase is washed with brine, dried over MgSO$_4$, and concentrated in vacuo to give the title compound. LC (method 2): $t_R$=1.09 min; Mass spectrum (ESI$^+$): m/z=762 [M+H]$^+$.

Step 6: N-(4-{4-[2-[(3R,3aR,6R,6aS)-6-(tert-Butyl-dimethyl-silanyloxy)-hexahydro-furo[3,2-b]furan-3-yloxy]-6-chloro-3-(2-trimethylsilanyl-ethoxymethyl)-3H-imidazo[4,5-b]pyridin-5-yl]-phenyl}-cyclohexanyl)-(methyl)oxido-$\lambda^4$-sulfanylidene])-2,2,2-trifluoro-acetamide The title compound is prepared from cis-2-[(3R,3aR,6R,6aS)-6-(tert-butyl-dimethyl-silanyloxy)-hexahydro-furo[3,2-b]furan-3-yloxy]-6-chloro-5-[4-(4-methanesulfinyl-cyclohexyl)-phenyl]-3-(2-trimethylsilanyl-ethoxymethyl)-3H-imidazo[4,5-b]pyridine following a procedure analogous to that described for Intermediate 28 (Step 3). LC (method 2): $t_R$=1.20 min.

Intermediate 37

N-(2-{4-[6-Chloro-2-43R,3aR,6R,6aR)-6-hydroxy-hexahydrofuro[3,2-b]furan-3-yloxy)-3-(2-trimethyl-silanyl-ethoxymethyl)-3H-imidazo[4,5-b]pyridin-5-yl]-phenyl}-pyrimidin-5-yl)-S,S-dimethylsulfoximide

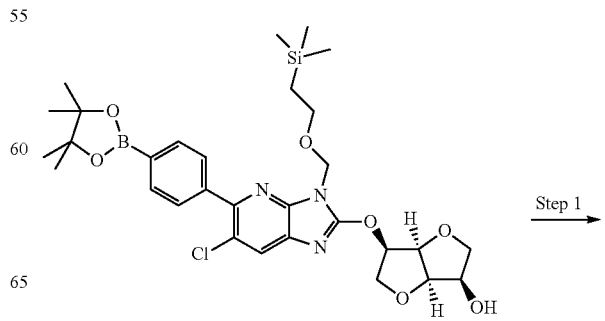

Step 1 →

83

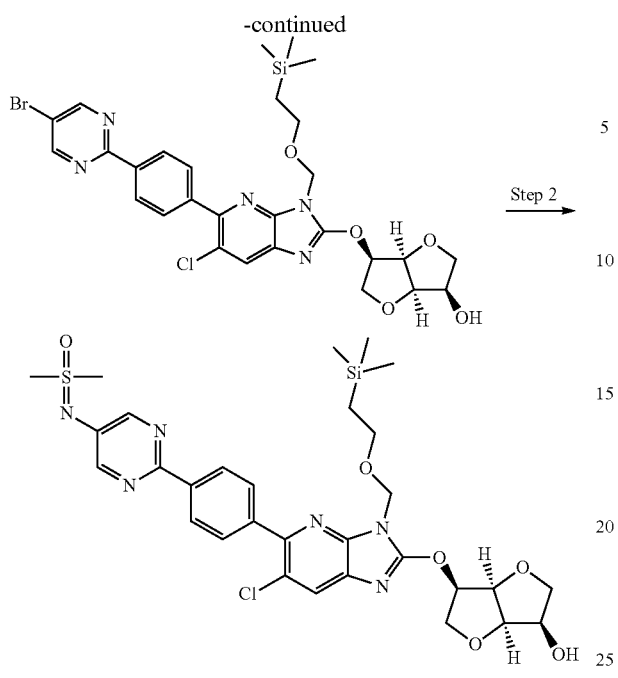

Step 1: (3R,3aR,6R,6aR)-6-[5-[4-(5-Bromo-pyrimidin-2-yl)-phenyl]-6-chloro-3-(2-trimethylsilanyl-ethoxymethyl)-3H-imidazo[4,5-b]pyridin-2-yloxy]-hexahydro-furo[3,2-b]furan-3-ol The title compound is prepared from (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol and 5-bromo-2-iodopyrimidine following a procedure analogous to that described for Intermediate 2 (Step 1). LC (method 1): $t_R$=1.28 min; Mass spectrum (ESI$^+$): m/z=660, 662 [M+H]$^+$.

Step 2: N-(2-{4-[6-Chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl]-phenyl}-pyrimidin-5-yl)-S,S-dimethylsulfoximide The title compound is prepared from (3R,3aR,6R,6aR)-6-[5-[4-(5-bromo-pyrimidin-2-yl)-phenyl]-6-chloro-3-(2-trimethylsilanyl-ethoxymethyl)-3H-imidazo[4,5-b]pyridin-2-yloxy]-hexahydro-furo[3,2-b]furan-3-ol and S,S-dimethylsulfoximine following a procedure analogous to that described for Intermediate 9. LC (method 1): $t_R$=1.03 min; Mass spectrum (ESI$^+$): m/z=673 [M+H]$^+$.

Intermediate 38

N-(2-(4-(6-Chloro-2-((3R,3aR,6R,6aR)-6-hydroxy-hexahydrofuro[3,2-b]furan-3-yloxy)-3-(2-trimethyl-silanyl-ethoxymethyl)-3H-imidazo[4,5-b]pyridin-5-yl)phenyl)pyridin-6-ylmethyl)-S,S-dimethylsulfoximide

Step 1: N-(6-Bromo-pyridin-2-ylmethyl)-S,S-dimethylsulfoximide

Potassium hydride (105 mg) is added to an ice-cooled mixture of S,S-dimethylsulfoximine (34 mg) and tetrabutylammonium bromide (6 mg) in tetrahydrofuran (2 mL) under an argon atmosphere and the resulting mixture is stirred at 0° C. for 1 h. 2-Bromo-6-bromomethyl-pyridine (101 mg) is added, the mixture is allowed to warmed to room temperature overnight and quenched with water. The organic phase washed with brine, dried over MgSO$_4$, and concentrated in vacuo. The residue is chromatographed on silica gel (dichloromethane/methanol acetate 99:1→90:10) to give the title compound. LC (method 1): $t_R$=0.62 min; Mass spectrum (ESI$^+$): m/z=264, 266 [M+H]$^+$.

Step 2: N-(2-(4-(6-chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)phenyl)pyridin-6-ylmethyl)-S,S-dimethylsulfoximide The title compound is prepared from (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol and N-(6-bromo-pyridin-2-ylmethyl)-S,S-dimethylsulfoximide following a procedure analogous to that described for Intermediate 2 (Step 1). LC (method 1): $t_R$=0.95 min; Mass spectrum (ESI$^+$): m/z=686 [M+H]$^+$.

Intermediates 39 and 40

N-(4-{4-[6-Chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl]-phenyl}-pyridin-2-yl)-S,S-dimethylsulfoximide and N-(2-{4-[6-Chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl]-phenyl}-pyridin-4-yl)-S,S-dimethylsulfoximide

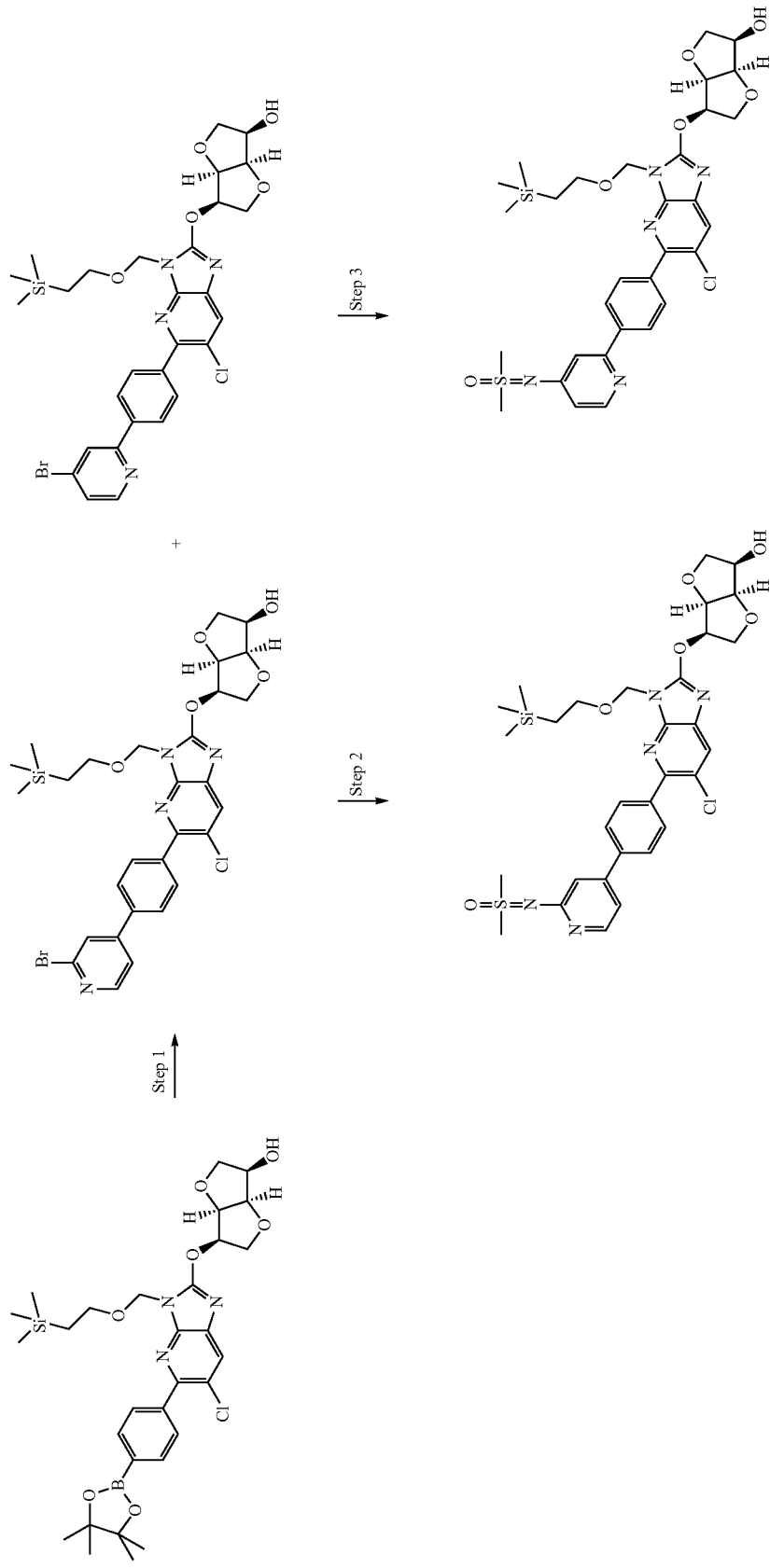

Step 1: (3R,3aR,6R,6aR)-6-[5-[4-(2-Bromo-pyridin-4-yl)-phenyl]-6-chloro-3-(2-tri-methylsilanyl-ethoxymethyl)-3H-imidazo[4,5-b]pyridin-2-yloxy]-hexahydro-furo[3,2-b]furan-3-ol and (3R,3aR,6R,6aR)-6-[5-[4-(4-Bromo-pyridin-2-yl)-phenyl]-6-chloro-3-(2-trimethylsilanyl-ethoxymethyl)-3H-imidazo[4,5-b]pyridin-2-yloxy]-hexahydro-furo[3,2-b]furan-3-ol The title compounds are prepared from (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol and 2,4-dibromopyridine following a procedure analogous to that described for Intermediate 2 (Step 1).

Isomer 39.1: LC (method 1): $t_R$=1.27 min; Mass spectrum (ESI$^+$): m/z=659, 661 [M+H]$^+$.
Isomer 40.1: LC (method 1): $t_R$=1.25 min; Mass spectrum (ESI$^+$): m/z=659, 661 [M+H]$^+$.

Step 2: N-(4-{4-[6-Chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl]-phenyl}-pyridin-2-yl)-S,S-dimethylsulfoximide The title compound is prepared from (3R,3aR,6R,6aR)-6-[5-[4-(2-bromo-pyridin-4-yl)-phenyl]-6-chloro-3-(2-trimethylsilanyl-ethoxymethyl)-3H-imidazo[4,5-b]pyridin-2-yloxy]-hexahydro-furo[3,2-b]furan-3-ol (Isomer 39.1) and S,S-dimethylsulfoximine following a procedure analogous to that described for Intermediate 9. LC (method 1): $t_R$=0.93 min; Mass spectrum (ESI$^+$): m/z=672 [M+H]$^+$.

Step 3: N-(2-{4-[6-Chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl]-phenyl}-pyridin-4-yl)-S,S-dimethylsulfoximide The title compound is prepared from (3R,3aR,6R,6aR)-6-[5-[4-(4-bromo-pyridin-2-yl)-phenyl]-6-chloro-3-(2-trimethylsilanyl-ethoxymethyl)-3H-imidazo[4,5-b]pyridin-2-yloxy]-hexahydro-furo[3,2-b]furan-3-ol (Isomer 40.1) and S,S-dimethylsulfoximine following a procedure analogous to that described for Intermediate 9. LC (method 1): $t_R$=0.94 min; Mass spectrum (ESI$^+$): m/z=672 [M+H]$^+$.

Intermediate 41

N-(4'-(6-Chloro-2-((3R,3aR,6R,6aR)-6-hydroxy-hexahydrofuro[3,2-b]furan-3-yloxy)-3-(2-trimethyl-silanyl-ethoxymethyl)-3H-imidazo[4,5-b]pyridin-5-yl)biphenyl-3-ylmethyl)-S,S-dimethylsulfoximide

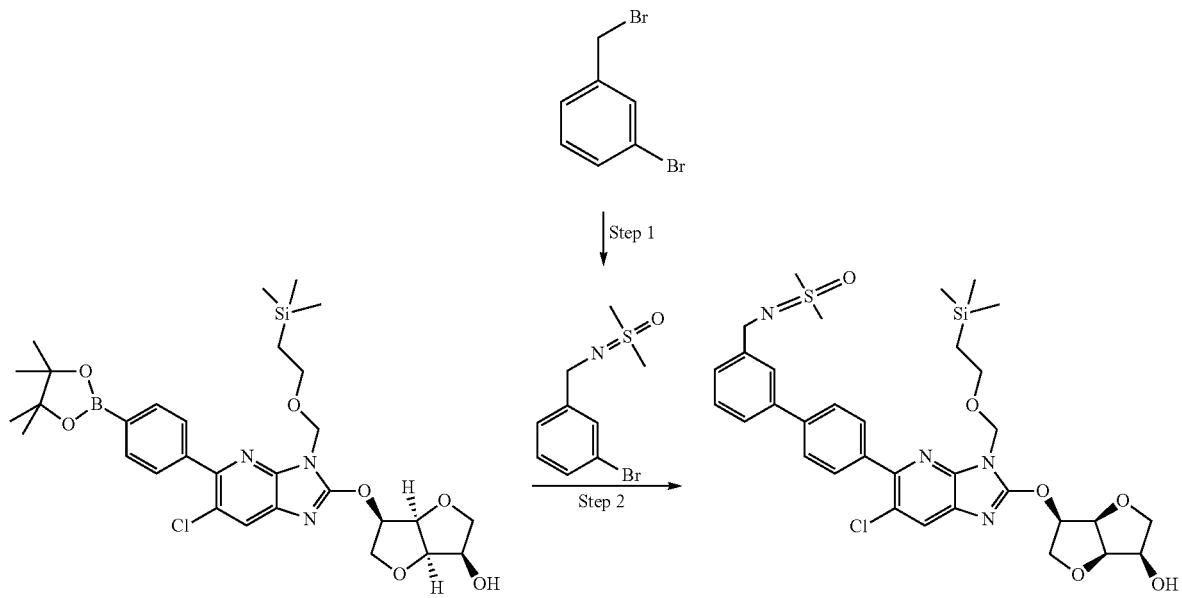

Step 1:
N-(3-Bromo-benzyl)-S,S-dimethylsulfoximide

The title compound is prepared from 1-bromo-3-bromomethyl-benzene and S,S-dimethylsulfoximine following a procedure analogous to that described for Intermediate 38 (Step 1). LC (method 4): $t_R$=0.72 min; Mass spectrum (ESI$^+$): m/z=262, 264 [M+H]$^+$.

Step 2: N-(4'-(6-Chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)biphenyl-3-ylmethyl)-S,S-dimethylsulfoximide The title compound is prepared from (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol and N-(3-bromo-benzyl)-S,S-dimethylsulfoximide following a procedure analogous to that described for Intermediate 2 (Step 1). LC (method 4): $t_R$=0.97 min; Mass spectrum (ESI$^+$): m/z=685 [M+H]$^+$.

Intermediate 42

N-(5-{4-[6-Chloro-2-((3R,3aR,6R,6aR)-6-hydroxy-hexahydrofuro[3,2-b]furan-3-yloxy)-3-(2-trimethyl-silanyl-ethoxymethyl)-3H-imidazo[4,5-b]pyridin-5-yl]-phenyl}-pyrazin-2-yl)-S,S-dimethylsulfoximide

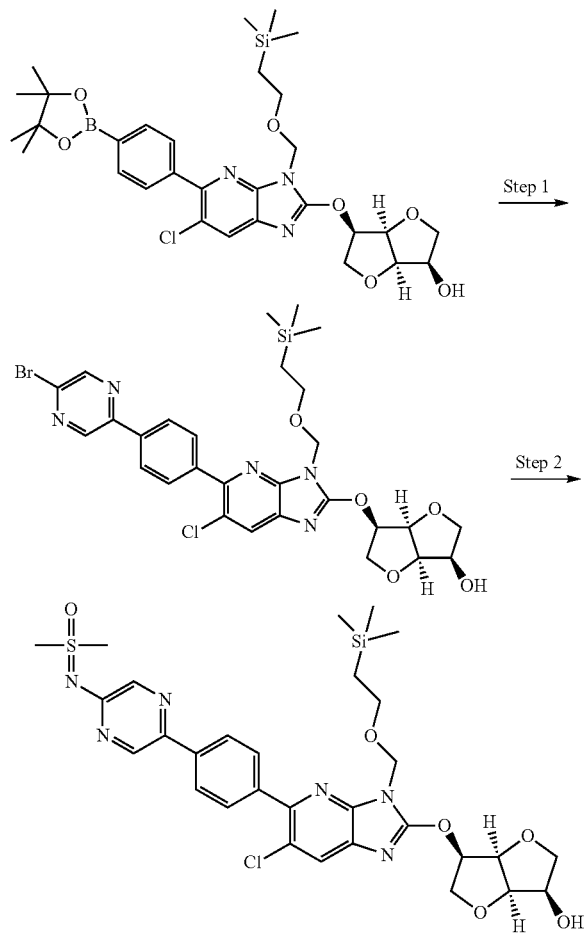

Step 1: (3R,3aR,6R,6aR)-6-[5-[4-(5-Bromo-pyrazin-2-yl)-phenyl]-6-chloro-3-(2-trimethylsilanyl-ethoxymethyl)-3H-imidazo[4,5-b]pyridin-2-yloxy]-hexahydrofuro[3,2-b]furan-3-ol The title compound is prepared from (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol and 2,5-dibromo-pyrazine following a procedure analogous to that described for Intermediate 2 (Step 1). LC (method 1): $t_R$=1.26 min; Mass spectrum (ESI⁺): m/z=660, 662 [M+H]⁺.

Step 2: N-(5-{4-[6-Chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl]-phenyl}-pyrazin-2-yl)-S,S-dimethylsulfoximide The title compound is prepared from (3R,3aR,6R,6aR)-6-[5-[4-(5-bromo-pyrazin-2-yl)-phenyl]-6-chloro-3-(2-trim-ethylsilanyl-ethoxymethyl)-3H-imidazo[4,5-b]pyridin-2-yloxy]-hexahydrofuro[3,2-b]furan-3-ol and S,S-dimethylsulfoximine following a procedure analogous to that described for Intermediate 9. LC (method 1): $t_R$=1.03 min; Mass spectrum (ESI⁺): m/z=673 [M+H]⁺.

Intermediate 43

N-(4-{4-[6-Chloro-2-((3R,3aR,6R,6aR)-6-hydroxy-hexahydrofuro[3,2-b]furan-3-yloxy)-3-(2-trimethyl-silanyl-ethoxymethyl)-3H-imidazo[4,5-b]pyridin-5-yl]-phenyl}-1-oxo-1,2,3,6-tetrahydro-1$\lambda^6$-thiopyran-1-ylidene)-2,2,2-trifluoro-acetamide

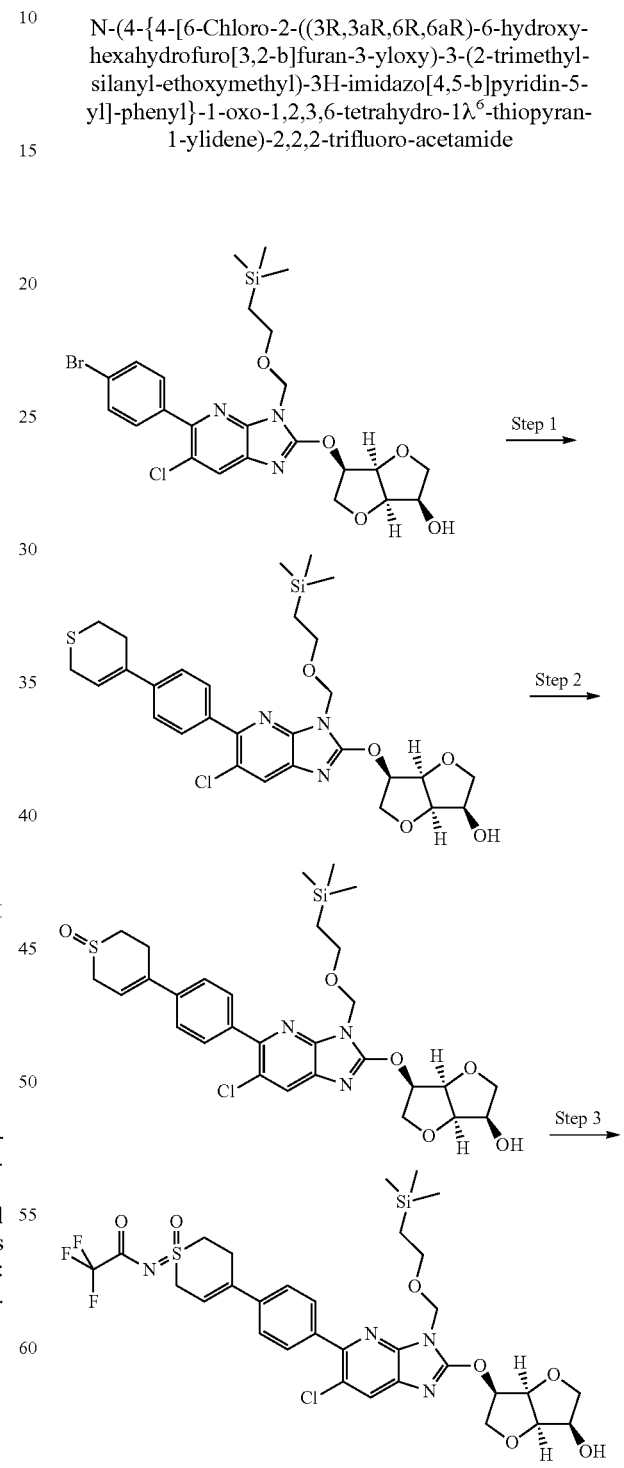

Step 1: (3R,3aR,6R,6aR)-6-[6-Chloro-5-[4-(3,6-dihydro-2H-thiopyran-4-yl)-phenyl]-3-(2-trimethylsilanyl-ethoxymethyl)-3H-imidazo[4,5-b]pyridin-2-yloxy]-hexahydro-furo[3,2-b]furan-3-ol The title compound is prepared from (3R,3aR,6R,6aR)-6-[5-(4-bromo-phenyl)-6-chloro-3-(2-trimethylsilanyl-ethoxymethyl)-3H-imidazo[4,5-b]pyridin-2-yloxy]-hexahydro-furo[3,2-b]furan-3-ol and 2-(3,6-dihydro-2H-thiopyran-4-yl)-4,4,5,5-tetramethyl-[1,3,2]dioxaborolane following a procedure analogous to that described for Intermediate 2 (Step 1). LC (method 1): $t_R$=1.26 min; Mass spectrum (ESI$^+$): m/z=602 [M+H]$^+$.

Step 2: (3R,3aR,6R,6aR)-6-[6-Chloro-5-[4-(1-oxo-1,2,3,6-tetrahydro-1λ$^4$-thiopyran-4-yl)-phenyl]-3-(2-trimethylsilanyl-ethoxymethyl)-3H-imidazo[4,5-b]pyridin-2-yloxy]-hexahydro-furo[3,2-b]furan-3-ol The title compound is prepared from (3R,3aR,6R,6aR)-6-[6-chloro-5-[4-(3,6-dihydro-2H-thiopyran-4-yl)-phenyl]-3-(2-trimethylsilanyl-ethoxymethyl)-3H-imidazo[4,5-b]pyridin-2-yloxy]-hexahydro-furo[3,2-b]furan-3-ol following a procedure analogous to that described for Intermediate 36 (Step 5). LC (method 1): $t_R$=1.00 min; Mass spectrum (ESI$^+$): m/z=618 [M+H]$^+$.

Step 3: N-(4-{4-[6-Chloro-2-((3R,3aR,6R,6aR)-6-hydroxy-hexahydrofuro[3,2-b]furan-3-yloxy)-3-(2-trimethylsilanyl-ethoxymethyl)-3H-imidazo[4,5-b]pyridin-5-yl]-phenyl}-1-oxo-1,2,3,6-tetrahydro-1λ$^6$-thiopyran-1-ylidene)-2,2,2-trifluoro-acetamide The title compound is prepared from (3R,3aR,6R,6aR)-6-[6-chloro-5-[4-(1-oxo-1,2,3,6-tetrahydro-1λ$^4$-thiopyran-4-yl)-phenyl]-3-(2-trimethylsilanyl-ethoxymethyl)-3H-imidazo[4,5-b]pyridin-2-yloxy]-hexahydro-furo[3,2-b]furan-3-ol following a procedure analogous to that described for Intermediate 28 (Step 3). LC (method 1): $t_R$=1.14 min; Mass spectrum (ESI$^+$): m/z=729 [M+H]$^+$.

Intermediate 44

(3R,3aR,6R,6aR)-6-(6-Chloro-5-(3'-(N-(2,2,2-trifluoroacetyl)-S-methyl-sulfonimido-yl)biphenyl-4-yl)-3-(2-trimethylsilanyl-ethoxymethyl)-3H-imidazo[4,5-b]pyridin-2-yloxy)hexahydrofuro[3,2-b]furan-3-ol

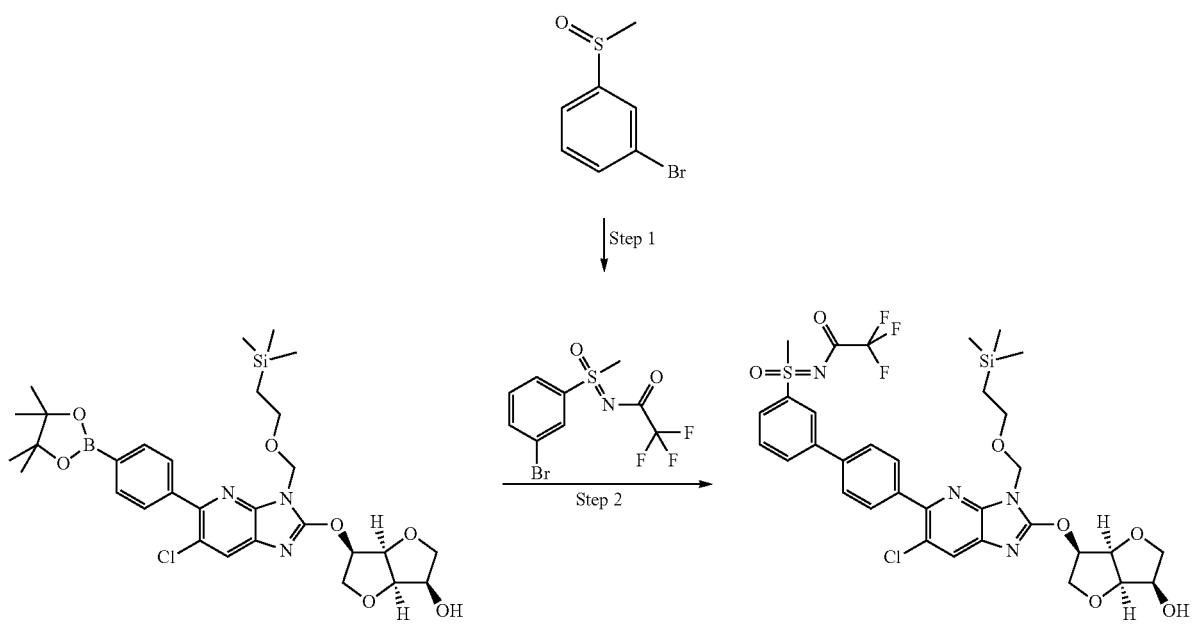

Step 1: 1-Bromo-3-(N-(2,2,2-trifluoroacetyl)-S-methylsulfonimidoyl)-benzene

The title compound is prepared from 1-bromo-3-methylsulfinyl-benzene following a procedure analogous to that described for Intermediate 28 (Step 3). LC (method 4): $t_R$=1.23 min; Mass spectrum (ESI$^+$): m/z=330, 332 [M+H]$^+$.

Step 2: (3R,3aR,6R,6aR)-6-(6-Chloro-5-(3'-(N-(2,2,2-trifluoroacetyl)-S-methyl-sulfonimidoyl)biphenyl-4-yl)-3-(2-trimethylsilanyl-ethoxymethyl)-3H-imidazo[4,5-b]pyridin-2-yloxy)hexahydrofuro[3,2-b]furan-3-ol The title compound is prepared from (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol and 1-bromo-3-(N-(2,2,2-trifluoroacetyl)-S-methylsulfonimidoyl)-benzene following a procedure analogous to that described for Intermediate 2 (Step 1). LC (method 6): $t_R$=0.81 min; Mass spectrum (ESI$^+$): m/z=753 [M+H]$^+$.

Intermediate 45

N-(4-{5-[6-Chloro-2-((3R,3aR,6R,6aR)-6-hydroxy-hexahydrofuro[3,2-b]furan-3-yloxy)-3-(2-trimethyl-silanyl-ethoxymethyl)-3H-imidazo[4,5-b]pyridin-5-yl]-pyrimidin-2-yl}-phenyl)-S,S-dimethylsulfoximide

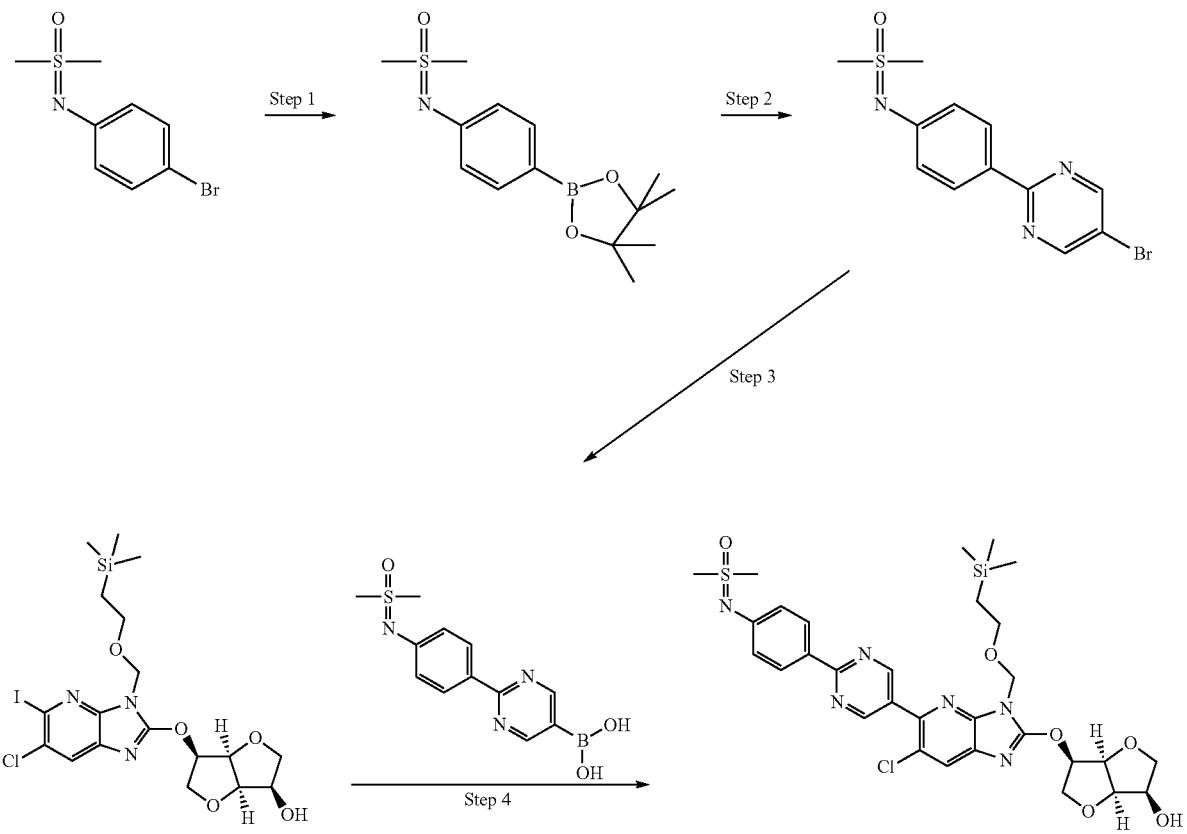

Step 1: N-[4-(4,4,5,5-Tetramethyl-[1,3,2]dioxaborolan-2-yl)-phenyl]-S,S-dimethylsulfoximide The title compound is prepared from N-(4-bromophenyl)-S,S-dimethylsulfoximine following a procedure analogous to that described for Intermediate 8 (Step 3). LC (method 1): $t_R$=0.93 min; Mass spectrum (ESI$^+$): m/z=296 [M+H]$^+$.

Step 2: N-[4-(5-Bromo-pyrimidin-2-yl)-phenyl]-S,S-dimethylsulfoximide

The title compound is prepared from N-[4-(4,4,5,5-tetramethyl-[1,3,2]dioxaborolan-2-yl)-phenyl]-S,S-dimethylsulfoximide and 5-bromo-2-iodopyrimidine following a procedure analogous to that described for Intermediate 2 (Step 1). LC (method 1): $t_R$=0.89 min; Mass spectrum (ESI$^+$): m/z=326, 328 [M+H]$^+$.

Step 3: 2-(N-(Dimethyloxido-λ$^4$-sulfanylidene)-phenyl)-pyrimidine-5-boronic acid The title compound is prepared from N-[4-(5-bromo-pyrimidin-2-yl)-phenyl]-S,S-dimethylsulfoximide following a procedure analogous to that described for Intermediate 8 (Step 3). The free boronic acid is formed directly under these conditions. LC (method 1): $t_R$=0.63 min; Mass spectrum (ESI$^+$): m/z=292 [M+H]$^+$.

Step 4: N-(4-{5-[6-Chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-2-yl]-pyrimidin-2-yl}-phenyl)-S,S-dimethylsulfoximide The title compound is prepared from 3R,3aR,6R,6aR)-6-(6-chloro-5-iodo-3-(2-trimethylsilanyl-ethoxymethyl)-3H-imidazo-[4,5-b]pyridin-2-yloxy)hexahydrofuro[3,2-b]furan-3-ol and 2-(N-(dimethyloxido-λ$^4$-sulfanylidene)-phenyl)-pyrimidine-5-boronic acid following a procedure analogous to that described for Intermediate 2 (Step 1). LC (method 1): $t_R$=1.03 min; Mass spectrum (ESI$^+$): m/z=673 [M+H]$^+$.

Intermediate 46

N-(2-{4-[6-Chloro-2-((3R,3aR,6R,6aR)-6-hydroxy-hexahydrofuro[3,2-b]furan-3-yloxy)-3-(2-trimethyl-silanyl-ethoxymethyl)-3H-imidazo[4,5-b]pyridin-5-yl]-phenyl}-2,3-dihydro-1H-isoindol-5-yl)-S,S-dimethylsulfoximide

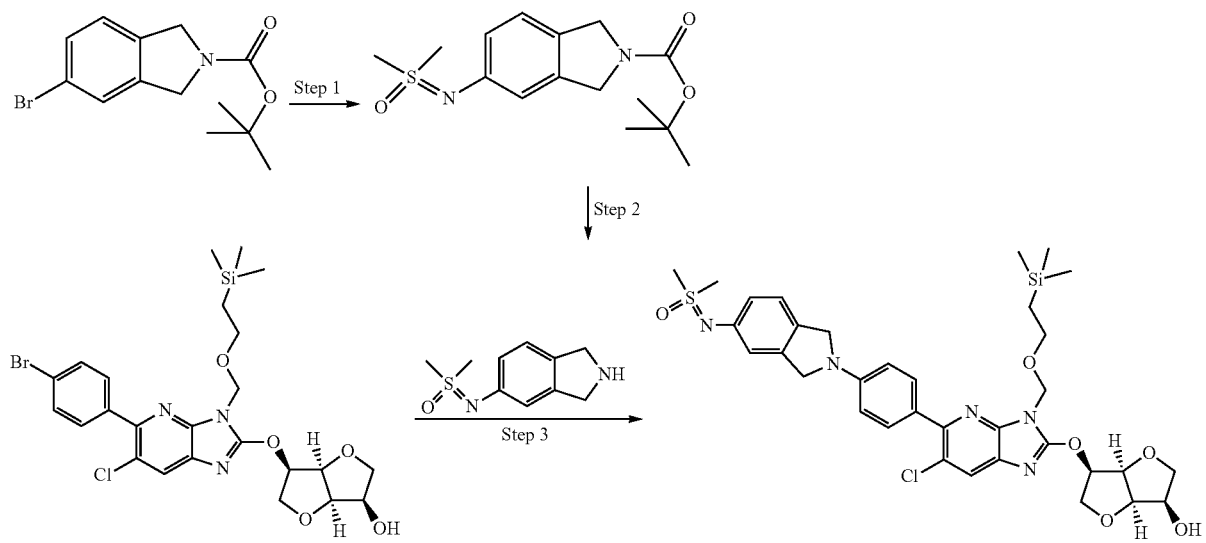

Step 1: 5-[N-(Dimethyloxido-$\lambda^4$-sulfanylidene)]-1,3-dihydroisoindole-2-carboxylic acid tert-butyl ester The title compound is prepared from 5-bromo-1,3-dihydroisoindole-2-carboxylic acid tert-butyl ester and S,S-dimethylsulfoximine following a procedure analogous to that described for Intermediate 9. LC (method 4): $t_R$=0.93 min; Mass spectrum (ESI$^+$): m/z=311 [M+H]$^+$.

Step 2: N-(2,3-Dihydro-1H-isoindol-5-yl)-S,S-dimethylsulfoximide hydrochloride The title compound is prepared from 5-[N-(dimethyl-oxido-$\lambda^4$-sulfanylidene)]-1,3-dihydroisoindole-2-carboxylic acid tert-butyl ester by treatment with HCl in 1,4-dioxane (4 N) at 60° C. LC (method 4): $t_R$=0.10 min; Mass spectrum (ESI$^+$): m/z=211 [M+H]$^+$.

Step 3: N-(2-{4-[6-Chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl]-phenyl}-2,3-dihydro-1H-isoindol-5-yl)-S,S-dimethylsulfoximide A mixture of (3R,3aR,6R,6aR)-6-[5-(4-bromo-phenyl)-6-chloro-3-(2-trimethylsilanyl-ethoxymethyl)-3H-imidazo[4,5-b]pyridin-2-yloxy]-hexahydrofuro[3,2-b]furan-3-ol (300 mg), N-(2,3-dihydro-1H-isoindol-5-yl)-S,S-dimethylsulfoximide hydrochloride (164 mg), and Cs$_2$CO$_3$ (590 mg) in 1,4-dioxane (15 mL) is purged with argon for 5 minutes. 2-Dicyclohexylphosphino-2',6'-diisopropoxybiphenyl (RuPhos, 17 mg) and palladium(II) acetate (8 mg) are added and the mixture is stirred under an argon atmosphere overnight at 105° C. More RuPhos (25 mg) and palladium(II) acetate (10 mg) are added and the mixture is stirred another night at 105° C. under an argon atmosphere. After cooling to room temperature, the mixture is diluted with ethyl acetate and water. The organic phase washed with water, dried over MgSO$_4$, and concentrated in vacuo. The residue is purified by HPLC to give the title compound. LC (method 4): $t_R$=1.14 min; Mass spectrum (ESI$^+$): m/z=712 [M+H]$^+$.

Intermediate 47

N-(6-{4-[6-Chloro-2-((3R,3aR,6R,6aR)-6- hydroxy-hexahydrofuro[3,2-b]furan-3-yloxy)-3-(2- trimethyl-silanyl-ethoxymethyl)-3H-imidazo[4,5-b] pyridin-5-yl]-phenyl}-6,7-dihydro-5H-pyrrolo[3,4-b] pyridin-2-yl)-S,S-dimethylsulfoximide

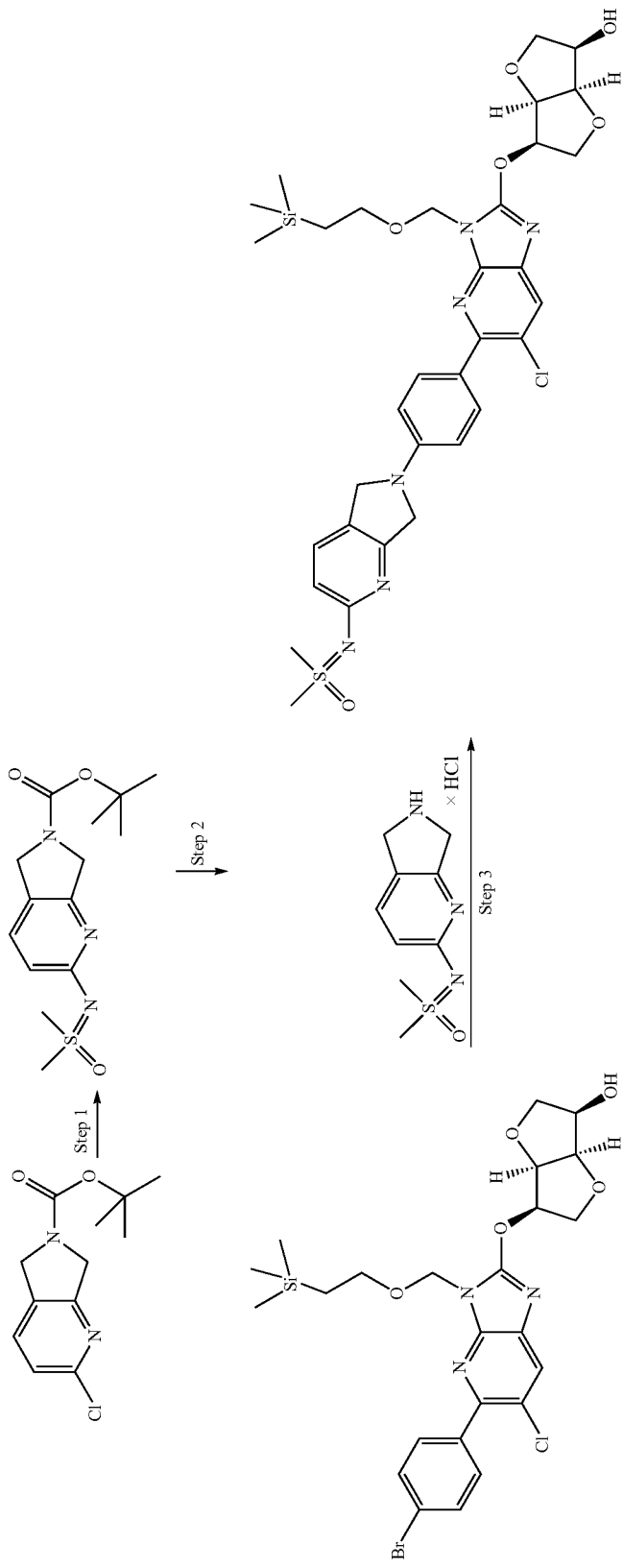

101

Step 1: 2-[N-(Dimethyloxido-λ⁴-sulfanylidene)]-5,7-dihydro-6H-pyrrolo[3,4-b]pyridine-6-carboxylic acid tert-butyl ester

The title compound is prepared from 2-chloro-5,7-dihydro-6H-pyrrolo[3,4-b]pyridine-6-carboxylic acid tert-butyl ester and S,S-dimethylsulfoximine following a procedure analogous to that described for Intermediate 23 (Step 1) using toluene as a solvent. LC (method 4): $t_R$=0.77 min; Mass spectrum (ESI⁺): m/z=312 [M+H]⁺.

Step 2: N-(6,7-Dihydro-5H-pyrrolo[3,4-b]pyridin-2-yl)-S,S-dimethylsulfoximide hydrochloride

The title compound is prepared from 2-[N-(dimethyl-oxido-λ⁴-sulfanylidene)]-5,7-dihydro-6H-pyrrolo[3,4-b]pyridine-6-carboxylic acid tert-butyl ester by treatment with HCl in 1,4-dioxane (4 N) at 100° C. LC (method 4): $t_R$=0.10 min; Mass spectrum (ESI⁺): m/z=212 [M+H]⁺.

Step 3: N-(6-{4-[6-Chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl]-phenyl}-6,7-dihydro-5H-pyrrolo[3,4-b]pyridin-2-yl)-S,S-dimethylsulfoximide

The title compound is prepared from (3R,3aR,6R,6aR)-6-[5-(4-bromo-phenyl)-6-chloro-3-(2-trimethylsilanyl-ethoxymethyl)-3H-imidazo[4,5-b]pyridin-2-yloxy]-hexahydrofuro[3,2-b]furan-3-ol and N-(6,7-dihydro-5H-pyrrolo[3,4-b]pyridin-2-yl)-S,S-dimethylsulfoximide hydrochloride following a procedure analogous to that described for Intermediate 46 (Step 3). LC (method 4): $t_R$=0.97 min; Mass spectrum (ESI⁺): m/z=713 [M+H]⁺.

Intermediate 48
N-(4'-(6-Chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)biphenyl-4-ylmethyl)-S,S-dimethylsulfoximide

102

Step 1:
N-(4-Bromo-benzyl)-S,S-dimethylsulfoximide

The title compound is prepared from 4-bromobenzyl-bromide and S,S-dimethylsulfoximine following a procedure analogous to that described for Intermediate 38 (Step 1). LC (method 4): $t_R$=0.72 min; Mass spectrum (ESI⁺): m/z=262, 264 [M+H]⁺.

Step 2: N-(4'-(6-Chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)biphenyl-4-ylmethyl)-S,S-dimethylsulfoximide

The title compound is prepared from (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol and N-(4-bromo-benzyl)-S,S-dimethylsulfoximide following a procedure analogous to that described for Intermediate 2 (Step 1). LC (method 4): $t_R$=0.96 min; Mass spectrum (ESI⁺): m/z=685 [M+H]⁺.

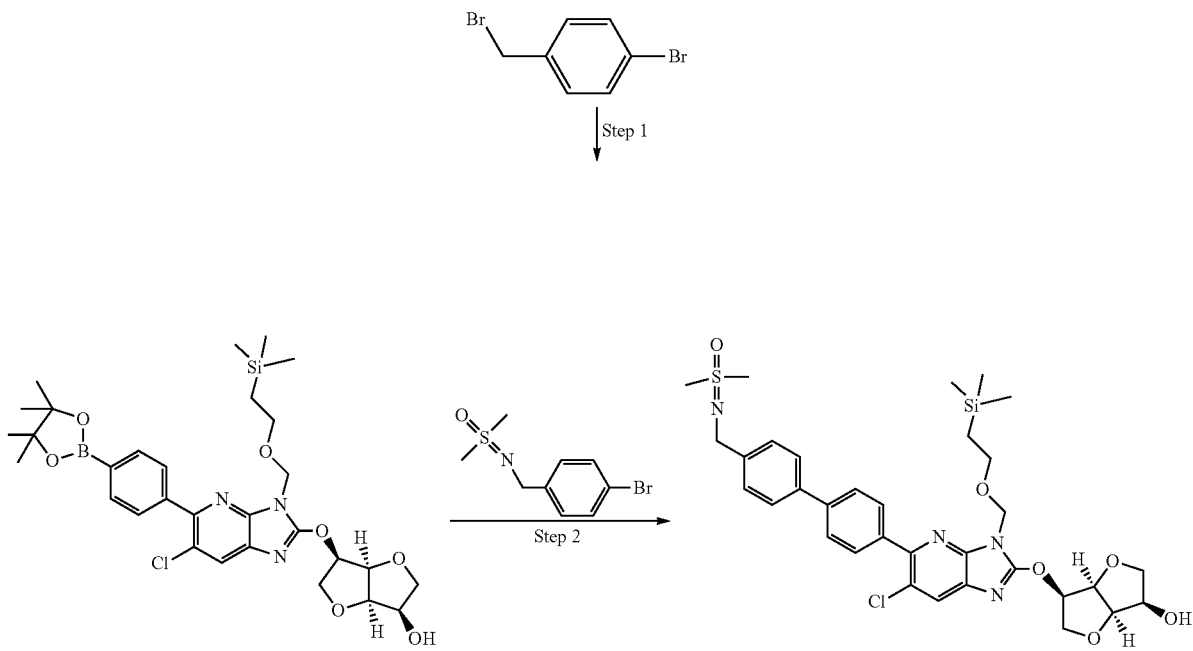

Intermediate 49

N-(2-(4-(6-Chloro-2-((3R,3aR,6R,6aR)-6-hydroxy-hexahydrofuro[3,2-b]furan-3-yloxy)-3-(2-trimethyl-silanyl-ethoxymethyl)-3H-imidazo[4,5-b]pyridin-5-yl)phenyl)pyridin-4-ylmethyl)-S,S-dimethylsulfoximide

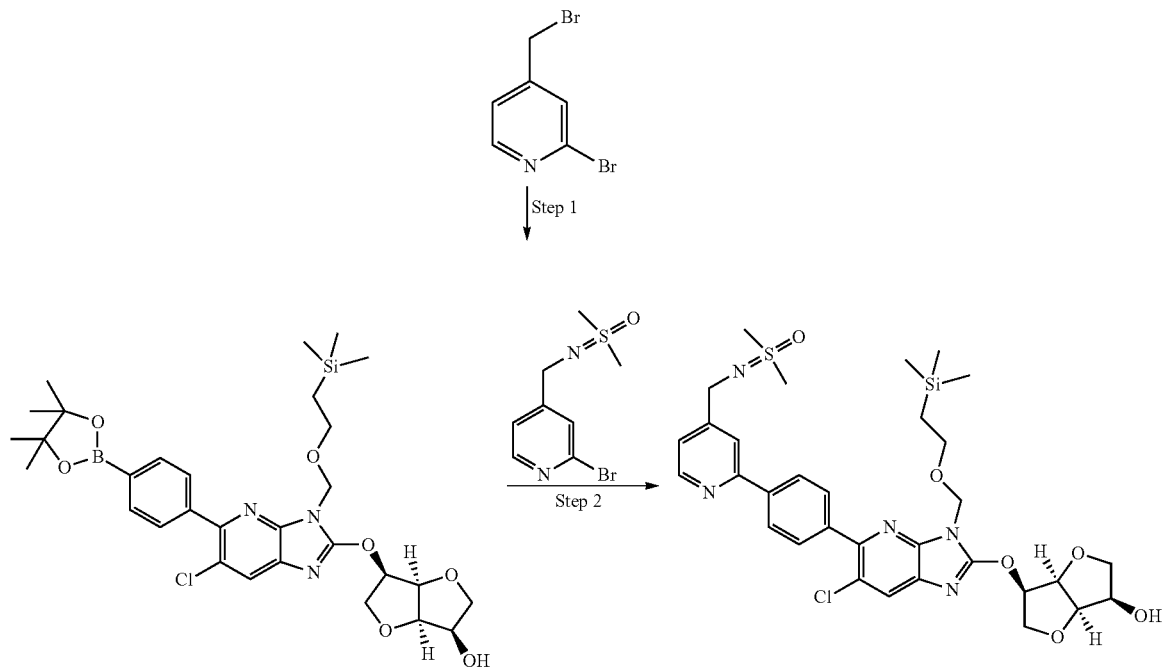

Step 1: N-(2-Bromo-pyridin-4-ylmethyl)-S,S-dimethylsulfoximide

The title compound is prepared from 2-bromo-4-bromomethyl-pyridine and S,S-dimethylsulfoximine following a procedure analogous to that described for Intermediate 38 (Step 1). LC (method 1): $t_R$=0.54 min; Mass spectrum (ESI$^+$): m/z=263, 265 [M+H]$^+$.

Step 2: N-(2-(4-(6-Chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)phenyl)pyridin-4-ylmethyl)-S,S-dimethylsulfoximide The title compound is prepared from (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol and N-(2-bromo-pyridin-4-ylmethyl)-S,S-dimethylsulfoximide following a procedure analogous to that described for Intermediate 2 (Step 1). LC (method 1): $t_R$=0.93 min; Mass spectrum (ESI$^+$): m/z=686 [M+H]$^+$.

Intermediate 50

N-(6-{4-[6-Chloro-2-((3R,3aR,6R,6aR)-6-hydroxy-hexahydrofuro[3,2-b]furan-3-yloxy)-3-(2-trimethyl-silanyl-ethoxymethyl)-3H-imidazo[4,5-b]pyridin-5-yl]-phenyl}-pyridin-2-yl)-S,S-dimethylsulfoximide

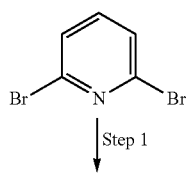

Step 1

-continued

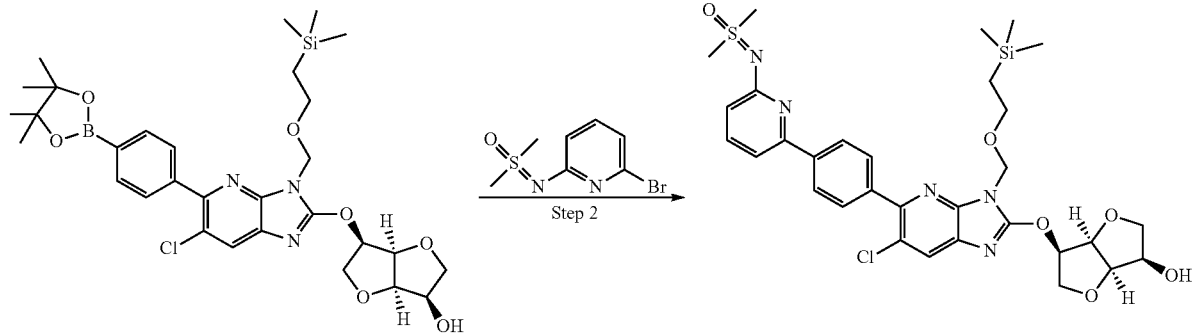

Step 1:
N-(6-Bromo-pyridin-2-yl)-S,S-dimethylsulfoximine

A mixture of 2,6-dibromo-pyridine (300 mg), S,S-dimethylsulfoximine (118 mg), rac. 2,2'-bis(diphenylphosphino)-1,1'-binapthyl (24 mg), and sodium tert-butoxide (122 mg) in toluene (6 mL) in a microwave vial is purged with argon for 5 minutes. Bis(dibenzylideneacetone)palladium(0) (22 mg) is added, the vial is sealed, and the mixture heated to 120° C. for 30 minutes. The product mixture is filtered over celite, using diethyl ether as eluent. The filtrate is concentrated in vacuo and the residue is triturated with toluene/hexane. The precipitate is filtered off and dried to give the title compound. LC (method 1): $t_R$=0.76 min; Mass spectrum (ESI$^+$): m/z=249, 251 [M+H]$^+$.

Step 2: N-(6-{4-[6-Chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl]-phenyl}-pyridin-2-yl)-S,S-dimethylsulfoximide The title compound is prepared from (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol and N-(6-bromo-pyridin-2-yl)-S,S-dimethylsulfoximine following a procedure analogous to that described for Intermediate 2 (Step 1). LC (method 1): $t_R$=0.97 min; Mass spectrum (ESI$^+$): m/z=672 [M+H]$^+$.

Intermediate 51

N-(6-(4-(6-Chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)phenyl)pyridin-3-ylmethyl)-S,S-dimethylsulfoximide

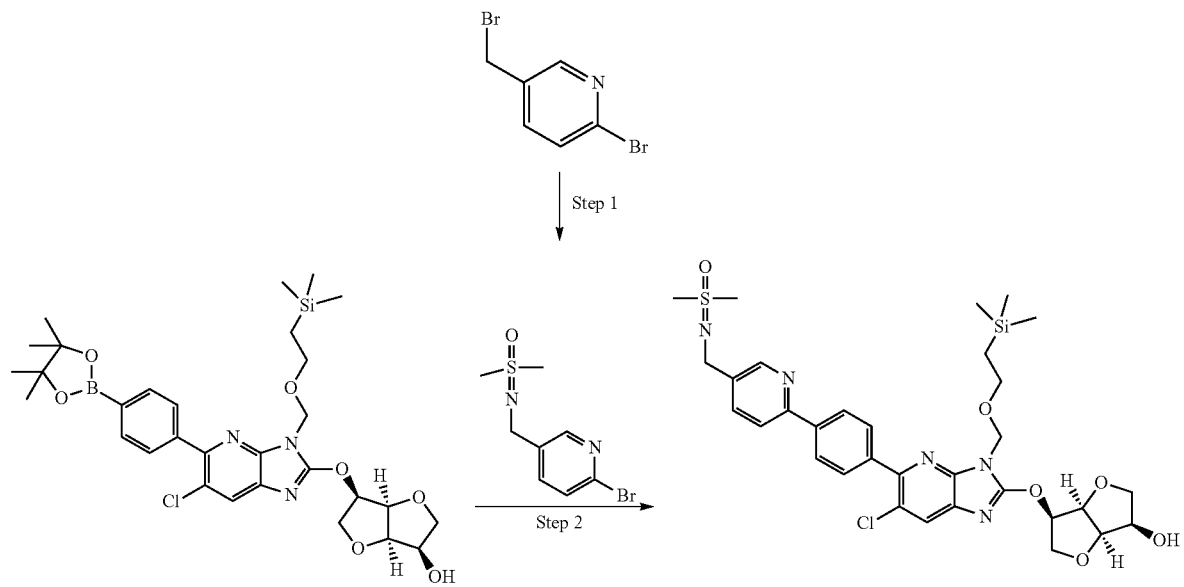 [SMILES: BrCc1ccc(Br)nc1 ; CC1(C)OB(c2ccc(-c3nc4c(cc3Cl)nc(O[C@@H]3CO[C@H]5[C@@H]3OC[C@H]5O)n4COCC[Si](C)(C)C)cc2)OC1(C)C ; CS(C)(=O)=NCc1ccc(Br)nc1 ; C[Si](C)(C)CCOCn1c(O[C@@H]2CO[C@H]3[C@@H]2OC[C@H]3O)nc2cc(Cl)c(-c3ccc(-c4ccc(CN=S(C)(C)=O)cn4)cc3)nc21]

107

Step 1: N-(6-Bromo-pyridin-3-ylmethyl)-S,S-dimethylsulfoximide

The title compound is prepared from 2-bromo-5-bromomethyl-pyridine and S,S-dimethylsulfoximine following a procedure analogous to that described for Intermediate 38 (Step 1). LC (method 1): $t_R$=0.57 min; Mass spectrum (ESI$^+$): m/z=263, 265 [M+H]$^+$.

Step 2: N-(6-(4-(6-Chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)phenyl)pyridin-3-ylmethyl)-S,S-dimethylsulfoximide The title compound is prepared from (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol and N-(6-bromo-pyridin-3-ylmethyl)-S,S-dimethylsulfoximide following a procedure analogous to that described for Intermediate 2 (Step 1). LC (method 1): $t_R$=0.90 min; Mass spectrum (ESI$^+$): m/z=686 [M+H]$^+$.

Intermediate 52

(3R,3aR,6R,6aR)-6-(6-Chloro-5-(4-(5-(N-(2,2,2-trifluoroacetyl)-S-methylsulfonimidoyl)pyrimidin-2-yl)phenyl)-3-(2-trimethylsilanyl-ethoxy-methyl)-3H-imidazo[4,5-b]pyridin-2-yloxy)hexahydrofuro[3,2-b]furan-3-ol

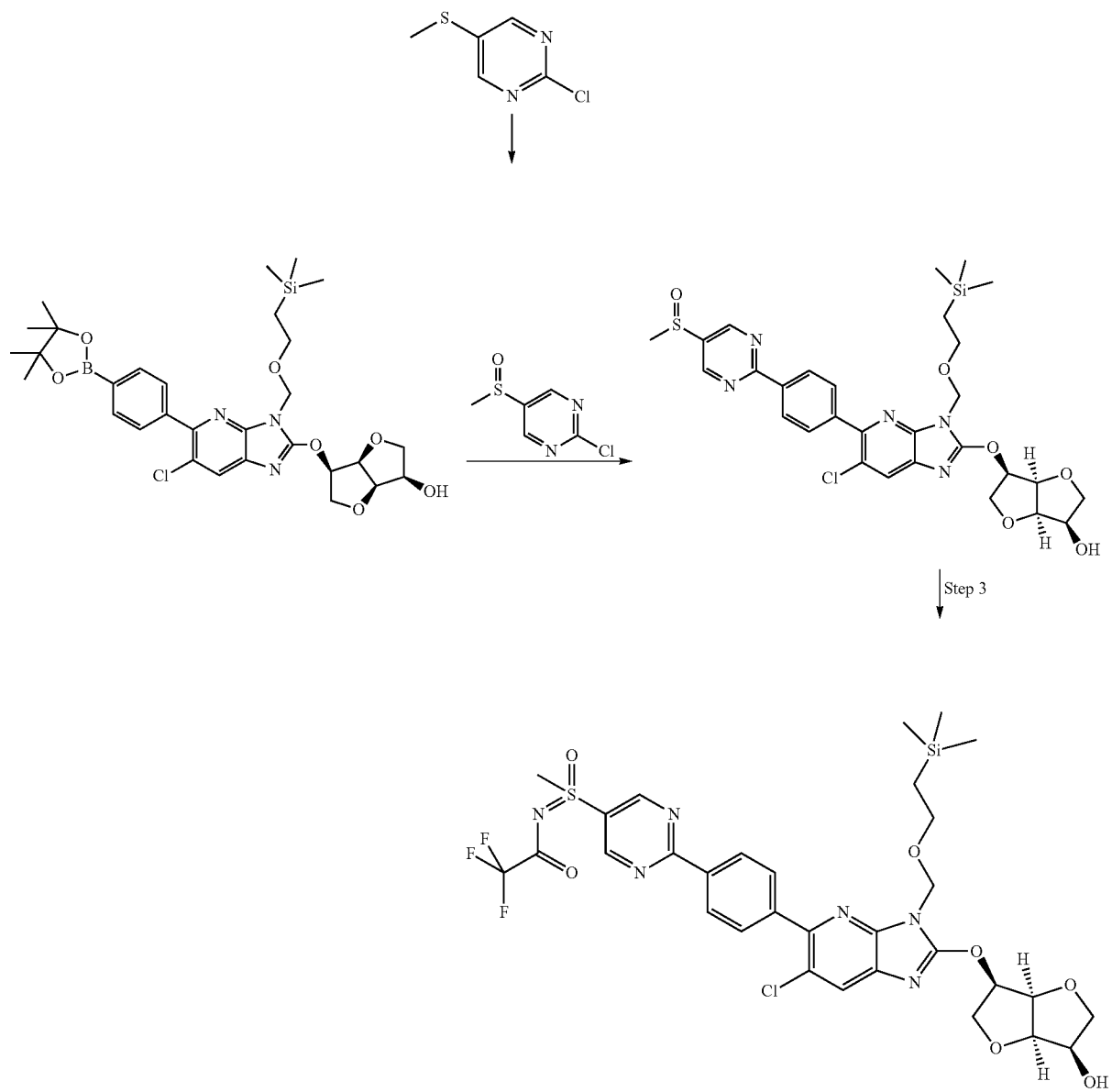

Step 1: 2-Chloro-S-methylsulfinyl-pyrimidine

A mixture of 2-Chloro-S-methylsulfanyl-pyrimidine (264 mg), sodium metaperiodate (487 mg), methanol (12 mL), and water (3 mL) is stirred at 40° C. for 6 h. More sodium metaperiodate (150 mg) is added and the reaction mixture is stirred at 30° C. overnight. The reaction mixture is diluted with water and extracted with dichloromethane. The combined extracts are washed with brine, dried over $MgSO_4$ and concentrated in vacuo. The crude product is used for the next reaction step without further purification. LC (method 1): $t_R$=0.25 min; Mass spectrum (ESI$^+$): m/z=177 [M+H]$^+$.

Step 2: (3R,3aR,6R,6aR)-6-[6-Chloro-5-[4-(5-methanesulfinyl-pyrimidin-2-yl)-phenyl]-3-(2-trimethyl-silanyl-ethoxymethyl)-3H-imidazo[4,5-b]pyridin-2-yloxy]-hexahydro-furo[3,2-b]furan-3-ol The title compound is prepared from (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol and 2-chloro-5-methylsulfinyl-pyrimidine following a procedure analogous to that described for Intermediate 28 (Step 2) using ethanol as solvent. LC (method 1): $t_R$=1.04 min; Mass spectrum (ESI$^+$): m/z=644 [M+H]$^+$.

Step 3: (3R,3aR,6R,6aR)-6-(6-chloro-5-(4-(5-(N-(2,2,2-trifluoroacetyl)-S-methyl-sulfonimidoyl)pyrimidin-2-yl)phenyl)-3-(2-trimethylsilanyl-ethoxymethyl)-3H-imidazo[4,5-b]pyridin-2-yloxy)hexahydrofuro[3,2-b]furan-3-ol The title compound is prepared from (3R,3aR,6R,6aR)-6-[6-chloro-5-[4-(5-methanesulfinyl-pyrimidin-2-yl)-phenyl]-3-(2-trimethylsilanyl-ethoxymethyl)-3H-imidazo[4,5-b]pyridin-2-yloxy]-hexahydro-furo[3,2-b]furan-3-ol following a procedure analogous to that described for Intermediate 28 (Step 3). LC (method 1): $t_R$=1.17 min; Mass spectrum (ESI$^+$): m/z=755 [M+H]$^+$.

Intermediate 53

N-(6-{4-[6-Chloro-2-((3R,3aR,6R,6aR)-6-hydroxy-hexahydrofuro[3,2-b]furan-3-yloxy)-3-(2-trimethylsilanyl-ethoxymethyl)-3H-imidazo[4,5-b]pyridin-5-yl]-phenyl}-pyridazin-3-yl)-S,S-dimethylsulfoximide

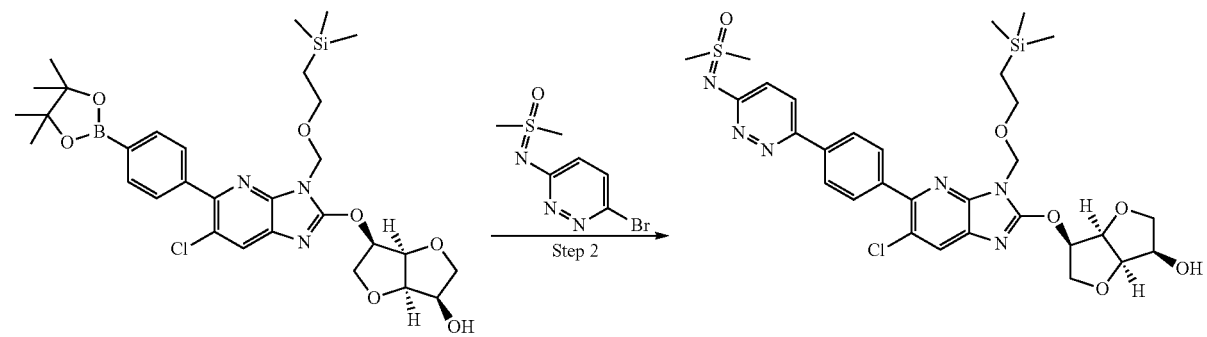

111

Step 1: N-(6-Bromo-pyridazin-3-yl)-S,S-dimethylsulfoximide

The title compound is prepared from 3,6-dibromo-pyridazine and S,S-dimethylsulfoximine following a procedure analogous to that described for Intermediate 15 (Step 1) using sodium tert-butoxide instead of cesium carbonate. LC (method 7): $t_R$=0.59 min; Mass spectrum (ESI$^+$): m/z=250, 252 [M+H]$^+$.

Step 2: N-(6-{4-[6-Chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl]-phenyl}-pyridazin-3-yl)-S,S-dimethylsulfoximide The title compound is prepared from (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol and N-(6-bromo-pyridazin-3-yl)-S,S-dimethylsulfoximide following a procedure analogous to that described for Intermediate 2 (Step 1) using ethanol as solvent. LC (method 1): $t_R$=0.95 min; Mass spectrum (ESI$^+$): m/z=673 [M+H]$^+$.

Intermediate 54

N-(5-{4-[6-Chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl]-phenyl}-pyridin-2-ylmethyl)-S,S-dimethylsulfoximide

112

Step 1: N-(5-Bromo-pyridin-2-ylmethyl)-S,S-dimethylsulfoximide

The title compound is prepared from 5-bromo-2-bromomethyl-pyridine and S,S-dimethylsulfoximine following a procedure analogous to that described for Intermediate 38 (Step 1). LC (method 1): $t_R$=0.59 min; Mass spectrum (ESI$^+$): m/z=263, 265 [M+H]$^+$.

Step 2: N-(5-{4-[6-Chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl]-phenyl}-pyridin-2-ylmethyl)-S,S-dimethylsulfoximide The title compound is prepared from (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol and N-(5-bromo-pyridin-2-ylmethyl)-S,S-dimethylsulfoximide following a procedure analogous to that described for Intermediate 2 (Step 1). LC (method 1): $t_R$=0.92 min; Mass spectrum (ESI$^+$): m/z=686 [M+H]$^+$.

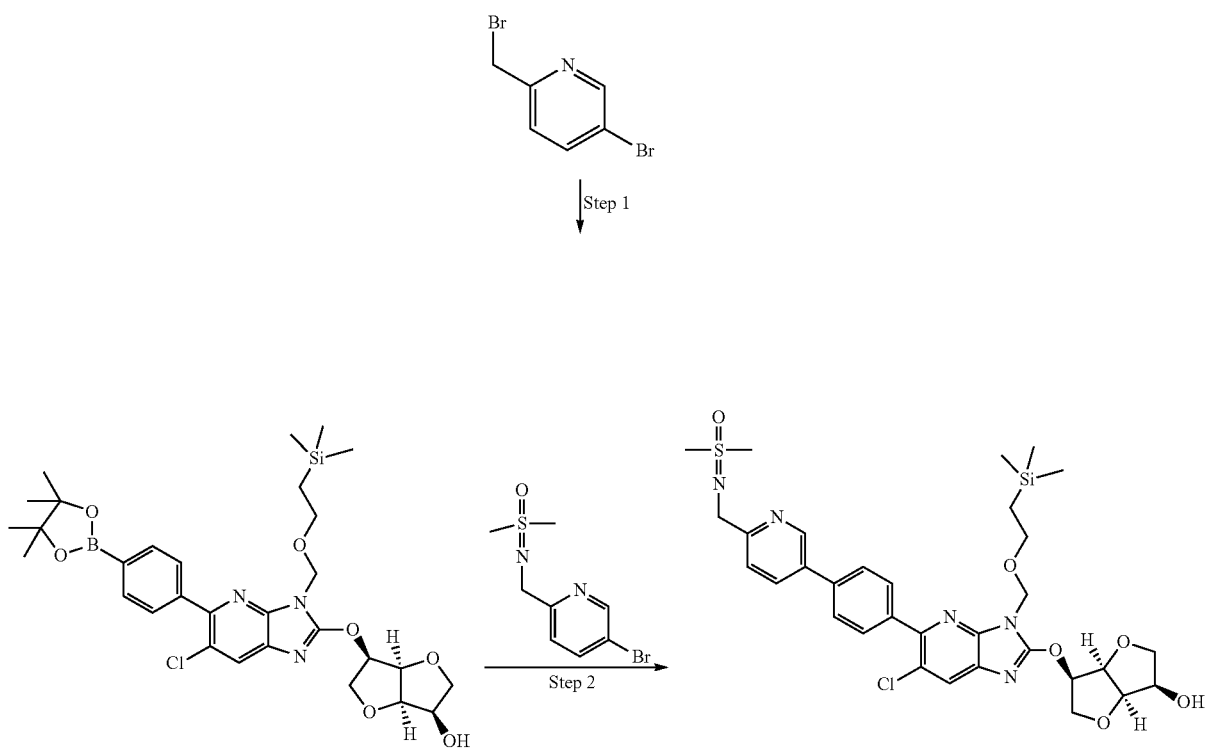

Intermediate 55

(3R,3aR,6R,6aR)-6-(6-Chloro-5-(4'-(N-(2,2,2-trifluoroacetyl)-S-methyl-sulfonimidoylmethyl)biphenyl-4-yl)-3-(2-trimethylsilanyl-ethoxy-methyl)-3H-imidazo[4,5-b]pyridin-2-yloxy)hexahydrofuro[3,2-b]furan-3-ol

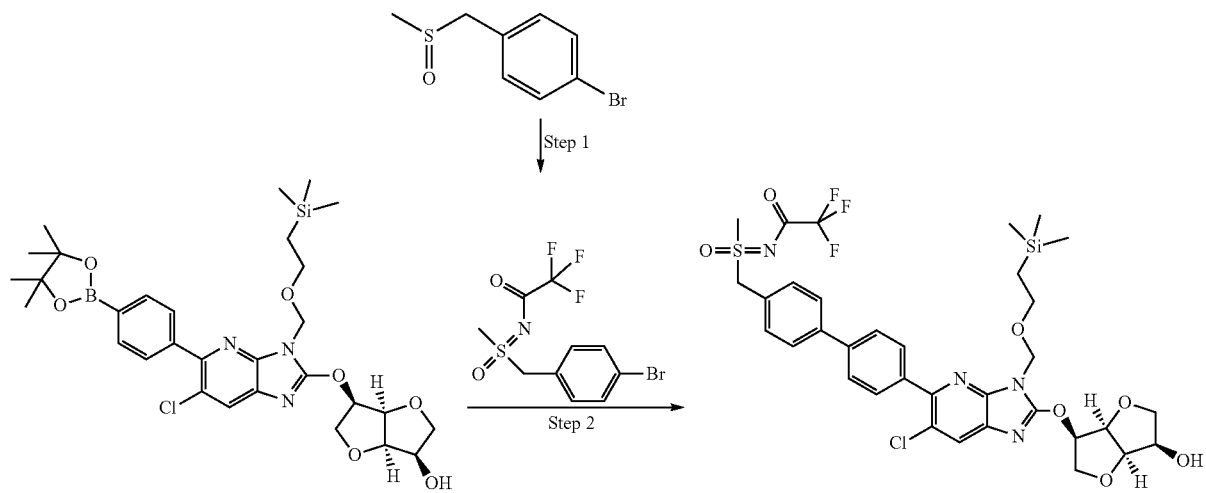

Step 1: 1-Bromo-4-(N-(2,2,2-trifluoroacetyl)-S-methylsulfonimidoylmethyl)-benzene The title compound is prepared from 1-bromo-4-methanesulfinylmethyl-benzene following a procedure analogous to that described for Intermediate 28 (Step 3). LC (method 1): $t_R$=1.00 min; Mass spectrum (ESI$^+$): m/z=345 [M+H]$^+$.

Step 2: (3R,3aR,6R,6aR)-6-(6-Chloro-5-(4'-(N-(2,2,2-trifluoroacetyl)-S-methyl-sulfonimidoylmethyl) biphenyl-4-yl)-3-(2-trimethylsilanyl-ethoxy-methyl)-3H-imidazo[4,5-b]pyridin-2-yloxy)hexahydrofuro[3,2-b]furan-3-ol The title compound is prepared from (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol and 1-bromo-4-(N-(2,2,2-trifluoroacetyl)-S-methylsulfonimidoylmethyl)-benzene following a procedure analogous to that described for Intermediate 2 (Step 1). LC (method 1): $t_R$=1.17 min; Mass spectrum (ESI$^+$): m/z=767 [M+H]$^+$.

Intermediate 56

N-(4-{4-[6-Chloro-2-((3R,3aR,6R,6aR)-6-hydroxy-hexahydrofuro[3,2-b]furan-3-yloxy)-3-(2-trimethyl-silanyl-ethoxymethyl)-3H-imidazo[4,5-b]pyridin-5-yl]-phenyl}-pyridin-2-ylmethyl)-S,S-dimethylsulfoximide

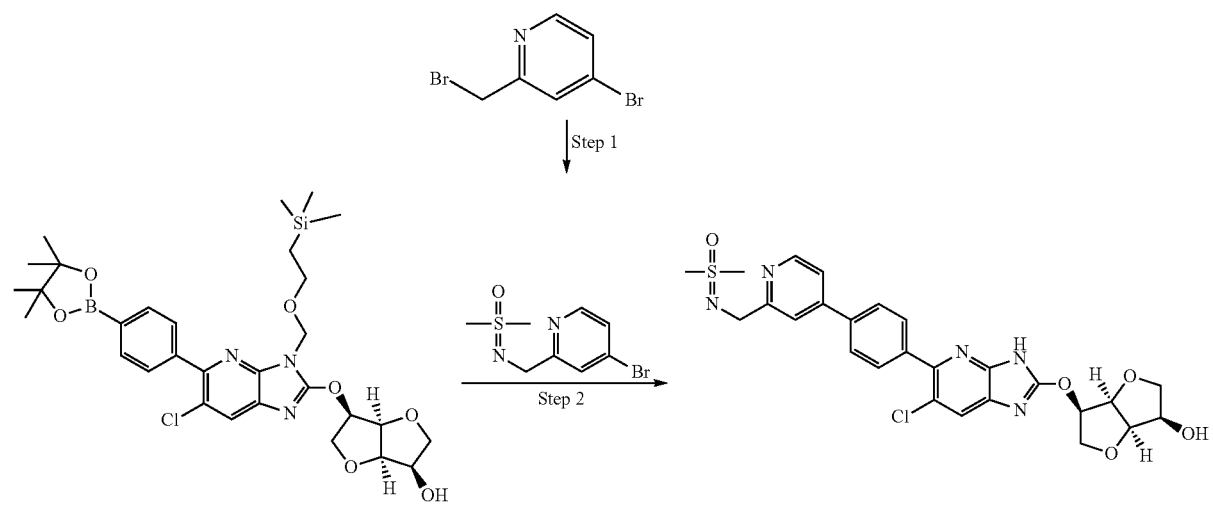 [SMILES: BrCc1cc(Br)ccn1 ; CC1(C)OB(c2ccc(-c3nc4c(cc3Cl)nc(O[C@@H]3CO[C@H]5[C@@H]3OC[C@H]5O)n4COCC[Si](C)(C)C)cc2)OC1(C)C ; CS(C)(=O)=NCc1cc(Br)ccn1 ; CS(C)(=O)=NCc1cc(-c2ccc(-c3nc4[nH]c(O[C@@H]5CO[C@H]6[C@@H]5OC[C@H]6O)nc4cc3Cl)cc2)ccn1]

Step 1 N-(4-Bromo-pyridin-2-ylmethyl)-S,S-dimethylsulfoximide

A mixture of S,S-dimethylsulfoximine (359 mg), potassium tert-butylate (425 mg) and dioxane (6 mL) and tetrahydrofuran (5 mL) is stirred for 1 h under an argon atmosphere at 0° C. in an ice bath. 4-Bromo-2-bromomethyl-pyridine (792 mg) dissolved in tetrahydrofuran is added, the ice bath is removed and the resulting mixture is stirred for 4 h at room temperature. The reaction mixture is diluted with ethyl acetate (50 ml) and water (20 mL). The aqueous phase is extracted with ethyl acetate and the combined organic phases are dried over MgSO$_4$ and concentrated in vacuo. The residue is purified by HPLC to give the title compound. LC (method 5): $t_R$=0.66 min; Mass spectrum (ESI$^+$): m/z=263, 265 [M+H]$^+$.

Step 2: N-(4-{4-[6-Chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl]-phenyl}-pyridin-2-ylmethyl)-S,S-dimethylsulfoximide The title compound is prepared from (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol and N-(4-bromo-pyridin-2-ylmethyl)-S,S-dimethylsulfoximide following a procedure analogous to that described for Intermediate 2 (Step 1). LC (method 4): $t_R$=0.88 min; Mass spectrum (ESI$^+$): m/z=686 [M+H]$^+$.

Intermediate 57

(3R,3aR,6R,6aR)-6-{6-Chloro-5-[4-(1-imino-1-oxo-hexahydro-1λ$^6$-thiopyran-4-yl)-phenyl]-1-(2-trimethylsilanyl-ethoxy-methyl)-1H-imidazo[4,5-b]pyridin-2-yloxy}-hexahydro-furo[3,2-b]furan-3-ol (Diastereomer 1 and Diastereomer 2)

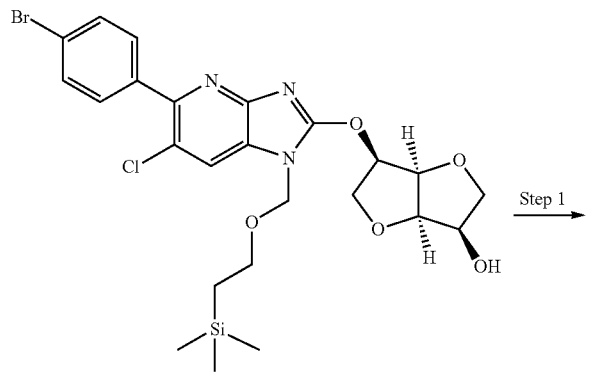

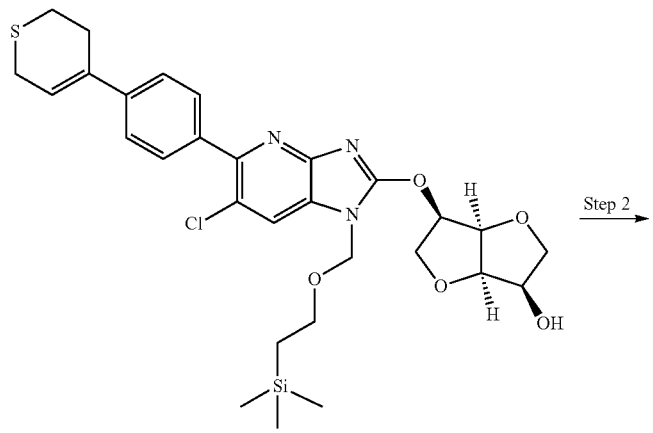

-continued
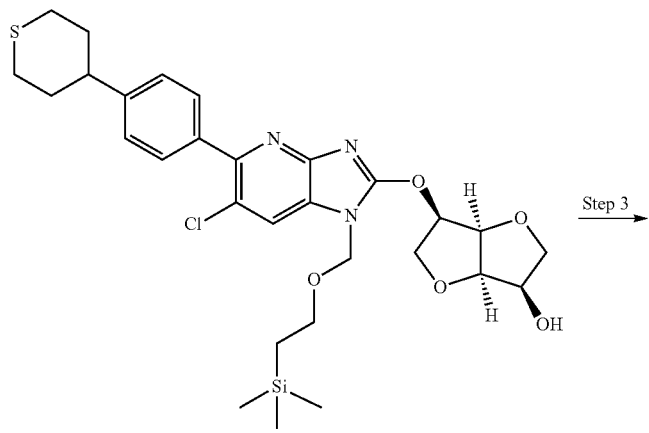
Step 3
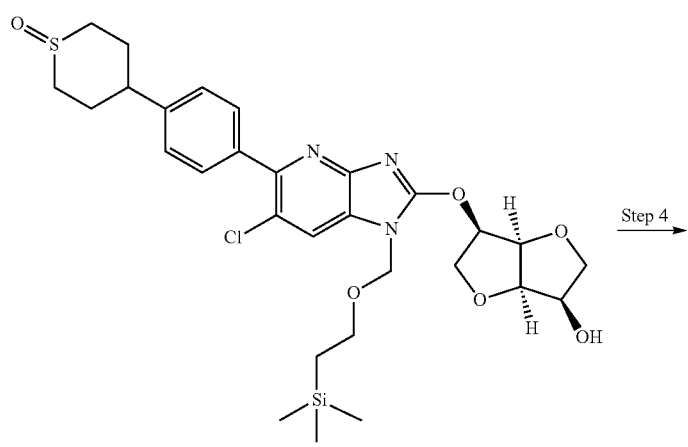
Step 4
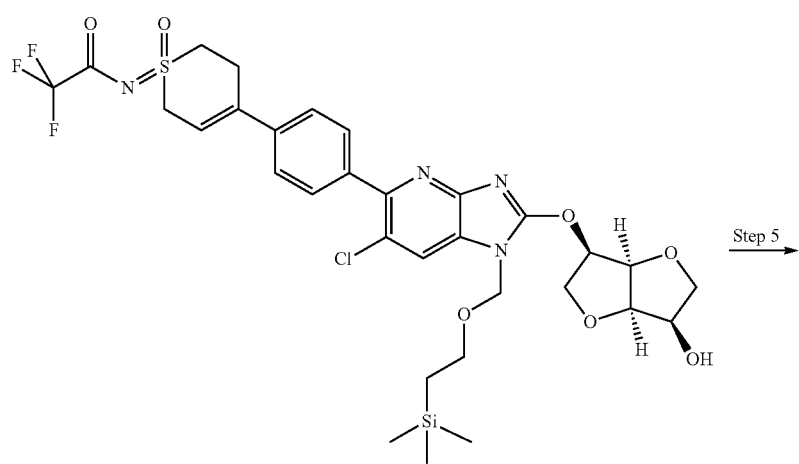
Step 5

-continued

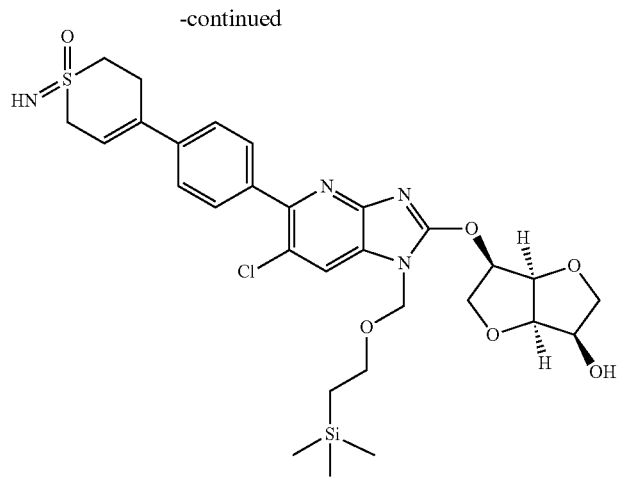

Step 1: (3R,3aR,6R,6aR)-6-[6-Chloro-5-[4-(3,6-dihydro-2H-thiopyran-4-yl)-phenyl]-1-(2-trimethyl-silanyl-ethoxymethyl)-1H-imidazo[4,5-b]pyridin-2-yloxy]-hexahydro-furo[3,2-b]furan-3-ol The title compound is prepared from (3R,3aR,6R,6aR)-6-[5-(4-bromo-phenyl)-6-chloro-1-(2-trimethylsilanyl-ethoxymethyl)-1H-imidazo[4,5-b]pyridin-2-yloxy]-hexahydro-furo[3,2-b]furan-3-ol and 2-(3,6-dihydro-2H-thiopyran-4-yl)-4,4,5,5-tetramethyl-[1,3,2]dioxaborolane following a procedure analogous to that described for Intermediate 2 (Step 1). LC (method 1): $t_R$=0.93 min; Mass spectrum (ESI$^+$): m/z=602 [M+H]$^+$.

Step 2: (3R,3aR,6R,6aR)-6-[6-Chloro-5-[4-(tetra-hydro-thiopyran-4-yl)-phenyl]-1-(2-trimethylsilanyl-ethoxymethyl)-1H-imidazo[4,5-b]pyridin-2-yloxy]-hexahydro-furo[3,2-b]furan-3-ol The title compound is prepared by hydrogenation of (3R,3aR,6R,6aR)-6-[6-chloro-5-[4-(3,6-dihydro-2H-thiopyran-4-yl)-phenyl]-1-(2-trimethylsilanyl-ethoxymethyl)-1H-imidazo[4,5-b]pyridin-2-yloxy]-hexahydro-furo[3,2-b]furan-3-ol in the presence of palladium on charcoal (10%) in tetrahydrofuran at room temperature. LC (method 1): $t_R$=1.27 min; Mass spectrum (ESI$^+$): m/z=604 [M+H]$^+$.

Step 3: (3R,3aR,6R,6aR)-6-[6-Chloro-5-[4-(1-oxo-hexahydro-1λ$^4$-thiopyran-4-yl)-phenyl]-1-(2-trimethylsilanyl-ethoxymethyl)-1H-imidazo[4,5-b]pyridin-2-yloxy]-hexahydro-furo[3,2-b]furan-3-ol The title compound is prepared from (3R,3aR,6R,6aR)-6-[6-chloro-5-[4-(tetrahydro-thiopyran-4-yl)-phenyl]-1-(2-trimethylsilanyl-ethoxymethyl)-1H-imidazo[4,5-b]pyridin-2-yloxy]-hexahydro-furo[3,2-b]furan-3-ol following a procedure analogous to that described for Intermediate 36 (Step 5). LC (method 1): $t_R$=1.01 min; Mass spectrum (ESI$^+$): m/z=620 [M+H]$^+$.

Step 4: N-(4-{4-[6-Chloro-2-((3R,3aR,6R,6aR)-6-hydroxy-hexahydrofuro[3,2-b]furan-3-yloxy)-1-(2-trimethylsilanyl-ethoxymethyl)-1H-imidazo[4,5-b]pyridin-5-yl]-phenyl}-1-oxo-hexahydro-1λ$^6$-thiopyran-1-ylidene)-2,2,2-trifluoro-acetamide The title compound is prepared from (3R,3aR,6R,6aR)-6-[6-chloro-5-[4-(1-oxo-hexahydro-1λ$^4$-thiopyran-4-yl)-phenyl]-1-(2-trimethylsilanyl-ethoxymethyl)-1H-imidazo[4,5-b]pyridin-2-yloxy]-hexahydro-furo[3,2-b]furan-3-ol following a procedure analogous to that described for Intermediate 28 (Step 3). LC (method 1): $t_R$=1.14 min; Mass spectrum (ESI$^+$): m/z=731 [M+H]$^+$.

Step 5: (3R,3aR,6R,6aR)-6-{6-Chloro-5-[4-(1-imino-1-oxo-hexahydro-1λ$^6$-thiopyran-4-yl)-phenyl]-1-(2-trimethylsilanyl-ethoxy-methyl)-1H-imidazo[4,5-b]pyridin-2-yloxy}-hexahydro-furo[3,2-b]furan-3-ol (Diastereomer 1 and Diastereomer 2)

The title compound is prepared from N-(4-{4-[6-chloro-2-((3R,3aR,6R,6aR)-6-hydroxy-hexahydrofuro[3,2-b]furan-3-yloxy)-1-(2-trimethylsilanyl-ethoxymethyl)-1H-imidazo[4,5-b]pyridin-5-yl]-phenyl}-1-oxo-hexahydro-1λ$^6$-thiopyran-1-ylidene)-2,2,2-trifluoro-acetamide by treatment with potassium carbonate in methanol at room temperature. Diastereomers can be separated by silica gel chromatography (ethyl acetate/methanol 95:5→80:20)

Diastereomer 1: LC (method 1): $t_R$=0.92 min; Mass spectrum (ESI$^+$): m/z=635 [M+H]$^+$.

Diastereomer 2: LC (method 1): $t_R$=0.93 min; Mass spectrum (ESI$^+$): m/z=635 [M+H]$^+$.

Intermediate 58

N-(4-(6-Chloro-2-((3R,3aR,6R,6aR)-6-hydroxy-hexahydrofuro[3,2-b]furan-3-yloxy)-3-(2-trimethyl-silanyl-ethoxy-methyl)-3H-imidazo[4,5-b]pyridin-5-yl)phenyl)-S,S-dimethyl-sulfondiimine

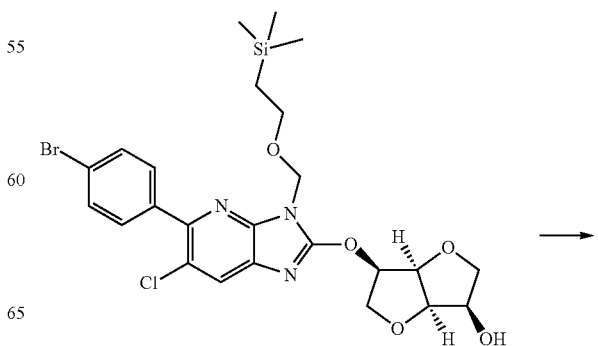

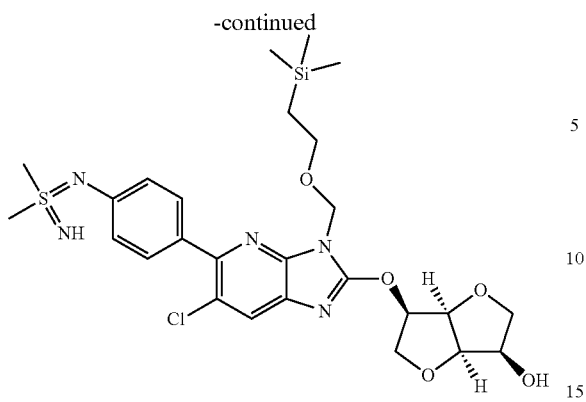

The title compound is prepared from (3R,3aR,6R,6aR)-6-[5-(4-bromo-phenyl)-6-chloro-1-(2-trimethylsilanyl-ethoxymethyl)-1H-imidazo[4,5-b]pyridin-2-yloxy]-hexahydro-furo[3,2-b]furan-3-ol and S,S-dimethyl-sulfondiimine following a procedure analogous to that described for Intermediate 2 (Step 2). LC (method 1): $t_R$=0.89 min; Mass spectrum (ESI$^+$): m/z=594 [M+H]$^+$.

Intermediate 59

(3R,3aR,6R,6aR)-6-{6-Chloro-5-[4-(2-methylimino-2-oxo-hexahydro-2λ$^6$-thieno[3,4-c]pyrrol-5-yl)-phenyl]-3-(2-trimethylsilanyl-ethoxy-methyl)-3H-imidazo[4,5-b]pyridin-2-yloxy}-hexahydro-furo[3,2-b]furan-3-ol

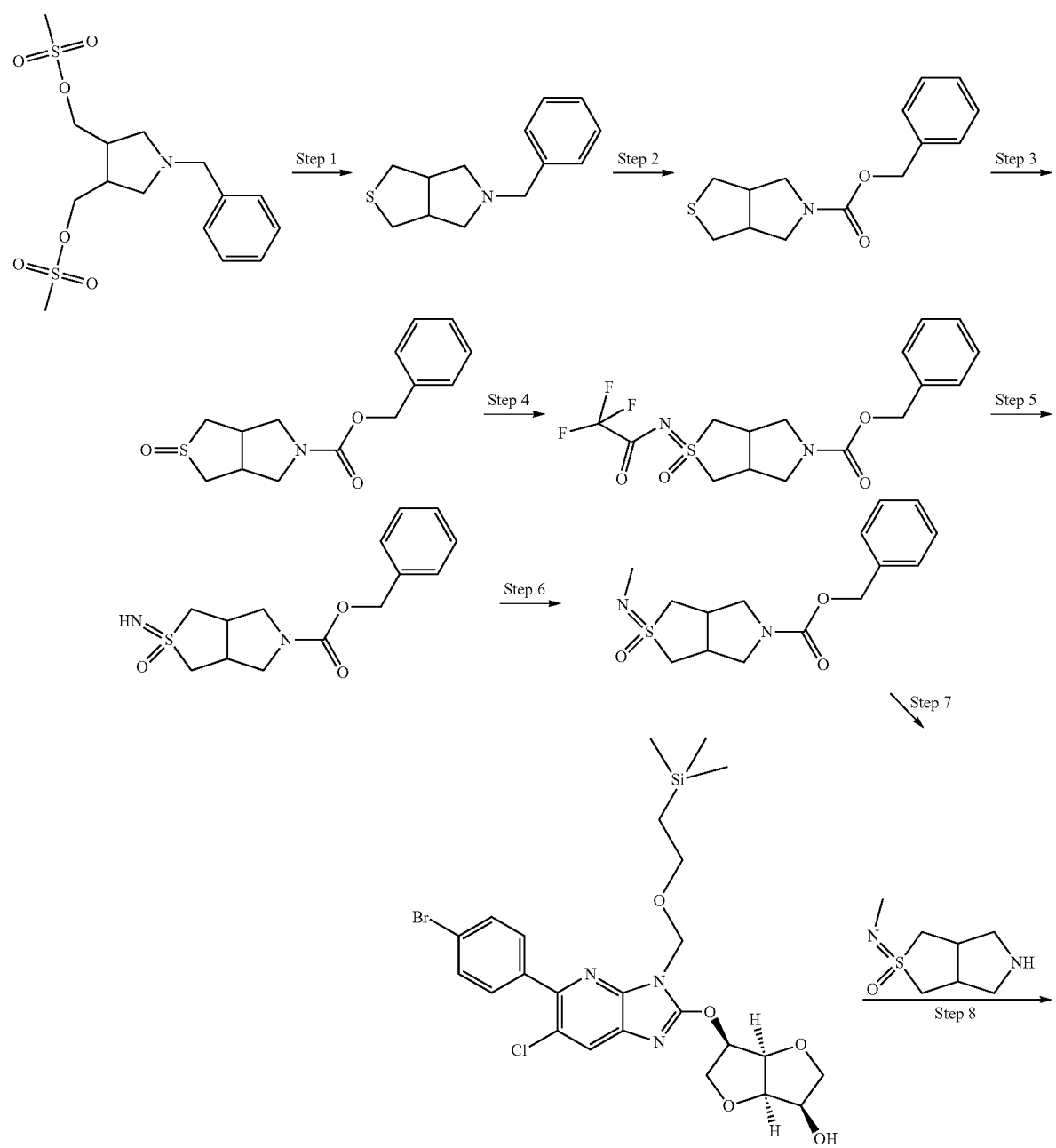

-continued

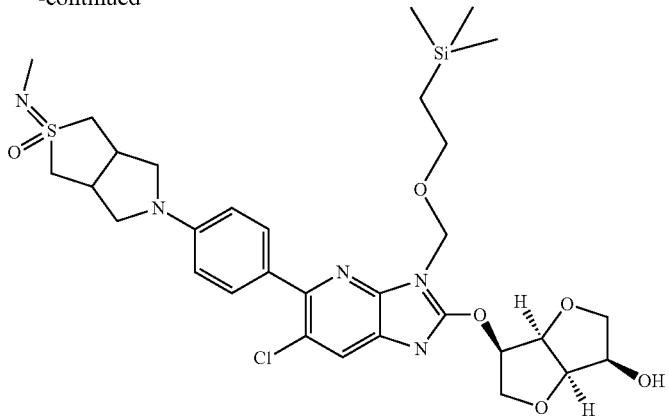

Step 1: 5-Benzyl-hexahydro-thieno[3,4-c]pyrrole

A mixture of 1-benzyl-3,4-di(methylsulfonyloxy)methyl-pyrrolidine (6.00 g), sodium sulfide (1.61 g), Aliquat-336 (1.29 g), toluene and water is stirred overnight at 90° C. The aqueous phase is extracted with ethyl acetate and the combined organic phases are washed with water and brine, dried over MgSO$_4$, and concentrated in vacuo. The residue is chromatographed on silica gel (ethyl acetate/cyclohexane 50:50→100:0) to give the title compound. LC (method 4): $t_R$=0.66 min; Mass spectrum (ESI$^+$): m/z=220 [M+H]$^+$.

Step 2: 5-Benzyloxycarbonyl-hexahydro-thieno[3,4-c]pyrrole

Benzyl chloroformate (2.72 g) is added drop wise to an ice-cooled solution of 5-benzyl-hexahydro-thieno[3,4-c]pyrrole (1.00 g) in dichloromethane. The resulting mixture is stirred overnight at room temperature, concentrated in vacuo, diluted with acetonitrile, basified with ammonium hydroxide solution, and filtered. The filtrate is purified by reversed phase HPLC to give the title compound. LC (method 5): $t_R$=1.00 min; Mass spectrum (ESI$^+$): m/z=264 [M+H]$^+$.

Step 3: 2-Oxo-hexahydro-2λ$^4$-thieno[3,4-c]pyrrole-5-carboxylic acid benzyl ester The title compound is prepared by oxidation of 5-benzyloxycarbonyl-hexahydro-thieno[3,4-c]pyrrole with sodium metaperiodate in a mixture of methanol and water at room temperature. LC (method 5): $t_R$=0.77 min; Mass spectrum (ESI$^+$): m/z=280 [M+H]$^+$.

Step 4: 2-Oxo-2-(2,2,2-trifluoro-acetylimino)-hexahydro-2λ$^6$-thieno[3,4-c]pyrrole-5-carboxylic acid benzyl ester The title compound is prepared from 2-oxo-hexahydro-2λ$^4$-thieno[3,4-c]pyrrole-5-carboxylic acid benzyl ester following a procedure analogous to that described for Intermediate 28 (Step 3). LC (method 5): $t_R$=0.97 min; Mass spectrum (ESI$^+$): m/z=391 [M+H]$^+$.

Step 5: 2-Imino-2-oxo-hexahydro-2λ$^6$-thieno[3,4-c]pyrrole-5-carboxylic acid benzyl ester The title compound is prepared from 2-oxo-2-(2,2,2-trifluoro-acetylimino)-hexahydro-2λ$^6$-thieno[3,4-c]pyrrole-5-carboxylic acid benzyl ester by treatment with potassium carbonate in methanol at room temperature. LC (method 5): $t_R$=0.75 min; Mass spectrum (ESI$^+$): m/z=295 [M+H]$^+$.

Step 6: 2-Methylimino-2-oxo-hexahydro-2λ$^6$-thieno[3,4-c]pyrrole-5-carboxylic acid benzyl ester The title compound is prepared from 2-imino-2-oxo-hexahydro-2λ$^6$-thieno[3,4-c]pyrrole-5-carboxylic acid benzyl ester following a procedure analogous to that described for Intermediate 11 (Step 2). LC (method 5): $t_R$=0.79 min; Mass spectrum (ESI$^+$: m/z=309 [M+H]$^+$.

Step 7: Methyl-(2-oxo-octahydro-2λ$^6$-thieno[3,4-c]pyrrol-2-ylidene)-amine hydrobromide The title compound is prepared from 2-methylimino-2-oxo-hexahydro-2λ$^6$-thieno[3,4-c]pyrrole-5-carboxylic acid benzyl ester by treatment with hydrobromic acid in acetic acid at room temperature. LC (method 5): $t_R$=0.14 min; Mass spectrum (ESI$^+$): m/z=175 [M+H]$^+$.

Step 8: (3R,3aR,6R,6aR)-6-[6-Chloro-5-[4-(2-methylimino-2-oxo-hexahydro-2λ$^6$-thieno[3,4-c]pyrrol-5-yl)-phenyl]-3-(2-trimethylsilanyl-ethoxymethyl)-3H-imidazo[4,5-b]pyridin-2-yloxy]-hexahydro-furo[3,2-b]furan-3-ol The title compound is prepared from (3R,3aR,6R,6aR)-6-[5-(4-bromo-phenyl)-6-chloro-1-(2-trimethylsilanyl-ethoxymethyl)-1H-imidazo[4,5-b]pyridin-2-yloxy]-hexahydro-furo[3,2-b]furan-3-ol and methyl-(2-oxo-octahydro-2λ$^6$-thieno[3,4-c]pyrrol-2-ylidene)-amine hydrobromide following a procedure analogous to that described for Intermediate 46 (Step 2). LC (method 5): $t_R$=1.01 min; Mass spectrum (ESI$^+$): m/z=676 [M+H]$^+$.

Example 1

N-(4-(6-Chloro-2-((3R,3aR,6R,6aR)-6-hydroxy-hexahydrofuro[3,2-b]furan-3-yloxy)-3H-imidazo[4,5-b]pyridin-5-yl)phenyl)}-S,S-dimethylsulfoximide

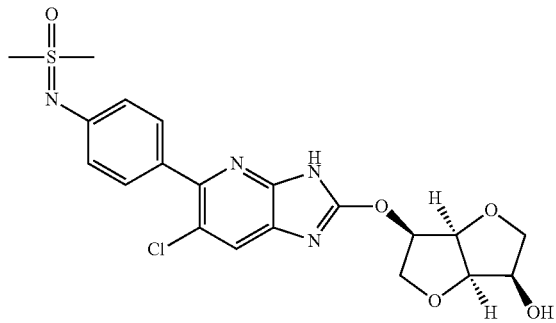 [SMILES: CS(C)(=O)=Nc1ccc(-c2nc3[nH]c(O[C@@H]4CO[C@H]5[C@@H]4OC[C@H]5O)nc3cc2Cl)cc1]

A mixture of N-(4-(6-chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)phenyl)-S,S-dimethylsulfoximide (60 mg) and KHSO$_4$ (2 M aqueous solution, 45 µL) in formic acid (1.2 mL) is stirred for 2 h at 60° C. The mixture is cooled to 0° C. in an ice bath and the pH is adjusted to 11 by adding NaOH (10 M aqueous solution). Tetrahydrofurane (3 mL) is added and the mixture is stirred for 1 h at room temperature. Hydrochloric acid (4 N) is added until the pH reaches 6. The mixture is diluted with ethylacetate, washed with water and brine, and dried over MgSO$_4$. The solvents are evaporated in vacuo and the residue is purified by HPLC on reversed phase to give the title compound. LC (method 1): $t_R$=0.73 min; Mass spectrum (ESI$^+$): m/z=465 [M+H]$^+$.

Example 2

N-(4'-(6-Chloro-2-((3R,3aR,6R,6aR)-6-hydroxy-hexahydrofuro[3,2-b]furan-3-yloxy)-3H-imidazo[4,5-b]pyridin-5-yl)biphenyl-4-yl)-S,S-dimethylsulfoximide

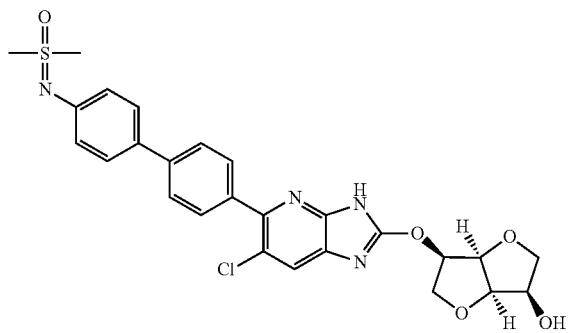 [SMILES: CS(C)(=O)=Nc1ccc(-c2ccc(-c3nc4[nH]c(O[C@@H]5CO[C@H]6[C@@H]5OC[C@H]6O)nc4cc3Cl)cc2)cc1]

The title compound is prepared from N-(4'-(6-chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)biphenyl-4-yl)-S,S-dimethylsulfoximide following a procedure analogous to that described for Example 1. LC (method 1): $t_R$=0.85 min; Mass spectrum (ESI$^+$): m/z=541 [M+H]$^+$.

Example 3

N-4-(6-Chloro-2-((3R,3aR,6R,6aR)-6-hydroxyhexa-hydrofuro[3,2-b]furan-3-yloxy)-3H-imidazo[4,5-b]pyridin-5-yl)benzoyl)-S,S-dimethylsulfoximide

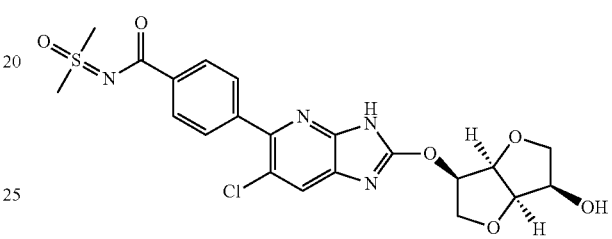

The title compound is prepared from 4-(6-chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)benzoyl dimethylsulfoximide following a procedure analogous to that described for Example 1. LC (method 1): $t_R$=0.76 min; Mass spectrum (ESI$^+$): m/z=493 [M+H]$^+$.

Example 4

(3R,3aR,6R,6aR)-6-(6-Chloro-5-(4-(S-imino-5-oxo-thiomorpholin-4-yl)-phenyl)-3H-imidazo[4,5-b]pyri-din-2-yloxy)-hexahydro-furo[3,2-b]furan-3-ol

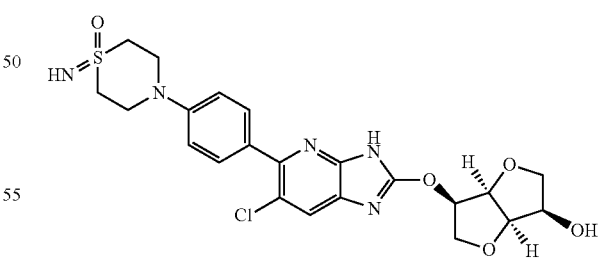

The title compound is prepared from (3R,3aR,6R,6aR)-6-(6-chloro-5-(4-(S-(N-acetylimino)-S-oxo-thiomorpholin-4-yl)-phenyl)-3-(2-trimethylsilanyl-ethoxymethyl)-3H-imidazo[4,5-b]pyridin-2-yloxy)-hexahydro-furo[3,2-b]furan-3-ol following a procedure analogous to that described for Example 1. LC (method 1): $t_R$=0.71 min; Mass spectrum (ESI$^+$): m/z=506 [M+H]$^+$.

Example 5

(3R,3aR,6R,6aR)-6-(6-Chloro-5-(4-(S-methylimino-5-oxo-thiomorpholin-4-yl)-phenyl)-3H-imidazo[4,5-b]pyridin-2-yloxy)-hexahydro-furo[3,2-b]furan-3-ol

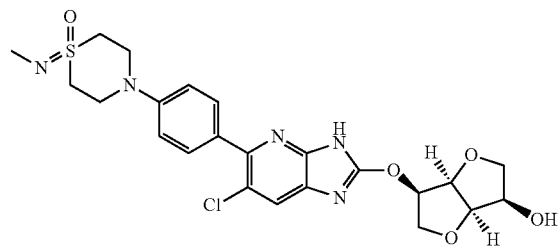 [SMILES: CN=S1(=O)CCN(c2ccc(-c3nc4[nH]c(O[C@@H]5CO[C@H]6[C@@H]5OC[C@H]6O)nc4cc3Cl)cc2)CC1]

The title compound is prepared from (3R,3aR,6R,6aR)-6-(6-chloro-5-(4-(S-methylimino-5-oxo-thiomorpholin-4-yl)-phenyl)-3-(2-trimethylsilanyl-ethoxymethyl)-3H-imidazo[4,5-b]pyridin-2-yloxy)-hexahydro-furo[3,2-b]furan-3-ol following a procedure analogous to that described for Example 1. LC (method 1): $t_R$=0.71 min; Mass spectrum (ESI$^+$): m/z=520 [M+H]$^+$.

Example 6

N-4'-(6-Chloro-2-((3R,3aR,6R,6aR)-6-hydroxyhexahydrofuro[3,2-b]furan-3-yloxy)-3H-imidazo[4,5-b]pyridin-5-yl)biphenyl-4-carbonyl-S,S-dimethylsulfoximide

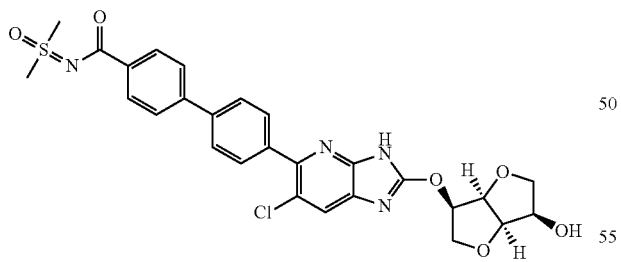

The title compound is prepared from N-4'-(6-chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)biphenyl-4-carbonyl-S,S-dimethylsulfoximide following a procedure analogous to that described for Example 1. LC (method 1): $t_R$=0.87 min; Mass spectrum (ESI$^+$): m/z=569 [M+H]$^+$.

Example 7

S-(4'-(6-Chloro-2-((3R,3aR,6R,6aR)-6-hydroxy-hexahydrofuro[3,2-b]furan-3-yloxy)-3H-imidazo[4,5-b]pyridin-5-yl)biphenyl-4-yl)-S-methyl-N-cyano-sulfoximide

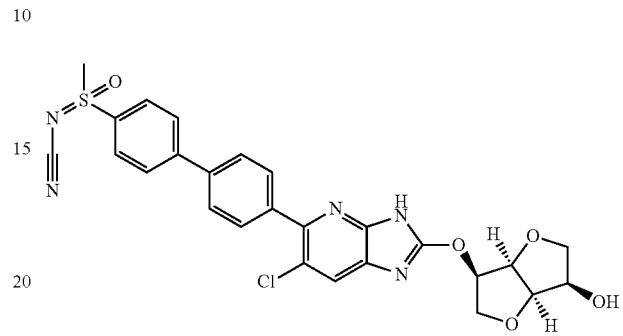

The title compound is prepared from S-(4'-(6-chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)biphenyl-4-yl)-S-methyl-N-cyano-sulfoximide following a procedure analogous to that described for Example 1. LC (method 1): $t_R$=0.89 min; Mass spectrum (ESI$^+$): m/z=552 [M+H]$^+$.

Example 8

(3R,3aR,6R,6aR)-6-{6-Chloro-5-[4'-(1-oxo-tetrahydro-1λ4-thiophen-1-ylideneamino)-biphenyl-4-yl]-3H-imidazo[4,5-b]pyridin-2-yloxy}-hexahydro-furo[3,2-b]furan-3-ol

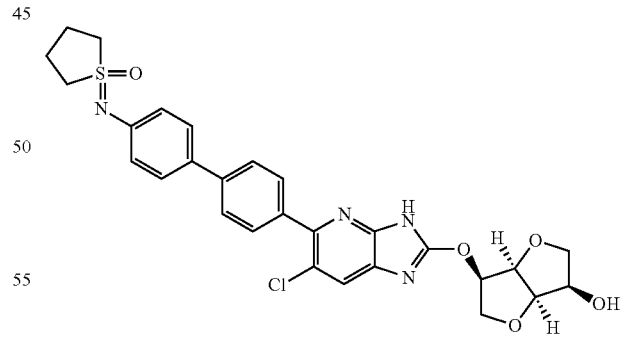

The title compound is prepared from (3R,3aR,6R,6aR)-6-{6-chloro-5-[4'-(1-oxo-tetrahydro-1λ4-thiophen-1-ylideneamino)-biphenyl-4-yl]-3-(2-trimethylsilanyl-ethoxymethyl)-3H-imidazo[4,5-b]pyridin-2-yloxy}-hexahydro-furo[3,2-b]furan-3-ol following a procedure analogous to that described for Example 1. LC (method 1): $t_R$=0.90 min; Mass spectrum (ESI$^+$): m/z=567 [M+H]$^+$.

Example 9

(S)-N-(4-(6-Chloro-2-((3R,3aR,6R,6aR)-6-hydroxy-hexahydrofuro[3,2-b]furan-3-yloxy)-3H-imidazo[4,5-b]pyridin-5-yl)phenyl)-S-methyl-S-phenylsulfoximide

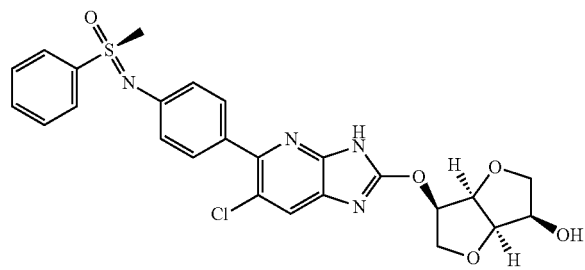 [SMILES: C[S@@](=O)(=Nc1ccc(-c2nc3[nH]c(O[C@@H]4CO[C@H]5[C@@H]4OC[C@H]5O)nc3cc2Cl)cc1)c1ccccc1]

The title compound is prepared from (S)-N-(4-(6-chloro-2-((3R,3aR,6R,6aR)-6-hydroxyhexahydrofuro[3,2-b]furan-3-yloxy)-3-(2-trimethylsilanyl-ethoxy-methyl)-3H-imidazo[4,5-b]pyridin-5-yl)phenyl)-S-methyl-5-phenylsulfoximide following a procedure analogous to that described for Example 1. LC (method 3): $t_R$=0.85 min; Mass spectrum (ESI$^+$): m/z=527 [M+H]$^+$.

Example 10

(3R,3aR,6R,6aR)-6-(6-Chloro-5-(4'-(N,S-dimethyl-sulfonimidoyl)biphenyl-4-yl)-3H-imidazo[4,5-b]pyridin-2-yloxy)hexahydrofuro[3,2-b]furan-3-ol

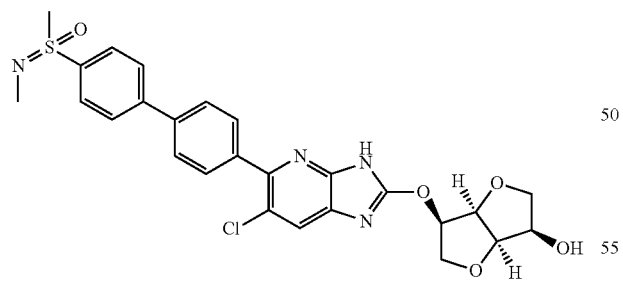

The title compound is prepared from (3R,3aR,6R,6aR)-6-(6-chloro-5-(4'-(N,S-dimethylsulfonimidoyl)biphenyl-4-yl)-3-(2-trimethylsilanyl-ethoxy-methyl)-3H-imidazo-[4,5-b]pyridin-2-yloxy)hexahydrofuro[3,2-b]furan-3-ol following a procedure analogous to that described for Example 1. LC (method 1): $t_R$=0.83 min; Mass spectrum (ESI$^+$): m/z=541 [M+H]$^+$.

Example 11

N-(4'-(6-Chloro-2-((3R,3aR,6R,6aR)-6-hydroxy-hexahydrofuro[3,2-b]furan-3-yloxy)-3H-imidazo[4,5-b]pyridin-5-yl)biphenyl-4-yl)-S,S-diethylsulfoxim-ide

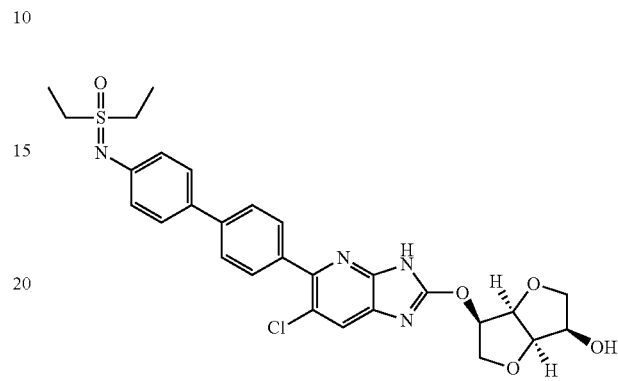

The title compound is prepared from N-(4'-(6-chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)biphenyl-4-yl)-S,S-diethylsulfoximide following a procedure analogous to that described for Example 1. LC (method 1): $t_R$=0.91 min; Mass spectrum (ESI$^+$): m/z=569 [M+H]$^+$.

Example 12

(R)-N-(4-(6-Chloro-2-((3R,3aR,6R,6aR)-6-hydroxy-hexahydrofuro[3,2-b]furan-3-yloxy)-3H-imidazo[4,5-b]pyridin-5-yl)phenyl)-S-methyl-S-phenylsulfoxim-ide

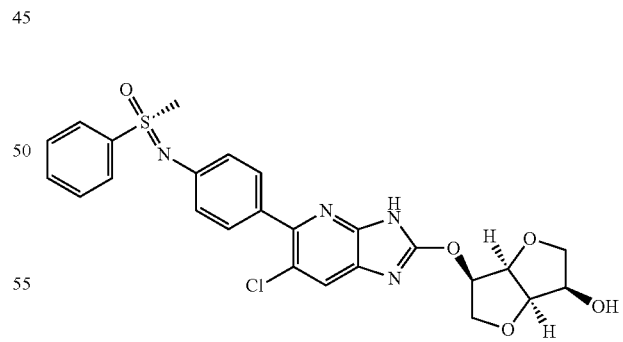

The title compound is prepared from (R)-N-(4-(6-chloro-2-((3R,3aR,6R,6aR)-6-hydroxyhexahydrofuro[3,2-b]furan-3-yloxy)-3-(2-trimethylsilanyl-ethoxy-methyl)-3H-imidazo[4,5-b]pyridin-5-yl)phenyl)-S-methyl-5-phenylsulfoximide following a procedure analogous to that described for Example 1. LC (method 3): $t_R$=0.85 min; Mass spectrum (ESI$^+$): m/z=527 [M+H]$^+$.

Example 13

N-(4'-(6-Chloro-2-((3R,3aR,6R,6aR)-6-hydroxy-hexahydrofuro[3,2-b]furan-3-yloxy)-3H-imidazo[4,5-b]pyridin-5-yl)biphenyl-4-yl)-S-ethyl-S-methylsulfoximide

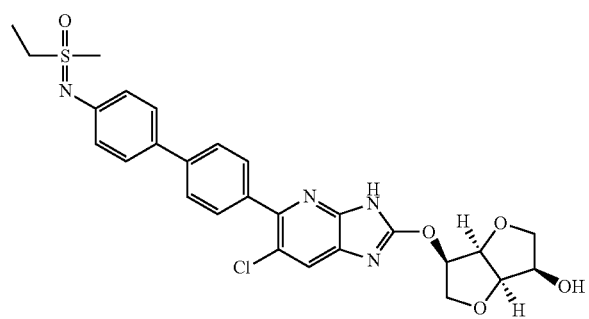 [SMILES: CCS(C)(=O)=Nc1ccc(-c2ccc(-c3nc4[nH]c(O[C@@H]5CO[C@H]6[C@@H]5OC[C@H]6O)nc4cc3Cl)cc2)cc1]

The title compound is prepared from N-(4'-(6-chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)biphenyl-4-yl)-S-ethyl-S-methylsulfoximide following a procedure analogous to that described for Example 1. LC (method 1): $t_R$=0.89 min; Mass spectrum (ESI$^+$): m/z=555 [M+H]$^+$.

Example 14

N-(4'-(6-Chloro-2-((3R,3aR,6R,6aR)-6-hydroxy-hexahydrofuro[3,2-b]furan-3-yloxy)-3H-imidazo[4,5-b]pyridin-5-yl)biphenyl-3-yl)-S,S-dimethylsulfoximide

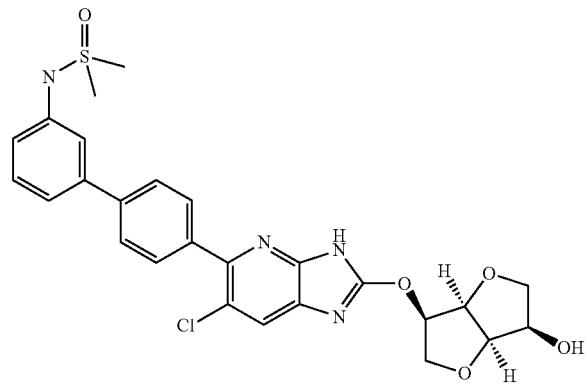

The title compound is prepared from N-(4'-(6-chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)biphenyl-3-yl)-S,S-dimethylsulfoximide following a procedure analogous to that described for Example 1. LC (method 3): $t_R$=0.85 min; Mass spectrum (ESI$^+$): m/z=541 [M+H]$^+$.

Example 15

N-(4'-(6-Chloro-2-((3R,3aR,6R,6aR)-6-hydroxy-hexahydrofuro[3,2-b]furan-3-yloxy)-3H-imidazo[4,5-b]pyridin-5-yl)biphenyl-4-yl)-S-cyclopropyl-S-methylsulfoximide

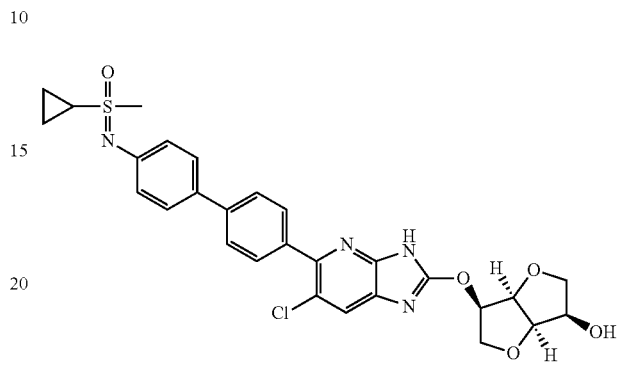

The title compound is prepared from N-(4'-(6-chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)biphenyl-4-yl)-S-cyclopropyl-S-methylsulfoximide following a procedure analogous to that described for Example 1. LC (method 1): $t_R$=0.91 min; Mass spectrum (ESI$^+$): m/z=567 [M+H]$^+$.

Example 16

(S)-N-4-(6-Chloro-2-((3R,3aR,6R,6aR)-6-hydroxy-hexahydrofuro[3,2-b]furan-3-yloxy)-3H-imidazo[4,5-b]pyridin-5-yl)benzoyl-S-methyl-5-phenylsulfoximine

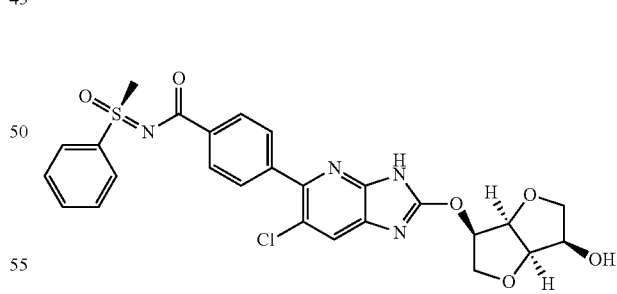

The title compound is prepared from (S)-N-4-(6-chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)benzoyl-S-methyl-5-phenylsulfoximine following a procedure analogous to that described for Example 1. LC (method 1): $t_R$=0.88 min; Mass spectrum (ESI$^+$): m/z=555 [M+H]$^+$.

Example 17

N-(4'-(6-Chloro-2-((3R,3aR,6R,6aR)-6-hydroxy-hexahydrofuro[3,2-b]furan-3-yloxy)-3H-imidazo[4,5-b]pyridin-5-yl)biphenyl-4-yl)-S,S-dimethyl-sulfondiimine

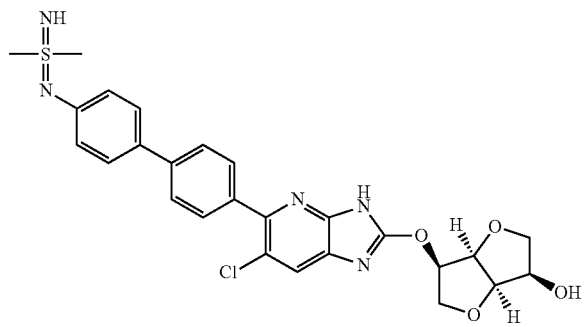 [SMILES: CS(C)(=N)=Nc1ccc(-c2ccc(-c3nc4[nH]c(O[C@@H]5CO[C@H]6[C@@H]5OC[C@H]6O)nc4cc3Cl)cc2)cc1]

The title compound is prepared from N-(4'-(6-chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)biphenyl-4-yl)-S,S-dimethyl-sulfondiimine following a procedure analogous to that described for Example 1. LC (method 1): $t_R$=0.80 min; Mass spectrum (ESI$^+$): m/z=540 [M+H]$^+$.

Example 18

N-(4'-(6-Chloro-2-((3R,3aR,6R,6aR)-6-hydroxy-hexahydrofuro[3,2-b]furan-3-yloxy)-3H-imidazo[4,5-b]pyridin-5-yl)biphenyl-4-yl)-S-isopropyl-S-methylsulfoximide

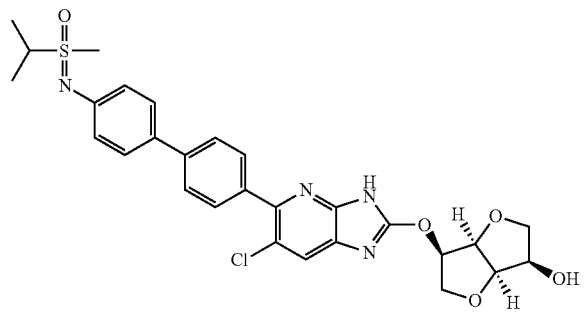

The title compound is prepared from N-(4'-(6-chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)biphenyl-4-yl)-S-isopropyl-S-methylsulfoximide following a procedure analogous to that described for Example 1. LC (method 1): $t_R$=0.93 min; Mass spectrum (ESI$^+$): m/z=569 [M+H]$^+$.

Example 19

N-4-(6-Chloro-2-((3R,3aR,6R,6aR)-6-hydroxyhexahydrofuro[3,2-b]furan-3-yloxy)-3H-imidazo[4,5-b]pyridin-5-yl)benzoyl-S-methyl-S-(pyridin-3-yl)-sulfoximine

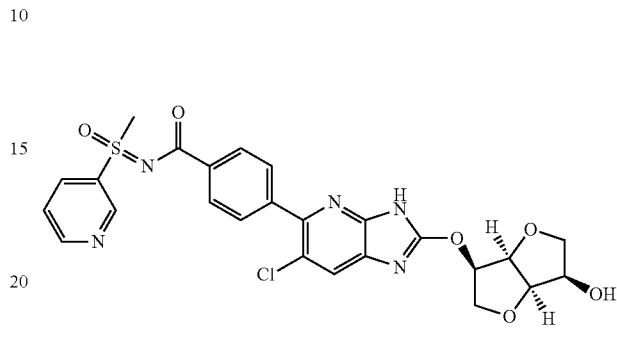

The title compound is prepared from N-4-(6-chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)benzoyl-S-methyl-S-(pyridin-3-yl)-sulfoximine following a procedure analogous to that described for Example 1. LC (method 1): $t_R$=0.80 min; Mass spectrum (ESI$^+$): m/z=556 [M+H]$^+$.

Example 20

N-4-(6-Chloro-2-((3R,3aR,6R,6aR)-6-hydroxyhexahydrofuro[3,2-b]furan-3-yloxy)-3H-imidazo[4,5-b]pyridin-5-yl)benzoyl-S-methyl-S-(tetrahydro-2H-pyran-4-yl)-sulfoximine

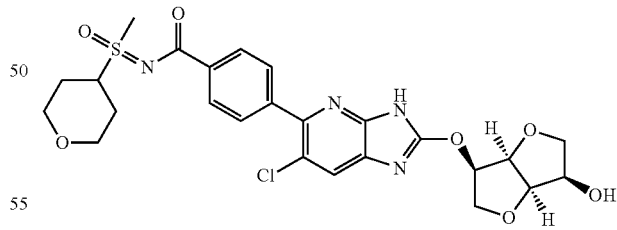

The title compound is prepared from N-4-(6-chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)benzoyl-S-methyl-S-(tetrahydro-2H-pyran-4-yl)-sulfoximine following a procedure analogous to that described for Example 1. LC (method 1): $t_R$=0.80 min; Mass spectrum (ESI$^+$): m/z=563 [M+H]$^+$.

Example 21

4-[6-Chloro-2-((3R,3aR,6R,6aR)-6-hydroxy-hexahydro-furo[3,2-b]furan-3-yloxy)-3H-imidazo[4,5-b]pyridin-5-yl]-N-(4-oxo-4λ6-[1,4]oxathian-4-ylidene)-benzamide

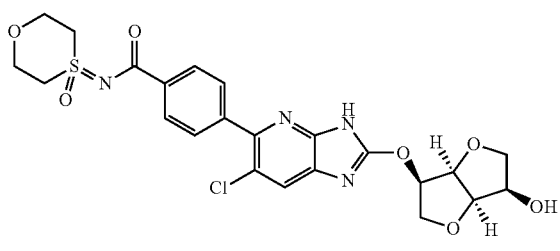 [SMILES: O=C(N=S1(=O)CCOCC1)c1ccc(-c2nc3[nH]c(O[C@@H]4CO[C@H]5[C@@H]4OC[C@H]5O)nc3cc2Cl)cc1]

The title compound is prepared from 4-[6-chloro-2-((3R,3aR,6R,6aR)-6-hydroxy-hexahydro-furo[3,2-b]furan-3-yloxy)-3-(2-trimethylsilanyl-ethoxymethyl)-3H-imidazo-[4,5-b]pyridin-5-yl]-N-(4-oxo-4λ6-[1,4]oxathian-4-ylidene)-benzamide following a procedure analogous to that described for Example 1. LC (method 1): $t_R$=0.78 min; Mass spectrum (ESI$^+$): m/z=535 [M+H]$^+$.

Example 22

N-(5-(4-(6-Chloro-2-((3R,3aR,6R,6aR)-6-hydroxyhexahydrofuro[3,2-b]furan-3-yloxy)-3H-imidazo[4,5-b]pyridin-5-yl)phenyl)pyridin-2-yl)-S,S-dimethyl-sulfoximide

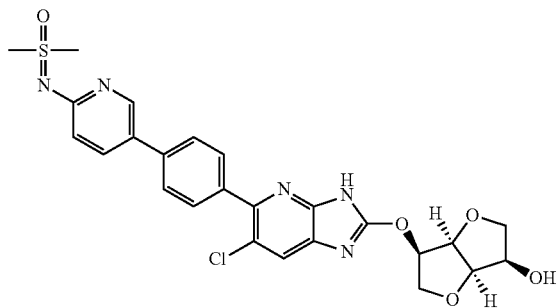 [SMILES: CS(C)(=O)=Nc1ccc(-c2ccc(-c3nc4[nH]c(O[C@@H]5CO[C@H]6[C@@H]5OC[C@H]6O)nc4cc3Cl)cc2)cn1]

The title compound is prepared from N-(5-(4-(6-chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)phenyl)pyridin-2-yl)-S,S-dimethylsulfoximide following a procedure analogous to that described for Example 1. LC (method 1): $t_R$=0.74 min; Mass spectrum (ESI$^+$): m/z=542 [M+H]$^+$.

Example 23

(3R,3aR,6R,6aR)-6-(6-Chloro-5-(4'-(S-methylsulfonimidoyl)biphenyl-4-yl)-3H-imidazo[4,5-b]pyridin-2-yloxy)hexahydrofuro[3,2-b]furan-3-ol

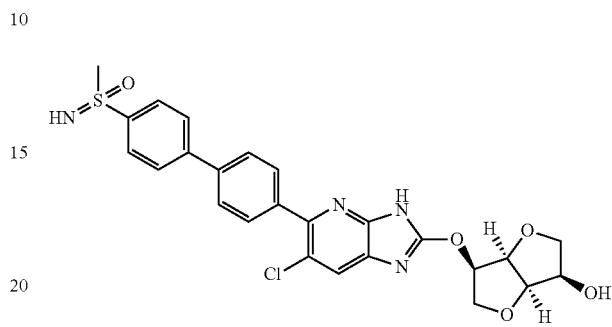

The title compound is prepared from (3R,3aR,6R,6aR)-6-(6-chloro-5-(4'-(N-tert-butoxycarbonyl-S-methylsulfonimidoyl)biphenyl-4-yl)-3-(2-trimethylsilanyl-ethoxymethyl)-3H-imidazo[4,5-b]pyridin-2-yloxy)hexahydrofuro[3,2-b]furan-3-ol following a procedure analogous to that described for Example 1. LC (method 1): $t_R$=0.78 min; Mass spectrum (ESI$^+$): m/z=527 [M+H]$^+$.

Example 24

4-[6-Chloro-2-((3R,3aR,6R,6aR)-6-hydroxy-hexahydro-furo[3,2-b]furan-3-yloxy)-3H-imidazo[4,5-b]pyridin-5-yl]-N-(1-oxo-hexahydro-1λ6-thiopyran-1-ylidene)-benzamide

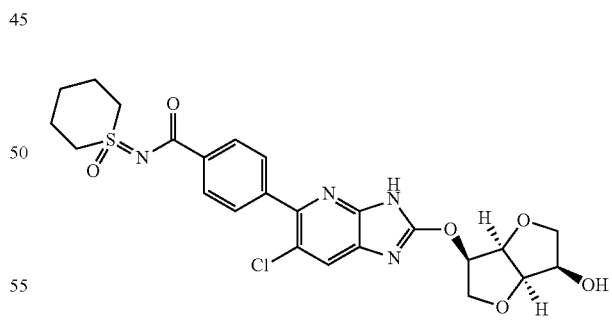

The title compound is prepared from 4-[6-chloro-2-((3R,3aR,6R,6aR)-6-hydroxy-hexahydro-furo[3,2-b]furan-3-yloxy)-3-(2-trimethylsilanyl-ethoxymethyl)-3H-imidazo-[4,5-b]pyridin-5-yl]-N-(1-oxo-hexahydro-1λ6-thiopyran-1-ylidene)-benzamide following a procedure analogous to that described for Example 1. LC (method 1): $t_R$=0.83 min; Mass spectrum (ESI$^+$): m/z=533 [M+H]$^+$.

Example 25

(R)-N-4-(6-Chloro-2-((3R,3aR,6R,6aR)-6-hydroxy-hexahydrofuro[3,2-b]furan-3-yloxy)-3H-imidazo[4,5-b]pyridin-5-yl)-benzoyl-S-methyl-5-phenylsulfoximine

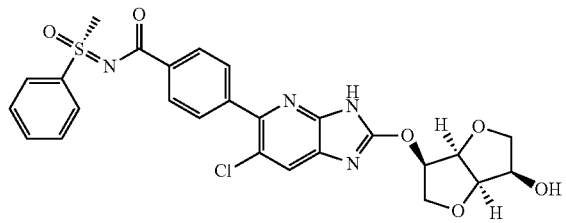 [SMILES: C[S@](=O)(=NC(=O)c1ccc(-c2nc3[nH]c(O[C@@H]4CO[C@H]5[C@@H]4OC[C@H]5O)nc3cc2Cl)cc1)c1ccccc1]

The title compound is prepared from (R)-N-4-(6-chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)benzoyl-S-methyl-5-phenylsulfoximine following a procedure analogous to that described for Example 1. LC (method 1): $t_R$=0.87 min; Mass spectrum (ESI$^+$): m/z=555 [M+H]$^+$.

Example 26

N-(4-(6-Chloro-2-((3R,3aR,6R,6aR)-6-hydroxy-hexahydrofuro[3,2-b]furan-3-yloxy)-3H-imidazo[4,5-b]pyridin-5-yl)phenyl)-S-methyl-S-(pyridin-4-yl)-sulfoximide

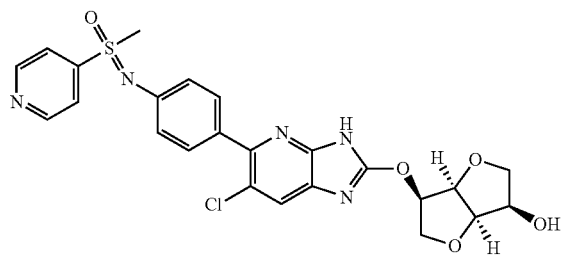 [SMILES: CS(=O)(=Nc1ccc(-c2nc3[nH]c(O[C@@H]4CO[C@H]5[C@@H]4OC[C@H]5O)nc3cc2Cl)cc1)c1ccncc1]

The title compound is prepared from N-(4-(6-chloro-2-((3R,3aR,6R,6aR)-6-hydroxyhexahydrofuro[3,2-b]furan-3-yloxy)-3-(2-trimethylsilanyl-ethoxy-methyl)-3H-imidazo[4,5-b]pyridin-5-yl)phenyl)-S-methyl-S-(pyridin-4-yl)-sulfoximide following a procedure analogous to that described for Example 1. LC (method 1): $t_R$=0.77 min; Mass spectrum (ESI$^+$): m/z=528 [M+H]$^+$.

Example 27

3R,3aR,6R,6aR)-6-(6-Chloro-5-(4-(5-(S-methylsulfonimidoyl)pyridin-2-yl)phenyl)-3H-imidazo[4,5-b]pyridin-2-yloxy)hexahydrofuro[3,2-b]furan-3-ol

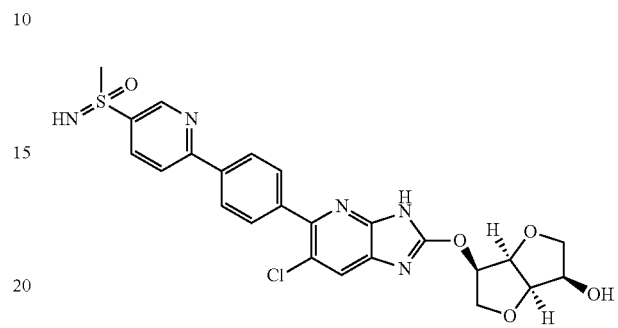

The title compound is prepared from (3R,3aR,6R,6aR)-6-(6-chloro-5-(4-(5-(N-tert-butoxycarbonyl-S-methylsulfonimidoyl)pyridin-2-yl)phenyl)-3-(2-trimethylsilanyl-ethoxy-methyl)-3H-imidazo[4,5-b]pyridin-2-yloxy) hexahydrofuro[3,2-b]furan-3-ol following a procedure analogous to that described for Example 1. LC (method 1): $t_R$=0.76 min; Mass spectrum (ESI$^+$): m/z=528 [M+H]$^+$.

Example 28

(3R,3aR,6R,6aR)-6-(6-Chloro-5-(4-(5-(N,S-dimethylsulfonimidoyl)pyridin-2-yl)phenyl)-3H-imidazo[4,5-b]pyridin-2-yloxy)hexahydrofuro[3,2-b]furan-3-ol

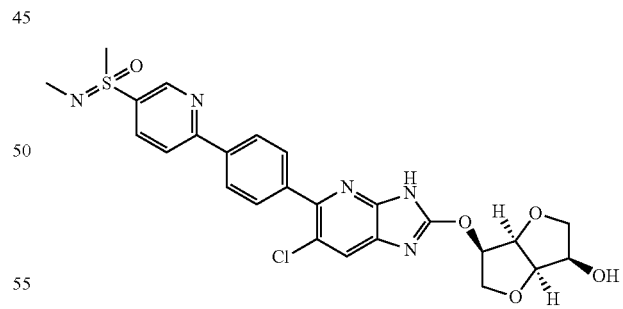

The title compound is prepared from (3R,3aR,6R,6aR)-6-(6-chloro-5-(4-(5-(N,S-dimethylsulfonimidoyl)pyridin-2-yl)phenyl)-3-(2-trimethylsilanyl-ethoxy-methyl)-3H-imidazo[4,5-b]pyridin-2-yloxy)hexahydrofuro[3,2-b]furan-3-ol following a procedure analogous to that described for Example 1. LC (method 1): $t_R$=0.78 min; Mass spectrum (ESI$^+$): m/z=542 [M+H]$^+$.

Example 29

(3R,3aR,6R,6aR)-6-(6-Chloro-5-(4-(4-(N,S-dimethylsulfonimidoyl)phenyl)piperazin-1-yl)-3H-imidazo[4,5-b]pyridin-2-yloxy)hexahydrofuro[3,2-b]furan-3-ol

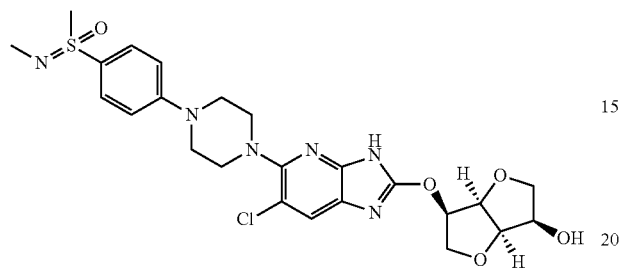

The title compound is prepared from (3R,3aR,6R,6aR)-6-(6-chloro-5-(4-(4-(N,S-dimethylsulfonimidoyl)phenyl)piperazin-1-yl)-3-(2-trimethylsilanyl-ethoxy-methyl)-3H-imidazo[4,5-b]pyridin-2-yloxy)hexahydrofuro[3,2-b]furan-3-ol following a procedure analogous to that described for Example 1. LC (method 1): $t_R$=0.78 min; Mass spectrum (ESI$^+$): m/z=549 [M+H]$^+$.

Example 30

N-(2-(4-(6-Chloro-2-((3R,3aR,6R,6aR)-6-hydroxyhexahydrofuro[3,2-b]furan-3-yloxy)-3H-imidazo[4,5-b]pyridin-5-yl)phenyl)pyridin-5-yl)-S,S-dimethylsulfoximide

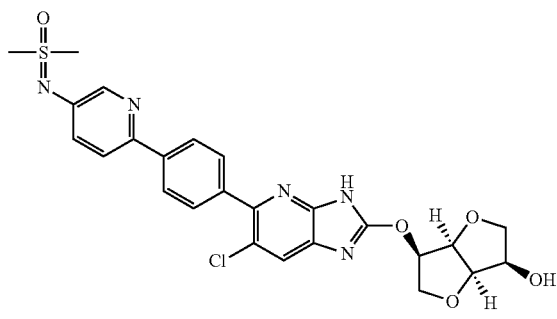 [SMILES: CS(C)(=O)=Nc1ccc(-c2ccc(-c3nc4[nH]c(O[C@@H]5CO[C@H]6[C@@H]5OC[C@H]6O)nc4cc3Cl)cc2)nc1]

The title compound is prepared from N-(2-(4-(6-chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)phenyl)pyridin-5-yl)-S,S-dimethylsulfoximide following a procedure analogous to that described for Example 1. LC (method 1): $t_R$=0.73 min; Mass spectrum (ESI$^+$): m/z=542 [M+H]$^+$.

Example 31

N-(1-(4-(6-Chloro-2-((3R,3aR,6R,6aR)-6-hydroxyhexahydrofuro[3,2-b]furan-3-yloxy)-3H-imidazo[4,5-b]pyridin-5-yl)phenyl)piperidin-4-ylmethyl)-S,S-dimethylsulfoximide

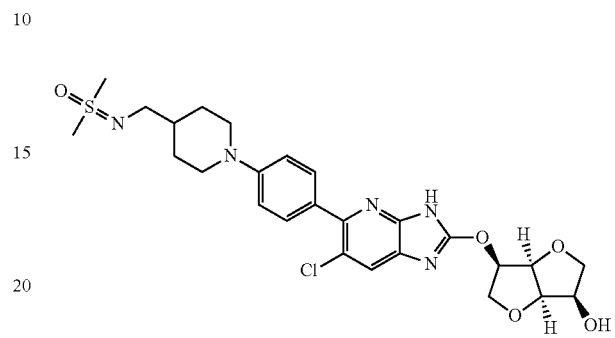

The title compound is prepared from N-(1-(4-(6-chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)phenyl)piperidin-4-ylmethyl)-S,S-dimethylsulfoximide following a procedure analogous to that described for Example 1. LC (method 4): $t_R$=0.66 min; Mass spectrum (ESI$^+$): m/z=562 [M+H]$^+$.

Example 32

N-(4-{5-[6-Chloro-2-((3R,3aR,6R,6aR)-6-hydroxyhexahydrofuro[3,2-b]furan-3-yloxy)-3H-imidazo[4,5-b]pyridin-5-yl]-pyridin-2-yl}-phenyl)-S,S-dimethylsulfoximide

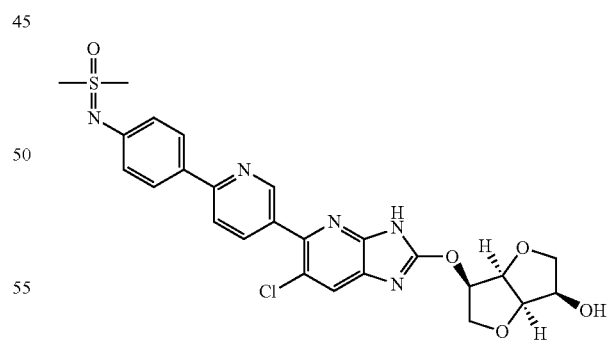

The title compound is prepared from N-(4-{5-[6-chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl]-pyridin-2-yl}-phenyl)-S,S-dimethylsulfoximide following a procedure analogous to that described for Example 1. LC (method 4): $t_R$=0.73 min; Mass spectrum (ESI$^+$): m/z=542 [M+H]$^+$.

Example 33 cis-(3R,3aR,6R,6aR)-6-(6-Chloro-5-[4-{4-(S-methylsulfonimidoyl)-cyclohexyl}-phenyl]-3H-imidazo[4,5-b]pyridin-2-yloxy)-hexahydro-furo[3,2-b]furan-3-ol

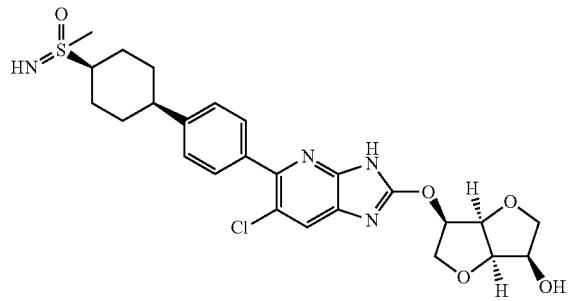 [SMILES: CS(=N)(=O)[C@H]1CC[C@@H](c2ccc(-c3nc4[nH]c(O[C@@H]5CO[C@H]6[C@@H]5OC[C@H]6O)nc4cc3Cl)cc2)CC1]

The title compound is prepared from N-(4-{4-[2-[(3R,3aR,6R,6aS)-6-(tert-butyl-dimethyl-silanyloxy)-hexahydro-furo[3,2-b]furan-3-yloxy]-6-chloro-3-(2-trimethylsilanyl-ethoxymethyl)-3H-imidazo[4,5-b]pyridin-5-yl]-phenyl}-cyclohexanyl)-(methyl)oxido-λ⁴-sulfanylidene])-2,2,2-trifluoro-acetamide following a procedure analogous to that described for Example 1. LC (method 1): $t_R$=0.77 min; Mass spectrum (ESI⁺): m/z=533 [M+H]⁺.

Example 34

N-(2-{4-[6-Chloro-2-((3R,3aR,6R,6aR)-6-hydroxyhexahydrofuro[3,2-b]furan-3-yloxy)-3H-imidazo[4,5-b]pyridin-5-yl]-phenyl}-pyrimidin-5-yl)-S,S-dimethylsulfoximide

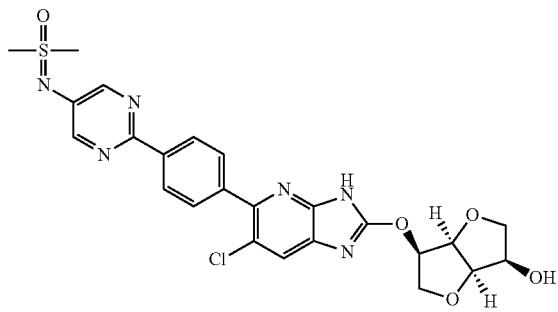 [SMILES: CS(C)(=O)=Nc1cnc(-c2ccc(-c3nc4[nH]c(O[C@@H]5CO[C@H]6[C@@H]5OC[C@H]6O)nc4cc3Cl)cc2)nc1]

The title compound is prepared from N-(2-{4-[6-chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl]-phenyl}-pyrimidin-5-yl)-S,S-dimethylsulfoximide following a procedure analogous to that described for Example 1. LC (method 1): $t_R$=0.79 min; Mass spectrum (ESI⁺): m/z=543 [M+H]⁺.

Example 35

N-(2-(4-(6-Chloro-2-((3R,3aR,6R,6aR)-6-hydroxyhexahydrofuro[3,2-b]furan-3-yloxy)-3H-imidazo[4,5-b]pyridin-5-yl)phenyl)pyridin-6-ylmethyl)-S,S-dimethylsulfoximide

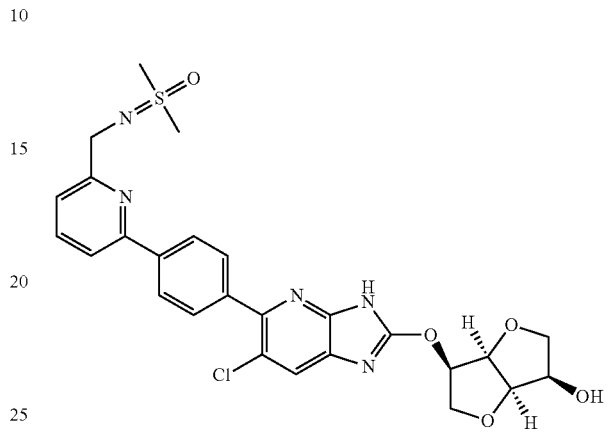

The title compound is prepared from N-(2-(4-(6-chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)phenyl)pyridin-6-ylmethyl)-S,S-dimethylsulfoximide following a procedure analogous to that described for Example 1. LC (method 1): $t_R$=0.75 min; Mass spectrum (ESI⁺): m/z=556 [M+H]⁺.

Example 36

N-(4-{4-[6-Chloro-2-((3R,3aR,6R,6aR)-6-hydroxyhexahydrofuro[3,2-b]furan-3-yloxy)-3H-imidazo[4,5-b]pyridin-5-yl]-phenyl}-pyridin-2-yl)-S,S-dimethylsulfoximide

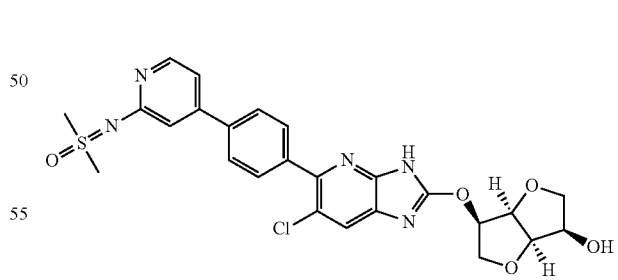

The title compound is prepared from N-(4-{4-[6-chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl]-phenyl}-pyridin-2-yl)-S,S-dimethylsulfoximide following a procedure analogous to that described for Example 1. LC (method 1): $t_R$=0.73 min; Mass spectrum (ESI⁺): m/z=542 [M+H]⁺.

Example 37

N-(2-{4-[6-Chloro-2-((3R,3aR,6R,6aR)-6-hydroxy-hexahydrofuro[3,2-b]furan-3-yloxy)-3H-imidazo[4,5-b]pyridin-5-yl]-phenyl}-pyridin-4-yl)-S,S-dimethylsulfoximide

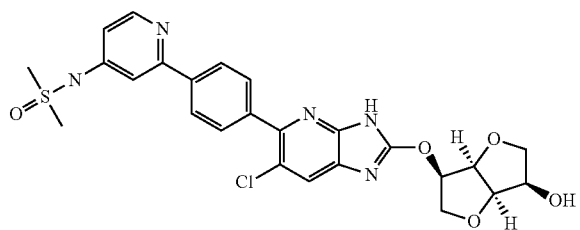

The title compound is prepared from N-(2-{4-[6-chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl]-phenyl}-pyridin-4-yl)-S,S-dimethylsulfoximide following a procedure analogous to that described for Example 1. LC (method 1): $t_R$=0.74 min; Mass spectrum (ESI$^+$): m/z=542 [M+H]$^+$.

Example 38

N-(4'-(6-Chloro-2-((3R,3aR,6R,6aR)-6-hydroxy-hexahydrofuro[3,2-b]furan-3-yloxy)-3H-imidazo[4,5-b]pyridin-5-yl)biphenyl-3-ylmethyl)-S,S-dimethylsulfoximide

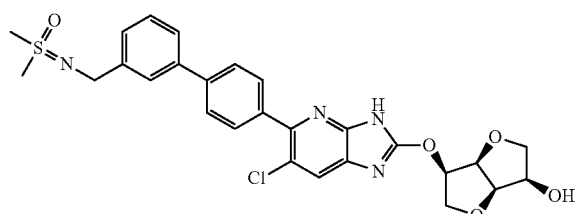

A mixture of N-(4'-(6-chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)biphenyl-3-ylmethyl)-S,S-dimethylsulfoximide (47 mg), methanol (50 µL), and trifluoroacetic acid (94 µL) in dichloromethane (3 mL) is stirred at 45° C. overnight. The mixture is diluted with dichloromethane (25 mL), washed with 2 N aqueous Na$_2$CO$_3$ solution, dried over MgSO$_4$, and concentrated in vacuo. The residue is purified by HPLC to give the title compound. LC (method 5): $t_R$=0.71 min; Mass spectrum (ESI$^+$): m/z=555 [M+H]$^+$.

Example 39

N-(5-{4-[6-Chloro-2-((3R,3aR,6R,6aR)-6-hydroxy-hexahydrofuro[3,2-b]furan-3-yloxy)-3H-imidazo[4,5-b]pyridin-5-yl]-phenyl}-pyrazin-2-yl)-S,S-dimethylsulfoximide

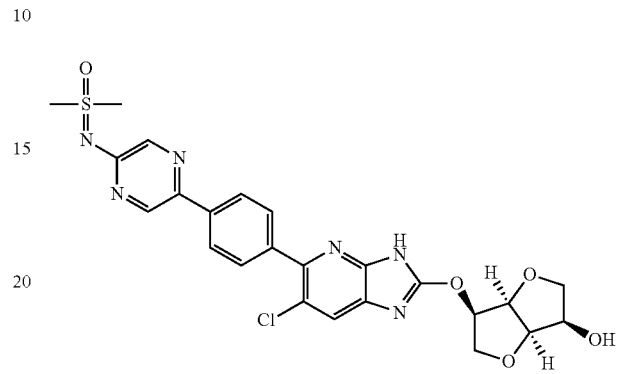

The title compound is prepared from N-(5-{4-[6-chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl]-phenyl}-pyrazin-2-yl)-S,S-dimethylsulfoximide following a procedure analogous to that described for Example 1. LC (method 1): $t_R$=0.80 min; Mass spectrum (ESI$^+$): m/z=543 [M+H]$^+$.

Example 40

3R,3aR,6R,6aR)-6-{6-Chloro-5-[4-(1-imino-1-oxo-1,2,3,6-tetrahydro-1$\lambda^6$-thiopyran-4-yl)-phenyl]-3H-imidazo[4,5-b]pyridin-2-yloxy}-hexahydro-furo[3,2-b]furan-3-ol

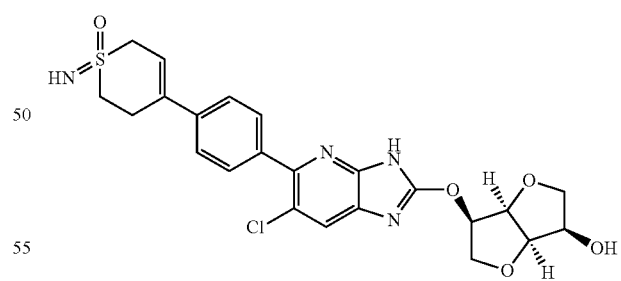

The title compound is prepared from N-(4-{4-[6-chloro-2-((3R,3aR,6R,6aR)-6-hydroxy-hexahydrofuro[3,2-b]furan-3-yloxy)-3-(2-trimethylsilanyl-ethoxymethyl)-3H-imidazo[4,5-b]pyridin-5-yl]-phenyl}-1-oxo-1,2,3,6-tetrahydro-1$\lambda^6$-thiopyran-1-ylidene)-2,2,2-trifluoroacetamide following a procedure analogous to that described for Example 1. LC (method 1): $t_R$=0.71 min; Mass spectrum (ESI$^+$): m/z=503 [M+H]$^+$.

Example 41

(3R,3aR,6R,6aR)-6-(6-Chloro-5-(3'-(S-methylsulfonimidoyl)biphenyl-4-yl)-3H-imidazo[4,5-b]pyridin-2-yloxy)hexahydrofuro[3,2-b]furan-3-ol

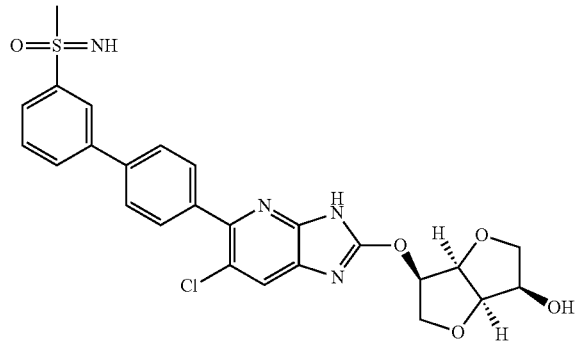 [SMILES: CS(=N)(=O)c1cccc(-c2ccc(-c3nc4[nH]c(O[C@@H]5CO[C@H]6[C@@H]5OC[C@H]6O)nc4cc3Cl)cc2)c1]

The title compound is prepared from (3R,3aR,6R,6aR)-6-(6-chloro-5-(3'-(N-(2,2,2-trifluoroacetyl)-S-methyl-sulfonimidoyl)biphenyl-4-yl)-3-(2-trimethylsilanyl-ethoxymethyl)-3H-imidazo[4,5-b]pyridin-2-yloxy)hexahydrofuro[3,2-b]furan-3-ol following a procedure analogous to that described for Example 1. LC (method 4): $t_R$=0.81 min; Mass spectrum (ESI$^+$): m/z=527 [M+H]$^+$.

Example 42

N-(4-{5-[6-Chloro-2-((3R,3aR,6R,6aR)-6-hydroxyhexahydrofuro[3,2-b]furan-3-yloxy)-3H-imidazo[4,5-b]pyridin-5-yl]-pyrimidin-2-yl}-phenyl)-S,S-dimethylsulfoximide

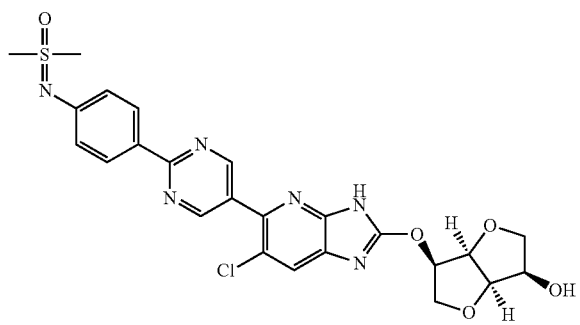

The title compound is prepared from N-(4-{5-[6-chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl]-pyrimidin-2-yl}-phenyl)-S,S-dimethylsulfoximide following a procedure analogous to that described for Example 38. LC (method 1): $t_R$=0.79 min; Mass spectrum (ESI$^+$): m/z=543 [M+H]$^+$.

Example 43

N-(2-{4-[6-Chloro-2-((3R,3aR,6R,6aR)-6-hydroxyhexahydrofuro[3,2-b]furan-3-yloxy)-3H-imidazo[4,5-b]pyridin-5-yl]-phenyl}-2,3-dihydro-1H-isoindol-5-yl)-S,S-dimethylsulfoximide

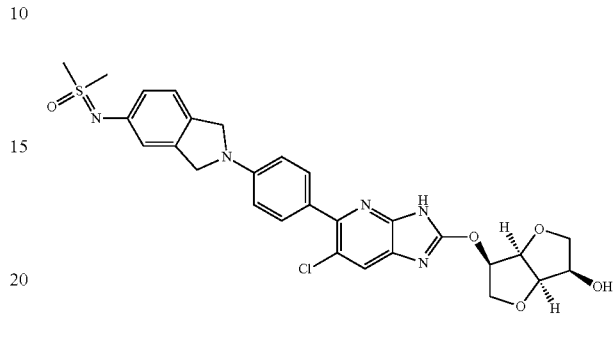

The title compound is prepared from N-(2-{4-[6-chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl]-phenyl}-2,3-dihydro-1H-isoindol-5-yl)-S,S-dimethylsulfoximide following a procedure analogous to that described for Example 38. LC (method 5): $t_R$=0.74 min; Mass spectrum (ESI$^+$): m/z=582 [M+H]$^+$.

Example 44

N-(6-{4-[6-Chloro-2-((3R,3aR,6R,6aR)-6-hydroxyhexahydrofuro[3,2-b]furan-3-yloxy)-3H-imidazo[4,5-b]pyridin-5-yl]-phenyl}-6,7-dihydro-5H-pyrrolo[3,4-b]pyridin-2-yl)-S,S-dimethylsulfoximide

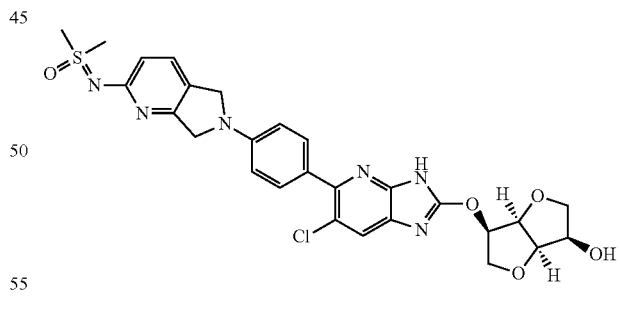

The title compound is prepared from N-(6-{4-[6-chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl]-phenyl}-6,7-dihydro-5H-pyrrolo[3,4-b]pyridin-2-yl)-S,S-dimethylsulfoximide following a procedure analogous to that described for Example 38. LC (method 5): $t_R$=0.72 min; Mass spectrum (ESI$^+$): m/z=583 [M+H]$^+$.

Example 45

N-(4'-(6-Chloro-2-((3R,3aR,6R,6aR)-6-hydroxy-hexahydrofuro[3,2-b]furan-3-yloxy)-3H-imidazo[4,5-b]pyridin-5-yl)biphenyl-4-ylmethyl)-S,S-dimethyl-sulfoximide

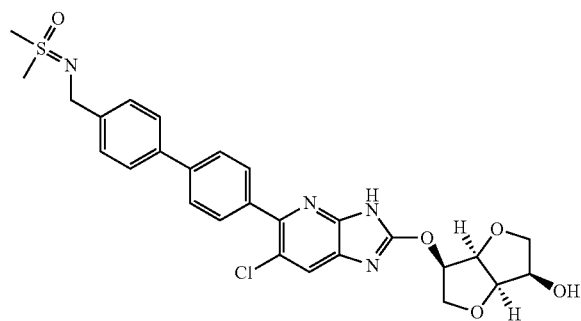 [SMILES: CS(C)(=O)=NCc1ccc(-c2ccc(-c3nc4[nH]c(O[C@@H]5CO[C@H]6[C@@H]5OC[C@H]6O)nc4cc3Cl)cc2)cc1]

The title compound is prepared from N-(4'-(6-chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)biphenyl-4-ylmethyl)-S,S-dimethylsulfoximide following a procedure analogous to that described for Example 38. LC (method 5): $t_R$=0.70 min; Mass spectrum (ESI$^+$): m/z=555 [M+H]$^+$.

Example 46

N-(2-(4-(6-Chloro-2-((3R,3aR,6R,6aR)-6-hydroxy-hexahydrofuro[3,2-b]furan-3-yloxy)-3H-imidazo[4,5-b]pyridin-5-yl)phenyl)pyridin-4-ylmethyl)-S,S-dimethylsulfoximide

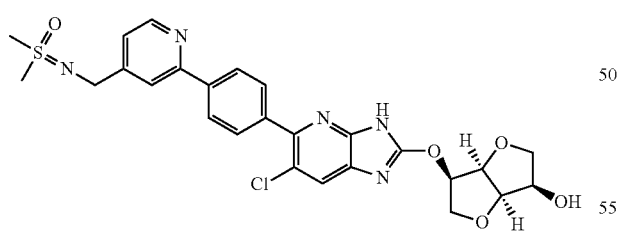

The title compound is prepared from N-(2-(4-(6-chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)phenyl)pyridin-4-ylmethyl)-S,S-dimethylsulfoximide following a procedure analogous to that described for Example 1. LC (method 3): $t_R$=0.68 min; Mass spectrum (ESI$^+$): m/z=556 [M+H]$^+$.

Example 47

N-(6-{4-[6-Chloro-2-((3R,3aR,6R,6aR)-6-hydroxy-hexahydrofuro[3,2-b]furan-3-yloxy)-3H-imidazo[4,5-b]pyridin-5-yl]-phenyl}-pyridin-2-yl)-S,S-dimethylsulfoximide

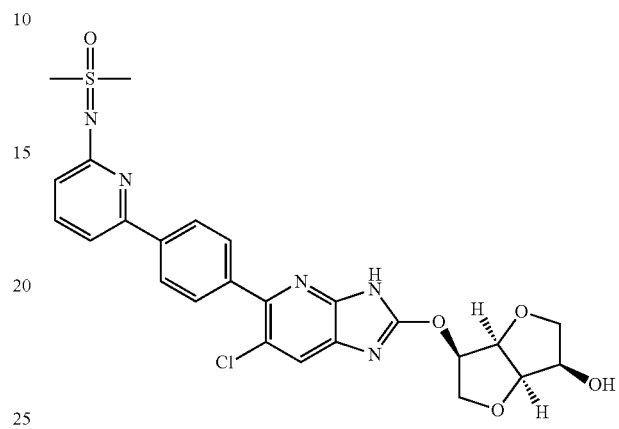

The title compound is prepared from N-(6-{4-[6-chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl]-phenyl}-pyridin-2-yl)-S,S-dimethylsulfoximide following a procedure analogous to that described for Example 1. LC (method 3): $t_R$=0.76 min; Mass spectrum (ESI$^+$): m/z=542 [M+H]$^+$.

Example 48

N-(6-(4-(6-Chloro-2-((3R,3aR,6R,6aR)-6-hydroxy-hexahydrofuro[3,2-b]furan-3-yloxy)-3H-imidazo[4,5-b]pyridin-5-yl)phenyl)pyridin-3-ylmethyl)-S,S-dimethylsulfoximide

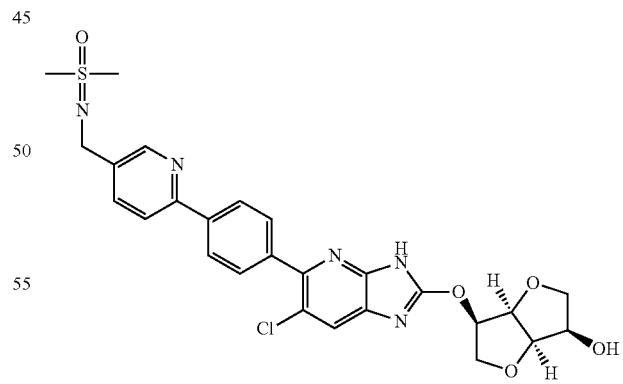

The title compound is prepared from N-(6-(4-(6-chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl)phenyl)pyridin-3-ylmethyl)-S,S-dimethylsulfoximide following a procedure analogous to that described for Example 1. LC (method 1): $t_R$=0.70 min; Mass spectrum (ESI$^+$): m/z=556 [M+H]$^+$.

Example 49

(3R,3aR,6R,6aR)-6-(6-Chloro-5-(4-(5-(S-methylsulfonimidoyl)pyrimidin-2-yl)phenyl)-3H-imidazo[4,5-b]pyridin-2-yloxy)hexahydrofuro[3,2-b]furan-3-ol

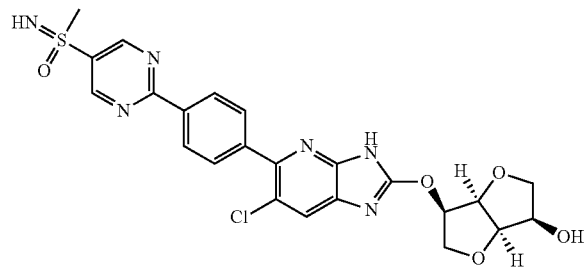 [SMILES: CS(=N)(=O)c1cnc(-c2ccc(-c3nc4[nH]c(O[C@@H]5CO[C@H]6[C@@H]5OC[C@H]6O)nc4cc3Cl)cc2)nc1]

A mixture of (3R,3aR,6R,6aR)-6-(6-chloro-5-(4-(5-(N-(2,2,2-trifluoroacetyl)-S-methylsulfonimidoyl)pyrimidin-2-yl)phenyl)-3-(2-trimethylsilanyl-ethoxy-methyl)-3H-imidazo[4,5-b]pyridin-2-yloxy)hexahydrofuro[3,2-b]furan-3-ol (238 mg) and trifluoroacetic acid (2 mL) in dichloromethane (3 mL) is stirred at room temperature overnight. The mixture concentrated in vacuo, methanol (5 mL) and 2 N aqueous Na$_2$CO$_3$ solution (0.50 mL) are added. The resulting mixture is stirred for two days at room temperature and concentrated in vacuo. The residue is chromatographed on silica gel (dichloromethane/methanol 95:5→60:40) to give the title compound. LC (method 1): $t_R$=0.78 min; Mass spectrum (ESI$^+$): m/z=529 [M+H]$^+$.

Example 50

N-(6-{4-[6-Chloro-2-((3R,3aR,6R,6aR)-6-hydroxy-hexahydrofuro[3,2-b]furan-3-yloxy)-3H-imidazo[4,5-b]pyridin-5-yl]-phenyl}-pyridazin-3-yl)-S,S-dimethylsulfoximide

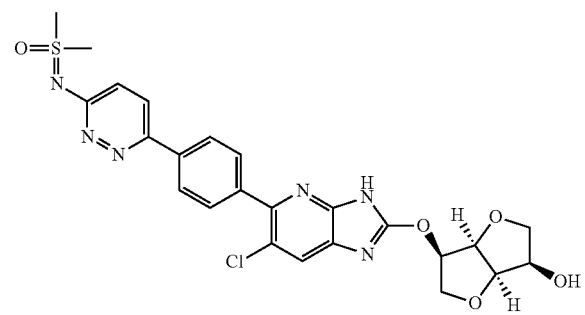 [SMILES: CS(C)(=O)=Nc1ccc(-c2ccc(-c3nc4[nH]c(O[C@@H]5CO[C@H]6[C@@H]5OC[C@H]6O)nc4cc3Cl)cc2)nn1]

The title compound is prepared from N-(6-{4-[6-chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl]-phenyl}-pyridazin-3-yl)-S,S-dimethylsulfoximide following a procedure analogous to that described for Example 38. LC (method 1): $t_R$=0.74 min; Mass spectrum (ESI$^+$): m/z=543 [M+H]$^+$.

Example 51

N-(5-{4-[6-Chloro-2-((3R,3aR,6R,6aR)-6-hydroxy-hexahydrofuro[3,2-b]furan-3-yloxy)-3H-imidazo[4,5-b]pyridin-5-yl]-phenyl}-pyridin-2-ylmethyl)-S,S-dimethylsulfoximide

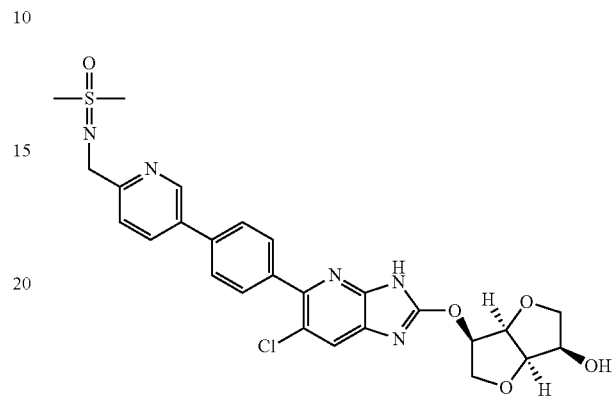

The title compound is prepared from N-(5-{4-[6-chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl]-phenyl}-pyridin-2-ylmethyl)-S,S-dimethylsulfoximide following a procedure analogous to that described for Example 1. LC (method 1): $t_R$=0.71 min; Mass spectrum (ESI$^+$): m/z=556 [M+H]$^+$.

Example 52

(3R,3aR,6R,6aR)-6-(6-Chloro-5-(4'-(S-methylsulfonimidoylmethyl)biphenyl-4-yl)-3H-imidazo[4,5-b]pyridin-2-yloxy)hexahydrofuro[3,2-b]furan-3-ol

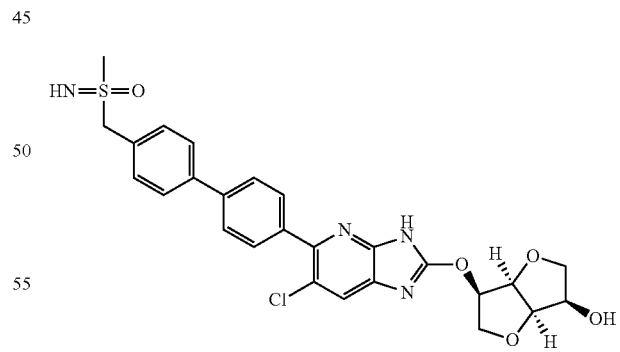

The title compound is prepared from (3R,3aR,6R,6aR)-6-(6-chloro-5-(4'-(N-(2,2,2-trifluoroacetyl)-S-methyl-sulfonimidoylmethyl)biphenyl-4-yl)-3-(2-trimethylsilanyl-ethoxy-methyl)-3H-imidazo[4,5-b]pyridin-2-yloxy) hexahydrofuro[3,2-b]furan-3-ol following a procedure analogous to that described for Example 1. LC (method 1): $t_R$=0.78 min; Mass spectrum (ESI$^+$): m/z=541 [M+H]$^+$.

Example 53

N-(4-{4-[6-Chloro-2-((3R,3aR,6R,6aR)-6-hydroxy-hexahydrofuro[3,2-b]furan-3-yloxy)-3-(2-trimethyl-silanyl-ethoxymethyl)-3H-imidazo[4,5-b]pyridin-5-yl]-phenyl}-pyridin-2-ylmethyl)-S,S-dimethylsulfoximide

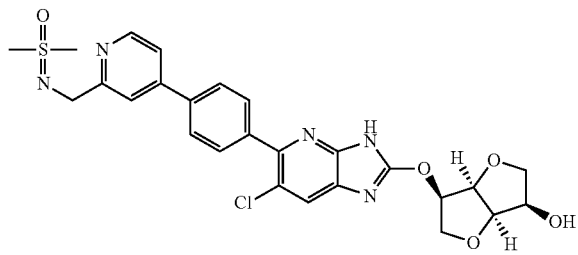 [SMILES: CS(C)(=O)=NCc1cc(-c2ccc(-c3nc4[nH]c(O[C@@H]5CO[C@H]6[C@@H]5OC[C@H]6O)nc4cc3Cl)cc2)ccn1]

The title compound is prepared from N-(4-{4-[6-chloro-2-((3R,3aR,6R,6aR)-6-hydroxyhexahydrofuro[3,2-b]furan-3-yloxy)-3-(2-trimethylsilanyl-ethoxymethyl)-3H-imidazo[4,5-b]pyridin-5-yl]-phenyl}-pyridin-2-ylmethyl)-S,S-dimethylsulfoximide following a procedure analogous to that described for Example 38. LC (method 4): $t_R$=0.71 min; Mass spectrum (ESI$^+$): m/z=556 [M+H]$^+$.

Example 54

(3R,3aR,6R,6aR)-6-{6-Chloro-5-[4-(1-imino-1-oxo-hexahydro-1λ$^6$-thiopyran-4-yl)-phenyl]-3H-imidazo[4,5-b]pyridin-2-yloxy}-hexahydro-furo[3,2-b]furan-3-ol (Diasteromer 1)

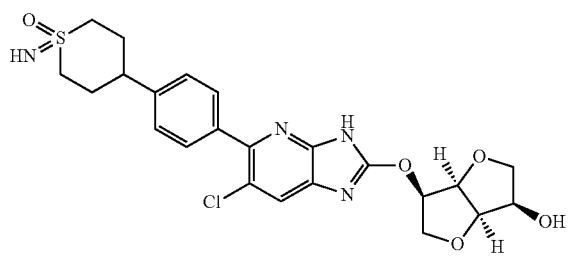 [SMILES: N=S1(=O)CCC(c2ccc(-c3nc4[nH]c(O[C@@H]5CO[C@H]6[C@@H]5OC[C@H]6O)nc4cc3Cl)cc2)CC1]

The title compound is prepared from (3R,3aR,6R,6aR)-6-{6-chloro-5-[4-(1-imino-1-oxo-hexahydro-1λ$^6$-thiopyran-4-yl)-phenyl]-1-(2-trimethylsilanyl-ethoxy-methyl)-1H-imidazo[4,5-b]pyridin-2-yloxy}-hexahydro-furo[3,2-b]furan-3-ol (Diastereomer 1) following a procedure analogous to that described for Example 1. LC (method 1): $t_R$=0.71 min; Mass spectrum (ESI$^+$): m/z=505 [M+H]$^+$.

Example 55

(3R,3aR,6R,6aR)-6-{6-Chloro-5-[4-(1-imino-1-oxo-hexahydro-1λ$^6$-thiopyran-4-yl)-phenyl]-3H-imidazo[4,5-b]pyridin-2-yloxy}-hexahydro-furo[3,2-b]furan-3-ol (Diasteromer 2)

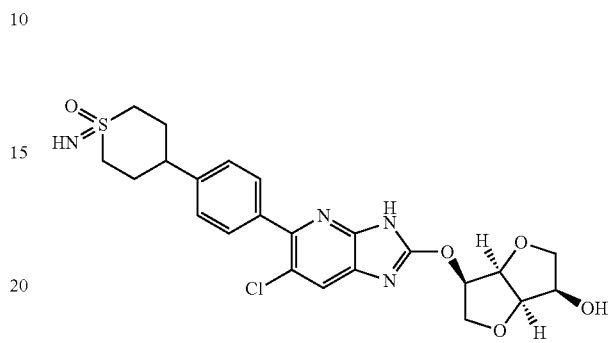

The title compound is prepared from (3R,3aR,6R,6aR)-6-{6-chloro-5-[4-(1-imino-1-oxo-hexahydro-1λ$^6$-thiopyran-4-yl)-phenyl]-1-(2-trimethylsilanyl-ethoxy-methyl)-1H-imidazo[4,5-b]pyridin-2-yloxy}-hexahydro-furo[3,2-b]furan-3-ol (Diastereomer 2) following a procedure analogous to that described for Example 1. LC (method 1): $t_R$=0.73 min; Mass spectrum (ESI$^+$): m/z=505 [M+H]$^+$.

Example 56

N-(4-(6-Chloro-2-((3R,3aR,6R,6aR)-6-hydroxy-hexahydrofuro[3,2-b]furan-3-yloxy)-3H-imidazo[4,5-b]pyridin-5-yl)phenyl)-S,S-dimethyl-sulfondiimine

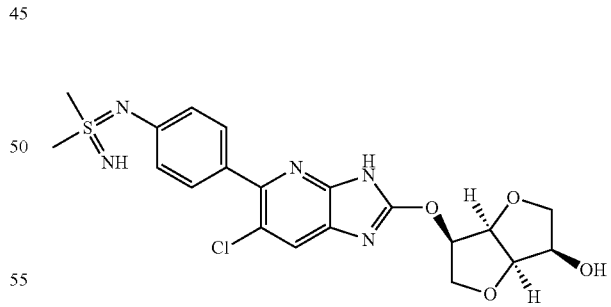

The title compound is prepared from N-(4-(6-chloro-2-((3R,3aR,6R,6aR)-6-hydroxyhexahydrofuro[3,2-b]furan-3-yloxy)-3-(2-trimethylsilanyl-ethoxy-methyl)-3H-imidazo[4,5-b]pyridin-5-yl)phenyl)-S,S-dimethyl-sulfondiimine following a procedure analogous to that described for Example 1. LC (method 1): $t_R$=0.67 min; Mass spectrum (ESI$^+$): m/z=464 [M+H]$^+$.

Example 57

(3R,3aR,6R,6aR)-6-{6-Chloro-5-[4-(2-methylimino-2-oxo-hexahydro-2λ⁶-thieno[3,4-c]pyrrol-5-yl)-phenyl]-3H-imidazo[4,5-b]pyridin-2-yloxy}-hexahydro-furo[3,2-b]furan-3-ol

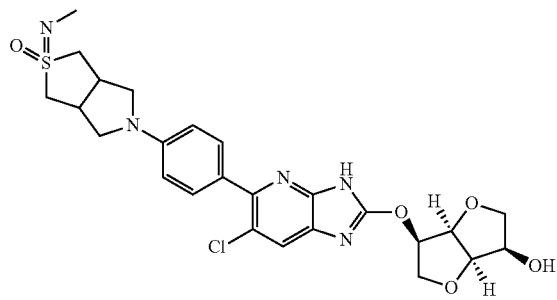 [SMILES: CN=S1(=O)CC2CN(c3ccc(-c4nc5[nH]c(O[C@@H]6CO[C@H]7[C@@H]6OC[C@H]7O)nc5cc4Cl)cc3)CC2C1]

The title compound is prepared from (3R,3aR,6R,6aR)-6-{6-chloro-5-[4-(2-methylimino-2-oxo-hexahydro-2λ6-thieno[3,4-c]pyrrol-5-yl)-phenyl]-3-(2-trimethylsilanyl-ethoxy-methyl)-3H-imidazo[4,5-b]pyridin-2-yloxy}-hexahydro-furo[3,2-b]furan-3-ol by treatment with trifluoroacetic acid in toluene at 50° C. LC (method 4): $t_R$=0.71 min; Mass spectrum (ESI⁺): m/z=546 [M+H]⁺.

The invention claimed is:

1. A compound of formula I,

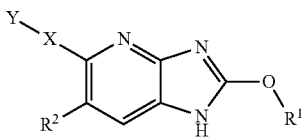

wherein

R¹ is selected from the group consisting of

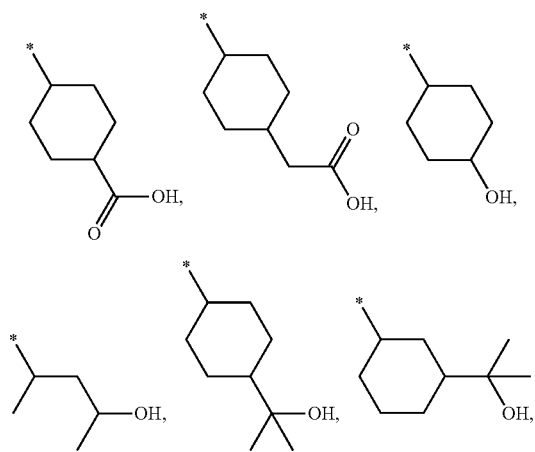

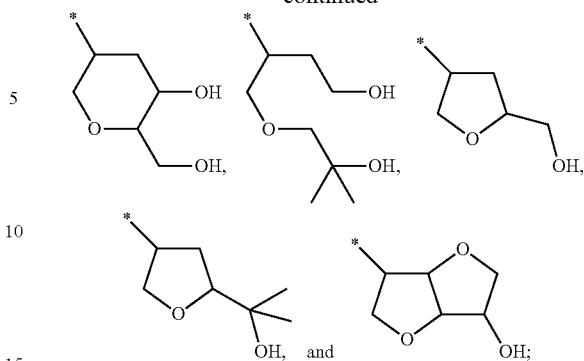

R² is selected from the group consisting of F, Cl, Br, $C_{1-4}$-alkyl, and $C_{1-4}$-alkyl-O—, wherein any alkyl group and subgroup is optionally substituted with 1 or more F atoms;

X is selected from the group consisting of a bond, a divalent piperidinyl, a divalent piperazinyl, a phenylene, pyridinylene, pyrimidinylene, and pyridazinylene group, wherein said divalent piperidinyl and piperazinyl group is optionally substituted with F, H₃C—, or H₃C—O—, and wherein said phenylene, pyridinylene, pyrimidinylene, and pyridazinylene group are optionally substituted with F, Cl, Br, NC—, HO₂C—, H₃C—, H₃C—O—, F₃C—, or F₃CO—; and Y is selected from the group consisting of cyclohexyl, cyclohexenyl, piperidinyl, phenyl, pyridinyl, pyridazinyl, pyrazinyl, isoindolinyl, azaisoindolinyl, and pyrimidinyl, which are mandatorily substituted with a group selected from $R^S R^{S'}(O=)S=N—$, $R^S R^{S'}(O=)S=N—C_{1-3}$-alkyl-, $R^S R^{S'}(O=)S=N—C(=O)—$, $(R^N)N=S(=O)(R^S)—$, $(R^N)N=S(=O)(R^S)—C_{1-3}$-alkyl-, and $R^S R^{S'}(R^{N'}—N=)S=N—$, and wherein said cyclohexyl, cyclohexenyl and piperidinyl groups are optionally substituted with F, H₃C—, and H₃C—O—, and wherein said phenyl, pyridinyl, pyridazinyl, pyrazinyl, isoindolinyl, azaisoindolinyl and pyrimidinyl groups are optionally substituted with F, Cl, Br, NC—, HO₂C—, H₃C—, H₃C—O—, F₃C—, or F₃CO—;

a saturated or partly unsaturated heterocyclyl group selected from cyclohexyl, cyclohexenyl, piperidinyl and aza- bicyclooctyl each containing a —S(=O)(=N—R^N)—group, optionally substituted with 1 to 3 groups independently selected from F, HO—, NC—, $C_{1-4}$-alkyl- and $C_{1-4}$-alkyl-O—, wherein $R^N$ is selected from H, NC—, $C_{1-4}$-alkyl, $C_{1-4}$-alkyl-C(=O)—, $C_{1-4}$-alkyl-O—C(=O)—, $C_{3-7}$-cycloalkyl, $C_{3-7}$-cycloalkyl-$C_{1-3}$-alkyl-, $C_{3-7}$-cycloalkyl-C(=O)—, heterocyclyl, heterocyclyl-CH₂—, heterocyclyl-C(=O)—, aryl, aryl-$C_{1-3}$-alkyl-, aryl -C(=O)—, heteroaryl, heteroaryl-$C_{1-3}$-alkyl-, and heteroaryl-C(=O)—, and $R^{N'}$ is selected from H, NC—, $C_{1-4}$-alkyl-, aryl, aryl-$C_{1-3}$-alkyl-, heteroaryl, heteroaryl-$C_{1-3}$-alkyl-, wherein any alkyl, cycloalkyl and heterocyclyl group is optionally substituted with 1 to 3 groups independently selected from F, $C_{1-3}$-alkyl-O—, ($C_{1-3}$- alkyl)$_2$-N—, HO$_2$C—, C$_{1-3}$-alkyl-C(=O)—, and C$_{1-3}$-alkyl-S(=O)$_2$—, and wherein any aryl and heteroaryl group is optionally substituted with 1 to 3 groups independently selected from F, Cl, Br, I, HO—, NC—, HO$_2$C—, C$_{1-3}$-alkyl, C$_{1-3}$-alkyl-O—, H$_2$N—, C$_{1-3}$-alkyl-NH—, (C$_{1-3}$-alkyl)$_2$-N—, and C$_{1-3}$-alkyl -S(=O)$_2$—, and wherein $R^{N'}$ is selected from H, NC—, C$_{1-4}$-alkyl, C$_{3-7}$-cycloalkyl, aryl-C$_{1-3}$-alkyl-, heteroaryl, heteroaryl-C$_{1-3}$-alkyl-, wherein any alkyl and cycloalkyl optionally substituted with 1 to 3 groups independently selected from F, C$_{1-3}$-alkyl-O—, (C$_{1-3}$-alkyl)$_2$-N—, HO$_2$C—, C$_{1-3}$-alkyl-C(=O)—, and C$_{1-3}$-alkyl-S(=O)$_2$—, and wherein any aryl and heteroaryl group is optionally substituted with 1 to 3 groups independently selected from F, Cl, Br, I, HO—, NC—, HO$_2$C—, C$_{1-3}$-alkyl, C$_{1-3}$-alkyl-O—, H$_2$N—, C$_{1-3}$-alkyl-NH—, (C$_{1-3}$-alkyl)$_2$-N—, and C$_{1-3}$-alkyl -S(=O)$_2$—, and wherein $R^S$ and $R^{S'}$ are independently selected from C$_{1-4}$-alkyl, C$_{3-7}$-cycloalkyl, C$_{3-7}$-cycloalkyl-C$_{1-3}$-alkyl-, heterocyclyl, heterocyclyl-C$_{1-3}$-alkyl-, aryl, aryl-CH$_2$—, heteroaryl, and heteroaryl-C$_{1-3}$-alkyl-, wherein any alkyl, cycloalkyl and heterocyclyl group is optionally substituted with 1 to 3 groups independently selected from C$_{1-3}$-alkyl-O—, (C$_{1-3}$-alkyl)$_2$-N—, HO$_2$C—, C$_{1-3}$-alkyl-C(=O)—, and C$_{1-3}$-alkyl-S(=O)$_2$—, and wherein any aryl and heteroaryl group is optionally substituted with 1 to 3 groups independently selected from F, Cl, Br, I, HO—, NC—, C$_{1-3}$-alkyl, C$_{1-3}$-alkyl-O—, H$_2$N—, C$_{1-3}$-alkyl-NH—, (C$_{1-3}$-alkyl)$_2$-N—, and C$_{1-3}$-alkyl-S(=O)$_2$, or $R^S$ and $R^{S'}$ together with the S-atom these groups are attached to form a 5-7 membered saturated monocyclic ring system containing 0 to 1 heteroatoms selected from —NR$^{N''}$— and O, optionally substituted with 1 to 3 groups independently selected from F, HO—, C$_{1-3}$-alkyl, C$_{1-3}$-alkyl-O—, H$_2$N—, C$_{1-3}$-alkyl-NH—, (C$_{1-3}$-alkyl)$_2$-N—, and C$_{1-3}$-alkyl-S(=O)$_2$—, and wherein $R^{N''}$ is selected from H, H$_3$C—, H$_5$C$_2$—, and cyclopropyl;

or a salt thereof.

2. A compound according to claim 1, wherein $R^1$ is selected from the group consisting of

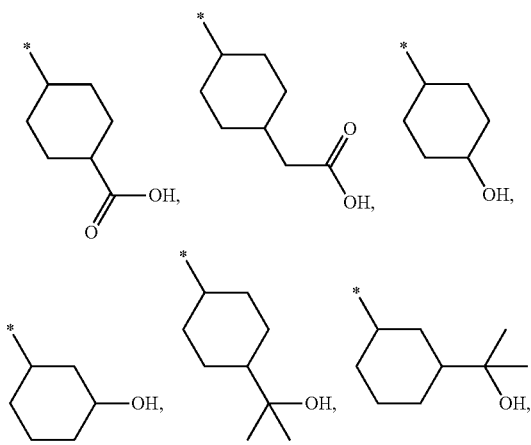

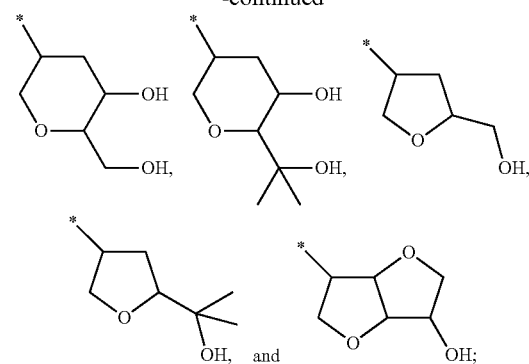

$R^2$ is defined as in claim 1; and

X is selected from the group consisting of a bond, a divalent piperidinyl, a divalent piperazinyl, a phenylene, pyridinylene, pyrimidinylene, and pyridazinylene group, wherein said divalent piperidinyl and piperazinyl group is optionally substituted with F, H$_3$C—, or H$_3$C—O—, and wherein said phenylene, pyridinylene, pyrimidinylene, and pyridazinylene group are optionally substituted with F, Cl, Br, NC—, HO$_2$C—, H$_3$C—, H$_3$C—O—, F$_3$C—, or F$_3$CO—; and Y is selected from the group consisting of a saturated or partly unsaturated monocyclic 5-7 membered ring system, optionally substituted with F, H$_3$C—, and H$_3$C—O—, wherein mandatorily one ring member is a —S(=O)(=N—R$^N$)— group and optionally one ring member is a —NR$^{N''}$-group, wherein $R^N$ and $R^{N''}$ are defined as in claim 1;

or a salt thereof.

3. A compound according to claim 1, wherein $R^1$ is selected from the group consisting of

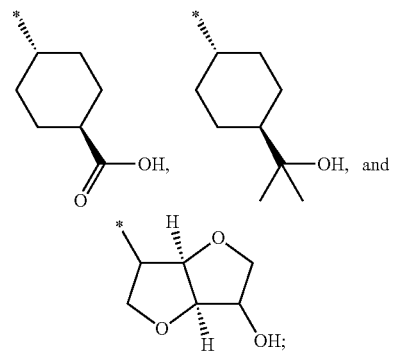

$R^2$ is selected from the group consisting of F, Cl, H$_3$C—, H$_3$C—O—, F$_3$C—, and F$_3$C—O—;

X is defined as in claim 1; and

Y is selected from the group consisting of cyclohexyl, piperidinyl, phenyl and pyridinyl, which are mandatorily substituted with a group selected from R$^S$R$^{S'}$(O=)S=N—, R$^S$R$^{S'}$(O=)S=N—CH$_2$—, R$^S$R$^{S'}$(O=)S=N—C(=O)—, (R$^N$)N=S(=O)(R$^S$)—, (R$^N$)N=S(=O)(R$^S$)—CH$_2$—, and R$^S$R$^{S'}$(R$^{N'}$—N=)S=N—, wherein $R^N$ is selected from H, NC—, H$_3$C—, (CH$_3$)$_3$C—O—C(=O)—, F$_3$C—C(=O)—, and $R^{N'}$ is H, wherein $R^S$ and $R^{S'}$ are independently selected from $H_3C$—, $H_5C_2$—, $(H_3C)_2CH$—, cyclopropyl, tetrahydropyranyl, phenyl, and pyridinyl, or $R^S$ and $R^{S'}$ linked together are selected from —$(CH_2)_4$—, —$(CH_2)_5$—, and —$(CH_2)_2$—O—$(CH_2)_2$—, and wherein any cyclohexyl, piperidinyl, phenyl and pyridinyl groups mentioned under Y or $R^S$ and $R^{S'}$ optionally are substituted with F, $H_3C$—, or $H_3C$—O—;

or a salt thereof.

4. A compound according to claim 1, wherein
$R^1$ is selected from the group consisting of

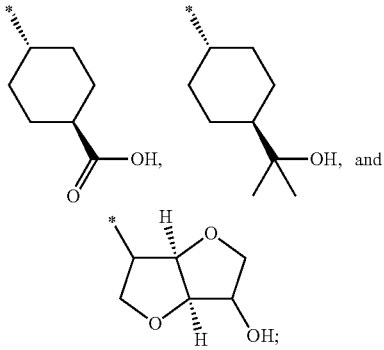

$R^2$ is selected from the group consisting of F, Cl, $H_3C$—, $H_3C$—O—, $F_3C$—, and $F_3C$—O—;
X is defined as in claim 1; and
Y is selected from the group consisting of

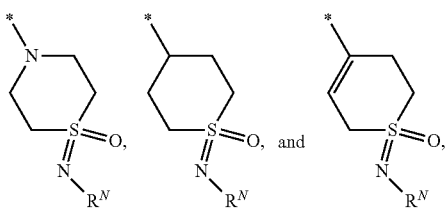

wherein $R^N$ is selected from H, NC—, $H_3C$—, $(H_3C)_3C$—O—C(=O)—, and $F_3C$—C(=O)—;
or a salt thereof.

5. A compound according to claim 1, wherein
$R^1$ is selected from the group consisting of

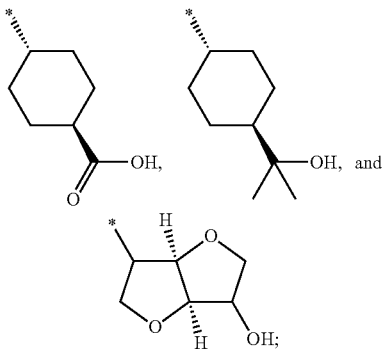

$R^2$ is selected from the group consisting of Cl, and $H_3C$—;
X is selected from the group consisting of a bond, a divalent piperazinyl, phenylene, and a pyridinylene, bound via para positions and optionally substituted with F or $H_3C$—; and
Y is selected from the group consisting of cyclohexyl, piperidinyl, phenyl and pyridinyl, which are mandatorily substituted with a group selected from $R^S R^{S'}(O=)S=N$—, $R^S R^{S'}(O=)S=N$—$CH_2$—, $R^S R^{S'}(O=)$S=N—C(=O)—, $(R^N)N=S(=O)(R^S)$—, $(R^N)N=S(=O)(R^S)$—$CH_2$—, and $R^S R^{S'}(R^{N'}$—N=)S=N—, wherein $R^N$ is selected from H, NC—, $H_3C$—, $(H_3C)_3C$—O—C(=O)—, $F_3C$—C(=O)—, and $R^{N'}$ is H, wherein $R^S$ and $R^{S'}$ are independently selected from $H_3C$—, $H_5C_2$—, $(H_3C)_2CH$—, cyclopropyl, tetrahydropyranyl, phenyl, and pyridinyl, or $R^S$ and $R^{S'}$ linked together are selected from —$(CH_2)_4$—, —$(CH_2)_5$—, and —$(CH_2)_2$—O—$(CH_2)_2$—, and wherein any cyclohexyl, piperidinyl, phenyl and pyridinyl groups mentioned under Y or $R^S$ and $R^{S'}$ optionally are substituted with F, $H_3C$—, or $H_3C$—O—;

or a salt thereof.

6. A compound according to claim 1, wherein
$R^1$ is selected from the group consisting of

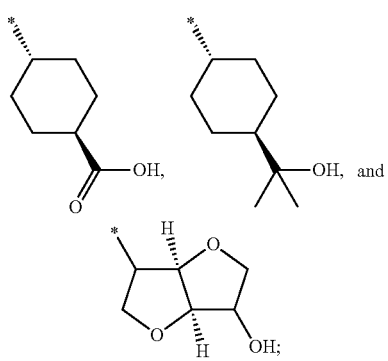

$R^2$ is selected from the group consisting of Cl, and $H_3C$—;
X is selected from the group consisting of a bond, a divalent piperazinyl, phenylene, and a pyridinylene, bound via para positions and optionally substituted with F or $H_3C$—; and
Y is selected from the group consisting of

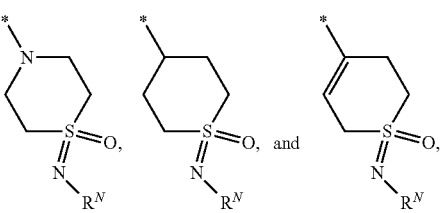

wherein $R^N$ is selected from H, NC—, $H_3C$—, $(H_3C)_3C$—O—C(=O)—, and $F_3C$—C(=O)—;
or a salt thereof.

7. A pharmaceutically acceptable salt of a compound according to claim 1.

8. A pharmaceutical composition comprising one or more compounds according to claim 1 or one or more pharmaceutically acceptable salts thereof, optionally together with one or more inert carriers and/or diluents.

9. A pharmaceutical composition comprising one or more compounds according to claim 1 or one or more pharmaceutically acceptable salts thereof and one or more additional therapeutic agents, optionally together with one or more inert carriers and/or diluents.

10. A pharmaceutical composition according to claim 9 wherein one additional therapeutic agent is selected from the group consisting of antidiabetic agents, agents for the treatment of overweight and/or obesity and agents for the treatment of high blood pressure, heart failure and/or atherosclerosis.

11. A compound of formula I, selected from a group consisting of:
1
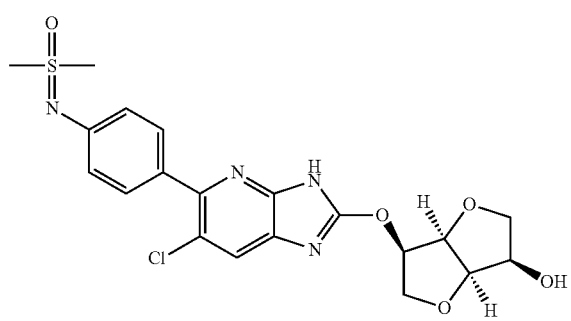
2
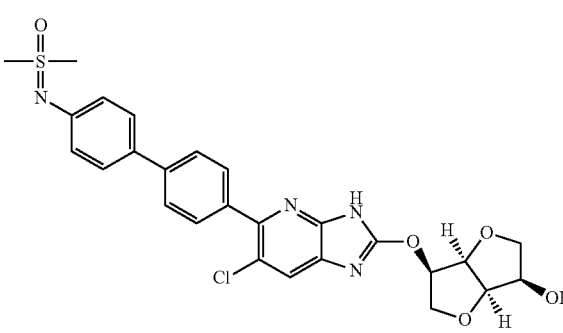
3
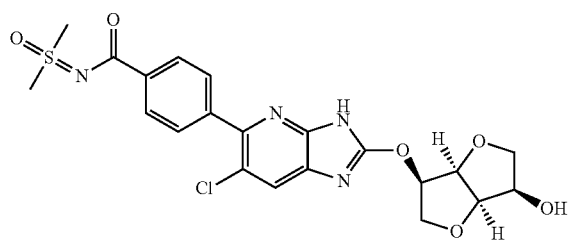
4
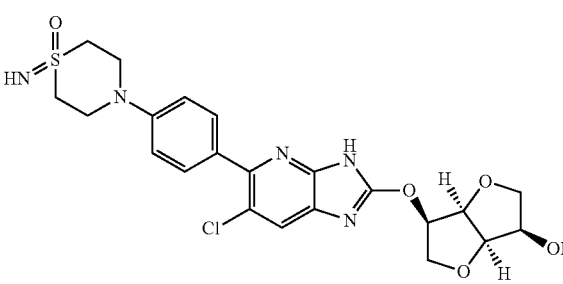
5
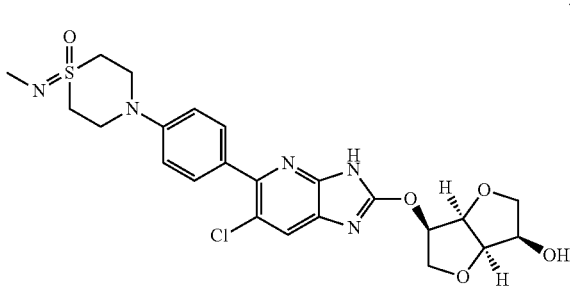
5
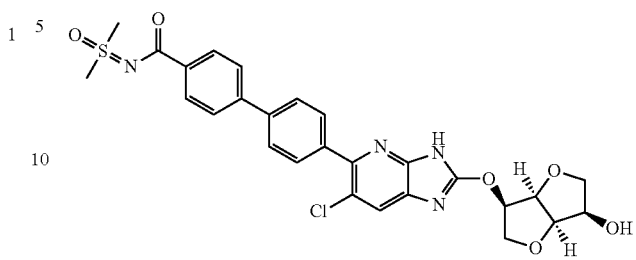
6
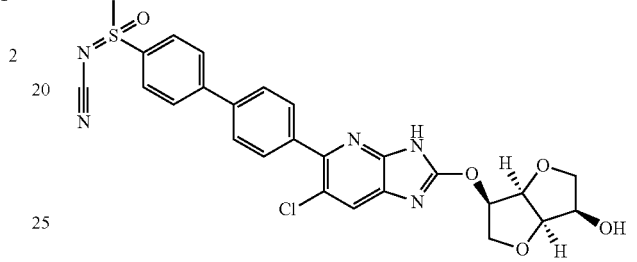
7
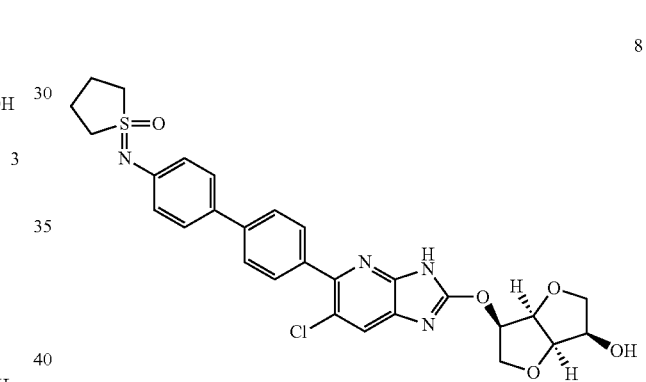
8
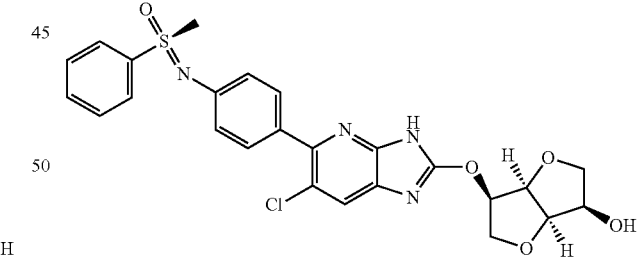
9
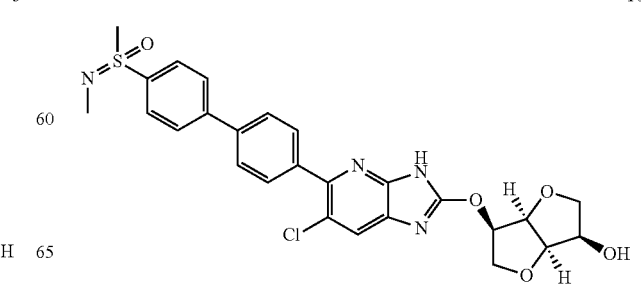

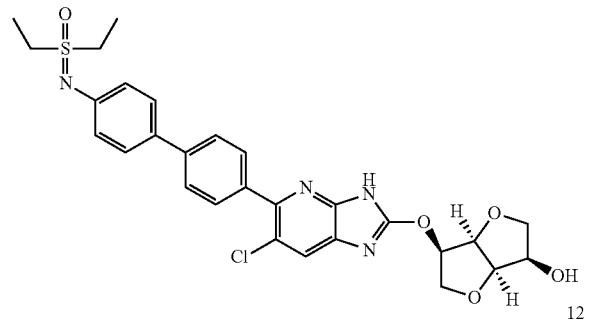
11
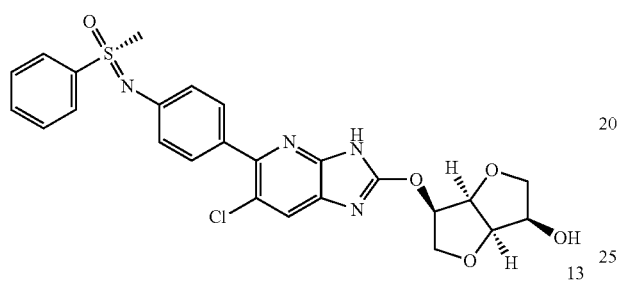
12
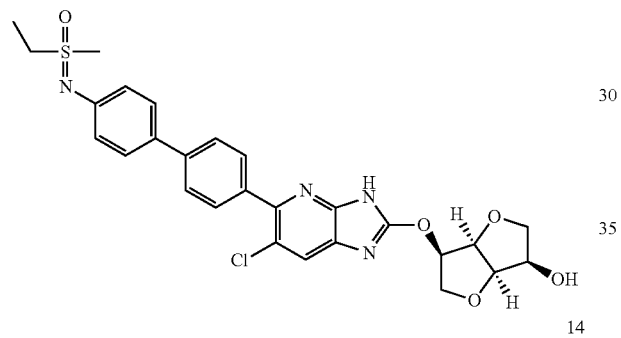
13
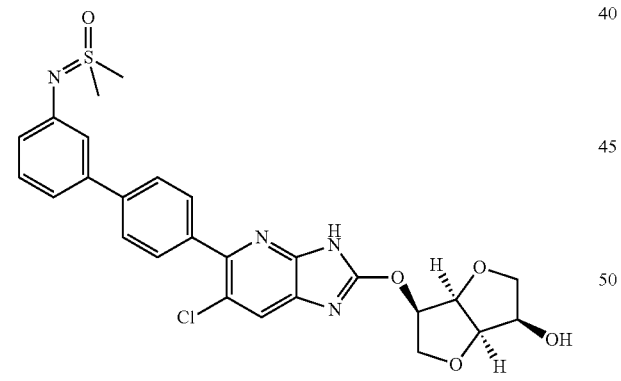
14
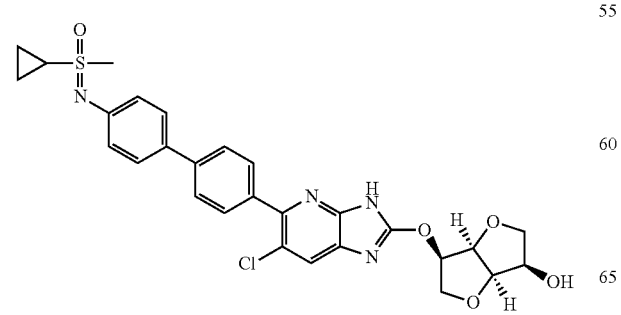
15
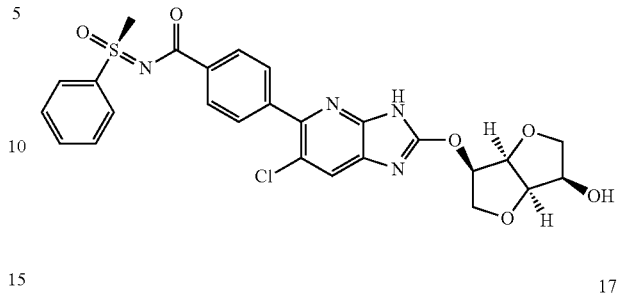
16
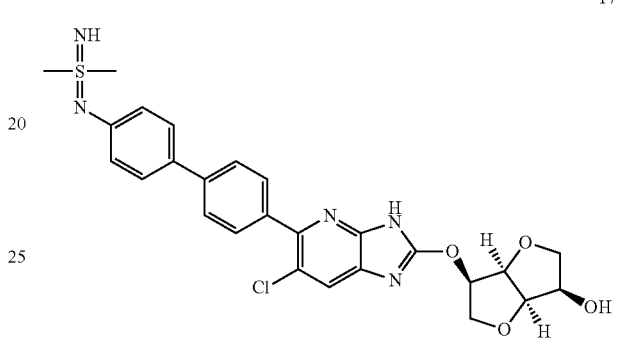
17
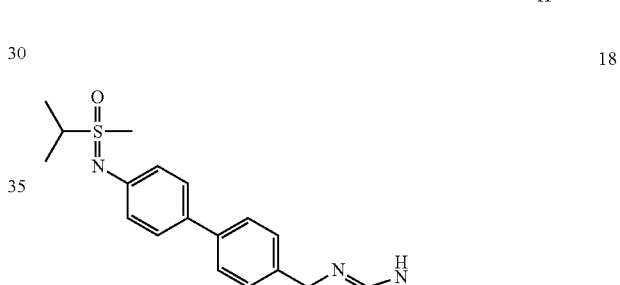
18
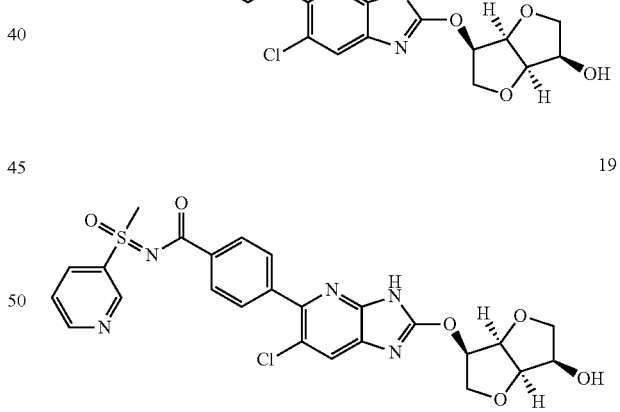
19
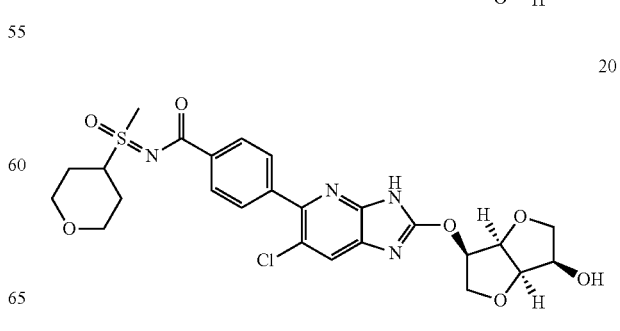
20

21
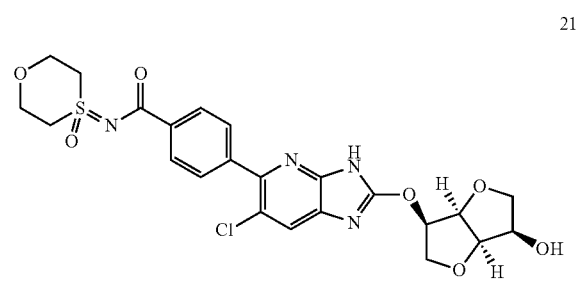
22
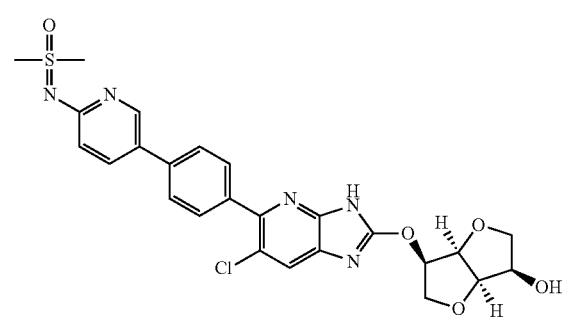
23
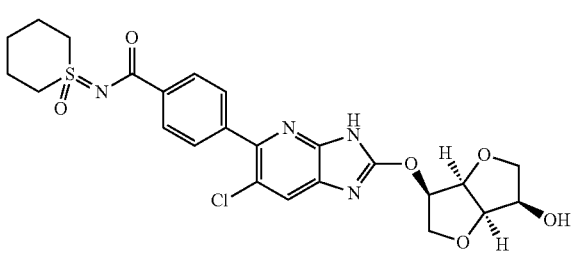
24
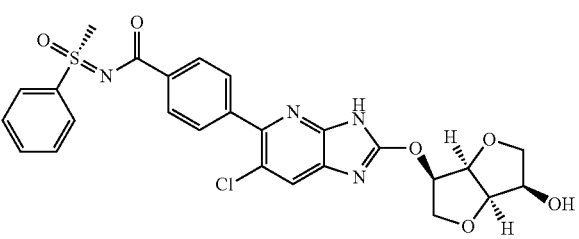
25
26
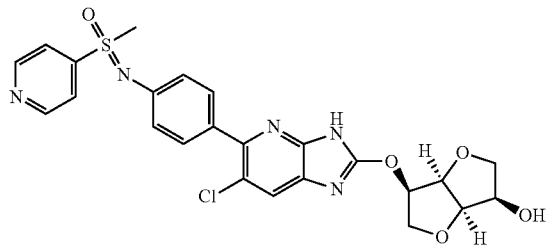
27
28
29
30
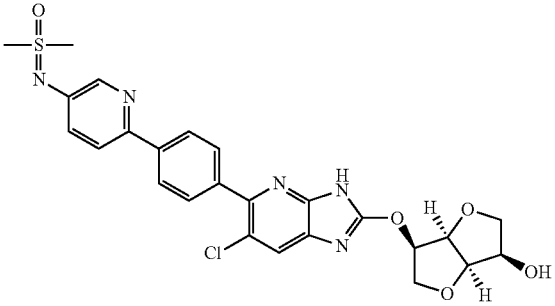

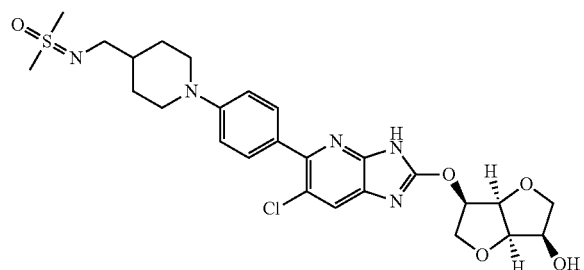
31
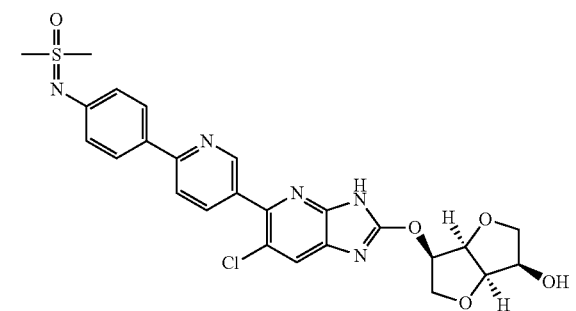
32
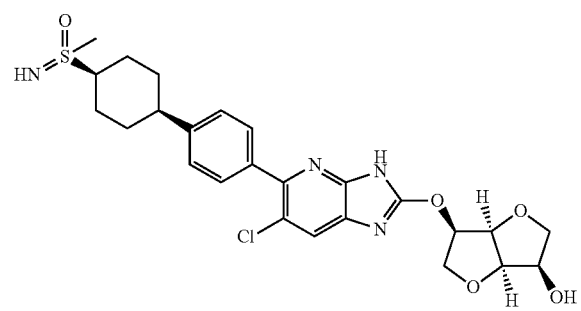
33
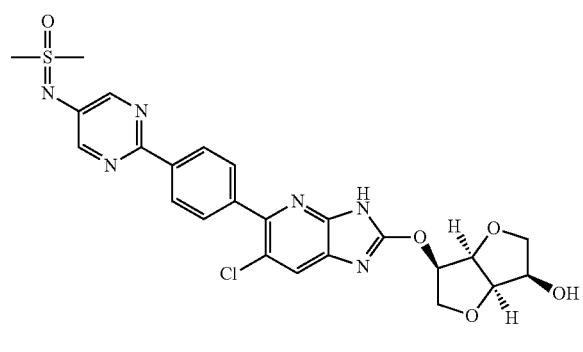
34
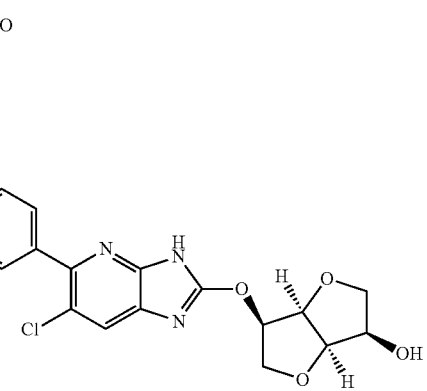
35
36
37
38
39

40
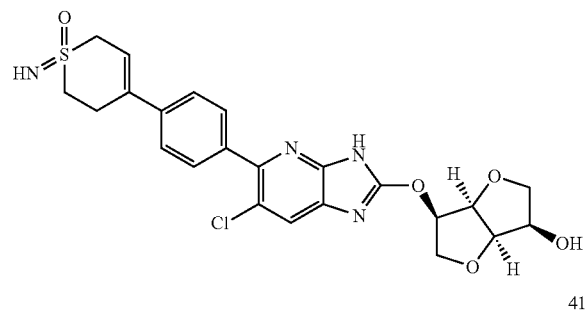
41
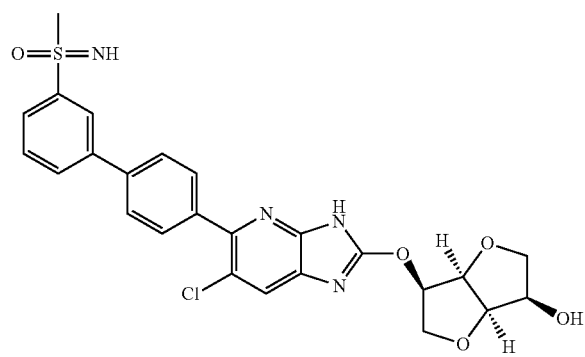
42
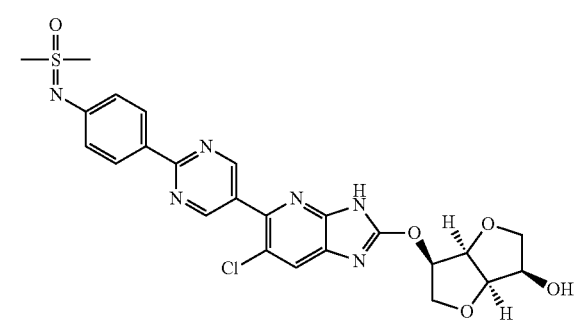
43
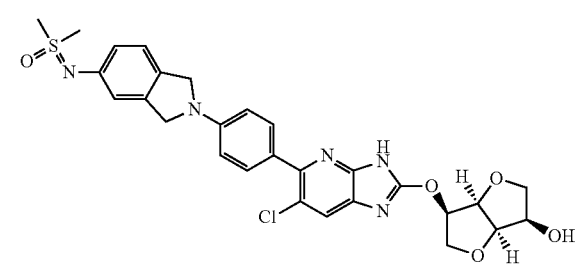
44
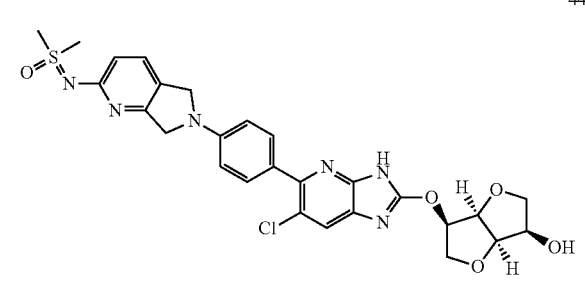
45
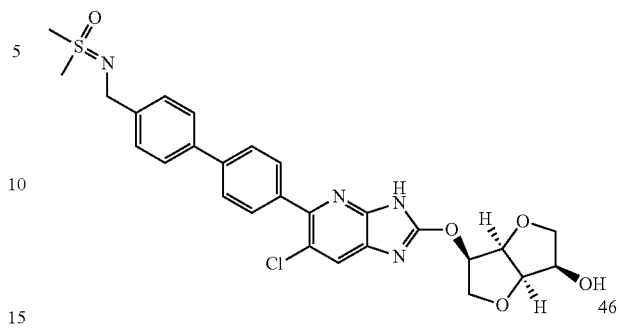
46
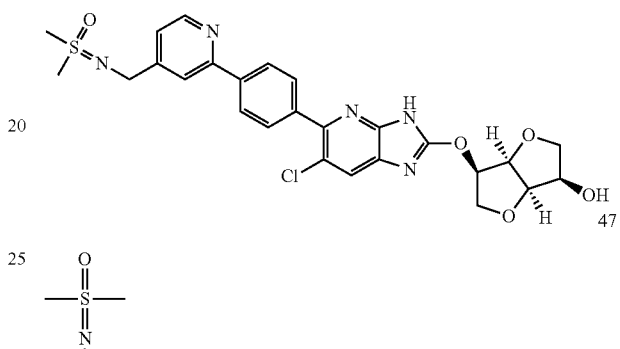
47
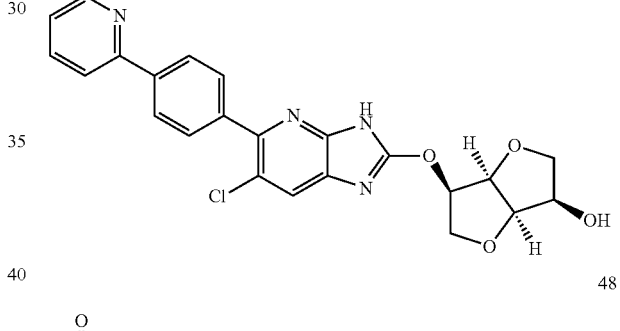
48
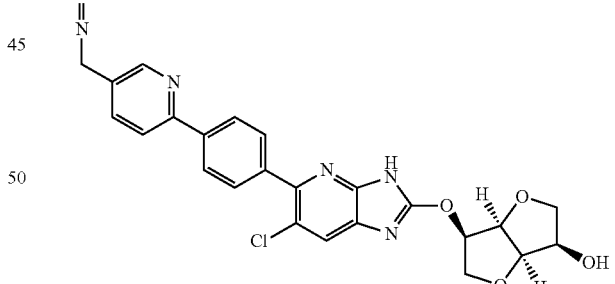
49
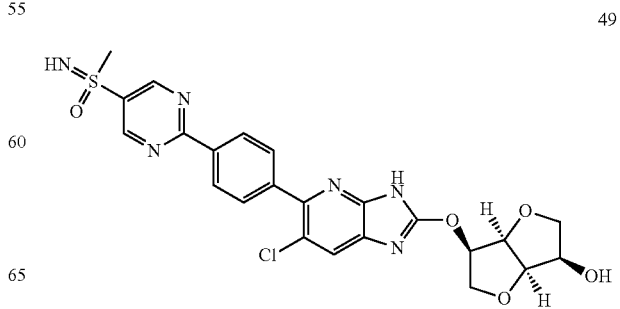

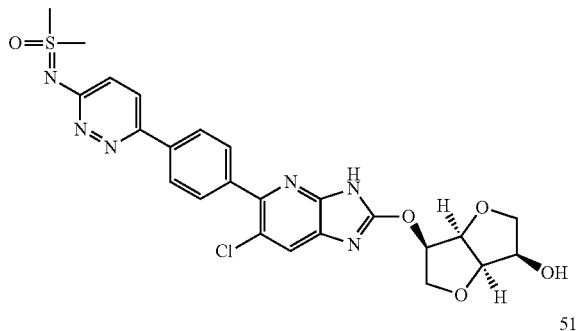
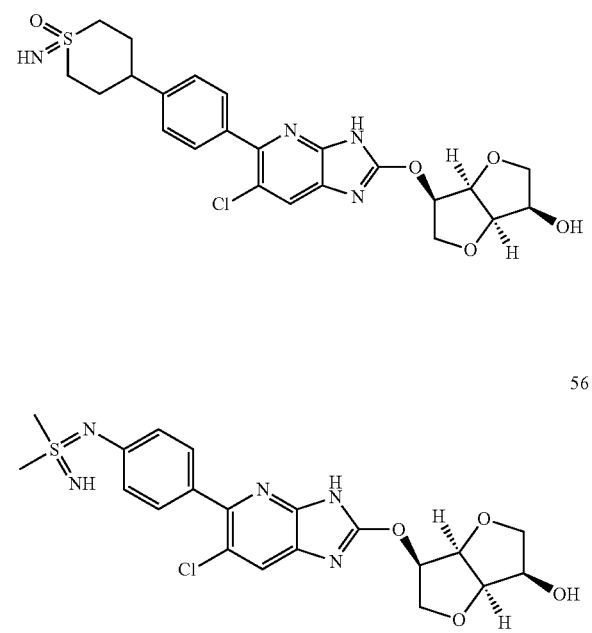
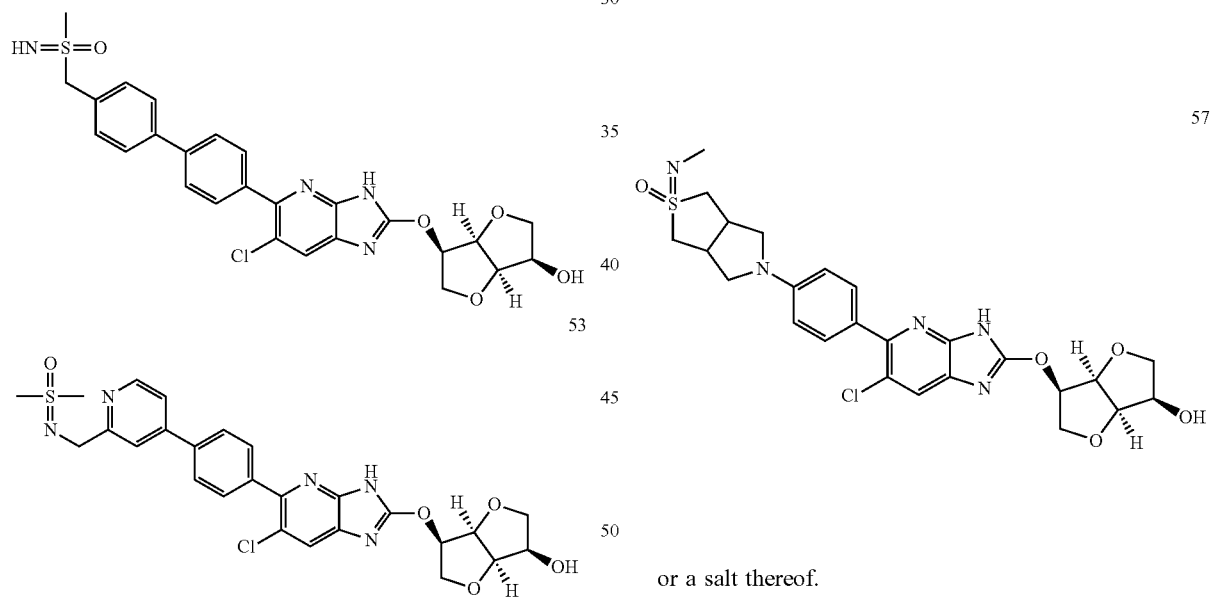
or a salt thereof.